United States Patent
Momose et al.

(10) Patent No.: US 7,423,159 B2
(45) Date of Patent: Sep. 9, 2008

(54) AGENT FOR PREVENTING OR TREATING NEUROPATHY

(75) Inventors: Yu Momose, Osaka (JP); Nozomu Sakai, Osaka (JP); Tsuyoshi Maekawa, Osaka (JP); Masatoshi Hazama, Osaka (JP); Toru Kawamura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 147 days.

(21) Appl. No.: 10/532,667

(22) PCT Filed: Oct. 30, 2003

(86) PCT No.: PCT/JP03/13901

§ 371 (c)(1),
(2), (4) Date: Apr. 27, 2005

(87) PCT Pub. No.: WO2004/039365

PCT Pub. Date: May 13, 2004

(65) Prior Publication Data

US 2006/0004069 A1    Jan. 5, 2006

(30) Foreign Application Priority Data

Nov. 1, 2002   (JP)   ............................. 2002-320153

(51) Int. Cl.
C07D 213/10   (2006.01)
(52) U.S. Cl. .................................... 548/356.1
(58) Field of Classification Search ............... 548/356.1
See application file for complete search history.

(56) References Cited

U.S. PATENT DOCUMENTS

| | | | |
|---|---|---|---|
| 3,702,330 A | 11/1972 | Hoff et al. | |
| 4,172,136 A | 10/1979 | Berger et al. | |
| 4,447,444 A * | 5/1984 | Stahler et al. | 514/407 |
| 4,835,280 A | 5/1989 | Martens et al. | |
| 5,250,504 A | 10/1993 | Maravetz | |
| 5,464,860 A | 11/1995 | Lepage et al. | |
| 5,552,420 A * | 9/1996 | Aldous et al. | 514/364 |
| 2004/0204417 A1 | 10/2004 | Perez et al. | |

FOREIGN PATENT DOCUMENTS

| | | |
|---|---|---|
| EP | 0 153 850 | 9/1985 |
| EP | 0 630 894 | 12/1994 |
| EP | 1 148 053 | 10/2001 |
| JP | 4-184435 | 7/1992 |
| WO | 86/00307 | 1/1986 |
| WO | 00/01679 | 1/2000 |
| WO | 00/75120 | 12/2000 |
| WO | 01/14372 | 3/2001 |
| WO | 02/098852 | 12/2002 |
| WO | 03/049702 | 6/2003 |
| WO | 03/072554 | 9/2003 |
| WO | 2003/099793 | 12/2003 |

OTHER PUBLICATIONS

T. M. Monteiro et al., "Synthesis and analgesic activity of new pyrazole-4-carboxanilides and (E)-3-pyrazol-4-ylpropenanilides", Revista Portuguesa De Farmacia, vol. 49, No. 4, 1999, pp. 153-160, with English translation.

M. K. Bratenko et al., "Functionally Substituted 3-Heterylpyrazoles: XI. 3-[3-Aryl (heteryl)pyrazol-4-yl]propenoic and Propanoic Acids", Russian Journal of Organic Chemistry, vol. 38, No. 8, 2002, pp. 1171-1177.

Patent Abstracts of Japan, vol. 1998, No. 12, Oct. 31, 1998 & JP 10 195063 A, Jul. 28, 1998 *abstract*.

M. Ohta et al., "Novel 5-Hydroxytryptamine (5-$HT_3$) Receptor Antagonists. I. Synthesis and Structure-Activity Relationships of Conformationally Restricted Fused Imidazole Derivatives" Chem. Phar. Bull. vol. 44, No. 5, 1996, pp. 991-999.

Y. Yuen-Lang et al., "Chemotherapeutic Studies on Schistosomiasis XXXIII. Synthesis of β-(5-Nitroimidazol-2-YI) Acrylamides and Related Compounds", Pharmaceutical Industry, vol. 17, No. 10, 1986, pp. 444-448, with English translation.

(Continued)

*Primary Examiner*—Rebecca L Anderson
*Assistant Examiner*—Robert Havlin
(74) *Attorney, Agent, or Firm*—Wenderoth, Lind & Ponack, L.L.P.

(57) ABSTRACT

The present invention provides an agent for preventing or treating neuropathy having superior action and low toxicity. This agent comprises a compound represented by the formula: wherein ring A is a 5-membered aromatic heterocycle containing 2 or more nitrogen atoms, which may further have substituent(s); B is an optionally substituted hydrocarbon group or an optionally substituted heterocyclic group; X is a divalent acyclic hydrocarbon group; Z is —O—, —S—, —$NR_2$—, —$CONR_2$— or —$NR_2CO$— ($R_2$ is a hydrogen atom or an optionally substituted alkyl group); Y is a bond or a divalent acyclic hydrocarbon group; $R_1$ is an optionally substituted cyclic group, an optionally substituted amino group or an optionally substituted acyl group, provided that when the 5-membered aromatic heterocycle represented by ring A is imidazole, then Z should not be —O—, or a salt thereof.

2 Claims, No Drawings

OTHER PUBLICATIONS

Y. Z. Ling et al., "17-Imidazolyl, Pyrazolyl, and Isoxazolyl Androstene Derivatives. Novel Steroidal Inhibitors of Human Cytochrome $C_{17,20}$-Lyase ($P450_{17a}$)", J. Med. Chem., vol. 40, No. 20, Sep. 26, 1997, pp. 3297-3304.

R. Plate et al., "Synthesis and Muscarinic Activities of 3-(Pyrazolyl)-1,2,5,6-tetrahydropyridine Derivatives", Bioorganic & Medicinal Chemistry, vol. 4, No. 2, Feb. 1996, pp. 227-237.

C. S. Lee et al., "Carbon-Carbon Linked (Pyrazolylphenyl)oxazolidinones with Antibacterial Activity Against Multiple Drug Resistant Gram-Positive and Fastidious Gram-Negative Bacteria", Bioorganic & Medicinal Chemistry, vol. 9, No. 12, Dec. 2001, pp. 3243-3253.

R. Plate et al., "Synthesis and In Vitro Muscarinic Activities of a Series of 3-(Pyrazol-3-yl)-1-azabicyclo[2.2.2]octanes", Bioorganic & Medicinal Chemistry, vol. 8, No. 2, Feb. 2000, pp. 449-454.

R. W. Harper et al., "Leukotriene $B_4$ ($LTB_4$) Receptor Antagonists: A Series of (Hydroxyphenyl)pyrazoles", J. Med. Chem., vol. 37, No. 15, Jul. 22, 1994, pp. 2411-2420.

G. R. Bebernitz et al., "The Effect of 1,3-Diaryl-[1H]-pyrazole-4-acetamides on Glucose Utilization in ob/ob Mice", J. Med. Chem., vol. 44, 2001, pp. 2601-2611.

Russian Office Action issued Jul. 16, 2007 in the corresponding Russian Application No. 2005-116689 with English translation.

"Heterocyclic compounds" ed. R.Elderfield, M. Foreign Literature, 1954, v.V, 9.45-47 In Russian with English translation.

* cited by examiner

AGENT FOR PREVENTING OR TREATING NEUROPATHY

This application is a U.S. national stage of International Application No. PCT/JP2003/013901 filed Oct. 30, 2003.

The present invention relates to an agent for preventing or treating neuropathy and an agent for promoting production or secretion of a neurotrophic factor.

Moreover, the present invention relates to a novel 5-membered aromatic heterocyclic compound having neurotrophic factor production or secretion promoting action, which is useful for the prophylaxis or treatment of neuropathy and the like.

BACKGROUND ART

As the 5-membered aromatic heterocyclic compound, the following compounds have been reported.

(1) As an adenosine A1 receptor antagonist, a compound represented by the formula:

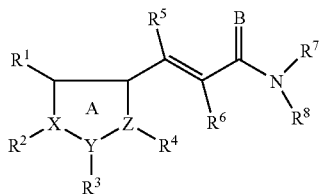

wherein A is an aromatic ring; X, Y and Z are each a carbon, a nitrogen, an oxygen or a sulfur; $R^1$ is an optionally substituted aryl or an optionally substituted heteroaryl; $R^2$, $R^3$ and $R^4$ are the same or different and each is a hydrogen, a lower alkyl, a lower alkenyl, a lower alkynyl and the like; $R^5$ and $R^6$ are the same or different and each is a hydrogen or a lower alkyl; B is an oxygen or a sulfur; $R^7$ and $R^8$ are the same or different and each is a hydrogen, a lower alkyl, a lower alkoxy, an optionally substituted aryl, an optionally substituted arylalkyl, an optionally substituted heteroaryl, an optionally substituted heteroarylalkyl, an optionally protected carboxyalkyl and the like has been reported (see EP-A-630894).

(2) As an antihyperlipidemic agent and anti-arteriosclerosis agent, a compound represented by the formula:

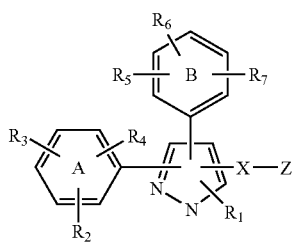

wherein $R_1$ is a $C_{1-6}$ alkyl; $R_2$ and $R_5$ are each independently a hydrogen, a $C_{1-4}$ alkyl, a $C_{1-4}$ alkoxy (except t-butoxy), a trifluoromethyl, a fluoro, a chloro, a phenyl, a phenoxy or a benzyloxy; $R_3$ and $R_6$ are each independently a hydrogen, a $C_{1-3}$ alkyl, a $C_{1-3}$ alkoxy, a trifluoromethyl, a fluoro, a chloro, a phenoxy or a benzyloxy; $R_4$ and $R_7$ are each independently a hydrogen, a $C_{1-3}$ alkyl, a $C_{1-2}$ alkoxy, a fluoro or a chloro;

X is —(CH$_2$)m- or —(CH$_2$)qCH=CH(CH$_2$)q- (m is 0, 1, 2 or 3, each q is 0, or one is 0 and the other is 1); and
Z is —CH(OH)—CH$_2$—C(OH)R$_{10}$—CH$_2$—COOH(R$_{10}$ is a hydrogen or a $C_{1-3}$ alkyl);

provided that each of ring A and B may have only one selected c; from trifluoromethyl, phenoxy and benzyloxy, and —X-Z is present at the 4- or 5-position of a pyrazole ring, and the ortho-position relative to $R_1$ has been reported (see WO86/00307).

(3) As a neurotrophin production or secretion promoter, a compound represented by the formula:

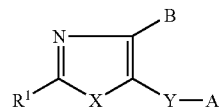

wherein $R^1$ is a halogen atom, an optionally substituted heterocyclic group, an optionally substituted hydroxy group, an optionally substituted thiol group or an optionally substituted amino group, A is an optionally substituted acyl group, an optionally substituted heterocyclic group, an optionally substituted hydroxy group or an optionally esterified or amidated carboxyl group, B is an optionally substituted aromatic group, X is an oxygen atom, a sulfur atom or an optionally substituted nitrogen atom, and Y is a divalent hydrocarbon group or a heterocyclic group has been reported (see WO01/14372).

(4) As a retinoid-related receptor function regulator, a compound represented by the formula

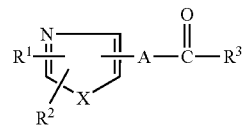

wherein $R^1$ is an optionally substituted aromatic hydrocarbon group or an optionally substituted aromatic heterocyclic group;
$R^2$ is a hydrogen or an optionally substituted hydrocarbon group;
X is O, S or a group represented by —NR$^4$— wherein $R^4$ is a hydrogen or an optionally substituted alkyl group; A is an optionally substituted aromatic hydrocarbon group or an optionally substituted aromatic heterocyclic group; $R^3$ is a group represented by the formula: —OR$^5$— wherein $R^5$ is a hydrogen or an optionally substituted hydrocarbon group or —NR$^6$R$^7$ wherein $R^6$ and $R^7$ are the same or different and each is a hydrogen or an optionally substituted hydrocarbon group, or $R^6$ and $R^7$ may form a ring together with the adjacent nitrogen atom has been reported (see WO00/01679).

SUMMARY OF THE INVENTION

An object of the present invention is to provide an agent for preventing or treating neuropathy, and an agent for promoting production or secretion of a neurotrophic factor, which have superior actions and which are low toxic.

A further object of the present invention is to provide a 5-membered aromatic heterocyclic compound having superior prophylactic or therapeutic action on neuropathy, which is low toxic.

The present inventors have found that a compound represented by the formula:

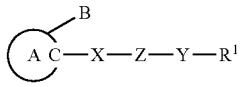

(I)

wherein
ring A is a 5-membered aromatic heterocycle containing 2 or more nitrogen atoms, which may further have substituent(s);
B is an optionally substituted hydrocarbon group or an optionally substituted heterocyclic group;
X, Z, Y and $R^1$ are as defined below,
provided that when the 5-membered aromatic heterocycle represented by ring A is imidazole, then Z should not be —O—, which is structurally characterized in that a group represented by the formula: —X-Z-Y—$R^1$ [X is a divalent acyclic hydrocarbon group; Z is —O—, —S—, —$NR^2$—, —$CONR^2$— or —$NR^2CO$— ($R^2$ is a hydrogen atom or an optionally substituted alkyl group); Y is a bond or a divalent acyclic hydrocarbon group; $R^1$ is an optionally substituted cyclic group, an optionally substituted amino group or an optionally substituted acyl group] is bonded on a ring-constituting carbon atom of a 5-membered aromatic heterocycle containing 2 or more nitrogen atoms, shows superior neurotrophic factor production or secretion action based on the characteristic chemical structure, and based on this finding, completed the present invention.

That is, the present invention relates to
1) an agent for preventing or treating neuropathy, which comprises a compound represented by the formula:

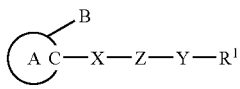

(I)

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;
Z is —O—, —S—, —$NR^2$—, —$CONR^2$— or —$NR^2CO$— ($R^2$ is a hydrogen atom or an optionally substituted alkyl group);
Y is a bond or a divalent acyclic hydrocarbon group; and
$R^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof;
2) the agent of the aforementioned 1), wherein the 5-membered aromatic heterocycle represented by ring A is a pyrazole, oxadiazole, thiadiazole, triazole or tetrazole ring;

3) the agent of the aforementioned 1), wherein the optionally substituted cyclic group represented by $R^1$ is a group represented by the formula:

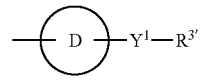

wherein D is a ring optionally further having substituent(s); $Y^1$ is a bond or a divalent acyclic hydrocarbon group; $R^{3'}$ is a group of the formula: —$SO_2R^4$, —$SOR^4$ or —$PO_3R^4R^5$ wherein $R^4$ and $R^5$ are the same or different and each is a hydrogen atom, a hydrocarbon group or a heterocyclic group, and $R^4$ and $R^5$ may form a heterocycle together with the adjacent oxo-substituted phosphorus atom and two oxygen atoms, or an optionally substituted heterocyclic group;
4) an agent for promoting production or secretion of a neurotrophic factor, which comprises a compound of the formula

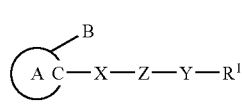

(I)

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;
Z is —O—, —S—, —$NR^2$—, —$CONR^2$— or —$NR^2CO$— ($R^2$ is a hydrogen atom or an optionally substituted alkyl group);
Y is a bond or a divalent acyclic hydrocarbon group; and
$R^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof;
5) the agent of the aforementioned 4), wherein the 5-membered aromatic heterocycle represented by ring A is a pyrazole, oxadiazole, thiadiazole, triazole or tetrazole ring;
6) an agent for ameliorating pain comprising a compound represented by the formula:

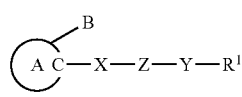

(I)

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;

Z is —O—, —S—, —NR$^2$—, —CONR$^2$— or —NR$^2$CO— (R$^2$ is a hydrogen atom or an optionally substituted alkyl group);

Y is a bond or a divalent acyclic hydrocarbon group; and

R$^1$ is an optionally substituted cyclic group, an optionally substituted amino group or an optionally substituted acyl group, provided that when the 5-membered aromatic heterocycle represented by ring A is imidazole, then Z should not be —O—, or a salt thereof;

7) the agent of the aforementioned 6), wherein the 5-membered aromatic heterocycle represented by ring A is a pyrazole, oxadiazole, thiadiazole, triazole or tetrazole ring;

8) a neuroprotective agent comprising a compound represented by the formula:

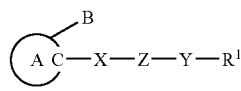

(I)

wherein ring A is a 5-membered aromatic heterocycle containing 2 or more nitrogen atoms, which may further have substituent(s);

B is an optionally substituted hydrocarbon group or an optionally substituted heterocyclic group;

X is a divalent acyclic hydrocarbon group;

Z is —O—, —S—, —NR$^2$—, —CONR$^2$— or —NR$^2$CO— (R$^2$ is a hydrogen atom or an optionally substituted alkyl group);

Y is a bond or a divalent acyclic hydrocarbon group; and

R$^1$ is an optionally substituted cyclic group, an optionally substituted amino group or an optionally substituted acyl group, provided that when the 5-membered aromatic heterocycle represented by ring A is imidazole, then Z should not be —O—, or a salt thereof;

9) a compound represented by the formula

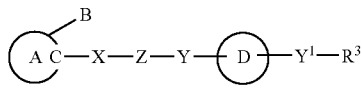

(II)

wherein ring A is a 5-membered aromatic heterocycle containing 2 or more nitrogen atoms, which may further have substituent(s);

B is an optionally substituted hydrocarbon group or an optionally substituted heterocyclic group;

X is a divalent acyclic hydrocarbon group;

Z is —O—, —S—, —NR$^2$—, —CONR$^2$— or —NR$^2$CO— (R$^2$ is a hydrogen atom or an optionally substituted alkyl group);

Y and Y$^1$ are the same or different and each is a bond or a divalent acyclic hydrocarbon group; and D is a ring optionally further having substituent(s);

R$^3$ is an optionally substituted acyl group or an optionally substituted heterocyclic group, provided that when the 5-membered aromatic heterocycle represented by ring A is imidazole, then Z should not be —O—, and provided that when the 5-membered aromatic heterocycle represented by ring A is pyrazole, X is methylene, Z is —S— and Y is a bond, then the ring represented by D should not be oxadiazole, or a salt thereof;

10) the compound of the aforementioned 9), wherein the 5-membered aromatic heterocycle represented by ring A is a pyrazole, oxadiazole, thiadiazole, triazole or tetrazole ring;

11) the compound of the aforementioned 9), wherein the optionally substituted acyl group represented by R$^3$ is a group of the formula: —SO$_2$R$^4$, —SOR$^4$ or —PO$_3$R$^4$R$^5$ wherein R$^4$ and R$^5$ are the same or different and each is a hydrogen atom, a hydrocarbon group or a heterocyclic group, and R$^4$ and R$^5$ may form a heterocycle together with the adjacent oxo-substituted phosphorus atom and two oxygen atoms;

12) the compound of the aforementioned 9), wherein the 5-membered aromatic heterocycle represented by ring A is a pyrazole ring;

13) the compound of the aforementioned 9), wherein B is an optionally substituted aromatic hydrocarbon group or an optionally substituted aromatic heterocyclic group;

14) the compound of the aforementioned 9), wherein X is a divalent C$_{1-8}$ aliphatic hydrocarbon group;

15) the compound of the aforementioned 9), wherein Z is —CONR$^2$— (R$^2$ is a hydrogen atom or an optionally substituted alkyl group);

16) the compound of the aforementioned 9), wherein Y is a bond or a C$_{1-4}$ alkylene;

17) the compound of the aforementioned 9), wherein Y$^1$ is a bond or a C$_{1-4}$ alkylene;

18) the compound of the aforementioned 9), wherein the ring represented by D is a C$_{6-14}$ aromatic hydrocarbon ring;

19) the compound of the aforementioned 9), which is diethyl [4-({(2E)-3-[5-(4-fluorophenyl)-1-methyl-1H-pyrazol-4-yl]prop-2-enoyl}amino)benzyl]phosphonate;

(2E)-N-{4-[(2,4-dioxo-1,3-thiazolidin-5-yl)methyl]phenyl}-3-[5-(4-fluorophenyl)-1-methyl-1H-pyrazol-4-yl]acrylamide;

(2E)-3-[5-(4-fluorophenyl)-1-methyl-1H-pyrazol-4-yl]-N-[4-(1H-imidazol-1-ylmethyl)phenyl]acrylamide;

(2E)-3-[5-(4-fluorophenyl)-1-methyl-1H-pyrazol-4-yl]-N-[4-(1H-pyrazol-1-ylmethyl)phenyl]acrylamide;

diethyl [4-({(2E)-3-[1-methyl-5-(2-thienyl)-1H-pyrazol-4-yl]prop-2-enoyl}amino)benzyl]phosphonate;

(2E)-3-[5-(4-fluorophenyl)-1-methyl-1H-pyrazol-4-yl]-N-{4-[(3-methyl-2,4-dioxo-1,3-thiazolidin-5-yl)methyl]phenyl}acrylamide;

(2E)-N-[4-(1H-benzimidazol-1-ylmethyl)phenyl]-3-[5-(4-fluorophenyl)-1-methyl-1H-pyrazol-4-yl]acrylamide;

(2E)-3-[5-(4-fluorophenyl)-1-methyl-1H-pyrazol-4-yl]-N-{4-[(methylsulfonyl)methyl]phenyl}acrylamide;

(2E)-3-[5-(4-fluorophenyl)-1-methyl-1H-pyrazol-4-yl]-N-{4-[hydroxy(2-pyridinyl)methyl]phenyl}acrylamide;

(2E)-3-[5-(4-fluorophenyl)-1-methyl-1H-pyrazol-4-yl]-N-[4-(4-morpholinylmethyl)phenyl]acrylamide; or (2E)-N-{4-[(ethylsulfonyl)methyl]phenyl}-3-[5-(4-fluorophenyl)-1-methyl-1H-pyrazol-4-yl]acrylamide;

20) a pharmaceutical agent comprising the compound of the aforementioned 9) or a prodrug thereof;

21) a method for preventing or treating neuropathy in a mammal, which comprises administering a compound represented by the formula:

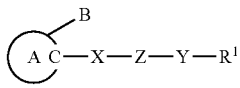

wherein
ring A is a 5-membered aromatic heterocycle containing 2 or more nitrogen atoms, which may further have substituent(s);
B is an optionally substituted hydrocarbon group or an optionally substituted heterocyclic group;
x is a divalent acyclic hydrocarbon group;
Z is —O—, —S—, —NR$^2$—, —CONR$^2$— or —NR$^2$CO— (R$^2$ is a hydrogen atom or an optionally substituted alkyl group);
Y is a bond or a divalent acyclic hydrocarbon group; and
R$^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof, to said mammal;

22) a method for promoting production or secretion of a neurotrophic factor in a mammal, which comprises administering a compound represented by the formula:

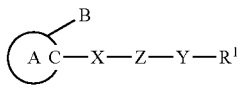

wherein
ring A is a 5-membered aromatic heterocycle containing 2 or more nitrogen atoms, which may further have substituent (s);
B is an optionally substituted hydrocarbon group or an optionally substituted heterocyclic group;
X is a divalent acyclic hydrocarbon group;
Z is —O—, —S—, —NR$^2$—, —CONR$^2$— or —NR$^2$CO— (R$^2$ is a hydrogen atom or an optionally substituted alkyl group);
Y is a bond or a divalent acyclic hydrocarbon group; and
R$^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof, to said mammal;

23) a method for ameliorating pain in a mammal, which comprises administering a compound represented by the formula:

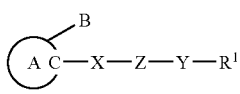

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;
Z is —O—, —S—, —NR$^2$—, —CONR$^2$— or —NR$^2$CO— (R$^2$ is a hydrogen atom or an optionally substituted alkyl group);
Y is a bond or a divalent acyclic hydrocarbon group; and
R$^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof, to said mammal;

24) a method for protecting a nerve in a mammal, which comprises administering a compound represented by the formula:

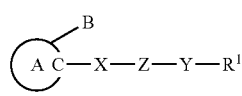

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;
Z is —O—, —S—, —NR$^2$—, —CONR$^2$— or —NR$^2$CO— (R$^2$ is a hydrogen atom or an optionally substituted alkyl group);
Y is a bond or a divalent acyclic hydrocarbon group; and
R$^1$ is an optionally substituted cyclic group, an optionally substituted amino group or an optionally substituted acyl group,
provided that when the 5-membered aromatic heterocycle represented by ring A is imidazole, then Z should not be —O—,
or a salt thereof, to said mammal;

25) use of a compound represented by the formula:

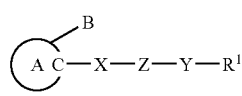

wherein
ring A is a 5-membered aromatic heterocycle containing 2 or more nitrogen atoms, which may further have substituent(s);
B is an optionally substituted hydrocarbon group or an optionally substituted heterocyclic group;
X is a divalent acyclic hydrocarbon group;
Z is —O—, —S—, —NR$^2$—, —CONR$^2$— or —NR$^2$CO— (R$^2$ is a hydrogen atom or an optionally substituted alkyl group);
Y is a bond or a divalent acyclic hydrocarbon group; and

9

$R^1$ is an optionally substituted cyclic group, an optionally substituted amino group or an optionally substituted acyl group, provided that when the 5-membered aromatic heterocycle represented by ring A is imidazole, then Z should not be —O—, or a salt thereof, for the production of an agent for preventing or treating neuropathy;

26) use of a compound represented by the formula:

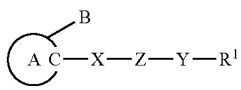
(I)

wherein ring A is a 5-membered aromatic heterocycle containing 2 or more nitrogen atoms, which may further have substituent(s);

B is an optionally substituted hydrocarbon group or an optionally substituted heterocyclic group;

X is a divalent acyclic hydrocarbon group;

Z is —O—, —S—, —$NR^2$—, —$CONR^2$— or —$NR^2CO$— ($R^2$ is a hydrogen atom or an optionally substituted alkyl group);

Y is a bond or a divalent acyclic hydrocarbon group; and $R^1$ is an optionally substituted cyclic group, an optionally substituted amino group or an optionally substituted acyl group, provided that when the 5-membered aromatic heterocycle represented by ring A is imidazole, then Z should not be —O—, or a salt thereof, for the production of an agent for promoting production or secretion of a neurotrophic factor;

27) use of a compound represented by the formula:

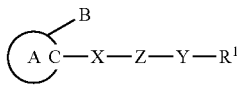
(I)

wherein ring A is a 5-membered aromatic heterocycle containing 2 or more nitrogen atoms, which may further have substituent(s);

B is an optionally substituted hydrocarbon group or an optionally substituted heterocyclic group;

X is a divalent acyclic hydrocarbon group;

Z is —O—, —S—, —$NR^2$—, —$CONR^2$— or —$NR^2CO$— ($R^2$ is a hydrogen atom or an optionally substituted alkyl group);

Y is a bond or a divalent acyclic hydrocarbon group; and $R^1$ is an optionally substituted cyclic group, an optionally substituted amino group or an optionally substituted acyl group, provided that when the 5-membered aromatic heterocycle represented by ring A is imidazole, then Z should not be —O—, or a salt thereof, for the production of an agent for ameliorating pain;

10

28) use of a compound represented by the formula:

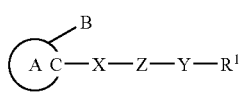
(I)

wherein ring A is a 5-membered aromatic heterocycle containing 2 or more nitrogen atoms, which may further have substituent(s);

B is an optionally substituted hydrocarbon group or an optionally substituted heterocyclic group;

X is a divalent acyclic hydrocarbon group;

Z is —O—, —S—, —$NR^2$—, —$CONR^2$— or —$NR^2CO$— ($R^2$ is a hydrogen atom or an optionally substituted alkyl group);

Y is a bond or a divalent acyclic hydrocarbon group; and $R^1$ is an optionally substituted cyclic group, an optionally substituted amino group or an optionally substituted acyl group, provided that when the 5-membered aromatic heterocycle represented by ring A is imidazole, then Z should not be —O—, or a salt thereof, for the production of a neuroprotective agent;

29) a production method of a compound represented by the formula:

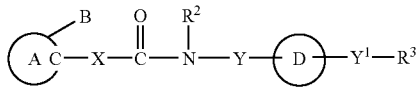

wherein ring A is a 5-membered aromatic heterocycle containing 2 or more nitrogen atoms, which may further have substituent (s);

B is an optionally substituted hydrocarbon group or an optionally substituted heterocyclic group;

X is a divalent acyclic hydrocarbon group;

$R^2$ is a hydrogen atom or an optionally substituted alkyl group;

Y and $Y^1$ are the same or different and each is a bond or a divalent acyclic hydrocarbon group;

D is a ring optionally further having substituent(s); and $R^3$ is an optionally substituted acyl group or an optionally substituted heterocyclic group, or a salt thereof, which comprises reacting a compound represented by the formula:

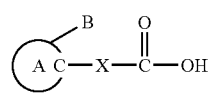
(III)

wherein each symbol is as defined above, or a salt thereof, with a compound represented by the formula:

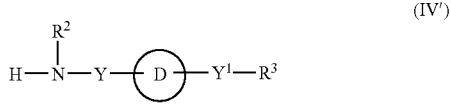

wherein each symbol is as defined above, or a salt thereof;
30) a production method of a compound represented by the formula:

wherein

B is an optionally substituted hydrocarbon group or an optionally substituted heterocyclic group, and $alk^4$ is a $C_{1-6}$ alkyl group or a $C_{7-13}$ aralkyl group, or a salt thereof, which comprises reacting a compound represented by the formula:

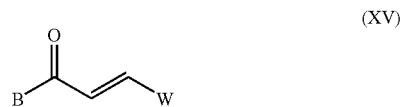

wherein W is —OH or —N($alk^2$)($alk^3$) wherein $alk^2$ and $alk^3$ are the same or different and each is a $C_{1-6}$ alkyl group, and B is as defined above, or a salt thereof, with a $C_{1-6}$ alkylhydrazine or a $C_{7-13}$ aralkylhydrazine in the presence of an acid; and the like.

DETAILED DESCRIPTION OF THE INVENTION

The terms used in the present specification are defined in detail in the following.

In the "5-membered aromatic heterocycle containing 2 or more nitrogen atoms, which may further have substituent(s)" denoted by ring A, as the "5-membered aromatic heterocycle containing 2 or more nitrogen atoms", for example, a 5-membered aromatic heterocycle containing 2 or more nitrogen atoms besides carbon atoms as ring-constituting atoms and optionally further containing 1 or 2 heteroatoms selected from an oxygen atom, a sulfur atom and a nitrogen atom can be mentioned.

As concrete examples of the "5-membered aromatic heterocycle containing 2 or more nitrogen atoms", for example, an imidazole ring, a pyrazole ring, an oxadiazole ring, a thiadiazole ring, a triazole ring, a tetrazole ring and the like can be mentioned. Of these a pyrazole ring, an oxadiazole ring, a thiadiazole ring, a triazole ring and a tetrazole ring are preferable, and a pyrazole ring is particularly preferable.

The "5-membered aromatic heterocycle containing 2 or more nitrogen atoms" may further have 1 or 2 substituents at substitutable positions. As such substituent, for example a halogen atom, an optionally substituted hydrocarbon group, an optionally substituted heterocyclic group, an optionally substituted hydroxy group, an optionally substituted thiol group, an optionally substituted amino group and the like can be mentioned.

As the aforementioned "halogen atom", for example, fluorine atom, chlorine atom, bromine atom and iodine atom can be mentioned. Of these, fluorine atom and chlorine atom are preferable.

As the "hydrocarbon group" in the aforementioned "optionally substituted hydrocarbon group", for example, an aliphatic hydrocarbon group, an alicyclic hydrocarbon group, an aromatic hydrocarbon group, an aromatic aliphatic hydrocarbon group, an alicyclic aliphatic hydrocarbon group and the like can be mentioned.

As the aliphatic hydrocarbon groups, for example, straight-chain or branched aliphatic hydrocarbon groups containing 1 to 15 carbon atoms, specifically an alkyl group, an alkenyl group, an alkynyl group, and the like can be mentioned.

As preferable examples of the alkyl groups, $C_{1-10}$ alkyl groups such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As preferable examples of the alkenyl groups, $C_{2-10}$ alkenyl groups such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As preferable examples of the alkynyl groups, $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the alicyclic hydrocarbon groups, for example, saturated or unsaturated alicyclic hydrocarbon groups containing 3 to 12 carbon atoms, specifically a cycloalkyl group, a cycloalkenyl group, a cycloalkadienyl group and the like, can be mentioned.

As preferable examples of the cycloalkyl groups, $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like can be mentioned.

As preferable examples of the cycloalkenyl groups, $C_{3-10}$ cycloalkenyl groups such as 2-cyclopenten-1-yl, 3-cyclopenten-1-yl, 2-cyclohexen-1-yl, 3-cyclohexen-1-yl and the like can be mentioned.

As preferable examples of the cycloalkadienyl groups, $C_{4-10}$ cycloalkadienyl groups such as 2,4-cyclopentadien-1-yl, 2,4-cyclohexadien-1-yl, 2,5-cyclohexadien-1-yl and the like can be mentioned.

As the aromatic hydrocarbon group, for example, a $C_{6-14}$ aryl group and the like can be mentioned. As preferable examples of the aryl group, phenyl, naphthyl, anthryl, phenanthryl, acenaphthylenyl, biphenylyl, indenyl and the like can be mentioned. Of these, phenyl, naphthyl and the like are preferable. The aryl group may be partially saturated and as the partially saturated aryl group, for example, dihydroindenyl and the like can be mentioned.

As the aromatic aliphatic hydrocarbon group, for example, a $C_{7-13}$ aromatic aliphatic hydrocarbon group, and concretely, an aralkyl group; an arylalkenyl group and the like, can be mentioned.

As preferable examples of the aralkyl group, a $C_{7-13}$ aralkyl group, such as benzyl, phenethyl, phenylpropyl, naphthylmethyl, benzhydryl and the like, can be mentioned.

As preferable examples of the arylalkenyl group, a $C_{8-13}$ arylalkenyl group, such as styryl and the like, can be mentioned.

As the alicyclic aliphatic hydrocarbon group, for example, a $C_{4-13}$ alicyclic aliphatic hydrocarbon group, and concretely, a cycloalkylalkyl group, a cycloalkylalkenyl group and the like can be mentioned.

As preferable examples of the cycloalkylalkyl group, a $C_{4-13}$ cycloalkylalkyl group, such as cyclopropylmethyl, cyclopropylethyl, cyclopentylmethyl, cyclopentylethyl, cyclohexylmethyl, cyclohexylethyl and the like, can be mentioned.

As preferable examples of the cycloalkylalkenyl group, a $C_{5-13}$ cycloalkylalkenyl group, such as cyclopropylethenyl, cyclopentylethenyl, cyclohexylethenyl and the like, can be mentioned.

The above-mentioned "hydrocarbon group" may have 1 to 3 substituents at substitutable positions. As such substituent, for example, a halogen atom, a nitro, an oxo, a $C_{1-3}$ alkylenedioxy, an optionally substituted aromatic heterocyclic group, an optionally substituted non-aromatic heterocyclic group, an optionally substituted amino group, an optionally substituted hydroxy group, an optionally substituted thiol group, an optionally substituted acyl group and the like can be mentioned.

As the halogen atoms, for example, a fluorine atom, a chlorine atom, a bromine atom and an iodine atom can be mentioned. Especially preferred are a fluorine atom and a chlorine atom.

As the $C_{1-3}$ alkylenedioxy, for example, methylenedioxy, ethylenedioxy and the like can be mentioned.

As the "aromatic heterocyclic group" of the "optionally substituted aromatic heterocyclic group", for example, a 5- to 7-membered monocyclic aromatic heterocyclic group which contains, as a ring-constituting atom besides carbon atoms, 1 to 4 heteroatoms selected from an oxygen atom, a sulfur atom and a nitrogen atom or a condensed aromatic heterocyclic group, can be mentioned. As the condensed aromatic heterocyclic group, for example, a group wherein these 5- to 7-membered monocyclic aromatic heterocyclic groups are condensed with a 6-membered ring containing 1 or 2 nitrogen atoms, a benzene ring, a 5-membered ring containing 1 sulfur atom, and the like can be mentioned.

As preferable examples of the "aromatic heterocyclic group", furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), oxazolyl (e.g., 2-oxazolyl, 4-oxazolyl, 5-oxazolyl), isoxazolyl, thiazolyl (e.g., 2-thiazolyl, 4-thiazolyl, 5-thiazolyl), isothiazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,4-triazol-5-yl, 1,2,3-triazol-1-yl, 1,2,3-triazol-2-yl, 1,2,3-triazol-4-yl), tetrazolyl (e.g., tetrazol-1-yl, tetrazol-5-yl), quinolyl (e.g., 2-quinolyl, 3-quinolyl, 4-quinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl), benzimidazolyl (e.g., benzimidazol-1-yl, benzimidazol-2-yl), indolyl (e.g., indol-1-yl, indol-3-yl), 1H-indazolyl (e.g., 1H-indazol-3-yl), 1H-pyrrolo[2,3-b]pyrazinyl (e.g., 1H-pyrrolo[2,3-b]pyrazin-2-yl), 1H-pyrrolopyridinyl (e.g., 1H-pyrrolo[2,3-b]pyridin-6-yl), 1H-imidazopyridinyl (e.g., 1H-imidazo[4,5-b]pyridin-2-yl, 1H-imidazo[4,5-c]pyridin-2-yl), 1H-imidazopyrazinyl (e.g., 1H-imidazo[4,5-b]pyrazin-2-yl), triazinyl, isoquinolyl, benzoxadiazolyl, benzothiadiazolyl, benztriazolyl and the like can be mentioned.

As the "non-aromatic heterocyclic group" of the "optionally substituted non-aromatic heterocyclic group", for example, a 5- to 7-membered monocyclic non-aromatic heterocyclic group which contains 1 to 4 heteroatoms selected from an oxygen atom, a sulfur atom and a nitrogen atom as a ring-constituting atom besides carbon atoms or a condensed non-aromatic heterocyclic group can be mentioned. As the condensed non-aromatic heterocyclic group, for example, a group wherein these 5- to 7-membered monocyclic non-aromatic heterocyclic groups are condensed with a 6-membered ring containing 1 or 2 nitrogen atoms, a benzene ring, a 5-membered ring containing 1 sulfur atom, and the like can be mentioned.

As preferable examples of the non-aromatic heterocyclic group, pyrrolidinyl (e.g., 1-pyrrolidinyl), piperidinyl (e.g., piperidino), morpholinyl (e.g., morpholino), thiomorpholinyl (e.g., thiomorpholino), piperazinyl (e.g., 1-piperazinyl), hexamethyleneiminyl (e.g., hexamethylenimin-1-yl), oxazolidinyl (e.g., oxazolidin-3-yl), thiazolidinyl (e.g., thiazolidin-3-yl), imidazolidinyl (e.g., imidazolidin-3-yl), imidazolinyl (e.g., imidazolin-1-yl, imidazolin-2-yl), oxazolinyl (e.g., oxazolin-2-yl), thiazolinyl (e.g., thiazolin-2-yl), oxazinyl (e.g., oxazin-2-yl), tetrahydrofuranyl, azepanyl, tetrahydropyridinyl (e.g., 1,2,3,6-tetrahydropyridin-1-yl), dihydrobenzofuranyl, dioxolanyl, dithiolanyl, dioxothiazolidinyl, dioxooxazolidinyl and the like can be mentioned.

The above-mentioned aromatic heterocyclic group and non-aromatic heterocyclic group may have 1 to 3 substituents at substitutable positions. As such substituent, for example, a nitro, a hydroxy, an amino, an oxo, a halogen atom (e.g., fluorine atom, chlorine atom, bromine atom, iodine atom), a $C_{1-6}$ alkyl optionally substituted by 1 to 3 halogen atoms (e.g., fluorine atom, chlorine atom, bromine atom, iodine atom) such as methyl and ethyl, a $C_{1-6}$ alkoxy group optionally substituted by 1 to 3 halogen atoms (e.g., fluorine atom, chlorine atom, bromine atom, iodine atom) such as methoxy and ethoxy, a $C_{6-14}$ aryl (e.g., phenyl) and the like can be mentioned.

As the "optionally substituted amino group", for example, an amino group optionally mono- or di-substituted by a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{1-13}$ acyl group or a heteroaryl group, each optionally having substituents can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group and $C_{7-13}$ aralkyl group, those exemplified as the "hydrocarbon group" of the "optionally substituted hydrocarbon group" exemplified as the substituents for ring A can be mentioned.

As the aforementioned $C_{1-13}$ acyl group, those exemplified as the acyl group of the "optionally substituted acyl group" to be mentioned later can be mentioned. The acyl group is preferably a formyl, a $C_{1-10}$ alkyl-carbonyl, a $C_{1-6}$ alkoxy-carbonyl, a $C_{6-14}$ aryl-carbonyl, a $C_{7-13}$ aralkyl-carbonyl, a 5- or 6-membered aromatic heterocyclic-carbonyl, a 5- or 6-membered non-aromatic heterocyclic-carbonyl and the like.

Here, as preferable examples of the $C_{1-10}$ alkyl-carbonyl, acetyl, propionyl, butyryl, isobutyryl, valeryl, isovaleryl, pivaloyl, hexanoyl, heptanoyl, octanoyl and the like can be mentioned.

As preferable examples of the $C_{1-6}$ alkoxy-carbonyl, for example, tert-butoxycarbonyl and the like can be mentioned.

As preferable examples of the $C_{6-14}$ aryl-carbonyl, benzoyl and the like can be mentioned.

As preferable examples of the $C_{7-13}$ aralkyl-carbonyl, benzylcarbonyl, phenethylcarbonyl and the like can be mentioned.

As preferable examples of the 5- or 6-membered aromatic heterocyclic-carbonyl, furylcarbonyl, pyrrolylcarbonyl, thienylcarbonyl, pyridylcarbonyl and the like can be mentioned.

As preferable examples of the 5- or 6-membered non-aromatic heterocyclic-carbonyl, tetrahydrofurylcarbonyl and the like can be mentioned.

As the aforementioned heteroaryl group, for example, the aromatic heterocyclic groups exemplified as the substituents of the "optionally substituted hydrocarbon group" exemplified as the substituents for ring A can be mentioned. Of these, pyridyl, imidazolyl, triazolyl, pyrimidinyl and the like are preferable These $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{1-13}$ acyl group and heteroaryl group may have 1 to 6, preferably 1 or 2 substituents at substitutable positions. As such substituent, for example, a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, a $C_{1-6}$ alkoxy group optionally substituted by 1 to 3 halogen atoms (e.g., fluorine atom, chlorine atom, bromine atom, iodine atom) such as methoxy and ethoxy, a hydroxy, a nitro, an amino, a $C_{1-6}$ alkylsulfonyl group (e.g., methylsulfonyl) and the like can be mentioned.

As the substituted amino group, for example, a mono- or di-$C_{1-10}$ alkylamino (e.g., methylamino, dimethylamino, ethylamino, diethylamino, ethylmethylamino, propylamino, dibutylamino), a mono- or di-$C_{2-10}$ alkenylamino (e.g., diallylamino), a mono- or di-$C_{3-10}$ cycloalkylamino (e.g., cyclohexylamino), a mono- or di-$C_{1-10}$ alkyl-carboxamide (e.g., acetylamino, propionylamino), a mono- or di-$C_{6-14}$ arylamino (e.g., phenylamino), a N-$C_{1-10}$ alkyl-N-$C_{6-14}$ arylamino (e.g., N-methyl-N-phenylamino), a N-$C_{1-10}$ alkyl-N-$C_{7-13}$ aralkylamino (e.g., N-methyl-N-benzylamino), a mono- or di-$C_{1-6}$ alkoxy-carboxamide (e.g., tert-butoxycarboxamide), a mono- or di-$C_{6-14}$ aryl-carboxamide (e.g., phenylcarboxamide), a mono- or di-$C_{7-13}$ aralkyl-carboxamide (e.g., benzylcarboxamide, phenethylcarboxamide), a mono- or di-5- or 6-membered aromatic heterocyclic-carboxamide (e.g., furylcarboxamide, pyrrolylcarboxamide, thienylcarboxamide, pyridylcarboxamide), a mono- or di-5- or 6-membered non-aromatic heterocyclic-carboxamide (e.g., tetrahydrofurylcarboxamide) and the like can be mentioned.

As the "optionally substituted hydroxy group", for example, a hydroxy group optionally substituted by a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{1-13}$ acyl group or a heteroaryl group, each of which is optionally substituted and the like, can be mentioned.

Here, as the $C_{1-10}$ alkyl group, $C_{2-10}$ alkenyl group, $C_{3-10}$ cycloalkyl group, $C_{3-10}$ cycloalkenyl group, $C_{6-14}$ aryl group and $C_{7-13}$ aralkyl group, those exemplified as the "hydrocarbon group" of the "optionally substituted hydrocarbon group" exemplified as the substituents for ring A can be mentioned.

As the $C_{1-13}$ acyl group, those exemplified as the substituent of the aforementioned "optionally substituted amino group" can be mentioned.

As the heteroaryl group, for example, aromatic heterocyclic groups exemplified as the substituents of the "optionally substituted hydrocarbon group" exemplified as the substituents for ring A can be mentioned. Of these, pyridyl, imidazolyl, triazolyl, pyrimidinyl and the like are preferable.

These $C_{3-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{1-13}$ acyl group and heteroaryl group may have 1 or 2 substituents at substitutable positions. As such substituent, for example, a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, a $C_1$ alkoxy group optionally substituted by 1 to 3 halogen atoms (e.g., fluorine atom, chlorine atom, bromine atom, iodine atom) such as methoxy and ethoxy, a hydroxy, a nitro, an amino, a $C_{1-6}$ alkylsulfonyl group (e.g., methylsulfonyl) and the like can be mentioned.

As the substituted hydroxy group, for example, an alkoxy group, an alkenyloxy group, a cycloalkyloxy group, a cycloalkenyloxy group, an aryloxy group, an aralkyloxy group, an acyloxy group, a heteroaryloxy group, each of which is optionally substituted and the like, can be mentioned.

As preferable examples of the alkoxy group, $C_{1-10}$ alkoxy group, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy and the like, can be mentioned.

As preferable examples of the alkenyloxy group, $C_{2-10}$ alkenyloxy group, such as allyloxy, crotyloxy, 2-pentenyloxy, 3-hexenyloxy and the like, can be mentioned.

As preferable examples of the cycloalkyloxy group, $C_{3-10}$ cycloalkyloxy group, such as cyclobutoxy, cyclopentyloxy, cyclohexyloxy and the like, can be mentioned.

As preferable examples of the cycloalkenyloxy group, $C_{3-10}$ cycloalkenyloxy group, such as 2-cyclopentenyloxy, 2-cyclohexenyloxy and the like, can be mentioned.

As preferable examples of the aryloxy group, $C_{6-14}$ aryloxy group, such as phenoxy, naphthyloxy and the like, can be mentioned.

As preferable examples of the aralkyloxy group, $C_{7-13}$ aralkyloxy group, such as benzyloxy, phenethyloxy, naphthylmethyloxy and the like, can be mentioned.

As preferable examples of the acyloxy group, $C_{2-13}$ acyloxy group, such as $C_{1-6}$ alkyl-carbonyloxy group (e.g., acetyloxy, propionyloxy, butyryloxy, isobutyryloxy) and the like, can be mentioned.

As preferable examples of the heteroaryloxy group, 5- to 7-membered monocyclic heteroaryloxy group, such as 2-pyridyloxy, 3-pyridyloxy, 2-imidazolyloxy, 2-pyrimidinyloxy, 1,2,4-triazol-5-yloxy and the like, can be mentioned.

The above-mentioned alkoxy group, alkenyloxy group, cycloalkyloxy group, cycloalkenyloxy group, aryloxy group, aralkyloxy group, acyloxy group and heteroaryloxy group may have 1 to 3, preferably 1 or 2 substituents at substitutable positions. As such substituent, for example, a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, a $C_{1-6}$ alkoxy group optionally substituted by 1 to 3 halogen atoms (e.g., fluorine atom, chlorine atom, bromine atom, iodine atom) such as methoxy and ethoxy, a hydroxy, a nitro, an amino, a $C_{1-6}$ alkylsulfonyl group (e.g., methylsulfonyl) and the like can be mentioned.

As the optionally substituted thiol group, for example, a thiol group optionally substituted by a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{1-13}$ acyl group or a heteroaryl group, each of which is optionally substituted, and the like can be mentioned.

Here, as the $C_{3-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{1-13}$ acyl group and heteroaryl group, those respectively exemplified in the aforementioned "optionally substituted hydroxy group" can be mentioned. These groups may have 1 or 2 substituents at substitutable positions. As such substituent, for example, a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, a $C_{1-6}$ alkoxy group optionally substituted by 1 to 3 halogen atoms (e.g., fluorine atom, chlorine atom, bromine atom, iodine atom) such as methoxy and ethoxy, a hydroxy, a nitro, an amino, a $C_{1-6}$ alkylsulfonyl group (e.g., ethylsulfonyl), an oxo and the like can be mentioned.

As the substituted thiol group, for example, an alkylthio group, an alkenylthio group, a cycloalkylthio group, a cycloalkenylthio group, an arylthio group, an aralkylthio group, an acylthio group, a heteroarylthio group, each of which is optionally substituted and the like, can be mentioned.

As preferable examples of the alkylthio group, a $C_{1-10}$ alkylthio group, such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio and the like, can be mentioned.

As preferable examples of the alkenylthio group, a $C_{2-10}$ alkenylthio group, such as allylthio, crotylthio, 2-pentenylthio, 3-hexenylthio and the like can be mentioned.

As preferable examples of the cycloalkylthio group, a $C_{3-10}$ cycloalkylthio group, such as cyclobutylthio, cyclopentylthio, cyclohexylthio and the like, can be mentioned.

As preferable examples of the cycloalkenylthio group, a $C_{3-10}$ cycloalkenylthio group, such as 2-cyclopentenylthio, 2-cyclohexenylthio and the like, can be mentioned.

As preferable examples of the arylthio group, a $C_{6-14}$ arylthio group, such as phenylthio, naphthylthio and the like, can be mentioned.

As preferable examples of the aralkylthio group, a $C_{7-13}$ aralkylthio group, such as benzylthio, phenethylthio, naphthylmethylthio and the like can be mentioned.

As preferable examples of the acylthio group, a $C_{2-13}$ acylthio group, such as a $C_{1-6}$ alkyl-carbonylthio group (e.g., acetylthio, propionylthio, butyrylthio, isobutyrylthio) and the like can be mentioned.

As preferable examples of the heteroarylthio group, a 5- to 7-membered monocyclic heteroarylthio group, such as 2-pyridylthio, 3-pyridylthio, 2-imidazolylthio, 2-pyrimidinylthio, 1,2,4-triazol-5-ylthio and the like can be mentioned.

The above-mentioned alkylthio group, alkenylthio group, cycloalkylthio group, cycloalkenylthio group, arylthio group, aralkylthio group, acylthio group and heteroarylthio group may have 1 or 2 substituents at substitutable positions. As such substituent, for example, a halogen atom (e.g., fluorine atom, chlorine atom, bromine atom, iodine atom), a $C_{1-6}$ alkyl optionally substituted by 1 to 3 halogen atoms (e.g., fluorine atom, chlorine atom, bromine atom, iodine atom) such as methyl and trifluoromethyl, a $C_{1-6}$ alkoxy optionally substituted by 1 to 3 halogen atoms (e.g., fluorine atom, chlorine atom, bromine atom, iodine atom) such as methoxy and ethoxy, a hydroxy, a nitro, an amino, a $C_{1-6}$ alkylsulfonyl (e.g., methylsulfonyl), an oxo and the like can be mentioned.

As the acyl group of the "optionally substituted acyl group", for example, a group represented by the formula: —$COR^4$, —CO—$OR^4$, —$SO_2R^4$, —$SOR^4$, —$PO_3R^4R^5$ [i.e., —P(=O)($OR^4$)($OR^5$)], —CO—$NR^{4a}R^{5a}$, —CS—$NR^{4a}R^{5a}$ and —$SO_2$—$NR^{4a}R^{5a}$ wherein R and $R^5$ are the same or different and each is a hydrogen atom, a hydrocarbon group or a heterocyclic group, or $R^4$ and $R^5$ may form a heterocycle together with the adjacent oxo-substituted phosphorus atom and 2 oxygen atoms; $R^{4a}$ and $R^{5a}$ are the same or different and each is a hydrogen atom, a hydrocarbon group or a heterocyclic group, or $R^{4a}$ and $R^{5a}$ may form a nitrogen-containing heterocycle together with the adjacent nitrogen atom, and the like can be mentioned.

As the "hydrocarbon group" for $R^4$, $R^5$, $R^{4a}$ or $R^{5a}$, those exemplified as the "hydrocarbon group" of the "optionally substituted hydrocarbon group" exemplified as the substituents for ring A can be mentioned.

The hydrocarbon group is preferably a $C_{1-10}$ alkyl group (preferably methyl, ethyl, propyl, butyl, tert-butyl, pentyl, 1-ethylpropyl, 2,2-dimethylpropyl); a $C_{2-10}$ alkynyl group (preferably 2-propynyl); a $C_{3-10}$ cycloalkyl group which may be condensed with a benzene ring (preferably cyclopropyl, cyclohexyl); a $C_{6-14}$ aryl group which may be condensed with a $C_{3-10}$ cycloalkane (preferably cyclopentane) (preferably phenyl, dihydroindenyl, biphenylyl); a $C_{7-13}$ aralkyl group (preferably benzyl, phenethyl, phenylpropyl, naphthylmethyl, benzhydryl) and the like.

As the "heterocyclic group" for $R^4$, $R^5$, $R^{4a}$ or $R^{5a}$, the aromatic heterocyclic group and the non-aromatic heterocyclic group exemplified as the substituents of the "optionally substituted hydrocarbon group" exemplified as the substituents for ring A can be mentioned.

The heterocyclic group is preferably thiazolyl, oxazolyl, isothiazolyl, isoxazolyl, pyrazolyl, pyridyl, pyrazinyl, benzoxazolyl, benzothiazolyl, benzothiadiazolyl, quinolyl, isoquinolyl, pyrrolidinyl, piperidinyl, piperazinyl and the like.

As the heterocycle formed by $R^4$ and $R^5$ together with the adjacent oxo-substituted phosphorus atom and 2 oxygen atoms, for example, a 4- to 7-membered heterocycle containing an oxo-substituted phosphorus atom and 2 oxygen atoms besides carbon atoms as a ring-constituting atom, which may further contain 1 or 2 heteroatoms selected from an oxygen atom, a nitrogen atom and a sulfur atom, and the like can be mentioned. As preferable examples of such heterocycle, 2-oxide-1,3,2-dioxaphosphinane; 2-oxide-1,3,2-dioxaphosphorane, 2-oxide-4,7-dihydro-1,3,2-dioxaphosphepine and the like can be mentioned.

As the "nitrogen-containing heterocycle" formed by $R^{4a}$ and $R^{5a}$ together with the adjacent nitrogen atom, for example, a 5- to 7-membered nitrogen-containing heterocycle containing at least one nitrogen atom besides carbon atoms as a ring-constituting atom, which may further contain 1 or 2 heteroatoms selected from an oxygen atom, a sulfur atom and a nitrogen atom, and the like can be mentioned. As preferable examples of such nitrogen-containing heterocycle, pyrrolidine, imidazolidine, pyrazolidine, piperidine, piperazine, morpholine, thiomorpholine and the like can be mentioned.

The acyl group may have 1 to 3 substituents at substitutable positions. As such substituent, for example, a $C_{1-6}$ alkyl optionally substituted by 1 to 3 halogen atoms (e.g., fluorine atom, chlorine atom, bromine atom, iodine atom) such as methyl and ethyl, a $C_{1-6}$ alkoxy optionally substituted by 1 to 3 halogen atoms (e.g., fluorine atom, chlorine atom, bromine atom, iodine atom) such as methoxy and ethoxy, a halogen atom (e.g., fluorine atom, chlorine atom, bromine atom, iodine atom), a nitro, a hydroxy, an amino optionally mono- or di-substituted by a $C_{1-6}$ alkyl (e.g., methyl, ethyl) and the like can be mentioned.

As preferable examples of the acyl group, a formyl, a carboxyl, a carbamoyl, a thiocarbamoyl, a $C_{1-10}$ alkyl-carbonyl (e.g., acetyl, propionyl, butyryl, isobutyryl, valeryl, isovaleryl, pivaloyl, hexanoyl, heptanoyl, octanoyl), a $C_{2-10}$ alkenyl-carbonyl (e.g., crotonoyl), a $C_{3-10}$ cycloalkyl-carbonyl (e.g., cyclobutanecarbonyl, cyclopentanecarbonyl, cyclohexanecarbonyl, cycloheptanecarbonyl), a $C_{3-10}$ cycloalkenyl-carbonyl (e.g., 2-cyclohexenecarbonyl), a $C_{6-14}$ aryl-carbonyl (e.g., benzoyl, 1-naphthoyl, 2-naphthoyl), a $C_{7-13}$ aralkylcarbonyl (e.g., benzylcarbonyl, phenethylcarbonyl), an aromatic heterocyclic carbonyl (e.g., nicotinoyl, isonicotinoyl), a non-aromatic heterocyclic carbonyl (e.g., pyrrolidinylcarbonyl, piperidinocarbonyl), a $C_{1-6}$ alkoxy-carbonyl (e.g., methoxycarbonyl, ethoxycarbonyl, propoxycarbonyl, butoxycarbonyl, tert-butoxycarbonyl), a $C_{6-14}$ aryloxy-carbonyl (e.g., phenyloxycarbonyl, naphthyloxycarbonyl), a $C_{7-13}$ aralkyloxy-carbonyl (e.g., benzyloxycarbonyl, phenethyloxycarbonyl), a mono- or di-($C_{1-6}$ alkyl optionally having 1 to 3 substituents selected from a halogen atom and a $C_{1-6}$ alkoxy-carbonyl)-carbamoyl (e.g., methylcarbamoyl, ethylcarbamoyl, dimethylcarbamoyl, diethylcarbamoyl, ethylmethylcarbamoyl, propylcarbamoyl, trifluoroethylcarbamoyl), a mono- or di- (a $C_{1-6}$ alkyl optionally substituted by 1 to 3 halogens)-thiocarbamoyl (e.g., methylthiocarbamoyl, ethylthiocarbamoyl), a $C_{6-14}$ aryl-carbamoyl (e.g. phenylcarbamoyl), a $C_{3-10}$ cycloalkyl-carbamoyl (e.g., cyclopropylcarbamoyl), a $C_{7-13}$ aralkyl-carbamoyl (e.g., benzylcarbamoyl), a $C_{1-6}$ alkoxy-carbamoyl (e.g., methoxycarbamoyl), a $C_{1-10}$ alkylsulfinyl group (e.g., methylsulfinyl, ethylsulfinyl), a $C_{1-10}$ alkylsulfonyl group (e.g., methylsulfonyl, ethylsulfonyl), a $C_{6-14}$ arylsulfonyl (e.g., phenylsulfonyl), a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl), a mono- or di- (a $C_{1-6}$ alkyl optionally substituted by 1 to 3 halogens)-sulfamoyl (e.g., methylsulfamoyl, ethylsulfamoyl) and the like can be mentioned.

The "hydrocarbon group" of the "optionally substituted hydrocarbon group" exemplified as the substituents for ring A is preferably a $C_{1-10}$ alkyl group, a $C_{6-14}$ aryl group, a $C_{3-10}$ cycloalkyl group, a $C_{7-13}$ aralkyl group, a $C_{8-13}$ arylalkenyl group, a $C_{4-13}$ cycloalkylalkyl group and the like. The hydrocarbon group is more preferably a $C_{1-10}$ alkyl group, a $C_{6-14}$ aryl group and the like.

The substituent of the "optionally substituted hydrocarbon group" is preferably a $C_{1-6}$ alkoxy group optionally substituted by 1 to 3 halogen atoms (e.g., fluorine atom, chlorine atom, bromine atom, iodine atom) such as methoxy and ethoxy, a halogen atom (e.g., fluorine atom, chlorine atom, bromine atom, iodine atom), a nitro, a hydroxy, an amino, a $C_{1-3}$ alkylenedioxy (e.g., methylenedioxy, ethylenedioxy) and the like. The number of the substituent is, for example, 1 to 3.

As the "heterocyclic group" of the "optionally substituted heterocyclic group" exemplified as the substituents for ring A, those exemplified as the aforementioned "heterocyclic group" for the aforementioned $R^4$ can be mentioned.

The heterocyclic group is preferably an azolyl group optionally condensed with a benzene ring, such as pyrrolyl, imidazolyl, pyrazolyl, oxazolyl, isoxazolyl, thiazolyl, isothiazolyl, oxadiazolyl, thiadiazolyl, triazolyl, tetrazolyl, and the like.

The above-mentioned heterocyclic group may have 1 to 3 substituents at substitutable positions. As such substituent, for example, an optionally substituted aliphatic hydrocarbon group an optionally substituted alicyclic hydrocarbon group, an optionally substituted aromatic hydrocarbon group, an optionally substituted aromatic heterocyclic group, an optionally substituted non-aromatic heterocyclic group, a halogen atom, a nitro, an optionally substituted amino group, an optionally substituted hydroxy group, an optionally substituted thiol group, an optionally substituted acyl group, a $C_{1-3}$ alkylenedioxy, an oxo and the like can be mentioned.

Here, as the "aliphatic hydrocarbon group", "alicyclic hydrocarbon group" and "aromatic hydrocarbon group" of the "optionally substituted aliphatic hydrocarbon group", "optionally substituted alicyclic hydrocarbon group" and "optionally substituted aromatic hydrocarbon group", those exemplified as the "hydrocarbon group" of the "optionally substituted hydrocarbon group" exemplified as the substituents for ring A can be mentioned.

As the substituents of the "aliphatic hydrocarbon group", "alicyclic hydrocarbon group" and "aromatic hydrocarbon group", those exemplified as the "substituent" of the "optionally substituted hydrocarbon group" exemplified as the substituents for ring A can be mentioned. The position of substitution and the number of substitution are not particularly limited. The number of the substitution is preferably 1 to 3.

As the "optionally substituted aromatic heterocyclic group" and "optionally substituted non-aromatic heterocyclic group", those exemplified as the substituents of the "optionally substituted hydrocarbon group" exemplified as the substituents for ring A can be mentioned.

Furthermore, as the "halogen atom", "optionally substituted amino group", "Optionally substituted hydroxy group", "optionally substituted thiol group", "optionally substituted acyl group" and "$C_{1-3}$ alkylenedioxy", those exemplified as the substituents of the "optionally substituted hydrocarbon group" exemplified as the substituents for ring A can be mentioned.

As the "optionally substituted hydroxy group", "optionally substituted thiol group" and "optionally substituted amino group" exemplified as the substituents for ring A, those exemplified as the substituents of the "optionally substituted hydrocarbon group" exemplified as the substituents for ring A can be mentioned.

The substituent for ring A is preferably an optionally substituted hydrocarbon group, more preferably a $C_{1-10}$ alkyl group, a $C_{6-14}$ aryl group, a $C_{7-13}$ aralkyl group and the like. The substituent for ring A is particularly preferably a $C_{1-6}$ alkyl group (preferably methyl etc.).

The ring A is preferably an imidazole ring, a pyrazole ring, an oxadiazole ring, a thiadiazole ring, a triazole ring or a tetrazole ring (preferably a pyrazole ring, an oxadiazole ring, a thiadiazole ring, a triazole ring or a tetrazole ring, more preferably a pyrazole ring), each of which may have 1 or 2 substituents (preferably a $C_{1-6}$ alkyl group such as methyl and the like) selected from a $C_{1-10}$ alkyl group, a $C_{6-14}$ aryl group and a $C_{7-13}$ aralkyl group.

As the "optionally substituted hydrocarbon group" and "optionally substituted heterocyclic group" for B, those exemplified as the substituents for ring A are respectively used. Here, the hydrocarbon group of the "optionally substituted hydrocarbon group" is preferably an alicyclic hydrocarbon group or an aromatic hydrocarbon group. In addition, the heterocyclic group of the "optionally substituted heterocyclic group" is preferably an aromatic heterocyclic group.

B is preferably an optionally substituted aromatic hydrocarbon group or an optionally substituted aromatic heterocyclic group.

B is further preferably an optionally substituted $C_{6-14}$ aryl group, an optionally substituted 5- to 7-membered monocyclic aromatic heterocyclic group and the like. As preferable concrete examples of B, a $C_{6-14}$ aryl group (preferably phenyl, naphthyl) and a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms (e.g., fluorine atom, chlorine atom, bromine atom, iodine atom) such as methyl and ethyl, a $C_{1-6}$ alkoxy optionally substituted by 1 to 3 halogen atoms (e.g., fluorine atom, chlorine atom, bromine atom, iodine atom) such as methoxy and ethoxy, a halogen atom (e.g., fluorine atom, chlorine atom, bromine atom, iodine atom), a nitro, a formyl and a $C_{1-3}$ alkylenedioxy (e.g., methylenedioxy), can be mentioned.

Of these, a $C_{6-14}$ aryl group (preferably phenyl) and a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms (e.g., fluorine atom, chlorine atom, bromine atom, iodine atom), a $C_{1-6}$ alkoxy optionally substituted by 1 to 3 halogen atoms (e.g., fluorine atom, chlorine atom, bromine atom, iodine atom) and a halogen atom (preferably fluorine atom, chlorine atom, bromine atom), are preferable.

B is particularly preferably a $C_{6-14}$ aryl group (preferably phenyl) optionally having a halogen atom (preferably fluorine atom).

The "divalent acyclic hydrocarbon group" for X may be straight-chain or branched and saturated or unsaturated, as long as it is an acyclic divalent hydrocarbon group.

As the "divalent acyclic hydrocarbon group", for example, "divalent aliphatic hydrocarbon group" can be mentioned.

Particularly, a divalent $C_{1-8}$ aliphatic hydrocarbon group exemplified by the following is preferable.

(1) a $C_{1-8}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —CH(CH$_3$)—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$— and the like);

(2) a $C_{2-8}$ alkenylene (e.g., —CH=CH—, —CH$_2$—CH=CH—; —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$— and the like) and the like.

The $C_{2-8}$ alkenylene encompasses both its E form and Z form.

The "divalent acyclic hydrocarbon group" is preferably a $C_{1-4}$ alkylene or a $C_{2-4}$ alkenylene, more preferably —CH$_2$—, —(CH$_2$)$_2$—, —CH=CH— and the like. X is particularly preferably —CH=CH— and the like.

Z is —O—, —S—, —NR$^2$—, —CONR$^2$— or —NR$^2$CO— (R$^2$ is a hydrogen atom or an optionally substituted alkyl group).

In the optionally substituted alkyl group for R$^2$, as the alkyl-group, for example, a $C_{1-6}$ alkyl group (e.g., methyl, ethyl, propyl, isopropyl) can be mentioned. The alkyl group may have 1 to 3 substituents. As such substituent, for example, a 26 halogen atom (e.g., fluorine atom, chlorine atom, bromine atom, iodine atom), a $C_{1-6}$ alkoxy optionally substituted by 1 to 3 halogen atoms (e.g., fluorine atom, chlorine atom, bromine atom, iodine atom) such as methoxy and ethoxy, a hydroxy, a nitro, an amino and the like can be mentioned.

R$^2$ is preferably a hydrogen atom or a $C_{1-6}$ alkyl group, more preferably a hydrogen atom.

Z is preferably —CONR$^2$— (R$^2$ is as defined above), more preferably —CONH— (in the present invention, the carbon atom (C) of —CONR$^2$— is linked with X and the nitrogen atom (N) therein is linked with Y).

As the divalent acyclic hydrocarbon group for Y, those exemplified as the aforementioned X can be mentioned.

Y is preferably a bond, a $C_{1-4}$ alkylene, more preferably a bond, —CH$_2$—, —(CH$_2$)$_2$—, —(CH$_2$)$_3$— and the like. Y is particularly preferably a bond.

As the "cyclic group" of the "optionally substituted cyclic group" for R$^1$ is, for example, an alicyclic hydrocarbon group, an aromatic hydrocarbon group, an aromatic heterocyclic group, a non-aromatic heterocyclic group and the like can be mentioned.

Here, as the "alicyclic hydrocarbon group" and "aromatic hydrocarbon group", those exemplified as the "hydrocarbon group" of the "optionally substituted hydrocarbon group" exemplified as the substituents for ring A can be mentioned.

As the "aromatic heterocyclic group" and "non-aromatic heterocyclic group", those exemplified as the substituents of the "optionally substituted hydrocarbon group" exemplified as the substituents for ring A can be mentioned.

The cyclic group is preferably an optionally partially saturated $C_{6-14}$ aryl group (preferably phenyl, dihydroindenyl), a $C_{3-10}$ cycloalkyl group (preferably cyclopropyl, cyclobutyl, cyclopentyl, cyclohexyl, cycloheptyl, cyclooctyl), a $C_{3-10}$ cycloalkenyl group (preferably cyclohexenyl), a 5- or 6-membered aromatic heterocyclic group optionally condensed with a benzene ring (preferably furyl, thienyl, oxazolyl, thiazolyl, isoxazolyl, imidazolyl, pyrazolyl, pyridyl, pyrazinyl, indolyl, quinolyl, isoquinolyl and benzothiadiazolyl), a 5- or 6-membered non-aromatic heterocyclic group optionally condensed with a benzene ring (preferably pyrrolidinyl, tetrahydrofuranyl, thiazolinyl, oxazolinyl, thiazolidinyl, oxazolidinyl, dioxolanyl, piperidinyl, piperazinyl, morpholinyl, thiomorpholinyl, dihydrobenzofuranyl, oxodihydrobenzoxazolyl) and the like. The cyclic group is more preferably a $C_{6-14}$ aryl group, and phenyl is particularly preferable.

The "cyclic group" for R$^1$ may have 1 to 4 substituents at the substitutable positions. As such substituent, for example, (1) a nitro;
(2) an oxo;
(3) a hydroxy;
(4) a cyano;
(5) a halogen atom (e.g., fluorine atom, chlorine atom; bromine atom, iodine atom);
(6) a $C_{1-6}$ alkylenedioxy (e.g., methylenedioxy, ethylenedioxy);
(7) a carboxyl;
(8) a $C_{1-6}$ alkyl group (e.g., methyl, ethyl, propyl, isopropyl, butyl, isobutyl, pentyl, neopentyl) optionally substituted by 1 to 3 substituents selected from a halogen atom (e.g., fluorine atom, chlorine atom, bromine atom, iodine atom); a hydroxy; a cyano; a $C_{1-6}$ alkoxy (e.g., methoxy); an amino optionally mono- or di-substituted by a $C_{1-6}$ alkyl and a $C_{1-6}$ alkyl-carbonyl (e.g., acetyl, propionyl, butyryl, isobutyryl, isovaleryl), such as amino, methylamino, dimethylamino, acetylamino, butyrylamino, isobutyrylamino and isovalerylamino; a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl, pyrimidinyl) optionally substituted by 1 to 3 substituents selected from a $C_{1-6}$ alkyl, a hydroxy-$C_{1-6}$ alkyl, carboxyl, carbamoyl and a $C_{1-6}$ alkoxy-carbonyl (e.g., methoxycarbonyl); an aromatic fused heterocyclic group (e.g., benzimidazolyl, benzopyrazolyl, benzothiazolyl, benzoxazolyl, benzotriazolyl, quinolyl, indazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl (e.g., methoxycarbonyl); a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl (e.g., methoxycarbonyl); a non-aromatic fused heterocyclic group (e.g., oxodihydrobenzoxazolyl, tetrahydrobenzothiazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxycarbonyl (e.g., methoxycarbonyl); a carboxyl group; a $C_{1-6}$ alkoxy-carbonyl (e.g., methoxycarbonyl, ethoxycarbonyl, propoxycarbonyl, butoxycarbonyl, tert-butoxycarbonyl); a (mono- or di-$C_{1-10}$ alkyl) phosphono group optionally forming a ring (e.g., dimethylphosphono; diethylphosphono; diisopropylphosphono; dibutylphosphono; 2-oxide-1,3,2-dioxaphosphinanyl); a carbamoyl optionally substituted by an amino; a mono- or di-$C_{1-6}$ alkylcarbamoyl optionally substituted by 1 to 3 substituents selected from a halogen atom, a hydroxy and a $C_{1-6}$ alkoxy-carbonyl, such as methylcarbamoyl, ethylcarbamoyl, dimethylcarbamoyl, diethylcarbamoyl, ethylmethylcarbamoyl, propylcarbamoyl, trifluoroethylcarbamoyl, methoxycarbonylethylcarbamoyl, 2-hydroxy-1-methoxycarbonyl-ethylcarbamoyl and 2-hydroxy-1-methoxycarbonyl-propylcarbamoyl; a mono- or di-$C_{6-14}$ aryl-carbamoyl optionally substituted by 1 to 3 substituents selected from an optionally halogenated $C_{1-6}$ alkyl and a $C_{1-6}$ alkoxy, such as phenylcarbamoyl, methoxyphenylcarbamoyl and trifluoromethylphenylcarbamoyl; a mono- or di-$C_{7-13}$ aralkyl-carbamoyl optionally substituted by 1 to 3 substituents selected from an amino optionally mono- or di-substituted by a $C_{1-6}$ alkyl, an optionally halogenated $C_{1-6}$ alkyl, a hydroxy and a $C_{1-6}$ alkoxycarbonyl, such as benzylcarbamoyl, phenethylcarbamoyl, dimethylaminobenzylcarbamoyl, methoxycarbonylphenethylcarbamoyl and trifluoromethylbenzylcarbamoyl; a sulfamoyl; an optionally halogenated mono- or di-$C_{1-6}$ alkylsulfamoyl (e.g., methylsulfamoyl, ethylsulfamoyl); a $C_{1-6}$ alkylthio (e.g., methylthio, ethylthio and tert-butylthio); a $C_{1-6}$ alkylsulfinyl (e.g., methylsulfinyl, ethylsulfinyl and tert-butylsulfinyl); a $C_{1-6}$ alkylsulfonyl (e.g., methylsulfonyl, ethylsulfonyl and tert-butylsulfonyl); a $C_{1-6}$ alkyl-carbonyl (e.g., acetyl); a mono- or di-$C_{6-14}$ aryl-carboxamide (e.g., phenylcarboxamide); a $C_{6-14}$ arylthio (e.g., phenylthio); a 5- or 6-membered aromatic heterocyclic thio (e.g., triazolylthio and tetrazolylthio) optionally substituted by a $C_{1-6}$ alkyl; a $C_{6-14}$ arylsulfinyl (e.g., phenylsulfinyl); a 5- or 6-membered aromatic heterocyclic sulfinyl (e.g., triazolylsulfinyl and tetrazolylsulfinyl) optionally substituted by a $C_{1-6}$ alkyl; a $C_{6-14}$ arylsulfonyl (e.g., phenylsulfonyl); a 5- or 6-membered aromatic heterocyclic sulfonyl (e.g., triazolylsulfonyl and tetrazolylsulfonyl) optionally substituted by a $C_{1-6}$ alkyl;

(9) a $C_{3-10}$ cycloalkyl group (e.g., cyclohexyl) optionally substituted by 1 to 3 halogen atoms (e.g., fluorine atom, chlorine atom, bromine atom, iodine atom);

(10) a $C_{6-14}$ aryl (e.g., phenyl) optionally substituted by 1 to 3 halogen atoms (e.g., fluorine atom, chlorine atom, bromine atom, iodine atom);

(11) a $C_{7-13}$ aralkyl (e.g., benzyl) optionally substituted by 1 to 3 substituents selected from a halogen atom (e.g., fluorine atom, chlorine atom, bromine atom, iodine atom) and a hydroxy;

(12) a 5- or 6-membered aromatic heterocyclic group (e.g., thiadiazolyl and imidazolyl) optionally substituted by 1 to 3 substituents selected from a halogen atom (e.g., fluorine atom, chlorine atom, bromine atom, iodine atom), a $C_{1-6}$ alkyl and a $C_{6-14}$ aryl (e.g., phenyl) optionally substituted by 1 to 3 halogen atoms (e.g., fluorine atom, chlorine atom, bromine atom and iodine atom);

(13) a $C_{1-6}$ alkoxy group, (e.g., methoxy, ethoxy), optionally substituted by 1 to 3 substituents selected from a halogen atom (e.g., fluorine atom, chlorine atom, bromine atom, iodine atom), a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl and pyrimidinyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxycarbonyl (e.g., methoxycarbonyl); an aromatic fused heterocyclic group (e.g., benzimidazolyl, benzopyrazolyl, benzothiazolyl, benzoxazolyl, benzotriazolyl, quinolyl and indazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxycarbonyl (e.g., methoxycarbonyl); a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl (e.g., methoxycarbonyl); a non-aromatic fused heterocyclic group (e.g., oxodihydrobenzoxazolyl and tetrahydrobenzothiazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl (e.g., methoxycarbonyl);

(14) a $C_{1-6}$ alkylthio (e.g., methylthio) optionally substituted by 1 to 3 substituents selected from a 5- or 6-membered aromatic heterocyclic group (e.g., thiazolyl, oxazolyl, triazolyl, tetrazolyl, pyridyl, pyrimidinyl) optionally substituted by a $C_{1-6}$ alkyl and a halogen atom (e.g., fluorine atom, chlorine atom, bromine atom, iodine atom);

(15) a $C_{6-14}$ aryloxy (e.g., phenoxy) optionally substituted by 1 to 3 halogen atoms (e.g., fluorine atom, chlorine atom, bromine atom, iodine atom);

(16) an amino optionally mono- or di-substituted by a $C_{1-6}$ alkyl, such as amino, methylamino, dimethylamino, ethylamino, diethylamino, ethylmethylamino, propylamino and dibutylamino;

(17) a phosphono-$C_{1-6}$ alkylamino optionally mono- or di-substituted by a $C_{1-10}$ alkyl, such as phosphonomethylamino and diethylphosphonomethylamino;

(18) a mono- or di-$C_{1-6}$ alkyl-carboxamide optionally substituted by 1 to 6, preferably 1 to 3, substituents selected from a halogen atom (e.g., fluorine atom, chlorine atom, bromine atom, iodine atom), a $C_{1-6}$ alkyl and a $C_{1-6}$ alkoxycarbonyl (e.g., methoxycarbonyl and ethoxycarbonyl), such as acetylamino, hexanoylamino, trifluoroacetylamino, N-acetyl-N-methylamino, pentafluoropropionylamino and ethoxycarbonylpropionylamino;
(19) a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl);
(20) a $C_{1-6}$ alkyl-carbonyl (e.g., acetyl) optionally substituted by 1 to 3 halogen atoms (e.g., fluorine atom, chlorine atom, bromine atom, iodine atom);
(21) a $C_{1-6}$ alkylsulfinyl (e.g., methylsulfinyl) optionally substituted by a 5- or 6-membered aromatic heterocyclic group (e.g., thiazolyl, oxazolyl, triazolyl, tetrazolyl, pyridyl, pyrimidinyl) optionally substituted by a $C_{1-6}$ alkyl;
(22) a $C_{1-6}$ alkyl-sulfonyl (e.g., methylsulfonyl and ethylsulfonyl) optionally substituted by a 5- or 6-membered aromatic heterocyclic group (e.g., thiazolyl, oxazolyl, triazolyl, tetrazolyl, pyridyl, pyrimidinyl) optionally substituted by a $C_{1-6}$ alkyl;
(23) a $C_{3-10}$ cycloalkyl-carbonyl (e.g., cyclohexylcarbonyl) optionally substituted by 1 to 3 halogen atoms (e.g., fluorine atom, chlorine atom, bromine atom, iodine atom);
(24) a $C_{6-14}$ aryl-carbonyl (e.g., benzoyl) optionally substituted by 1 to 3 halogen atoms (e.g., fluorine atom, chlorine atom, bromine atom, iodine atom);
(25) a $C_{7-13}$ aralkyl-carbonyl (e.g., benzylcarbonyl and phenethylcarbonyl) optionally substituted by 1 to 3 halogen atoms (e.g., fluorine atom, chlorine atom, bromine atom, iodine atom);
(26) a $C_{6-14}$ aryl-$C_{2-6}$ alkenyl-carbonyl (e.g., styrylcarbonyl) optionally substituted by 1 to 3 halogen atoms (e.g., fluorine atom, chlorine atom, bromine atom, iodine atom);
(27) a $C_{1-6}$ alkoxy-carbonyl (e.g., methoxycarbonyl, ethoxycarbonyl and tert-butoxycarbonyl) optionally substituted by 1 to 3 halogen atoms (e.g., fluorine atom, chlorine atom, bromine atom, iodine atom);
(28) a 5- or 6-membered aromatic heterocyclic-carbonyl (e.g., furoyl, pyrrolylcarbonyl and pyridylcarbonyl) optionally substituted by a $C_{1-6}$ alkyl;
(29) a 5- or 6-membered non-aromatic heterocyclic-carbonyl (e.g., tetrahydrofuroyl) optionally substituted by a $C_{1-6}$ alkyl;
(30) a carbamoyl optionally mono- or di-substituted by a $C_{1-6}$ alkyl, such as carbamoyl and dimethylcarbamoyl;
(31) a sulfamoyl optionally substituted by 1 or 2 substituents selected from a 5- or 6-membered aromatic heterocyclic group (e.g., thiazolyl, oxazolyl, triazolyl, tetrazolyl, pyridyl, pyrimidinyl) optionally substituted by a $C_{1-6}$ alkyl and a $C_{1-6}$ alkyl, such as sulfamoyl and dimethylsulfamoyl;
(32) a $C_{7-13}$ aralkyloxy-carbonylthio (e.g., benzyloxycarbonylthio and phenethyloxycarbonylthio) optionally substituted by 1 to 3 halogen atoms (e.g., fluorine atom, chlorine atom, bromine atom, iodine atom);
(33) a $C_{1-6}$ alkoxy-carboxamide (e.g., tert-butoxycarboxamide);
(34) a $C_{6-14}$ aryl-sulfonyl (e.g., phenylsulfonyl) optionally substituted by 1 to 3 halogen atoms (e.g., fluorine atom, chlorine atom, bromine atom and iodine atom); and the like can be mentioned.

The substituent for the above-mentioned "cyclic group" is preferably
(1) a $C_{1-6}$ alkyl group (e.g., methyl, ethyl, propyl, isopropyl, butyl, isobutyl, pentyl, neopentyl) optionally substituted by 1 to 3 substituents selected from a hydroxy; a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl and pyrimidinyl) optionally substituted from a $C_{1-6}$ alkyl, a hydroxy-$C_{1-6}$ alkyl, a carboxyl, a carbamoyl and a $C_{1-6}$ alkoxy-carbonyl; an aromatic fused heterocyclic group (e.g., benzimidazolyl, benzopyrazolyl, benzothiazolyl, benzoxazolyl, benzotriazolyl, quinolyl and indazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl; a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl and dioxidethiomorpholinyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl; a non-aromatic fused heterocyclic group (e.g., oxodihydrobenzoxazolyl and tetrahydrobenzothiazolyl) optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl; a (mono- or di-$C_{1-10}$ alkyl) phosphono group optionally forming a ring (e.g., dimethylphosphono; diethylphosphono; diisopropylphosphono; dibutylphosphono; 2-oxide-1,3,2-dioxaphosphinanyl); a $C_{1-6}$ alkylthio; a $C_{1-6}$ alkylsulfinyl; and a $C_{1-6}$ alkylsulfonyl;
(2) a 5- or 6-membered aromatic heterocyclic group (e.g., thiadiazolyl and imidazolyl) optionally substituted by 1 to 3 substituents selected from a halogen atom, a $C_{1-6}$ alkyl and a $C_{6-14}$ aryl optionally substituted by 1 to 3 halogen atoms; or
(3) a $C_{1-6}$ alkyl-sulfonyl (e.g., methylsulfonyl and ethylsulfonyl) optionally substituted by a 5- or 6-membered aromatic heterocyclic group (e.g., thiazolyl, oxazolyl, triazolyl, tetrazolyl, pyridyl and pyrimidinyl) optionally substituted by a $C_{1-6}$ alkyl.

The substituent for the "cyclic group" is more preferably a $C_{1-6}$ alkyl group optionally substituted by 1 to 3 substituents selected from a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl and pyrimidinyl) optionally substituted by a $C_{1-6}$ alkyl; an aromatic fused heterocyclic group (e.g., benzimidazolyl, benzopyrazolyl, benzothiazolyl, benzoxazolyl, benzotriazolyl, quinolyl and indazolyl) optionally substituted by a $C_{1-6}$ alkyl; a 5- or 6-membered non-aromatic heterocyclic group (e.g., tetrahydrofuryl, morpholinyl thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl and dioxidethiomorpholinyl) optionally substituted by a $C_{1-6}$ alkyl; a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); a $C_{1-6}$ alkylsulfinyl; and a $C_{1-6}$ alkylsulfonyl.

As the "optionally substituted amino group" and "optionally substituted acyl group" for $R^1$, those exemplified as the substituents of the "optionally substituted hydrocarbon group" exemplified as the substituents for ring A are used.

As preferable examples of the "optionally substituted amino group" for $R^1$,
1) an amino optionally mono- or di-substituted by substituents selected from a $C_{1-6}$ alkyl optionally substituted by a hydroxy, a $C_{6-14}$ aryl, and a 5- or 6-membered aromatic heterocyclic group (e.g., pyridyl) optionally substituted by a nitro, such as amino, methylamino, dimethylamino, diisopropylamino, phenylamino and N-phenyl-N-methylamino;
2) a mono- or di-$C_{1-6}$ alkyl-carboxamide optionally substituted by 1 to 3 substituents selected from halogen atoms (e.g., fluorine, chlorine, bromine, iodine) and a $C_{1-6}$ alkyl, such as acetylamino, hexanoylamino, trifluoroacetylamino, N-acetyl-N-methylamino and pentafluoropropionylamino;

3) a $C_{1-6}$ alkoxy-carboxamide optionally substituted by a $C_{1-6}$ alkyl, such as tert-butoxycarboxamide and N-tert-butoxycarbonyl-N-methylamino;

4) a $C_{6-14}$ aryl-carboxamide (e.g., phenylcarboxamide) optionally substituted by a $C_{1-6}$ alkyl;

5) a $C_{7-13}$ aralkyl-carboxamide (e.g., benzylcarboxamide and phenethylcarboxamide) optionally substituted by a $C_{1-6}$ alkyl;

6) a 5- or 6-membered aromatic heterocyclic-carboxamide (e.g., furylcarboxamide, pyrrolylcarboxamide, thienylcarboxamide, pyridylcarboxamide) optionally substituted by a $C_{1-6}$ alkyl;

7) a 5- or 6-membered non-aromatic heterocyclic-carboxamide (e.g., tetrahydrofurylcarboxamide) optionally substituted by a $C_{1-6}$ alkyl; and the like can be mentioned.

As preferable examples of the "optionally substituted acyl group" for $R^1$, (1) a carboxyl;
(2) a $C_{1-6}$ alkyl-carbonyl (e.g., acetyl);
(3) a $C_{1-6}$ alkoxy-carbonyl (e.g., methoxycarbonyl, ethoxycarbonyl);
(4) a $C_{1-6}$ alkylsulfonyl (e.g., methylsulfonyl, ethylsulfonyl);
(5) a carbamoyl optionally mono- or di-substituted by a $C_{1-6}$ alkyl, such as carbamoyl and dimethylcarbamoyl;
(6) a sulfamoyl optionally mono- or di-substituted by a $C_{1-6}$ alkyl, such as sulfamoyl and dimethylsulfamoyl;
(7) a mono- or di-$C_{6-14}$ aryl-carbamoyl (e.g., phenylcarbamoyl);
(8) a mono- or di-$C_{7-13}$ aralkyl-carbamoyl (e.g., benzylcarbamoyl);
(9) a (mono- or di-$C_{1-10}$ alkyl)phosphono group optionally forming a ring (e.g., dimethylphosphono; diethylphosphono; diisopropylphosphono; dibutylphosphono; 2-oxide-1,3,2dioxaphosphinanyl; and the like can be mentioned.

$R^1$ is preferably an optionally substituted cyclic group, and more preferably, a $C_{6-14}$ aryl group (preferably phenyl) optionally substituted by a $C_{1-6}$ alkyl group optionally substituted by 1 to 3 substituents selected from a 5- or 6-membered aromatic heterocyclic group (e.g., thiazolyl, oxazolyl, imidazolyl, pyrazolyl, oxadiazolyl, thiazolyl, triazolyl, tetrazolyl, pyridyl and pyrimidinyl) optionally substituted by a $C_{1-6}$ alkyl; an aromatic fused heterocyclic group (e.g., benzimidazolyl, benzopyrazolyl, benzothiazolyl, benzoxazolyl, benzotriazolyl, quinolyl and indazolyl) optionally substituted by a $C_{1-6}$ alkyl; a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl and dioxidethiomorpholinyl) optionally substituted by a $C_{1-6}$ alkyl; a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); a $C_{1-6}$ alkylsulfinyl; and a $C_{1-6}$ alkylsulfonyl.

When, in the formula (I), the 5-membered aromatic heterocycle represented by ring A is imidazole, then Z should not be —O—.

As preferable examples of the compound represented by the formula (I), the following compounds can be mentioned.

A compound wherein ring A is an imidazole ring, a pyrazole ring, an oxadiazole ring, a thiadiazole ring, a triazole ring or a tetrazole ring (preferably a pyrazole ring, an oxadiazole ring, a thiadiazole ring, a triazole ring and a tetrazole ring, more preferably a pyrazole ring), each of which may have 1 or 2 substituents selected from a $C_{1-10}$ alkyl group, a $C_{6-14}$ aryl group and a $C_{7-13}$ aralkyl group;

B is a $C_{6-14}$ aryl group (preferably phenyl) or a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms (e.g., fluorine atom, chlorine atom, bromine atom, iodine atom), a $C_{1-6}$ alkoxy optionally substituted by 1 to 3 halogen atoms (e.g., fluorine atom, chlorine atom, bromine atom, iodine atom) and a halogen atom (preferably fluorine atom, chlorine atom, bromine atom);

X is a $C_{1-4}$ alkylene or a $C_{2-4}$ alkenylene;

Z is —CONR$^2$— (wherein R$^2$ is as defined above, preferably a hydrogen atom or a $C_{1-6}$ alkyl group, and the carbon atom (C) of —CONR$^2$— is linked with X and the nitrogen atom (N) therein is linked with Y);

Y is a bond or a $C_{1-4}$ alkylene; and $R^1$ is a $C_{6-14}$ aryl group (preferably phenyl) optionally substituted by a $C_{1-6}$ alkyl group optionally substituted by 1 to 3 substituents selected from a 5- or 6-membered aromatic heterocyclic group (e.g., thiazolyl, oxazolyl, imidazolyl, pyrazolyl, oxadiazolyl, thiazolyl, triazolyl, tetrazolyl, pyridyl and pyrimidinyl) optionally substituted by a $C_{1-6}$ alkyl; an aromatic fused heterocyclic group (e.g., benzimidazolyl, benzopyrazolyl, benzothiazolyl, benzoxazolyl, benzotriazolyl, quinolyl and indazolyl) optionally substituted by a $C_{1-6}$ alkyl; a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl and dioxidethiomorpholinyl) optionally substituted by a $C_{1-6}$ alkyl; a (mono- or di-$C_{1-10}$ alkyl) phosphono group optionally forming a ring (e.g., dimethylphosphono; diethylphosphono; diisopropylphosphono; dibutylphosphono; 2-oxide-1,3,2-dioxaphosphinanyl); a $C_{1-6}$ alkylsulfinyl; and a $C_{1-6}$ alkylsulfonyl.

As, the optionally substituted cyclic group for $R^1$, a group represented by the formula:

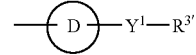

wherein, as defined in the following, D is a ring optionally further having substituent(s); $Y^1$ is a bond or a divalent acyclic hydrocarbon group; $R^3$ is a group of the formula: —SO$_2$R$^4$, —SOR$^4$ or —PO$_3$R$^4$R$^5$ wherein R$^4$ and R$^6$ are the same or different and each is a hydrogen atom, a hydrocarbon group or a heterocyclic group, and R$^4$ and R$^5$ may form a heterocycle together with the adjacent oxo-substituted phosphorus atom and two oxygen atoms, or an optionally substituted heterocyclic group, is preferable.

The "hydrocarbon group" for R$^4$ or R$^5$ is as defined above.

The "heterocyclic group" for R$^4$ or R$^5$ is as defined above.

The heterocycle formed by R$^4$ and R$^5$ together with the adjacent oxo-substituted phosphorus atom and two oxygen atoms is as defined above.

As the divalent acyclic hydrocarbon group for $Y^1$, those exemplified as the aforementioned X can be mentioned.

$Y^1$ is preferably a bond or a $C_{1-4}$ alkylene, more preferably a bond, —CH$_2$—, —(CH$_2$)$_2$—, —(CH$_2$)$_3$— and the like.

As the ring of the ring optionally further having substituent(s) for D, for example, the ring corresponding to the "cyclic group" for the aforementioned $R^1$ can be mentioned.

The ring for D is preferably an optionally partially saturated $C_{6-14}$ aromatic hydrocarbon ring (preferably benzene, dihydroindene), a $C_{3-10}$ cycloalkane (preferably cyclopropane, cyclobutane, cyclopentane, cyclohexane, cycloheptane, cyclooctane), a $C_{3-10}$ cycloalkene (preferably cyclohexene), a 5- or 6-membered aromatic heterocycle optionally condensed with a benzene ring (preferably furan, thiophene, oxazole, thiazole, isoxazole, imidazole, pyrazole, pyridine, pyrazine, indole, quinoline, isoquinoline and benzothiadiazole), a 5- or 6-membered non-aromatic heterocycle optionally condensed with a enzene ring (preferably pyrrolidine, tetrahydrofuran, thiazoline, oxazoline, thiazolidine, oxazolidine, dioxolane, piperidine, piperazine, morpholine, thiomorpholine, dihydrobenzofuran and oxodihydrobenzoxazole), and the like. The above-mentioned ring is more preferably a $C_{6-14}$ aromatic hydrocarbon, and benzene is particularly preferable.

The above-mentioned ring may have 1 to 3 substituents at substitutable positions. As such substituent, for example, a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, a $C_{1-6}$ alkoxy group optionally substituted by 1 to 3 halogen atoms (e.g., fluorine atom, chlorine atom, bromine atom, iodine atom) such as methoxy and ethoxy, and the like can be mentioned.

As the "optionally substituted acyl group" for $R^3$, for example, those exemplified as the substituents of the "optionally substituted hydrocarbon group" exemplified as the substituents for ring A can be mentioned. As the "optionally substituted heterocyclic group" for $R^3$ or $R^{3'}$, for example, those exemplified as the substituents for ring A can be mentioned.

As preferable examples of the "optionally substituted acyl group" for $R^3$, a carboxyl group; a $C_{1-6}$ alkoxy-carbonyl (e.g., methoxycarbonyl, ethoxycarbonyl, propoxycarbonyl, butoxycarbonyl, tert-butoxycarbonyl); a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); a carbamoyl optionally substituted by an amino; a mono- or di-$C_{1-6}$ alkylcarbamoyl optionally substituted by 1 to 3 substituents selected from a halogen atom, a hydroxy and a $C_{1-6}$ alkoxy-carbonyl, such as methylcarbamoyl, ethylcarbamoyl, dimethylcarbamoyl, diethylcarbamoyl, ethylmethylcarbamoyl, propylcarbamoyl, trifluoroethylcarbamoyl, methoxycarbonylethylcarbamoyl, 2-hydroxy-1-methoxycarbonyl-ethylcarbamoyl and 2-hydroxy-1-methoxycarbonyl-propylcarbamoyl; a mono- or di-$C_{6-14}$ aryl-carbamoyl optionally substituted by 1 to 3 substituents selected from an optionally halogenated $C_{1-6}$ alkyl and a $C_{1-6}$ alkoxy, such as phenylcarbamoyl, methoxyphenylcarbamoyl and trifluoromethylphenylcarbamoyl; a mono- or di-$C_{7-13}$ aralkyl-carbamoyl optionally substituted by 1 to 3 substituents selected from an amino optionally mono- or di-substituted by a $C_{1-6}$ alkyl, an optionally halogenated $C_{1-6}$ alkyl, a hydroxy and a $C_{1-6}$ alkoxycarbonyl, such as benzylcarbamoyl, phenethylcarbamoyl, dimethylaminobenzylcarbamoyl, methoxycarbonylphenethylcarbamoyl and trifluoromethylbenzylcarbamoyl; a sulfamoyl; an optionally halogenated mono- or di-$C_{1-6}$ alkylsulfamoyl (e.g., methylsulfamoyl, ethylsulfamoyl); a $C_{1-6}$ alkylsulfinyl (e.g., methylsulfinyl, ethylsulfinyl, tert-butylsulfinyl); a $C_{1-6}$ alkylsulfonyl (e.g., methylsulfonyl, ethylsulfonyl, tert-butylsulfonyl); a $C_{1-6}$ alkyl-carbonyl (e.g., acetyl); a 5- or 6-membered aromatic heterocyclic sulfinyl (e.g., triazolylsulfinyl and tetrazolylsulfinyl) optionally substituted by a $C_{1-6}$ alkyl; a $C_{6-14}$ arylsulfonyl (e.g., phenylsulfonyl); a 5- or 6-membered aromatic heterocyclic sulfonyl (e.g., triazolylsulfonyl and tetrazolylsulfonyl) optionally substituted by a $C_{1-6}$ alkyl; and the like can be mentioned. As the "optionally substituted acyl group" for $R^3$, a group of the formula: $-SO_2R^4$, $-SOR^4$ or $-PO_3R^4R^5$ (wherein each symbol is as defined above) are preferable.

The "optionally substituted acyl group" for $R^3$ is particularly preferably a $C_{1-6}$ alkylsulfonyl; and a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl).

Preferable examples of the "optionally substituted heterocyclic group" for $R^3$ or $R^{3'}$ include a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl, pyrimidinyl); an aromatic fused heterocyclic group (e.g., benzimidazolyl, benzopyrazolyl, benzothiazolyl, benzoxazolyl, benzotriazolyl, quinolyl, indazolyl); a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl); and a non-aromatic fused heterocyclic group (e.g., oxodihydrobenzoxazolyl, tetrahydrobenzothiazolyl), each of which is optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl (e.g., methoxycarbonyl).

Of these, a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl, pyrimidinyl), an aromatic fused heterocyclic group (e.g., benzimidazolyl, benzopyrazolyl, benzothiazolyl, benzoxazolyl, benzotriazolyl, quinolyl, indazolyl), and a 5- or 6-membered non-aromatic heterocyclic group (e.g., tetrahydrofuranyl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl), each of which is optionally substituted by a $C_{1-6}$ alkyl, are preferable.

When, in the formula (II), the 5-membered aromatic heterocycle represented by ring A is imidazole, then Z should not be —O—; when the 5-membered aromatic heterocycle represented by ring A is pyrazole, X is methylene, Z is —S— and Y is a bond, then the ring represented by D should not be oxadiazole.

As preferable examples of the compound represented by the formula (II), the following compound can be mentioned.

[Compound A]

A compound wherein ring A is an imidazole ring, a pyrazole ring, an oxadiazole ring, a thiadiazole ring, a triazole ring or a tetrazole ring (preferably a pyrazole ring, an oxadiazole ring, a thiadiazole ring, a triazole ring and a tetrazole ring, more preferably a pyrazole ring), each of which may have 1 or 2 substituents selected from a $C_{1-10}$ alkyl group, a $C_{6-14}$ aryl group and a $C_{7-13}$ aralkyl group;

B is an optionally substituted aromatic hydrocarbon group or an optionally substituted aromatic heterocyclic group, more preferably a $C_{6-14}$ aryl group (preferably phenyl) or a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms (e.g., fluorine atom, chlorine atom, bromine atom, iodine atom), a $C_{1-6}$ alkoxy optionally substituted by 1 to 3 halogen atoms (e.g., fluorine atom, chlorine atom, bromine atom, iodine atom), and a halogen atom (preferably fluorine atom, chlorine atom, bromine atom);

X is a divalent $C_{1-8}$ aliphatic hydrocarbon group, more preferably a $C_{1-4}$ alkylene or a $C_{2-4}$ alkenylene;

Z is —CONR$^2$— (wherein R$^2$ is as defined above and preferably a hydrogen atom or a $C_{1-6}$ alkyl group, and the carbon atom (C) of —CONR$^2$— is linked with X and the nitrogen atom (N) therein is linked with Y);

Y and Y$^1$ are the same or different and each is a bond or a $C_{1-4}$ alkylene;

D is a $C_{6-14}$ aromatic hydrocarbon group optionally further having substituent(s), more preferably a $C_{6-14}$ aromatic hydrocarbon (preferably, benzene) optionally having 1 to 3 substituents selected from a halogen atom (e.g., fluorine atom, chlorine atom, bromine atom, iodine atom), a $C_{1-6}$ alkyl group optionally substituted by 1 to 3 halogen atoms (e.g., fluorine atom, chlorine atom, bromine atom, iodine atom) such as methyl and trifluoromethyl, and a $C_{1-6}$ alkoxy group optionally substituted by 1 to 3 halogen atoms (e.g., fluorine atom, chlorine atom, bromine atom, iodine atom) such as methoxy and ethoxy;

R$^3$ is a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); or a 5- or 6-membered aromatic heterocyclic group (e.g., thiazolyl, oxazolyl, triazolyl, tetrazolyl, pyridyl, pyrimidinyl) or a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl), each of which is optionally substituted by 1 to 3 $C_{1-6}$ alkyl.

[Compound B]

A compound wherein ring A is an imidazole ring, a pyrazole ring, an oxadiazole ring, a thiadiazole ring, a triazole ring or a tetrazole ring (preferably a pyrazole ring, an oxadiazole ring, a thiadiazole ring, a triazole ring or a tetrazole ring, more preferably a pyrazole ring), each of which may have 1 or 2 substituents selected from a $C_{1-10}$ alkyl group, a $C_{6-14}$ aryl group and a $C_{7-13}$ aralkyl group (preferably a $C_{1-6}$ alkyl group such as methyl and the like);

B is a $C_{6-14}$ aryl group (preferably phenyl) or a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms, a $C_{1-6}$ alkoxy optionally substituted by 1 to 3 halogen atoms and a halogen atom; more preferably a $C_{6-14}$ aryl group (preferably phenyl) optionally having a halogen atom (preferably a fluorine atom);

X is a $C_{1-4}$ alkylene or a $C_{2-4}$ alkenylene; more preferably —CH$_2$—, —(CH$_2$)$_2$—, —CH=CH—; particularly preferably —CH=CH—;

Z is —CONR$^2$— (wherein R$^2$ is as defined above, and the carbon atom (C) of —CONR$^2$— is linked with X and the nitrogen atom (N) therein is linked with Y); more preferably —CONH—;

Y is a bond or a $C_{1-4}$ alkylene; more preferably a bond, —CH$_2$—, —(CH$_2$)$_2$—, —(CH$_2$)$_3$—; particularly preferably a bond;

Y$^1$ is a bond or a $C_{1-4}$ alkylene; more preferably a bond, —CH$_2$—, —(CH$_2$)$_2$—, —(CH$_2$)$_3$—;

D is a $C_{6-14}$ aromatic hydrocarbon (preferably benzene) optionally having 1 to 3 substituents selected from a halogen atom, a $C_{1-6}$ alkyl group optionally substituted by 1 to 3 halogen atoms and a $C_{1-6}$ alkoxy group optionally substituted by 1 to 3 halogen atoms; and R$^3$ is a carboxyl group; a $C_{1-6}$ alkoxy-carbonyl; a (mono- or di-$C_{1-10}$ alkyl)phosphono group optionally forming a ring (e.g., dimethylphosphono; diethylphosphono; diisopropylphosphono; dibutylphosphono; 2-oxide-1,3,2-dioxaphosphinanyl); a carbamoyl optionally substituted by an amino; a mono- or di-$C_{1-6}$ alkylcarbamoyl optionally substituted by 1 to 3 substituents selected from a halogen atom, a hydroxy and a $C_{1-6}$ alkoxy-carbonyl; a mono- or di-$C_{6-14}$ aryl-carbamoyl optionally substituted by 1 to 3 substituents selected from an optionally halogenated $C_{1-6}$ alkyl and a $C_{1-6}$ alkoxy; a mono- or di-$C_{7-13}$ aralkyl-carbamoyl optionally substituted by 1 to 3 substituents selected from an amino optionally mono- or di-substituted by a $C_{1-6}$ alkyl, an optionally halogenated $C_{1-6}$ alkyl, a hydroxy and a $C_{1-6}$ alkoxy-carbonyl; a sulfamoyl; an optionally halogenated mono- or di-$C_{1-6}$ alkylsulfamoyl; a $C_{1-6}$ alkylsulfinyl; a $C_{1-6}$ alkylsulfonyl (e.g., methylsulfonyl, ethylsulfonyl); a $C_{1-6}$ alkyl-carbonyl; a 5- or 6-membered aromatic heterocyclic sulfinyl (e.g., triazolylsulfinyl, tetrazolylsulfinyl) optionally substituted by a $C_{1-6}$ alkyl; a $C_{6-14}$ arylsulfonyl (e.g., phenylsulfonyl); a 5- or 6-membered aromatic heterocyclic sulfonyl (e.g., triazolylsulfonyl, tetrazolylsulfonyl) optionally substituted by a $C_{1-6}$ alkyl; more preferably a $C_{1-6}$ alkylsulfonyl (e.g., methylsulfonyl, ethylsulfonyl); a (mono- or di-$C_{1-10}$ alkyl) phosphono group optionally forming a ring (e.g., dimethylphosphono; diethylphosphono; diisopropylphosphono; dibutylphosphono; 2-oxide-1,3,2-dioxaphosphinanyl).

[Compound C]

A compound wherein ring A is an imidazole ring, a pyrazole ring, an oxadiazole ring, a thiadiazole ring, a triazole ring or a tetrazole ring (preferably a pyrazole ring, an oxadiazole ring, a thiadiazole ring, a triazole ring and a tetrazole ring, more preferably a pyrazole ring), each of which may have 1 or 2 substituents selected from a $C_{1-10}$ alkyl group, a $C_{6-14}$ aryl group and a $C_{7-13}$ aralkyl group (preferably a $C_{1-6}$ alkyl group such as methyl and the like);

B is a $C_{6-14}$ aryl group (preferably a phenyl) or a 5- to 7-membered monocyclic aromatic heterocyclic group (preferably furyl, thienyl, pyridyl, pyrimidinyl), each optionally having 1 to 3 substituents selected from a $C_{1-6}$ alkyl optionally substituted by 1 to 3 halogen atoms, a $C_{1-6}$ alkoxy optionally substituted by 1 to 3 halogen atoms and a halogen atom; more preferably a $C_{6-14}$ aryl group (preferably phenyl) optionally having a halogen atom (preferably a fluorine atom);

X is a $C_{1-4}$ alkylene or a $C_{2-4}$ alkenylene; more preferably —CH$_2$—, —(CH$_2$)$_2$—, —CH=CH—; particularly preferably —CH=CH—;

Z is —CONR$^2$— (wherein R$^2$ is as defined above, and the carbon atom (C) of —CONR$^2$— is linked with X and the nitrogen atom (N) therein is linked with Y); more preferably —CONH—;

Y is a bond or a $C_{1-4}$ alkylene; more preferably a bond, —CH$_2$—, —(CH$_2$)$_2$—, —(CH$_2$)$_3$—; particularly preferably a bond;

Y$^1$ is a bond or a $C_{1-4}$ alkylene; more preferably a bond, —CH$_2$—, —(CH$_2$)$_2$—, —(CH$_2$)$_3$—;

D is a $C_{6-14}$ aromatic hydrocarbon (preferably benzene) optionally having 1 to 3 substituents selected from a halogen atom, a $C_{1-6}$ alkyl group optionally substituted by 1 to 3 halogen atoms and a $C_{1-6}$ alkoxy group optionally substituted by 1 to 3 halogen atoms; and $R^3$ is a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl, pyrimidinyl); an aromatic fused heterocyclic group (e.g., benzimidazolyl, benzopyrazolyl, benzothiazolyl, benzoxazolyl, benzotriazolyl, quinolyl, indazolyl); a 5- or 6-membered non-aromatic heterocyclic group (e.g., tetrahydrofuryl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl); a non-aromatic fused heterocyclic group (e.g., oxodihydrobenzoxazolyl, tetrahydrobenzothiazolyl), each of which is optionally substituted by 1 to 3 substituents selected from a $C_{1-6}$ alkyl, a hydroxy-$C_{1-6}$ alkyl, a carboxyl, a carbamoyl and a $C_{1-6}$ alkoxy-carbonyl; more preferably a 5- or 6-membered aromatic heterocyclic group (e.g., thiazolyl, oxazolyl, imidazolyl, pyrazolyl, oxadiazolyl, thiadiazolyl, triazolyl, tetrazolyl, pyridyl, pyrimidinyl), an aromatic fused heterocyclic group (e.g., benzimidazolyl, benzopyrazolyl, benzothiazolyl, benzoxazolyl, benzotriazolyl, quinolyl, indazolyl) or a 5- or 6-membered non-aromatic heterocyclic group (e.g., tetrahydrofuranyl, morpholinyl, thiomorpholinyl, piperidinyl, pyrrolidinyl, piperazinyl, dioxothiazolidinyl, dioxooxazolidinyl, oxodihydrooxadiazolyl, dioxoimidazolidinyl, dioxopiperazinyl, dioxidethiomorpholinyl), each of which is optionally substituted by a $C_{1-6}$ alkyl.

[Compound D]

diethyl [4-({(2E)-3-[5-(4-fluorophenyl)-1-methyl-1H-pyrazol-4-yl]prop-2-enoyl}amino)benzyl]phosphonate (Example No. 2);

(2E)-N-{4-[(2,4-dioxo-1,3-thiazolidin-5-yl)methyl]phenyl}-3-[5-(4-fluorophenyl)-1-methyl-1H-pyrazol-4-yl]acrylamide (Example No. 60);

(2E)-3-[5-(4-fluorophenyl)-1-methyl-1H-pyrazol-4-yl]-N-[4-(1H-imidazol-1-ylmethyl)phenyl]acrylamide (Example No. 159);

(2E)-3-[5-(4-fluorophenyl)-1-methyl-1H-pyrazol-4-yl]-N-[4-(1H-pyrazol-1-ylmethyl)phenyl]acrylamide (Example No. 161);

diethyl [4-({(2E)-3-[1-methyl-5-(2-thienyl)-1H-pyrazol-4-yl]prop-2-enoyl}amino)benzyl]phosphonate (Example No. 149);

(2E)-3-[5-(4-fluorophenyl)-1-methyl-1H-pyrazol-4-yl]-N-{4-[(3-methyl-2,4-dioxo-1,3-thiazolidin-5-yl)methyl]phenyl}acrylamide (Example No. 110);

(2E)-N-[4-(1H-benzimidazol-1-ylmethyl)phenyl]-3-[5-(4-fluorophenyl)-1-methyl-1H-pyrazol-4-yl]acrylamide (Example No. 185);

(2E)-3-[5-(4-fluorophenyl)-1-methyl-1H-pyrazol-4-yl]-N-{4-[(methylsulfonyl)methyl]phenyl}acrylamide (Example No. 222);

(2E)-3-[5-(4-fluorophenyl)-1-methyl-1H-pyrazol-4-yl]-N-{4-[hydroxy(2-pyridinyl)methyl]phenyl}acrylamide (Example No. 49);

(2E)-3-[5-(4-fluorophenyl)-1-methyl-1H-pyrazol-4-yl]-N-[4-(4-morpholinylmethyl)phenyl]acrylamide (Example No. 192); and (2E)-N-{4-[(ethylsulfonyl)methyl]phenyl}-3-[5-(4-fluorophenyl)-1-methyl-1H-pyrazol-4-yl]acrylamide (Example No. 223).

The salts of a compound represented by the formula (I) or (II), a compound used in synthesizing the compound represented by the formula (I) or (II) and a compound used in the present invention are preferably pharmacologically acceptable ones and may be, for example, a salt with an inorganic base, a salt with an organic base, a salt with an inorganic acid, a salt with an organic acid and a salt with a basic or acidic amino acid.

Preferable examples of the salt with an inorganic base include alkali metal salts such as sodium salt, potassium salt and the like; alkaline earth metal salts such as calcium salt, magnesium salt and the like; and aluminum salt, ammonium salt and the like.

Preferable examples of the salt with an organic base include salts with trimethylamine, triethylamine, pyridine, picoline, ethanolamine, diethanolamine, triethanolamine, dicyclohexylamine, N,N-dibenzylethylenediamine, and the like.

Preferable examples of the salt with an inorganic acid include salts with hydrochloric acid, hydrobromic acid, nitric acid, sulfuric acid, and phosphoric acid and the like.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salt with a basic amino acid include salts with arginine, lysine and ornithine and the like.

Preferable examples of the salt with an acidic amino acid include salts with aspartic acid, glutamic acid, and the like.

Among these salts, a sodium salt, a potassium salt, hydrochloride and the like are most preferred.

A prodrug of the compound represented by the formula (I) or (II) or a salt thereof (hereinafter sometimes abbreviated as the compound of the present invention) means a compound capable of being converted to the compound of the present invention in vivo by the action of an enzyme or gastric juice and the like under physiological conditions, namely a compound capable of being converted to the compound of the present invention upon enzymatic oxidation, reduction or hydrolysis and the like, or a compound capable of being converted to the compound of the present invention upon hydrolysis and the like by gastric juice and the like. As the prodrug of the compound of the present invention, compounds derived by acylation, alkylation or phosphorylation of the amino group of the compound of the present invention (e.g. compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of the compound of the present invention, and the like); compounds derived by acylation, alkylation, phosphorylation or boration of the hydroxy group of the compound of the present invention (e.g. compounds derived by acetylation, palmitoylation, propanoylation, pivaloylation, succinylation, fumarylation; alanylation or dimethylaminomethylcarbonylation of the hydroxy group of the compound of the present invention, and the like); and compounds derived by esterification or amidation of the carboxyl group of the compound of the present invention (e.g. compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of the compound of the present invention, and the like), and the like can be mentioned. These compounds can be produced from the compound of the present invention by methods known per se.

The prodrug of the compound of the present invention may be one capable of being converted to the compound of the present invention under physiological conditions, as described in "Iyakuhin no Kaihatsu (Development of Drugs)", vol. 7, Molecular Designing, published by Hirokawa Shoten, 1990, pages 163-198.

The compound of the present invention may be labeled with an isotope (e.g., $^3H$, $^{14}C$, $^{35}S$, $^{125}I$, and the like) and the like.

Furthermore, the compound of the present invention may be an anhydride or a hydrate.

The compound of the present invention and a prodrug thereof are low toxic and can be used for mammals (e.g. human, mouse, rat, rabbit, dog, cat, cattle, horse, swine, monkey and the like), as an agent for preventing or treating neuropathy, an agent for promoting production or secretion of a neurotrophic factor and the like, either as such or by admixing with a pharmacologically acceptable carrier or the like to give a pharmaceutical composition.

As the above-mentioned pharmacologically acceptable carrier, various organic or inorganic carrier substances which are conventionally used as pharmaceutical preparation materials can be mentioned. They are incorporated as excipients, lubricants, binders, disintegrants or the like in solid preparations; as solvents, solubilizers, suspending agents, isotonizing agents, buffers, soothing agents or the like in liquid preparations. Where necessary, additives such as preservatives, antioxidants, coloring agents, sweeteners and the like may be used.

As preferable examples of the excipients, lactose, sucrose, D-mannitol, D-sorbitol, starch, pre-gelatinized starch, dextrin, crystalline cellulose, low-substituted hydroxypropylcellulose, carboxymethylcellulose sodium, powdered acacia, pullulan, light silicic anhydride, synthetic aluminum silicate, magnesium aluminometasilicate and the like can be mentioned.

As preferable examples of the lubricants, magnesium stearate, calcium stearate, talc, colloidal silica and the like can be mentioned.

As preferable examples of the binders, pre-gelatinized starch, sucrose, gelatin, powdered acacia, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like can be mentioned.

As preferable examples of the disintegrants, lactose, sucrose, starch, carboxymethylcellulose, carboxymethylcellulose calcium, croscarmellose sodium, carboxymethylstarch sodium, light silicic anhydride, low-substituted hydroxypropylcellulose and the like can be mentioned.

As preferable examples of the solvents water for injection, physiological saline, Ringer's solution, alcohol, propylene glycol, polyethylene glycol, sesame oil, corn oil, olive oil, cotton seed oil and the like can be mentioned.

As preferable examples of the solubilizers, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As preferable examples of the suspending agents, surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene-hardened castor oil, and the like can be mentioned.

As preferable examples of the isotonizing agents, sodium chloride, glycerol, D-mannitol, D-sorbitol, glucose and the like can be mentioned.

As preferable examples of the buffers, buffer solutions of phosphate, acetate, carbonate, citrate and the like can be mentioned.

As preferable examples of the soothing agents, benzyl alcohol and the like can be mentioned.

As preferable examples of the preservatives, para-hydroxybenzoates, chlorobutanol, benzyl alcohol, phenethyl alcohol, dehydroacetic acid, sorbic acid and the like can be mentioned.

As preferable examples of the antioxidants, sulfites, ascorbates and the like can be mentioned.

As preferable examples of the coloring agents, water-soluble edible tar dyes (e.g. food colors such as Food Color Red No. 2 and No. 3, Food Color Yellow No. 4 and No. 5, Food Color Blue No. 1 and No. 2), water-insoluble lake colors (e.g. the aluminum salt of the above water-soluble edible tar dyes and the like), natural colors (e.g. β-carotene, chlorophyll, red iron oxide and the like), and the like can be mentioned.

As preferable examples of the sweeteners, saccharin sodium, dipotassium glycyrrhizinate, aspartame, stevia and the like can be mentioned.

As the dosage form of the aforementioned pharmaceutical composition, oral preparations such as tablets (including sublingual tablet and intraorally disintegrating tablet), capsules (including soft capsules and microcapsules), granules, powders, troches, syrups, emulsions, suspensions and the like; or parenteral preparations such as injections (e.g. subcutaneous injection, intravenous injection, intramuscular injection, intraperitoneal injection, drip infusions and the like), external preparations (e.g. transdermal preparations, ointments and the like), suppositories (e.g. rectal suppositories, vaginal suppositories and the like), pellets, transnasal agents, transpulmonary agents (inhalant), eye drops etc., and the like can be mentioned, and these preparations can be safely administered orally or parenterally.

These preparations may be controlled-release preparations (e.g., sustained-release microcapsules and the like) such as rapid release preparations, sustained-release preparations and the like.

The pharmaceutical composition can be produced by the methods well established in fields of the pharmaceutical manufacturing techniques, for example, by the methods described in the Japanese Pharmacopoeia and the like. In the following, some concrete methods for producing such preparations are described in detail. The content of the compound of the invention in a pharmaceutical composition varies depending on the dosage form, dose of the compound of the invention and the like, but it is, for example, about 0.1-100 wt %.

For example, an oral preparation can be produced by adding an excipient (e.g., lactose, sucrose, starch, D-mannitol and the like), a disintegrant (e.g., carboxymethylcellulose calcium and the like), a binder (e.g., pre-gelatinized starch, powdered acacia, carboxymethylcellulose, hydroxypropylcellulose, polyvinylpyrrolidone and the like), a lubricant (e.g., talc, magnesium stearate, polyethylene glycol 6000 and the like) and the like to the active ingredient and compression-molding the mixture, and then, if desirable, by coating the molded product by a method known per se with a coating base for the purpose of masking of taste, or imparting enteric property or durability. As the coating base, for example, a sugar coating base, a water-soluble film coating base, an enteric film coating base, a sustained-release film coating base and the like can be mentioned.

As the sugar coating base, sucrose is used and, further, one or more kinds of ingredients selected from talc, precipitated calcium carbonate, gelatin, powdered acacia, pullulan, carnauba wax and the like may be used in combination.

As the water-soluble film coating base, for example, cellulose polymers such as hydroxypropylcellulose, hydroxypropylmethylcellulose, hydroxyethylcellulose, methylhydroxyethylcellulose and the like; synthetic polymers such as polyvinylacetal diethylaminoacetate, aminoalkyl methacrylate copolymer E [Eudragit E (trademark), Rohm Pharma], polyvinylpyrrolidone and the like; polysaccharides such as pullulan and the like, and the like can be mentioned.

As the enteric film coating base, for example, cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trademark), Rohm Pharma], methacrylic acid copolymer LD [Eudragit L-30D55 (trademark), Rohm Pharma], methacrylic acid copolymer S [Eudragit S (trademark), Rohm Pharma] and the like; natural products such as shellac and the like, and the like can be mentioned.

As the sustained-release film coating base, for example, cellulose polymers such as ethylcellulose and the like; acrylic acid polymers such as aminoalkyl methacrylate copolymer RS [Eudragit RS (trademark), Rhom Pharma], an ethyl acrylate-methyl methacrylate copolymer suspension [Eudragit NE (trademark), Rohm Pharma] and the like; and the like can be mentioned.

Two or more of the above coating bases may be used in admixture in appropriate proportions. On the occasion of coating, a shading agent such as titanium oxide, ferric oxide and the like may be used.

Injections are produced by dissolving, suspending or emulsifying the active ingredient in an aqueous solvent (e.g. distilled water, physiological saline, Ringer's solution) or an oleaginous solvent (e.g. vegetable oils such as olive oil, sesame oil, cotton seed oil, corn oil and the like; propylene glycol and the like), together with dispersants (e.g. polysorbate 80, polyoxyethylene-hardened castor oil 60, polyethylene glycol, carboxymethylcellulose, sodium alginate and the like), preservatives (e.g. methylparaben, propylparaben, benzyl alcohol, chlorobutanol, phenol and the like), isotonizing agents (e.g. sodium chloride, glycerol, D-mannitol, D-sorbitol, glucose and the like) and the like. If desirable, additives such as solubilizers (e.g. sodium salicylate, sodium acetate and the like), stabilizers (e.g. human serum albumin and the like), soothing agents (e.g. benzyl alcohol and the like) and the like, may be used.

The compound of the present invention has superior neurotrophic factor production or secretion promoting action.

As the neurotrophic factor, for example, neurotrophin, TGF-β superfamily, neurokine family, growth factor and the like can be mentioned.

The neurotrophin is a general name of the nerve growth actor (NGF) gene family, and refers to a protein that plays an important role in differentiation and functional homeostasis of the cells of the central and peripheral nervous systems, formation of synapse, regeneration and repair of damage and the like. As concrete examples of the neurotrophin, NGF, BDNF (brain-derived neurotrophic factor), NT-3 (neurotrophin-3), NT-4/5 (neurotrophin-4/5), NT-6 (neurotrophin-6) and the like can be mentioned. The neurotrophin preferably includes NGF, BDNF, NT-3 and the like.

The TGF-β superfamily means a protein group known to have a structure characterized by the position of cysteine in a mature molecule, and exhibit a great diversity of actions on various cells and tissues. As concrete examples thereof, TGF-β1, TGF-β2, TGF-β3, BMP (osteogenic factor, bone morphogehetic protein)-2, BMP-3, BMP-4, BMP-5, BMP-6, BMP-7, BMP-8A, BMP-8B, BMP-14 (GDF-5), GDNF (glial cell line-derived neurotrophic factor), neurturin, artemin, persephin, GDF-1, GDF-8, GDF (growth/differentiation factor)-15, inhibin α, inhibin β, DAF (dauer formation) 7 and the like can be mentioned. The TGF-β superfamily is preferably GDNF, GDF-15 and the like.

As the neurokine family, for example, ciliary neurotrophic factor (CNTF), interleukin 6 (IL-6) and the like can be mentioned.

As the growth factor, for example, insulin growth factor-1 (IGF-1), basic fibroblast growth factor and the like can be mentioned.

The neurotrophic factor is preferably neurotrophin, TGF-β superfamily and the like, more preferably NGF, BDNF, NT-3, GDNF, GDF-15 and the like.

The compound of the present invention has a nerve function improving action.

Moreover, the compound of the present invention has a motor nerve or sensory nerve conduction velocity improving action, pain (e.g., neuropathic pain) ameliorating action and neuroprotective action.

Here, the "neuroprotective action" means a neurite outgrowth action, a neurite network formation action, a suppressive action of neurite retraction, a suppressive action of nerve terminal degeneration, and the like.

The compound of the present invention is useful as an agent for preventing or treating, for example, neuropathies (e.g., peripheral neuropathies such as diabetic neuropathy, cancer treatment-induced neuropathy and the like, Guillain-barre syndrome); neurodegenerative diseases (e.g., Alzheimer's senile dementia, Parkinson's syndrome, Huntington's chorea, amyotrophic lateral sclerosis (ALS), Down's syndrome); diabetic cardiac myopathy; peripheral nerve injury; spinal injury; spinal canal stenosis; multiple sclerosis; cerebral ischemic disease; epilepsy; depression; trembling; restless legs syndrome; inflammatory bowel disease (e.g., inflammatory colitis); neuropathic pains (e.g., painful neuropathy, postherpetic neuralgia, back pain, trigeminal neuralgia, carpal tunnel syndrome, phantom limb pain, spinal injury, multiple sclerosis); chronic pain (e.g., cancer pain); behavioral abnormalities accompanied by dementia (e.g., wandering, aggressive behavior); anxiety disorder; numbness caused by wound; autonomic abnormalities (e.g., diabetic autonomic disorder, asymptomatic hypoglycemia, gastroparesis, neuropathic diarrhea and constipation, erectile dysfunction, orthostatic hypotension, arrhythmia, heart failure, painless cardiac infarction, dyshidrosis, neuropathic bladder, sudden deafness, chronic arterial occlusion, facial flush); bladder dysfunction (e.g., bladder reflex disorder); hearing impairment; diabetic foot lesion; bone disease (e.g., osteoporosis); joint disease (e.g., Charcot's joint, osteoarthritis, rheumatism); Hirschsprung's disease and the like.

In addition, the compound of the present invention is also useful as an agent for preventing or treating diseases such as diabetes (e.g., type-1 diabetes, type-2 diabetes, gestational diabetes etc.), impaired glucose tolerance (IGT), hyperlipidemia (e.g., hypertriglyceridemia, hypercholesterolemia, hypo-HDL-emia, postprandial hyperlipidemia), hyperinsulinemia, obesity, hyperphagia, hypertension, cardiovascular disease (e.g., atherosclerosis) and the like; or a syndrome (e.g., syndrome X, visceral obesity syndrome) comprising combination of some of these diseases.

Moreover, the compound of the present invention is used for secondary prophylaxis or suppression of progression (e.g., suppression of progression of impaired glucose tolerance into diabetes) of the above-mentioned various diseases (e.g., cardiac infarction).

Furthermore, the compound of the present invention is useful as an ameliorating agent of peripheral neuropathy or brain metabolic disorder; a promoter of curing skin injury caused by metabolic or endocrine system disease such as diabetes, and by wound; pancreatic regeneration agent (pancreatic function recovering agent); renal regeneration agent (renal function recovering agent); ameliorating or suppressing agent of pain (e.g., neuropathic pain); prophylactic agent of amputation of lower limb; a prophylactic agent of sudden death and the like.

While the dose of the compound of the present invention varies depending on the administration subject, administration route, target disease, condition and the like, it is, for example, in the case of oral administration to an adult patient with peripheral neuropathy (e.g., diabetic neuropathy), generally about 0.01-100 mg/kg body weight, preferably 0.05-30 mg/kg body weight, more preferably 0.1-2 mg/kg body weight, per dose, which amount is desirably administered once to 3 times a day.

The compound of the present invention can be used in combination with a pharmaceutical agent (hereinafter to be abbreviated as a combination drug) such as a therapeutic agent of diabetes, a therapeutic agent of diabetic complications, an antiepileptic agent, an antidepressant, an opioid agonist, an antihyperlipemic agent, an antihypertensive agent, an antiarrhythmic agent, an antiobesity agent, a diuretic, a chemotherapeutic agent, an immunotherapeutic agent, an antithrombotic agent, a therapeutic agent of osteoporosis, an antidementia agent, an agent for ameliorating erectile dysfunction, a therapeutic agent of incontinentia or pollakiuria, a therapeutic agent for dysuria, a non-steroidal anti-inflammatory drug, a local anesthetic, vitamines and the like. These combination drugs may be a low molecular weight compound, or may be a high molecular weight protein, polypeptide, antibody, vaccine and the like.

As the therapeutic agent of diabetes, insulin preparations (e.g. animal insulin preparations obtained by extraction from the bovine or swine pancreas; human insulin preparations synthesized by a genetic engineering technique using *Escherichia coli* or a yeast; insulin-zinc; protamine-insulin-zinc, a fragment or derivative of insulin (e.g., INS-1 etc.), oral insulin preparations and the like), insulin sensitizers (e.g. pioglitazone or its salt (preferably hydrochloride), rosiglitazone or its salt (preferably maleate), reglixane (JTT-501), GI-262570, netoglitazone (MCC-555), YM-440, DRF-2593, BM-13.1258, KRP-297, R-119702, CS-011, FK-614, the compounds described in WO99/58510 (e.g., (E)-4-[4-(5-methyl-2-phenyl-4-oxazolylmethoxy)benzyloxyimino]-4-phenylbutyric acid), the compounds described in WO01/38325, tesaglitazar (AZ-242), ragaglitazar (NN-622), BMS-298585, ONO-5816, BM-13-1258, LM-4156, NBX-102, LY-519818, MX-6054, LY-510929, balaglitazone (NN-2344), T-131 or its salt, THR-0921 and the like), α-glucosidase inhibitors (e.g., voglibose, acarbose, miglitol, emiglitate etc.), biguanides (e.g., phenformin, metformin, buformin etc.), insulin secretagogues, [sulfonylureas (e.g., tolbutamide, glibenclamide, gliclazide, chlorpropamide, tolazamide, acetohexamide, glyclopyramide, glimepiride, glipizide, glybuzole etc.), repaglinide, senaglinide, nateglinide, mitiglinide or its calcium salt hydrate etc.], GPR40 agonists, GLP-1 receptor agonists [e.g., GLP-1, GLP-1MR, NN-2211, AC-2993 (exendin-4), BIM-51077, Aib(8,35)hGLP-1(7,37)$NH_2$, CJC-1131 etc.], amyrin agonists (e.g., pramlintide etc.), phosphotyrosine phosphatase inhibitors (e.g., vanadic acid etc.), dipeptidylpeptidase IV inhibitors (e.g., NVP-DPP-278, PT-100, P32/98, NVP-DDP-728, LAF237, TS-021 etc.), β3 agonists (e.g., CL-316243, SR-58611-A, UL-TG-307, SB-226552, AJ-9677, BMS-196085, AZ40140 etc.), gluconeogenesis inhibitors (e.g., glycogen phosphorylase inhibitors, glucose-6-phosphatse inhibitors, glucagon antagonists etc.), SGLT (sodium-glucose cotransporter) inhibitors (e.g., T-1095 etc.), 11β-hydroxysteroid dehydrogenase inhibitors (e.g., BVT-3498 etc.), adiponectin or its agonists, IKK inhibitors (e.g., AS-2868 etc.), leptin resistance improving drugs, somatostatin receptor agonists (compounds described in WO01/25228 and WO03/42204, compounds described in WO98/44921, WO98/45285 and WO99/22735 etc.), glucokinase activators (e.g., Ro-28-1675) and the like can be mentioned.

As the therapeutic agent of diabetic complications, aldose reductase inhibitors (e.g., tolrestat, epalrestat, zenarestat, zopolrestat, minalrestat, fidarestat, SNK-860, CT-112 and the like), neurotrophic factors and increasing drugs thereof (e.g., NGF, NT-3, BDNF, neurotrophin production or secretion promoters described in WO01/14372 (e.g., 4-(4-chlorophenyl)-2-(2-methyl-1-imidazolyl)-5-[3-(2-methylphenoxy)propyl] oxazole and the like) and the like), nerve regeneration enhancers (e.g., Y-128 and the like), PKC inhibitors (e.g., LY-333531 and the like), AGE inhibitors (e.g., ALT946, pimagedine, pyratoxanthine, N-henacylthiazolium bromide (ALT766), ALT-711, EXO-226, pyridorin, pyridoxamine, and the like), active oxygen scavengers (e.g., thioctic acid and the like), cerebral vasodilators (e.g., tiapride, mexiletine and the like), somatostatin receptor agonists (BIM23190), apoptosis signal regulating kinase-1 (ASK-1) inhibitors and the like can be mentioned.

As the antiepileptic agent, for example, gabapentin, gabapentin MR, trileptal, keppra, zonegran, pregabalin, harkoseride, carbamazepine and the like can be mentioned.

As the antidepressant, for example, amitriptyline, imipramine and the like can be mentioned.

As the opioid agonist, for example, morphine and the like can be mentioned.

As the antihyperlipemic agent, statin compounds (e.g., cerivastatin, pravastatin, simvastatin, lovastatin, atorvastatin, fluvastatin, itavastatin and salts thereof (e.g., sodium salt) and the like), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid and the like), fibrate compounds (e.g., bezafibrate, clofibrate, simfibrate, clinofibrate and the like), antioxidanls (e.g., lipoic acid, probucol), and the like can be mentioned.

As the antihypertensive agent, angiotensin converting enzyme inhibitors (e.g., captopril, enalapril, delapril and the like) or angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-bemzimidazole-7-carboxylic acid etc.), calcium antagonists (e.g., manidipine, nifedipine, amlodipine, efonidipine, nicardipine and the like), clonidine and the like can be mentioned.

As the antiarrhythmic agent, for example, mexiletine and the like can be mentioned.

As the antiobesity agent, for example, antiobesity drugs acting on the central nervous system (e.g. dexfenfluramine, fenfluramine, phentermine, sibutramine, anfepramon, dexamphetamine, mazindol, phenylpropanolamine, clobenzorex; MCH receptor antagonists (e.g., SB-568849; SNAP-7941; the compounds included in WO01/82925 and WO01/87834 etc.); neuropeptide Y antagonists (e.g., CP-422935 etc.); cannabinoid receptor antagonists (e.g., SR-141716, SR-147778 etc.); ghrelin antagonists; 11β-hydroxysteroid dehydrogenase inhibitors (e.g., BVT-3498 etc.) and the like), pancreatic lipase inhibitors (e.g., orlistat, ALT-962 etc.), β3 agonists (e.g., CL-316243, SR-58611-A, UL-TG-307, SB-226552, AJ-9677, BMS-196085, AZ40140 etc.), anorectic peptides (e.g., leptin, CNTF (ciliary neurotrophic factor) etc.), cholecystokinin agonists (e.g., lintitript, FPL-15849 etc.), anorectics (e.g., P-57 etc.) and the like can be mentioned.

As the diuretic, for example, xanthine derivatives (e.g., sodium salicylate and theobromine, calcium salicylate and theobromine, and the like), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide and the like), antialdosterone preparations (e.g., spironolactone, triamterene and the like), carbonic anhydrase inhibitors (e.g., acetazolamide and the like), chlorobenzenesulfonamide preparations (e.g., chlortalidone, mefruside, indapamide and the like), azosemide, isosorbide, etacrynic acid, piretanide, bumetanide, furosemide and the like can be mentioned.

As the chemotherapeutic agent, for example, alkylation agents (e.g., cyclophosphamide, ifosfamide and the like), metabolic antagonists (e.g., methotrexate, 5-fluorouracil and the like), anti-cancer antibiotics (e.g., mitomycin, adriamycin and the like), plant-derived anti-cancer agents (e.g., vincristin, vindesine, taxol and the like), cisplatin, carboplatin, etopoxide and the like can be mentioned. Of these, furtulon and neofurtulon, which are 5-fluorouracil derivatives, and the like are preferable.

As the immunotherapeutic agent, for example, microorganism or bacterial components (e.g., a muramyl dipeptide derivative, picibanil and the like), polysaccharides having immunity potentiating activity (e.g., lentinan, sizofiran, krestin and the like), cytokines obtained by genetic engineering techniques (e.g., interferon, interleukin (IL) and the like), colony stimulating factors (e.g., granulocyte colony stimulating factor, erythropoietin and the like) and the like can be mentioned, with preference given to interleukins such as IL-1, IL-2, IL-12 and the like.

As the antithrombotic agent, for example, heparin (e.g., heparin sodium, heparin calcium, dalteparin sodium and the like), warfarin (e.g., warfarin potassium and the like), antithrombin drugs (e.g., aragatroban and the like), thrombolytic agents (e.g., urokinase, tisokinase, alteplase, nateplase, monteplase, pamiteplase and the like), platelet aggregation inhibitors (e.g., ticlopidine hydrochloride, cilostazol, ethyl icosapentate, beraprost sodium, sarpogrelate hydrochloride and the like) and the like can be mentioned.

As the therapeutic agent of osteoporosis, for example, alfacalcidol, calcitriol, elcatonin, calcitonin salmon, estriol, ipriflavone, pamidronate disodium, alendronate sodium hydrate, incadronate disodium and the like can be mentioned.

As the antidementia agent, for example, tacrine, donepezil, rivastigmine, galantamine and the like can be mentioned.

As the agent for ameliorating erectile dysfunction, for example, apomorphine, sildenafil citrate and the like can be entioned.

As the therapeutic agent of incontinentia or pollakiuria, for example, flavoxate hydrochloride, oxybutynin hydrochloride, propiverine hydrochloride and the like can be mentioned.

As a therapeutic agent for dysuria, acetylcholine esterase inhibitors (e.g., distigmine) and the like can be mentioned.

As the non-steroidal anti-inflammatory drug, for example, aspirin, acetaminophen, indomethacin and the like can be mentioned.

As the local anesthetic, for example, lidocaine, capsaicin and the like can be mentioned. As vitamins, for example, vitamin B1, vitamin B12 and the like can be mentioned.

Furthermore, drugs having a cachexia-ameliorating action established in animal models or clinical situations, such as cyclooxygenase inhibitors (e.g., indomethacin and the like) [*Cancer Research*, Vol. 49, 5935-5939, 1989], progesterone derivatives (e.g., megesterol acetate) [*Journal of Clinical Oncology*, Vol. 12, 213-225, 1994], glucosteroid (e.g., dexamethasone and the like), metoclopramide agents, tetrahydrocannabinol agents (ibid.), fat metabolism improving agents (e.g., eicosapentaenoic acid and the like) [*British Journal of Cancer*, Vol. 68-314-318, 1993], growth hormones, IGF-1; or antibodies to a cachexia-inducing factor such as TNF-α, LIF, IL-6, Oncostatin M and the like, can be also used in combination with the compound of the present invention.

The combination drug is preferably an insulin preparation, an insulin sensitizer, α-glucosidase inhibitor, a biguanide, an insulin secretagogue (preferably a sulfonylurea), an aldose reductase inhibitor, a PKC inhibitor, an antiepileptic agent, an antidepressant, an antiarrhythmic agent, an opioid agonist, an antioxidant, a non-steroidal anti-inflammatory drug and the like.

The administration time of the aforementioned combination drug is not restricted, and the compound of the present invention and the combination drug can be administered to an administration subject simultaneously, or may be administered at staggered times. The dosage of the combination drug may be determined according to the dose clinically used, and can be appropriately selected depending on an administration subject, administration route, disease, combination and the like.

The administration mode of the combination drug is not particularly restricted, as long as the compound of the present invention and the combination drug are combined in administration. Examples of such administration mode include the following methods: (1) The compound of the present invention and the combination drug are simultaneously processed to give a single preparation which is administered. (2) The compound of the present invention and the combination drug are separately processed to give two kinds of preparations which are administered simultaneously by the same administration route. (3). The compound of the present invention and the combination drug are separately processed to give two kinds of preparations which are administered by the same administration route at staggered times. (4) The compound of the present invention and the combination drug are separately processed to give two kinds of preparations which are administered simultaneously by the different administration routes. (5) The compound of the present invention and the combination drug are separately processed to give two kinds of preparations which are administered by the different administration routes at staggered times (for example, the compound of the present invention and the combination drug are administered in this order, or in the reverse order), and the like.

The proportion of the compound of the present invention to the combination drug can be appropriately selected depending on an administration subject, administration route, diseases and the like. For example, when the administration subject is a human, 0.01-100 parts by weight of the combination drug is used relative to 1 part by weight of the compound of the present invention.

When the compound of the present invention is used in combination with a combination drug, the dose of the both components can be reduced within a safe range in consideration of the opposing effect of the components. Particularly, a combination drug such as an insulin sensitizer, an insulin secretagogue (preferably a sulfonylurea), a biguanide, an aldose reductase inhibitor, a PKC inhibitor, an antiepileptic agent, an antidepressant, an antiarrhythmic agent, an opioid agonist, an antioxidant, a non-steroidal anti-inflammatory drug and the like can be reduced from the normal dose. Therefore, the opposing effect caused by these combination drugs can be safely prevented.

The compound of the present invention may be used in combination with a treatment method involving a non-pharmacological means such as spinal electrical stimulation, acupuncture and moxibustion and the like.

Hereinafter the production methods of the compound of the present invention are explained.

Compound (I) can be produced according to a method known per se, such as Method A, Method D and Method F to be described in the following, or an analogous method thereto.

The compound (Ia) of the formula (I) wherein Z is —CONR$^2$— (R$^2$ is as defined above) can be produced according to, for example, the following Method A.

[Method A]

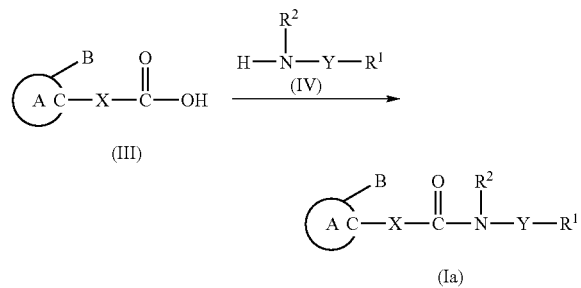

wherein the symbols are as defined above.

In this method, compound (III) is subjected to an amidation reaction to produce compound (Ia). This reaction is carried out according to a method known per se, such as a method for directly condensing compound (III) with compound (IV), a method for reacting a reactive derivative of compound (III) with compound (IV) and the like.

The method for directly condensing compound (III) with compound (IV) is generally carried out in the presence of a condensation agent, in a solvent that does not exert an adverse influence on the reaction.

As the condensation agent, conventional one such as carbodiimide type condensation reagents such as dicyclohexylcarbodiimide, diisopropylcarbodiimide, 1-ethyl-3-(3-dimethylaminopropyl)carbodiimide or its hydrochloride and the like; phosphoric acid type condensation reagents such as diethyl cyanophosphate, diphenylphosphoryl azide and the like; carbonyl diimidazole, 2-chloro-1,3-dimethylimidazolium tetrafluoroborate and the like can be mentioned.

As a solvent that does not exert an adverse influence on the reaction, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like can be mentioned. Two or more kinds of these solvents may be used in a mixture at appropriate ratios.

The amount of compound (IV) to be used is generally 0.1-10 molar equivalents, preferably 0.3-3 molar equivalents, relative to compound (III).

The amount of the condensation agent to be used is generally 0.1-10 molar equivalents, preferably 0.3-3 molar equivalents, relative to compound (III).

When the above-mentioned carbodiimide type condensation reagent is used as the condensation agent, the reaction efficiency can be improved by the use of a suitable condensation promoter (e.g., 1-hydroxy-1H-1,2,3-benzotriazole hydrate, 1-hydroxy-7-azabenzotriazole, 1-hydroxybenzotriazole, N-hydroxysuccinimide, N-hydroxyphthalimide and the like) where necessary. When the above-mentioned phosphoric acid type condensation reagent is used as the condensation agent, the reaction efficiency can be improved by generally adding an organic amine type base such as triethylamine and the like.

The amount of the above-mentioned condensation promoter and the organic amine type base to be used is generally 0.1-10 molar equivalents, preferably 0.3-3 molar equivalents, relative to compound (III).

The reaction temperature is generally −30° C. to 100° C.

The reaction time is generally 0.5-60 hrs.

As the reactive derivative of the aforementioned compound (III), for example, acid anhydride, acid halide (acid chloride, acid bromide), imidazolide, or mixed acid anhydride (e.g., anhydride with methyl carbonate, ethyl carbonate or isobutyl carbonate, and the like) and the like can be mentioned.

For example, when an acid anhydride or an acid halide is used as the reactive derivative, the reaction is generally carried out in the presence of a base, in a solvent that does not exert an adverse influence on the reaction.

As the base, for example, triethylamine, diisopropylethylamine, pyridine, N-methylmorpholine, N,N-dimethylaniline, 4-dimethylaminopyridine, lithium hydroxide, sodium hydroxide, potassium hydroxide, sodium hydrogen carbonate, sodium carbonate, potassium carbonate, cesium carbonate and the like can be mentioned.

As the solvent that does not exert an adverse influence on the reaction, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, acetonitrile, water and the like can be mentioned. Two or more kinds of these solvents may be used in a mixture at appropriate ratios. When the above-mentioned amides are used as the solvent that does not exert an adverse influence on the reaction, the reaction can be also carried out in the absence of a base.

The amount of the compound (IV) to be used is generally 0.1-10 molar equivalents, preferably 0.3-3 molar equivalents, relative to compound (III).

The amount of the base to be used is generally 0.1-10 molar equivalents, preferably 0.3-3 molar equivalents, relative to compound (III).

The reaction temperature is generally −30° C. to 100° C.

The reaction time is generally 0.5-20 hrs.

When a mixed acid anhydride is used as the reactive derivative, compound (III) is reacted with chlorocarbonic acid ester in the presence of a base and then reacted with compound (IV).

As the chlorocarbonic acid ester, for example, methyl chlorocarbonate, ethyl chlorocarbonate, isobutyl chlorocarbonate and the like can be mentioned.

As the base, for example, triethylamine, aniline, N-methylmorpholine, N,N-dimethylaniline, 4-dimethylaminopyridine, sodium hydroxide, potassium hydroxide, lithium hydroxide, sodium hydrogen carbonate, sodium carbonate, potassium carbonate, cesium carbonate and the like can be mentioned.

The amount of the compound (IV) to be used is generally 0.1-10 molar equivalents, preferably 0.3-3 molar equivalents, relative to compound (III).

The reaction temperature is generally −30° C. to 100° C.

The reaction time is generally 0.5-20 hrs.

The compound (Ia) thus obtained can be isolated and purified by a known separation and purification means, such as concentration, concentration under reduced pressure, solvent extraction, crystallization, recrystallization, phase transfer, chromatography and the like.

The compound (IV) to be used as a starting compound in the above-mentioned Method A can be produced by a method known per se.

The compound (III) to be used as a starting compound in the above-mentioned Method A can be produced by, for example, the following Method B.

[Method B]

$$\underset{(V)}{\overset{B}{\underset{A}{\bigcirc}}}C-X-\overset{O}{\underset{\|}{C}}-OR^6 \xrightarrow{\text{hydrolysis}} (III)$$

wherein $R^6$ is an optionally substituted hydrocarbon group, an optionally substituted heterocyclic group or an optionally substituted acyl group, and other symbols are as defined above.

As the "optionally substituted hydrocarbon group" and "optionally substituted heterocyclic group" for $R^6$, those respectively exemplified as the aforementioned B can be used.

As the "optionally substituted acyl group" for $R^6$, those exemplified as the aforementioned $R^1$ can be used.

$R^6$ is preferably a $C_{1-6}$ alkyl group (e.g., methyl, ethyl, propyl, isopropyl, tert-butyl), a $C_{7-13}$ aralkyl group (e.g., benzyl), a $C_{6-14}$ aryl group (e.g., phenyl) and the like.

In this method, compound (V) is subjected to a hydrolysis reaction to give compound (III).

This reaction is carried out according to a conventional method, in the presence of an acid or a base, in a water-containing solvent.

As the acid, for example, hydrochloric acid, sulfuric acid, acetic acid, hydrobromic acid and the like can be mentioned.

As the base, for example, alkali metal carbonates such as potassium carbonate, sodium carbonate, cesium carbonate and the like; alkaline earth metal carbonates such as barium carbonate, calcium carbonate and the like; alkali metal alkoxide such as sodium methoxide and the like; alkali metal hydroxide such as potassium hydroxide, sodium hydroxide, lithium hydroxide and the like; alkaline earth metal hydroxides such as barium hydroxide, calcium hydroxide and the like; and the like can be mentioned.

The amount of the acid or base to be used is generally an t excess amount relative to compound (V). Preferably, the amount of the acid to be used is about 2-about 50 equivalents relative to compound (V) and the amount of the base to be used is about 1.2-about 10 equivalents relative to compound (V).

As the water-containing solvent, for example, a mixed solvent of water and one or more kinds of solvents selected from alcohols such as methanol, ethanol and the like; ethers such as tetrahydrofuran, dioxane, diethyl ether and the like; dimethyl sulfoxide and acetone and the like, and the like can be mentioned. When an acid is used for hydrolysis reaction, an excess amount of the acid may be used as a solvent.

The reaction temperature is generally about −20 to about 150° C., preferably about −10 to about 100° C.

The reaction time is generally about 0.1-about 20 hrs.

The compound (III) thus obtained can be isolated and purified by a known separation and purification means, such as concentration, concentration under reduced pressure, solvent extraction, crystallization, recrystallization, phase transfer, chromatography and the like.

The compound (V) to be used as a starting compound in the above-mentioned Method B can be produced by a method known per se. For example, of compounds (V), compounds wherein X is —CH=CH— or —(CH$_2$)$_2$— [respectively compound (V-1) or (V-2)] can be produced according to the following Method C.

[Method C]

$$\underset{(VI)}{\overset{B}{\underset{A}{\bigcirc}}}C{\overset{B}{\underset{CO_2R^7}{}}} \xrightarrow{\text{Step 1a}} \underset{(VII)}{\overset{B}{\underset{A}{\bigcirc}}}C{\overset{B}{\underset{CH_2OH}{}}} \xrightarrow{\text{Step 2}} \underset{(IX)}{\overset{B}{\underset{A}{\bigcirc}}}C{\overset{B}{\underset{CHO}{}}}$$

$$\underset{(VIII)}{\overset{B}{\underset{A}{\bigcirc}}}C{\overset{}{\underset{CH_3}{}}} \xrightarrow{\text{Step 1b}} \quad \xrightarrow{\text{Step 1c}} \quad \xrightarrow{\text{Step 3}}$$

$$\underset{(V-1)}{\overset{B}{\underset{A}{\bigcirc}}}C{\overset{}{\underset{CH=CHCO_2R^6}{}}} \xrightarrow{\text{Step 4}} \underset{(V-2)}{\overset{B}{\underset{A}{\bigcirc}}}C{\overset{}{\underset{CH_2CH_2CO_2R^6}{}}}$$

wherein $R^7$ is an optionally substituted hydrocarbon group, an optionally substituted heterocyclic group or an optionally substituted acyl group, and other symbols are as defined above.

As the "optionally substituted hydrocarbon group", "optionally substituted heterocyclic group" and "optionally substituted acyl group" for $R^7$, those respectively exemplified as the aforementioned $R^6$ are used.

$R^7$ is preferably a $C_{1-6}$ alkyl group (e.g., methyl, ethyl, propyl, isopropyl, tert-butyl), a $C_{7-13}$ aralkyl group (e.g., benzyl), a $C_{6-14}$ aryl group (e.g., phenyl) and the like.

(Step 1a) Reduction Reaction

This reaction is carried out according to a conventional method in the presence of a reducing agent in a solvent that does not exert an adverse influence on the reaction.

As the reducing agent, for example, sodium borohydride, lithium borohydride, lithium aluminum hydride, diisobutylaluminum hydride, sodium dihydrobis (2-methoxyethoxy) aluminate, borane and its complex (e.g., borane-tetrahydrofuran, borane-pyridine, borane-dimethylsulfide and the like) and the like can be mentioned.

The amount of the reducing agent to be used is preferably about 0.5-about 10 molar equivalents relative to compound (VI).

As the solvent that does not exert an adverse influence on the reaction, for example, aromatic hydrocarbons such as benzene, toluene, xylene and the like; halogenated hydrocarbons such as chloroform, dichloromethane and the like; ethers such as tetrahydrofuran, dioxane, diethyl ether and the like; water; alcohols such as methanol, ethanol, isopropanol and the like; and the like can be mentioned. Two or more kinds of these solvents may be used in a mixture at appropriate ratios.

The reaction temperature is generally about −50 to about 150° C., preferably about −10 to about 100° C.

The reaction time is generally about 0.5-about 20-hrs.

The compound (VII) thus obtained can be isolated and purified by a known separation and purification means, such as concentration, concentration under reduced pressure, solvent extraction, crystallization, recrystallization, phase transfer, chromatography and the like. It is possible to use a reaction mixture containing compound (VII) as a starting material for the next reaction without separation or purifification of compound (VII).

The compound (VI) to be used as a starting compound in the above-mentioned Step 1a can be produced according a method known per se, such as methods described in *Tetrahedron Letters*, Vol. 41, p. 5453 (2000), WO 99/52882, *Journal of Chemical Society*, Perkin Trans. Vol. 1, No. 2, pp. 642-645 (1981) and the like, or a method analogous thereto.

(Step 1b) Halogenation and Hydroxylation Reactions

In this step, compound (VIII) is subjected to a halogenation reaction and then to hydroxylation reaction to give compound (VII).

Here, the halogenation reaction is carried out in the presence of a halogenating agent and, where necessary, a suitable reaction initiator, in a solvent that does not exert an adverse influence on the reaction.

As the halogenating agent, for example, N-halogenated imides such as N-bromosuccinimide, N-chlorosuccinimide and the like, and the like can be mentioned.

The amount of the halogenating agent to be used is preferably about 1-about 10 molar equivalents relative to compound (VIII).

As the reaction initiator, for example, organic azo compounds such as azobisisobutyronitrile and the like; organic peroxides such as benzoyl peroxide and the like; and the like can be mentioned.

The amount of the reaction initiator to be used is preferably about 0.001-about 1 molar equivalents relative to compound (VIII).

As the solvent that does not exert an adverse influence on the reaction, for example, ethers such as tetrahydrofuran, dioxane, diethyl ether and the like; halogenated hydrocarbons such as carbon tetrachloride, 1,2-dichloroethane, chloroform, dichloromethane and the like, acetonitrile, ethyl acetate, N,N-dimethylformamide and the like can be mentioned. Two or more kinds of these solvents may be used in a mixture at appropriate ratios.

The reaction temperature is generally −50 to 200° C., preferably 0 to 120° C.

The reaction time is generally 0.1-48 hrs.

The hydroxylation reaction is suitably carried out in the presence of a suitable base in a solvent that does not exert an adverse influence on the reaction.

As the base, for example, alkali metal acetates or formates such as sodium acetate, potassium acetate, sodium formate and the like; alkali metal carbonates such as potassium carbonate, sodium carbonate, cesium carbonate and the like; alkaline earth metal carbonates such as barium carbonate, calcium carbonate and the like; alkali metal alkoxides such as sodium methoxide and the like; alkali metal hydroxides such as potassium hydroxide, sodium hydroxide, lithium hydroxide and the like; alkaline earth metal hydroxides such as barium hydroxide, calcium hydroxide and the like; and the like can be mentioned.

The amount of the base to be used is generally an excess amount relative to compound (VIII). The amount of the base to be used is preferably about 1.2-about 30 equivalents, relative to compound (VIII).

As the solvent that does not exert an adverse influence on the reaction, for example, alcohols such as methanol, ethanol and the like; ethers such as tetrahydrofuran, dioxane, diethyl ether and the like; dimethyl sulfoxide, acetone and the like can be mentioned. Two or more kinds of these solvents may be used in a mixture at appropriate ratios, or may be used in mixture with water. When the aforementioned solvent is used in mixture with water, the mixing rate of water is, for example, 0.1-1000%, preferably 1-100%, in volume relative to the solvent.

The reaction temperature is generally about −20 to about 150° C., preferably about −10 to about 100° C.

The reaction time is generally about 0.1-about 20 hrs.

The compound (VII) thus obtained can be isolated and purified by a known separation and purification means, such as concentration, concentration under reduced pressure, solvent extraction, crystallization, recrystallization, phase transfer, chromatography and the like. It is also possible to use a reaction mixture containing compound (VII) as a starting material for the next reaction wihtout separating or purifying compound (VII).

(Step 1c) Dihalogenation and Hydrolysis Reaction

In this step, compound (VIII) is subjected to dihalogenation reaction and then to hydrolysis reaction to give compound (IX).

The dihalogenation reaction is carried out in the presence of a halogenating agent and, where necessary, a suitable reaction initiator in a solvent that does not exert an adverse influence on the reaction.

As the halogenating agent, reaction initiator and solvent that does not exert an adverse influence on the reaction, those respectively exemplified for the aforementioned halogenation reaction in Step 1b can be used.

The amount of the halogenating agent to be used is preferably about 2-about 20 molar equivalents, relative to compound (VIII).

The amount of the reaction initiator to be used is preferably about 0.001-about 1 molar equivalents relative to compound (VIII).

The reaction temperature is generally −50 to 200° C., preferably 0 to 120° C.

The reaction time is generally 0.1-48 hrs.

The hydrolysis reaction is carried out in the same manner as in the hydroxylation reaction in the aforementioned Step 1b.

The compound (IX) thus obtained can be isolated and purified by a known separation and purification means, such as concentration, concentration under reduced pressure, solvent extraction, crystallization, recrystallization, phase transfer, chromatography and the like. It is also possible to use a reaction mixture containing compound (IX) as a starting material for the next reaction without separation or purification of compound (IX).

The compound (VIII) to be used as a starting compound in the above-mentioned Steps 1b and 1c can be produced according to a method known per se, for example, the methods described in *Journal of Organic Chemistry*, Vol. 51, p. 4075 (1986) and the like, or a method analogous thereto.

(Step 2) Oxidization Reaction

This reaction is carried out according to a conventional method in the presence of an oxidant in a solvent that does not exert an adverse influence on the reaction.

As the oxidant, for example, metal oxidants such as manganese dioxide, pyridinium chlorochromate, pyridinium dichromate, ruthenium oxide and the like; and the like can be mentioned.

The amount of the oxidant to be used is preferably about 1-about 10 molar equivalents relative to compound (VII).

As the solvent that does not exert an adverse influence on the reaction, aromatic hydrocarbons such as benzene, toluene, xylene and the like; ethers such as tetrahydrofuran, dioxane, diethyl ether and the like; halogenated hydrocarbons such as chloroform, dichloromethane and the like; and the like can be mentioned. Two or more kinds of these solvents may be used in a mixture at appropriate ratios.

The reaction temperature is generally about −50 to about 150° C., preferably about −10 to about 100° C.

The reaction time is generally about 0.5-about 20 hrs.

In addition, compound (IX) can be also produced by adding a reaction reagent such as a sulfur trioxide pyridine complex or oxalyl chloride and the like to compound (VII) in a mixed solvent of sulfoxides such as dimethyl sulfoxide and the like, and halogenated hydrocarbons such as chloroform, dichloromethane and the like, and then reacting with an organic base such as triethylamine, N-methylmorpholine and the like.

The amount of the reaction reagent to be used is preferably about 1-about 10 molar equivalents, relative to compound (VII).

The amount of the organic base to be used is preferably about 1-about 10 molar equivalents, relative to compound (VII).

The reaction temperature is generally about −50 to about 150° C., preferably about −10 to about 100° C.

The reaction time is generally about 0.5-about 20 hrs.

The compound (IX) thus obtained can be isolated and purified by a known separation and purification means, such as concentration, concentration under reduced pressure, solvent extraction, crystallization, recrystallization, phase transfer, chromatography and the like. It is also possible to use a reaction mixture containing compound (IX) as a starting material for the next reaction without separation or purification of compound (IX).

(Step 3) Carbon-Addition Reaction

In this step, compound (V-1) is produced by the reaction of compound (IX) with an organic phosphorus reagent in the presence of a base in a solvent that does not exert an adverse influence on the reaction.

As the organic phosphorus reagent, for example, methyl dimethylphosphonoacetate, ethyl diethylphosphonoacetate, ethyl dimethylphosphonoacetate and the like can be mentioned.

The amount of the organic phosphorus reagent to be used is preferably about 1-about 10 molar equivalents relative to compound (IX).

As the base, for example, alkali metal salts such as potassium hydroxide, sodium hydroxide, sodium hydrogen carbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and the like can be mentioned.

The amount of these bases to be used is preferably about 1-about 5 molar equivalents relative to compound (IX).

As the solvent that does not exert an adverse influence on the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like can be mentioned. Two or more kinds of these solvents may be used in a mixture at appropriate ratios.

The reaction temperature is generally about −50 to about 150° C., preferably about −10 to about 100° C.

The reaction time is generally about 0.5-about 20 hrs.

The compound (V-1) thus obtained can be isolated and purified by a known separation and purification means, such as concentration, concentration under reduced pressure, solvent extraction, crystallization, recrystallization, phase transfer, chromatography and the like. It is also possible to use a reaction mixture containing compound (V-1) as a starting material for the next reaction without separation or purification of compound (V-1).

(Step 4) Hydrogenation Reaction

This reaction is carried out according to a conventional method under a hydrogen atmosphere or in the presence of hydrogen sources of formic acid and the like and a metal catalyst in a solvent that does not exert an adverse influence on the reaction.

As the metal catalyst, for example, transition metal catalysts such as palladium-carbon, palladium-barium carbonate, palladium black, platinum oxide, platinum-carbon, Raney-nickel, Wilkinson's catalyst and the like, and the like can be mentioned.

The amount of the metal catalyst to be used is preferably about 0.01-about 10 molar equivalents, relative to compound (V-1)

As the solvent that does not exert an adverse influence on the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; alcohols such as methanol, ethanol, isopropanol and the like; and the like can be mentioned. Two or more kinds of these solvents may be used in a mixture at appropriate ratios.

The reaction temperature is generally about −50 to about 150° C., preferably about −10 to about 100° C.

The reaction time is generally about 0.5-about 20 hrs. The compound (V-2) thus obtained can be isolated and purified by a known separation and purification means, such as concentration, concentration under reduced pressure, solvent extraction, crystallization, recrystallization, phase transfer, chromatography and the like.

The compound (Ib) of the formula (I) wherein Z is Za [Za is —O—, —S— or —NR$^2$— (R$^2$ is as defined above)] can be produced by, for example, the following Method D.

[Method D]

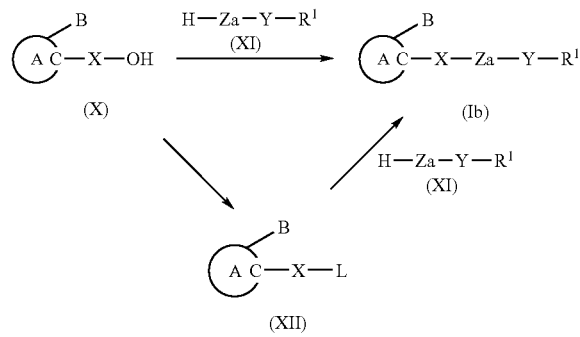

wherein L is a leaving group and other symbols are as defined above.

As the leaving group for L, for example, a halogen atom, —OSO$_2$R$^8$ (R$^8$ is a hydrogen atom, a C$_{1-4}$ alkyl group, a C$_{6-10}$ aryl group optionally substituted by a C$_{1-4}$ alkyl group, a C$_{7-14}$ aralkyl group optionally substituted by a C$_{1-4}$ alkyl group) and the like can be mentioned.

Here, as the halogen atom, fluorine, chlorine, bromine, iodine and the like can be mentioned.

As the C$_{1-4}$ alkyl group of "C$_{1-4}$ alkyl group", "C$_{6-10}$ aryl group optionally substituted by C$_{1-4}$ alkyl group" and "C$_{7-14}$ aralkyl group optionally substituted by C$_{1-4}$ alkyl group" for R$^8$, methyl, ethyl, propyl, isopropyl, butyl, isobutyl, sec-butyl and tert-butyl can be mentioned. Of these, methyl is preferable.

As the C$_{6-10}$ aryl group of the "C$_{6-10}$ aryl group optionally substituted by C$_{1-4}$ alkyl group" for R$^8$, phenyl and naphthyl can be mentioned. Of these, phenyl is preferable.

As the C$_{7-14}$ aralkyl group of the "C$_{7-14}$ aralkyl group optionally substituted by C$_{1-4}$ alkyl group" for R$^8$, benzyl, phenethyl and naphthylmethyl can be mentioned. Of these, benzyl is preferable.

The leaving group for L is preferably a halogen atom (preferably chlorine), methanesulfonyloxy and the like.

The compound (Ib) can be produced by, for example, subjecting compound (X) and compound (XI) to Mitsunobu reaction.

This reaction is carried out according to a conventional method in the presence of a phosphine and azo compound in a solvent that does not exert an adverse influence on the reaction.

As the phosphine compound, for example, trimethylphosphine, triethylphosphine, tributylphosphine, triphenylphosphine, diphenylpyridylphosphine, cyanomethylene tributylphosphorane and the like can be mentioned.

As the azo compound, for example, diethyl azodicarboxylate, diisopropyl azodicarboxylate, azodicarbonyldipiperidine and the like can be mentioned.

When cyanomethylene tributylphosphorane is used as the phosphine compound, the reaction can be carried out in the absence of an azo compound.

The amount of the compound (XI) to be used is generally 1-20 equivalents, preferably 1-10 equivalents, relative to compound (X).

The amount of the phosphine compound and azo compound to be used is generally 1-50 equivalents, preferably 1-10 equivalents, relative to compound (X).

As the solvent that does not exert an adverse influence on the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; and the like can be mentioned. Two or more kinds of these solvents may be used in a mixture at appropriate ratios.

The reaction temperature is generally about −20 to about 150° C., preferably about −10 to about 100° C.

The reaction time is generally about 0.1-about 20 hrs.

The compound (Ib) thus obtained can be isolated and purified by a known separation and purification means, such as concentration, concentration under reduced pressure, solvent extraction, crystallization, recrystallization, phase transfer, chromatography and the like.

The compound (Ib) can be also produced by converting compound (X) to a reactive derivative thereof, compound (XII), and reacting the compound (XII) with compound (XI).

The compound (XII) can be produced by reacting compound (X) with a suitable activating reagent in a solvent that does not exert an adverse influence on the reaction, where necessary, in the presence of a base.

Here, as the activating reagent, those corresponding to the aforementioned leaving group L can be used. Specific examples of the activating reagent include thionyl chloride, methanesulfonyl chloride and the like.

The amount of the activating reagent to be used is preferably about 1-about 10 molar equivalents relative to compound (X).

As the base, for example, alkali metal salts such as potassium hydroxide, sodium hydroxide, sodium hydrogen carbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and the like can be mentioned.

The amount of these bases to be used is preferably about 1-about 10 molar equivalents relative to compound (X).

As the solvent that does not exert an adverse influence on the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; and the like can be mentioned. Two or more kinds of these solvents may be used in a mixture at appropriate ratios, or may be used in mixture with water. When the aforementioned solvent is used in mixture with water, the mixing rate of water is, for example, 0.1-1000%, preferably 1-100%, in volume relative to the solvent.

The reaction temperature is generally about −20 to about 150° C., preferably about −10 to about 100° C.

The reaction time is generally about 0.1-about 20 hrs.

The compound (XII) thus obtained can be isolated and purified by a known separation and purification means, such as concentration, concentration under reduced pressure, solvent extraction, crystallization, recrystallization, phase transfer, chromatography and the like. It is also possible to use a reaction mixture containing compound (XII) as a starting material for the next reaction without separation or purification of compound (XII).

The reaction of compound (XII) with compound (XI) is carried out in a solvent that does not exert an adverse influence on the reaction, where necessary, in the presence of a base.

As the base, for example, alkali metal salts such as potassium hydroxide, sodium hydroxide, sodium hydrogen carbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and the like can be mentioned.

The amount of these bases to be used is preferably about 1-about 10 molar equivalents relative to compound (XII).

As the solvent that does not exert an adverse influence on the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; and the like can be mentioned. Two or more kinds of these solvents may be used in a mixture at appropriate ratios, or may be used in mixture with water. When the aforementioned solvent is used in mixture with water, the mixing rate of water is, for example, 0.1-1000%, preferably 1-100%, in volume relative to the solvent.

The amount of the compound (XI) to be used is generally 1-20 equivalents, preferably 1-10 equivalents, relative to compound (XII).

The reaction temperature is generally about −20 to about 150° C., preferably about −10 to about 100° C.

The reaction time is generally about 0.1-about 20 hrs.

The compound (Ib) thus obtained can be isolated and purified by a known separation and purification means, such as concentration, concentration under reduced pressure, solvent extraction, crystallization, recrystallization, phase transfer, chromatography and the like.

The compound (X) and compound (XI) to be used as starting compounds in the above-mentioned Method D can be produced by a method known per se or a method analogous thereto.

Of compounds (X), compound (Xa) wherein X is —(CH$_2$)$_3$— can be produced by, for example, the following Method E.

[Method E]

wherein the symbols are as defined above.

In this method, compound (V-2) is subjected to reduction reaction to give compound (Xa).

This reaction is carried out in the same manner as in Step 1a of the aforementioned Method C.

The compound (Xa) thus obtained can be isolated and purified by a known separation and purification means, such as concentration, concentration under reduced pressure, solvent extraction, crystallization, recrystallization, phase transfer, chromatography and the like.

Of the compounds (X), a compound wherein X is other than —(CH$_2$)$_3$— can be also produced by the above-mentioned Method E, or a method analogous thereto.

Compound (Ic) of the formula (I) wherein Z is —NR$^2$CO— (R$^2$ is as defined above) can be produced by, for example, the following Method F.

[Method F]

wherein the symbols are as defined above.

In this method, compound (XIII) is subjected to an amidation reaction to give compound (Ic). This reaction is carried out in the same manner as in the aforementioned Method A.

The compound (XIII) and compound (XIV) can be produced by a method known per se.

The compound (Ic) thus obtained can be isolated and purified by a known separation and purification means, such as concentration, concentration under reduced pressure, solvent extraction, crystallization, recrystallization, phase transfer, chromatography and the like.

Of the aforementioned compounds (Ia), compound (Iaa) represented by the formula:

wherein each symbol is as defined above, can be produced by reacting the aforementioned compound (III) with a compound represented by the formula:

$$H-N(R^2)-Y-(D)-Y^1-R^3 \quad (IV')$$

wherein each symbol is as defined above.

This reaction is carried out in the same manner as in the aforementioned Method A. In this reaction, compound (IV') to be used as a starting compound can be produced by a method known per se.

The compound (Iaa) thus obtained can be isolated or purified by known separation and purification methods, such as concentration, concentration under reduced pressure, solvent extraction, crystallization, recrystallization, phase transfer, chromatography and the like.

Of the aforementioned compounds (IX), compound (IXa), wherein ring A is a pyrazole substituted by a $C_{1-6}$ alkyl group, can be also produced by, for example, the following Method G.

[Method G]

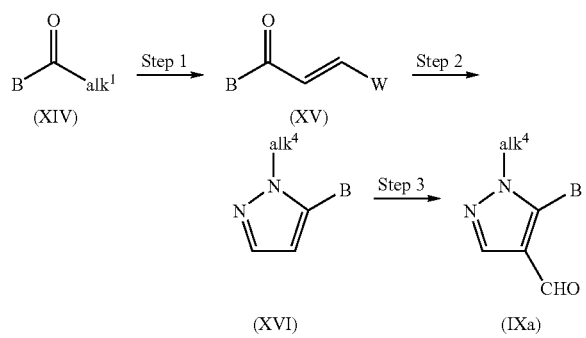

wherein B is as defined above; W is —OH or —N(alk$^2$)(alk$^3$); alk$^1$, alk$^2$, alk$^3$ and alk$^4$ are the same or different and each is a $C_{1-6}$ alkyl group.

As the $C_{1-6}$ alkyl group for alk$^1$, alk$^2$, alk$^3$ or alk$^4$, for example, methyl, ethyl, propyl, isopropyl, butyl, isobutyl, sec-butyl, tert-butyl and the like can be mentioned. Of these, methyl is preferable.

As the $C_{7-13}$ aralkyl group for alk$^4$, for example, benzyl and the like can be mentioned.

(Step 1)

This step can be performed according to a method known per se, such as the method described in *Inorganic Chemistry*, 28, 1093(1989), or a method analogous thereto.

First, compound (XIV) is reacted with a formic acid ester (e.g., lower alkyl ester such as methyl formate, ethyl formate, propyl formate and the like) in the presence of a base to give compound (XV) wherein W is —OH.

This reaction is generally carried out in a solvent that does not exert an adverse influence on the reaction. As the solvent that does not exert an adverse influence on the reaction, for example, alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butylmethyl ether, tetrahydrofuran, dioxane etc.), nitriles (e.g., acetonitrile, propionitrile etc.), dimethylformamide, dimethylacetamide, N-methylpyrrolidone, dimethyl sulfoxide, hexamethylphosphoramide and the like are used. Two or more kinds of these solvents may be used in a mixture at appropriate ratios.

As the base, for example, tertiary amines (e.g., trimethylamine, triethylamine, tributylamine, N-ethyldiisopropylamine, N-methylmorpholine, DBU (1,8-diazabicyclo[5.4.0]-7-undecene), DBN (1,5-diazabicyclo[4.3.0]-5-nonene) etc.), alkali metal carbonates (e.g., sodium hydrogen carbonate, potassium carbonate, sodium carbonate, cesium carbonate etc.), alkali metal hydroxides (e.g., potassium hydroxide, sodium hydroxide, calcium hydroxide etc.), alkoxides (e.g., sodium methoxide, sodium ethoxide, sodium propoxide, potassium tert-butoxide, sodium tert-butoxide etc.), potassium hydride, sodium hydride, sodium amide, potassium metal, sodium metal and the like are used.

The amount of the formic acid ester and the base to be used is generally 1-10 equivalents, preferably 1-5 equivalents, for each, relative to compound (XIV).

The reaction temperature is generally −20 to 150° C., preferably −10 to 100° C.

The reaction time is generally 30 min.-24 hrs., preferably 1 hr.-15 hrs.

In addition, compound (XV) wherein W is —N(alk$^2$)(alk$^3$) (alk$^2$ and alk$^3$ are the same or different and each is a $C_{1-6}$ alkyl group) can be produced by reacting compound (XIV) with dimethylformamide di-$C_{1-6}$ alkylacetals (e.g., dimethylformamide dimethylacetal, dimethylformamide diethylacetal, dimethylformamide dipropylacetal, dimethylformamide diisopropylacetal and the like), bisdimethylaminomethoxymethane or trisdimethylaminomethane.

This reaction is generally carried out in a solvent that does not exert an adverse influence on the reaction. As the solvent that does not exert an adverse influence on the reaction, for example, alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butylmethyl ether, tetrahydrofuran, dioxane etc.), nitriles (e.g., acetonitrile, propionitrile etc.), dimethylformamide, dimethylacetamide, N-methylpyrrolidone, dimethyl sulfoxide, hexamethylphosphoramide and the like are used. Two or more kinds of these solvents may be used in a mixture at appropriate ratios. It is also possible to carry out the reaction without solvent.

The amount of the above-mentioned dimethylformamide di-$C_{1-6}$ alkylacetals, bisdimethylaminomethoxymethane and trisdimethylaminomethane to be used is generally 1-10 equivalents, preferably 1-5 equivalents, for each, relative to compound (XIV).

The reaction temperature is generally −20 to 200° C., preferably −10 to 150° C.

The reaction time is generally 30 min.-24 hrs., preferably 1 hr.-15 hrs.

The compound (XV) thus obtained can be isolated or purified by known separation and purification methods, such as concentration, concentration under reduced pressure, solvent extraction, crystallization, recrystallization, phase transfer, chromatography and the like. A reaction mixture containing compound (XV) may be used as the starting material for the next reaction without separation or purification of compound (XV).

The compound (XIV) used as the starting compound in this reaction can be produced by a method known per se.

(Step 2)

Then, compound (XV) is reacted with a $C_{1-6}$ alkylhydrazine or a $C_{7-13}$ aralkylhydrazine in the presence of an acid to give compound (XVI).

As the $C_{1-6}$ alkylhydrazine, for example, methylhydrazine, ethylhydrazine and the like can be mentioned.

As the $C_{7-13}$ aralkylhydrazine, for example, benzylhydrazine and the like can be mentioned.

This reaction is generally carried out in a solvent that does not exert an adverse influence on the reaction. As the solvent that does not exert an adverse influence on the reaction, for example, alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butylmethyl ether, tetrahydrofuran, dioxane etc.), nitriles (e.g., acetonitrile, propionitrile etc.), esters (e.g., methyl acetate, ethyl acetate, ethyl propionate etc.); dimethylformamide, dimethylacetamide, N-methylpyrrolidone, dimethyl sulfoxide, hexamethylphosphoramide and the like are used. Two or more kinds of these solvents may be used in a mixture at appropriate ratios.

As the acid to be used for this reaction, for example, mineral acids (e.g., hydrochloric acid, hydrobromic acid, sulfuric acid, phosphoric acid etc.), organic acids (e.g., formic acid, acetic acid, propionic acid, butyric acid, methanesulfonic acid, ethanesulfonic acid, benzenesulfonic acid, toluenesulfonic acid and the like, camphor sulfonic acid etc.) and the like can be mentioned. Of these, sulfonic acids are preferable, and p-toluenesulfonic acid is particularly preferable.

The amount of the $C_{1-6}$ alkylhydrazine, the $C_{7-13}$ aralkylhydrazine and the acid to be used is generally 1-10 equivalents, preferably 1-5 equivalents, for each, relative to compound (XV).

In this reaction, the $C_{1-6}$ alkylhydrazine and the $C_{7-13}$ aralkylhydrazine may be used as an acid addition salt. As such acid addition salt, salts with inorganic acids (e.g., hydrochloride, sulfate) and salts with organic acids (e.g., p-toluenesulfonate) exemplified as the salts of compounds represented by the formula (I) can be mentioned. When $C_{1-6}$ alkylhydrazine and $C_{7-13}$ aralkylhydrazine are used as acid addition salts, the reaction can be also carried out without adding an acid.

In this reaction, the amount of the acid (inclusive of the acid forming an acid addition salt) to be used is preferably 1 equivalent relative to $C_{1-6}$ alkylhydrazine or $C_{7-13}$ aralkylhydrazine, and use of this amount results in the production of the objective compound in a high yield.

The reaction temperature is generally −20 to 150° C., preferably −10 to 100° C.

The reaction time is generally 30 min.-24 hrs., preferably 1 hr.-15 hrs.

The compound (XVI) thus obtained can be isolated or purified by known separation and purification methods, such as concentration, concentration under reduced pressure, solvent extraction, crystallization, recrystallization, phase transfer, chromatography and the like. A reaction mixture containing compound (XVI) may be used as the starting material for the next reaction without separation or purification of compound (XVI).

(Step 3)

Furthermore, compound (XVI) is subjected to formylation reaction in the presence of a halogenating agent (e.g., phosphorus oxychloride, phosphorus oxybromide, phosphorus trichloride, phosphorus pentachloride, thionyl chloride, phosgene and the like), and the like to give compound (IXa).

This reaction can be carried out according to a Vilsmeier-Haack reaction known per se, for example, the method reported in *J. Chem. Soc.*, Perkin I, 2334(1979) [D. Reid, R. Webster, S. McKenzie] or a method analogous thereto.

The formylation reaction is carried out using a formylating agent such as dimethylformamide, N-methylacetanilide, N-ethylacetanilide and the like.

This reaction is generally carried out in a solvent that does not exert an adverse influence on the reaction. As the solvent that does not exert an adverse influence on the reaction, for example, halogenated hydrocarbons (e.g., dichloromethane, chloroform, 1,2-dichloroethane, 1,1,2,2-tetrachloroethane etc.), aromatic hydrocarbons (e.g., chlorobenzene, dichlorobenzene, nitrobenzene etc.), ethers (e.g., ethyl ether, isopropyl ether, tert-butylmethyl ether, bis(2-methoxyethyl) ether, tetrahydrofuran, dioxane etc.), nitriles (e.g., acetonitrile, propionitrile etc.), esters (e.g., methyl acetate, ethyl acetate, ethyl propionate etc.) and the like are used. Two or more kinds of these solvents may be used in a mixture at appropriate ratios. In addition, the above-mentioned formylating agent may be used as the solvent. As the combination of the halogenating agent and the formylating agent to be used for this reaction, a combination of phosphorus oxychloride.dimethylformamide is preferable.

The amount of the formylation agent and halogenation agent to be used is generally 1-10 equivalents, preferably 1-5 equivalents, for each relative to compound (XVI).

The reaction temperature is generally −20 to 200° C., preferably −10 to 150° C.

The reaction time is generally 30 min.-24 hrs., preferably 1 hr.-15 hrs.

The compound (IXa) thus obtained can be isolated or purified by known separation and purification methods, such as concentration, concentration under reduced pressure, solvent extraction, crystallization, recrystallization, phase transfer, chromatography and the like.

Of the compounds (III) to be used as the starting compound in the above-mentioned Method A, compound (III-1) wherein X is —CH═CH— can be also produced according to the following Method H.

[Method H]

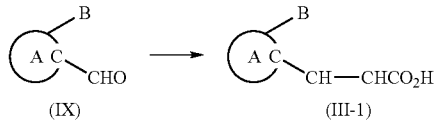

wherein each symbol is as defined above.

In this method, compound (IX) is reacted with malonic acid to give compound (III-1). This reaction can be carried out according to a method known per se, for example, methods described in *New Courses in Experiment Chemistry*; 14. Synthesis and Reaction of Organic Compounds [II] pp. 980-981; *Organic Syntheses*, Coll. Vol. 4, 731 (1963); *J. Am. Chem. Soc.*, 80, 3645 (1958) and the like, or a method analogous thereto.

For example, this reaction is carried out in the presence of a base in a solvent that does not exert an adverse influence on the reaction.

As the base, for example, aromatic amines (e.g., pyridine, lutidine, quinoline), secondary amines (e.g., piperidine, pyrrolidine, morpholine, dicyclohexylamine), tertiary amines (e.g., trimethylamine, triethylamine, tributylamine, N-ethyldiisopropylamine, N-methylmorpholine, DBU (1,8-diazabicyclo[5.4.0]-7-undecene), DBN (1,5-diazabicyclo[4.3.0]-5-nonene) etc.), alkali metal-carbonates (e.g., sodium hydrogen carbonate, potassium carbonate, sodium carbonate, cesium carbonate etc.), alkali metal hydroxides (e.g., potassium hydroxide sodium hydroxide; calcium hydroxide etc.), alkoxides (e.g., sodium methoxide, sodium ethoxide, sodium propoxide, potassium tert-butoxide, sodium tert-butoxide etc.), potassium hydride, sodium hydride, sodium amide, potassium metal, sodium metal and the like are used. Of the above-mentioned bases, liquid amines may be used as the solvent.

As the solvent that does not exert an adverse influence on the reaction, for example, alcohols (e.g., methanol, ethanol, propanol, isopropanol, butanol, tert-butanol, methoxyethanol etc.), halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, dichlorobenzene, nitrobenzene etc.), ethers (e.g., ethyl ether, isopropyl ether, tert-butylmethyl ether, bis (2-methoxyethyl) ether, tetrahydrofuran, dioxane etc.), nitriles (e.g., acetonitrile, propionitrile etc.), dimethylformamide, dimethylacetamide, N-methylpyrrolidone, dimethyl sulfoxide, hexamethylphosphoramide, water and the like are used. Two or more kinds of these solvents may be used in a mixture at appropriate ratios.

The amount of malonic acid to be used is generally 1-10 equivalents, preferably 1-5 equivalents, relative to compound (IX).

The amount of the base to be used is generally 1-10 equivalents, preferably 1-5 equivalents, relative to compound (IX).

The reaction temperature is generally −20 to 180° C., preferably 0 to 120° C.

The reaction time is generally 30 min.-36 hrs., preferably 1 hr.-18 hrs.

The compound (III-1) thus obtained can be isolated or purified by known separation and purification methods, such as concentration, concentration under reduced pressure, solvent extraction, crystallization, recrystallization, phase transfer, chromatography and the like.

In each of the aforementioned reactions, when the starting compound has amino, carboxy, hydroxy or carbonyl as a substituent, these groups may have a protecting group introduced therein, such as one generally used in peptide chemistry and the like. The objective compound can be obtained by removing the protecting group as necessary after the reaction.

As the amino-protecting group, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkoxy (e.g., methoxy, ethoxy, propoxy and the like) or nitro and the like.

As the carboxy-protecting group, for example, $C_{1-6}$ alkyl (e.g., methyl, ethyl, propyl, isopropyl, butyl, tert-butyl and the like), $C_{7-13}$ aralkyl (e.g., benzyl and the like), phenyl, trityl, silyl (e.g., trimethylsilyl, triethylsilyl, dimethylphenyl-silyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkoxy (e.g., methoxy, ethoxy, propoxy and the like) or nitro and the like.

As the hydroxy-protecting group, for example, $C_{1-6}$ alkyl (e.g., methyl, ethyl, propyl, isopropyl, butyl, tert-butyl and the like), phenyl, trityl, $C_{7-13}$ aralkyl (e.g., benzyl and the like), formyl, $C_{1-6}$ alkyl-carbonyl (e.g., acetyl, propionyl and the like), benzoyl, $C_{7-13}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like) or nitro and the like.

As the carbonyl-protecting group, for example, cyclic acetal (e.g., 1,3-dioxane and the like), non-cyclic acetal (e.g., di-$C_{1-6}$ alkyl acetal and the like) and the like can be mentioned.

The removing method of these protecting groups may be carried out by methods known per se, for example, the methods described in *Protective Groups in Organic Synthesis*, published by John Wiley and Sons, 1980, and the like. For example, employed are the methods using acids, bases, ultraviolet ray, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide, etc.), etc.; and reduction method, and the like.

When the starting compound can form a salt in each of the aforementioned reactions, the compound may be used in the form of a salt. As such salt, for example, those exemplified as the salt of the compound represented by the formula (I) can be used.

Where the compound of the present invention includes optical isomers, stereoisomers, regioisomers and rotational isomers, those are also encompassed in the compound of the present invention, and can be obtained as a single compound by synthetic methods and separation methods known per se. For example, when optical isomers of the compound of the present invention exist, optical isomers resolved from the compound are also encompassed in the compound of the present invention.

The optical isomers can be produced by a method known per se. Concretely, an optically active isomer can be obtained using an optically active synthetic intermediate or by optical resolution of a final racemate by a conventional method.

For optical resolution, a method known per se, such as a fractional recrystallization method, a chiral column method, a diastereomer method, and the like can be used.

1) Fractional Recrystallization Method

The method which comprises allowing a racemate and an optically-active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to form a salt, which is then separated through fractional recrystallization method, followed by, when desired, subjecting the salt to a neutralization step to give a free optical isomer.

2) Chiral Column Method

The method of separating by applying a racemate or a salt thereof, to a column for fractionating optical isomers (chiral column). In the case of, for example, liquid column chromatography, the optical isomers are separated by applying a mixture of optical isomers to a chiral column, such as ENANTIO-OVM (manufactured by Tosoh Corp.), CHIRAL SERIES (manufactured by Daicel Co.), etc., and developing with water, various buffers (e.g., phosphate buffer) and organic solvents (e.g., ethanol, ethanol, isopropanol, acetonitrile, trifluoroacetic acid, diethylamine, etc.), singly or as a suitable mixture of them. In the case of, for example, gas chromatography, a chiral column such as CP-Chirasil-DeX CB (manufactured by GL Science Co.), etc. is used for separation.)

3) Diastereomer Method

The method that a racemic mixture is chemically reacted with an optically-active reagent to give a mixture of diastereomer, which is subjected to an ordinary separation means (e.g., fractional recrystallization, chromatography, etc.) to give a single compound, which is then subjected to a chemical treatment (e.g., hydrolysis reaction etc.) to separate the optically-active reagent site from the compound to give an optical isomer. For example, where compound of the present invention has a hydroxy or a primary or secondary amino in the molecule, the compound and an optically-active organic acid (e.g., MTPA [α-methoxy-α-(trifluoromethyl)phenyl-acetic acid], (−)-menthoxyacetic acid, etc.) or the like are subjected to condensation reaction to give the respectively corresponding ester or amide diastereomer. On the other hand, where compound of the present invention has a carboxylic acid group, the compound and an optically-active amine or alcohol reagent are subjected to condensation reaction to give an amide or ester diastereomer. The separated diastereomer is then subjected to acidic or basic hydrolysis reaction, through which it is converted into the optical isomer of the original compound.

BEST MODE FOR PRACTICING THE INVENTION

The present invention is explained in detail in the following by referring to Reference. Examples, Examples, Experimental Examples and Formulation Examples, which are not to be construed as limitative.

In the following Reference Examples and Examples, "%" means percent by weight unless specifically indicated. In addition, room temperature means a temperature of 1-30° C.

In Reference Examples and Examples, HPLC was measured under the following conditions.
measurement tool: LC-10Avp system, Shimadzu Seisakusho
column: CAPSEL PAK C18UG120 S-3 μm, 2.0×50 mm
solvent:
  Solution A; 0.1% trifluoroacetic acid-containing water,
  Solution B; 0.1% trifluoroacetic acid-containing acetonitrile
gradient cycle: 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)
injection amount: 2 μl, flow rate: 0.5 ml/min, detection method: UV 220 nm In Reference Examples and Examples, mass spectrum (MS) was measured under the following conditions.
measurement tool: Micromass Ltd., platform II, Waters Corporation ZQ, or Waters Corporation ZMD
ionization method: Atmospheric Pressure Chemical Ionization (APCI) or Electron Spray Ionization (ESI)
preparative HPLC apparatus: Gilson, Inc., high through-put purification system
column: YMC Combiprep ODS-A S-5 μm, 20×50 mm
solvent:
  Solution A; 0.1% trifluoroacetic acid-containing water,
  Solution B; 0.1% trifluoroacetic acid-containing Acetonitrile
gradient cycle: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10)
flow rate: 25 ml/min, detection method: UV 220 nm

REFERENCE EXAMPLE 1

A mixture of ethyl 4-fluorobenzoylacetate (20.0 g) and N,N-dimethylformamide dimethylacetal (24.5 g) was stirred for 1 hr. with heating under reflux. The reaction mixture was concentrated, and methylhydrazine (9.3 g) and ethanol (100 mL) were added. The mixture was stirred for 3 hrs. with heating under reflux. The reaction mixture was concentrated, poured into water, and extracted with ethyl acetate. The organic layer was washed with water, dried over anhydrous sodium sulfate and concentrated to give a yellow oil (20.1 g). This yellow oil was dissolved in tetrahydrofuran (100 mL) and lithium aluminum hydride (3.26 g) was carefully added at 0° C. The mixture was stirred at 0° C. for 1 hr. Sodium sulfate decahydrate (38 g) was carefully added to the reaction mixture and the mixture was stirred at room temperature for 30 min. and filtered. The filtrate was concentrated to give 15.1 g of a yellow oil. From this yellow oil, 14.0 g thereof was dissolved in tetrahydrofuran (200 mL) and activated manganese dioxide (50 g) was added thereto. The mixture was stirred at room temperature for 14 hrs. The reaction mixture was filtered and the filtrate was concentrated. The residue was subjected to silica gel column chromatography to give 5-(4-fluorophenyl)-1-methyl-1H-pyrazole-4-carbaldehyde (4.25 g) as colorless crystals from a fraction eluted with hexane-ethyl acetate (2:1, v/v).

NMR(CDCl$_3$)δ: 3.81(3H, s), 7.2-7.3(2H, m), 7.35-7.45 (2H, m), 8.03(1H, s), 9.60(1H, s).

From the fraction eluted after the aforementioned compound, 3-(4-fluorophenyl)-1-methyl-1H-pyrazole-4-carbaldehyde (3.60 g) was obtained as colorless crystals.

NMR(CDCl$_3$)δ: 3.99 (3H, s), 7.1-7.2 (2H, m), 7.7-7.8 (2H, m), 7.98 (1H, s), 9.90 (1H, s).

Using known β-keto ester (including commercially available products) as a starting material and in the similar manner as in Reference Example 1, the compounds described in Reference Examples 2-13 and 16 were produced.

REFERENCE EXAMPLE 2

5-(4-Methoxyphenyl)-1-methyl-1H-pyrazole-4-carbaldehyde yield: 41%. Colorless prism crystals. melting point: 82-83° C. (recrystallized from ethyl acetate-hexane).

REFERENCE EXAMPLE 3

5-(4-Chlorophenyl)-1-methyl-1H-pyrazole-4-carbaldehyde yield: 28%. Colorless prism crystals. melting point: 78-80° C. (recrystallized from ethyl acetate-hexane).

REFERENCE EXAMPLE 4

5-(3-Chlorophenyl)-1-methyl-1H-pyrazole-4-carbaldehyde yield: 25%. Colorless prism crystals. melting point: 91-92° C. (recrystallized from ethyl acetate-hexane).

REFERENCE EXAMPLE 5

5-(4-Bromophenyl)-1-methyl-1H-pyrazole-4-carbaldehyde yield: 36%. Colorless solid.
NMR(CDCl$_3$)δ: 3.82 (3H, s), 7.25-7.35 (2H, m), 7.7-7.75 (2H, m), 8.05 (1H, s), 9.62 (1H, s).

REFERENCE EXAMPLE 6

1-Methyl-5-[4-(trifluoromethyl)phenyl]-1H-pyrazole-4-carbaldehyde yield: 31%. Colorless prism crystals. melting point: 66-67° C. (recrystallized from ethyl acetate-hexane).

REFERENCE EXAMPLE 7

5-(2-Fluorophenyl)-1-methyl-1H-pyrazole-4-carbaldehyde yield: 48%. Pale-yellow oil.
H-NMR(CDCl$_3$)δ: 3.80 (3H, s), 7.25-7.4 (3H, m), 7.5-7.6 (1H, m), 8.06 (1H, s), 9.61 (1H, s).

REFERENCE EXAMPLE 8

5-(3-Fluorophenyl)-1-methyl-1H-pyrazole-4-carbaldehyde yield: 20%. Colorless prism crystals. melting point: 115-116° C. (recrystallized from ethyl acetate-hexane).

REFERENCE EXAMPLE 9

1-Methyl-5-(4-methylphenyl)-1H-pyrazole-4-carbaldehyde yield: 33%. Colorless prism crystals. melting point: 55-56° C. (recrystallized from ethyl acetate-hexane).

REFERENCE EXAMPLE 10

1-Methyl-5-(1-naphthyl)-1H-pyrazole-4-carbaldehyde yield: 60%. Colorless prism crystals. melting point: 95-97° C. (recrystallized from ethyl acetate-hexane).

REFERENCE EXAMPLE 11

1-Methyl-5-phenyl-1H-pyrazole-4-carbaldehyde yield: 34%. Colorless prism crystals. melting point: 100-101° C. (recrystallized from ethyl acetate-hexane).

REFERENCE EXAMPLE 12

5-(2-Furyl)-1-methyl-1H-pyrazole-4-carbaldehyde yield: 37%. Colorless prism crystals. melting point: 121-122° C. (recrystallized from ethyl acetate-hexane).

REFERENCE EXAMPLE 13

1-Ethyl-5-(4-fluorophenyl)-1H-pyrazole-4-carbaldehyde yield: 24%. Pale-yellow oil.
NMR(CDCl$_3$)δ: 1.42 (3H, t, J=7 Hz), 4.08 (2H, q, J=7 Hz), 7.2-7.3 (2H, m), 7.35-7.45 (2H, m), 8.06 (1H, s), 9.58 (1H, s).

REFERENCE EXAMPLE 14

A mixture of ethyl 4-fluorobenzoylacetate (10.0 g) and N,N-dimethylformamide dimethylacetal (8.54 g) was stirred for 1 hr. with heating under reflux. The reaction mixture was concentrated, and benzylhydrazine-oxalate (15.2 g) and ethanol (100 mL) were added. The mixture was stirred for 3 hrs. with heating under reflux. The reaction mixture was concentrated, water was added, and the mixture was extracted with ethyl acetate. The organic layer was washed with water, dried over anhydrous magnesium sulfate and concentrated. The residue was subjected to silica gel column chromatography to give a mixture (11.83 g) of ethyl 1-benzyl-5-(4-fluorophenyl)-1H-pyrazole-4-carboxylate and ethyl 1-benzyl-3-(4-fluorophenyl)-1H-pyrazole-4-carboxylate from a fraction eluted with hexane-ethyl acetate (4:1, v/v).
NMR(CDCl$_3$)δ: 1.17 (3H×0.7, t, J=7.2 Hz), 1.26 (3H×0.3, t, J=7.2 Hz), 4.10-4.28 (2H, m), 5.17 (2H×0.7, s), 5.32 (2H×0.3, s), 6.94-7.82 (9H, m), 7.90 (1H×0.3, s), 8.05 (1H×0.7, s).

This mixture (11.83 g) was dissolved in tetrahydrofuran (200 mL), lithium aluminum hydride (1.38 g) was added carefully at 0° C. and the mixture was stirred at 0° C. for 1 hr. A 1N aqueous sodium hydroxide solution was added carefully to the reaction mixture until a solid ceased to precipitate. The mixture was stirred at room temperature for 30 min. and filtered. The filtrate was concentrated to give 10.29 g of a yellow oil. This yellow oil was dissolved in tetrahydrofuran (200 mL), activated manganese dioxide (30 g) was added and the mixture was stirred at room temperature for 14 hrs. The reaction mixture was filtered, and the filtrate was concentrated. The residue was subjected to silica gel column chromatography to give a mixture (7.8 g, yield 59%) of 1-benzyl-5-(4-fluorophenyl)-1H-pyrazole-4-carbaldehyde and 1-benzyl-3-(4-fluorophenyl)-1H-pyrazole-4-carbaldehyde from a fraction eluted with hexane-ethyl acetate (4:1-2:1, v/v).
NMR(CDCl$_3$)δ: 5.24 (2H×0.7, s), 5.35 (2H×0.3, s), 6.98-7.80 (9H, m), 7.92 (1H×0.3, s), 8.11 (1H×0.7, s), 9.59 (1H×0.7, s), 9.87 (1H×0.3, s).

REFERENCE EXAMPLE 15

A mixture of 4-fluoro-N-methylbenzohydrazide (5.0 g), ethyl acetoacetate (4.84 g) and ethanol (140 ml) was stirred for 14 hrs. with heating under reflux. The reaction mixture was concentrated, water was added, and the mixture was extracted with ethyl acetate. The organic layer was washed with water, dried over anhydrous magnesium sulfate and concentrated. The residue was subjected to silica gel column chromatography to give an oil from a fraction eluted with hexane-ethyl acetate (4:1-1:1, v/v). This oil was dissolved in ethanol (50 ml), 1,8-diazabicyclo[5.4.0]-7-undecene (0.5 ml) was added, and the mixture was stirred for 4 hrs. with heating under reflux. Water was added to the reaction mixture, and the mixture was extracted with ethyl acetate. The organic layer was washed with water, dried over anhydrous magnesium sulfate and concentrated to give ethyl 5-(4-fluorophenyl)-1,3-dimethyl-1H-pyrazole-4-carboxylate (3.41 g, yield 44%) as colorless crystals.

NMR(CDCl$_3$)δ: 1.11 (3H, t, J=7.0 Hz), 2.50 (3H, s), 3.63 (3H, s), 4.11 (2H, q, J=7.0 Hz), 7.10-7.24 (2H, m), 7.26-7.38 (2H, m).

Ethyl 5-(4-fluorophenyl)-1,3-dimethyl-1H-pyrazole-4-carboxylate (3.25 g) was dissolved in tetrahydrofuran (200 mL), lithium aluminum hydride (0.47 g) was added carefully at 0° C., and the mixture was stirred at room temperature for 2 hrs. A 2N aqueous sodium hydroxide solution was carefully added to the reaction mixture until a solid ceased to precipitate, and after stirring at room temperature for 30 min., the mixture was filtered. The filtrate was concentrated to give 2.59 g of a pale-yellow oil. This pale-yellow oil was dissolved in tetrahydrofuran (200 mL), and activated manganese dioxide (20 g) was added. The mixture was stirred at room temperature for 14 hrs. The reaction mixture was filtered and the filtrate was concentrated. The residue was subjected to silica gel column chromatography to give 5-(4-fluorophenyl)-1,3-dimethyl-1H-pyrazole-4-carbaldehyde (1.63 g, yield 61%) as a colorless powder from a fraction eluted with hexane-ethyl acetate (4:1-1:1, v/v). Recrystallization thereof from ethyl acetate-hexane gave colorless prism crystals. melting point: 130-131° C.

REFERENCE EXAMPLE 16

5-Cyclohexyl-1-methyl-1H-pyrazole-4-carbaldehyde yield: 36%. Colorless prism crystals. melting point: 83-84° C. (recrystallized from ethyl acetate-hexane).

REFERENCE EXAMPLE 17-1

A mixture of 4-fluoroaniline (11.1 g), ethyl formate (25.0 g) and ethanol (150 ml) was stirred at 65° C. for 2 hrs. Toluenesulfonylmethyl isocyanide (23.4 g) was added to the reaction mixture and the mixture was stirred for 2 hrs. with heating under reflux. The reaction mixture was concentrated and poured into water. The precipitated solids were collected by filtration, washed with water and dried to give ethyl 1-(4-fluorophenyl)-1H-imidazole-5-carboxylate (19.8 g, 85%). Recrystallization thereof from ethyl acetate-hexane gave pale-yellow prism crystals. melting point: 114-115° C.

REFERENCE EXAMPLE 17-2

To a solution of ethyl 1-(4-fluorophenyl)-1H-imidazole-5-carboxylate (9.37 g) in tetrahydrofuran (100 ml) was added dropwise diisobutylaluminum hydride (1.5 mol/l toluene solution, 60 ml) at 0° C. The mixture was stirred at 0° C. for 1 hr., sodium sulfate decahydrate (13.0 g) was added and the mixture was stirred at room temperature for 1 hr. The reaction mixture was filtered, and the organic layer was concentrated to give [1-(4-fluorophenyl)-1H-imidazol-5-yl]methanol (4.10 g, 53%) as crystals. Recrystallization thereof from ethyl acetate-isopropyl ether gave pale-yellow prism crystals. melting point: 96-98° C.

REFERENCE EXAMPLE 17-3

A mixture of [1-(4-fluorophenyl)-1H-imidazol-5-yl] methanol (2.50 g), activated manganese dioxide (10 g) and tetrahydrofuran (150 ml) was stirred at room temperature for 3 hrs. The reaction mixture was filtered, and the organic layer was concentrated to give 1-(4-fluorophenyl)-1H-imidazole-5-carbaldehyde (2.20 g, 89%) as crystals. Recrystallization thereof from ethyl acetate-hexane gave pale-yellow prism crystals. melting point: 131-133° C.

REFERENCE EXAMPLE 18

A mixture of 4'-fluoropropiophenone (7.50 g), p-toluenesulfonyl hydrazide (9.30 g), ethanol (100 ml) and acetic acid (1 ml) was stirred for 1 hr. with heating under reflux. The reaction mixture was cooled to room temperature and the precipitated solids were collected by filtration and dried to give N'-[1-(4-fluorophenyl)propylidene]-4-methylbenzenesulfonohydrazide (12.0 g, yield 73%) as white crystals.

NMR(CDCl$_3$)δ: 1.09 (3H, t, J=7.5 Hz), 2.42 (3H, s), 2.58 (2H, q, J=7.5 Hz), 6.95-7.05 (2H, m), 7.32 (2H, d, J=8.5 Hz), 7.55-7.65 (2H, m), 7.90 (2H, d, J=8.5 Hz), 8.07 (1H, broad s).

N'-[1-(4-Fluorophenyl)propylidene]-4-methylbenzenesulfonohydrazide (12.0 g) was dissolved in thionyl chloride (30 ml), and the mixture was stirred at room temperature for 1 hr. The reaction mixture was poured into a 1N aqueous sodium hydroxide solution. The precipitated solids were collected by filtration, washed with water and dried with airflow to give 4-(4-fluorophenyl)-5-methyl-1,2,3-thiadiazole (6.19 g, 65%) as a yellow solid.

NMR(CDCl$_3$)δ: 2.71 (3H, s), 7.15-7.25 (2H, m), 7.7-7.8 (2H, m).

A mixture of 4-(4-fluorophenyl)-5-methyl-1,2,3-thiadiazole (6.19 g), N-bromosuccinimide (12.4 g), 2,2'-azobis (isobutyronitrile) (100 mg) and carbon tetrachloride (100 ml) was stirred for 6 hrs. with heating under reflux. The reaction mixture was washed with water, dried over anhydrous magnesium sulfate and concentrated. Sodium acetate (30 g) and acetic acid (100 ml) were added to the residue and the mixture was stirred for 12 hrs. with heating under reflux. 6N Hydrochloric acid (50 ml) was added and the mixture was further stirred for 1 hr. with heating under reflux. The reaction mixture was concentrated, poured into a saturated aqueous sodium hydrogen carbonate solution and extracted with ethyl acetate. The organic layer was washed with saturated brine, dried over anhydrous magnesium sulfate and concentrated. The residue was subjected to silica gel column chromatography to give 4-(4-fluorophenyl)-1,2,3-thiadiazole-5-carbaldehyde (360 mg, yield 5.4%) as pale-yellow crystals from a fraction eluted with hexane-ethyl acetate (2:1, v/v).

NMR(CDCl$_3$)δ: 7.25-7.35 (2H, m), 7.8-7.9 (2H, m), 10.11 (1H, s).

REFERENCE EXAMPLE 19

A mixture of ethyl diethoxyacetate (17.6 g), hydrazine monohydrate (5.50 g) and ethanol (100 ml) was stirred for 6 hrs. with heating under reflux. The reaction mixture was concentrated, and the residue was dissolved in ethanol (50 ml). 4-Fluorophenyl isothiocyanate (15.3 g) was added and the mixture was stirred at room temperature for 15 min. A 2N aqueous sodium hydroxide solution (200 ml) was added and the mixture was stirred for 90 min. with heating under reflux. The reaction mixture was poured into a 6N aqueous hydrochloric acid solution and extracted with ethyl acetate. The organic layer was washed with saturated brine, dried over anhydrous magnesium sulfate, and concentrated to give 5-(diethoxymethyl)-4-(4-fluorophenyl)-2,4-dihydro-3H-1,2,4-triazole-3-thione (29.3 g, yield: 99%) as a yellow oil.

NMR(CDCl$_3$)δ: 1.13 (6H,t, J=7 Hz), 3.45-3.5 (2H, m), 3.6-3.7 (2H, m), 5.29 (1H, s), 7.15-7.25 (2H, m), 7.3-7.4 (2H, m), 11.21 (1H, broad s).

A 3.5N aqueous nitric acid solution (containing 0.3% of sodium nitrite) was added to 5-(diethoxymethyl)-4-(4-fluorophenyl)-2,4-dihydro-3H-1,2,4-triazole-3-thione (25.7 g) and the mixture was stirred at room temperature for 1 hr. The reaction mixture was poured into a saturated aqueous sodium carbonate solution and extracted with ethyl acetate. The organic layer was washed with saturated brine, dried over anhydrous magnesium sulfate, and concentrated to give a yellow oil (19.0 g). This yellow oil was dissolved in a 10% aqueous sulfuric acid solution (100 ml), heated to 70-75° C. and stirred for 2 hrs. The reaction mixture was poured into a 10% aqueous disodium hydrogen phosphate solution, and extracted with ethyl acetate. The organic layer was washed with saturated brine, dried over anhydrous magnesium sulfate, and concentrated to give 4-(4-fluorophenyl)-4H-1,2,4-triazole-3-carbaldehyde (7.25 g, 43%) as yellow crystals.

NMR(CDCl$_3$)δ: 7.15-7.25 (2H, m), 7.3-7.4(2H, m), 8.38 (1H, s), 10.14(1H, s).

REFERENCE EXAMPLE 20

A mixture of methyl 4-fluorobenzoylacetate (3.92 g), p-toluenesulfonyl azide (4.00 g), triethylamine (2.02 g) and acetonitrile (30 ml) was stirred at 0° C. for 1 hr. The reaction mixture was poured into water and extracted with ethyl acetate. The organic layer was washed with saturated brine, dried over anhydrous magnesium sulfate and concentrated to give a yellow oil. The Lawesson's reagent (8.10 g) and tetrahydrofuran (50 ml) were added to this yellow oil and the mixture was heated under reflux for 16 hrs. The reaction mixture was concentrated, and the residue was purified by silica gel column chromatography to give methyl 5-(4-fluorophenyl)-1,2,3-thiadiazole-4-carboxylate (1.95 g, yield 41%) as colorless crystals from a fraction eluted with ethyl acetate-hexane (1:3, v/v).

NMR(CDCl$_3$)δ: 3.99 (3H, s), 7.15-7.25 (2H, m), 7.55-7.6 (2H, m).

Diisobutylaluminum hydride (1.5N toluene solution, 10 ml) was added to a solution of methyl 5-(4-fluorophenyl)-1, 2,3-thiadiazole-4-carboxylate (1.19 g) in tetrahydrofuran (30 ml) at 0° C. and the mixture was stirred at 0° C. for 1 hr. The reaction mixture was poured into an aqueous dilute hydrochloric acid solution and extracted with ethyl acetate. The organic layer was washed with saturated brine, dried over anhydrous magnesium sulfate, and concentrated to give [5-(4-fluorophenyl)-1,2,3-thiadiazol-4-yl]methanol (0.80 g, yield 76%) as a yellow oil.

NMR(CDCl$_3$)δ: 5.05 (2H, s), 7.15-7.25 (2H, m), 7.55-7.6 (2H, m).

[5-(4-Fluorophenyl)-1,2,3-thiadiazol-4-yl]methanol (0.75 g) was dissolved in tetrahydrofuran (30 ml) and activated manganese dioxide (3 g) was added. The mixture was stirred at room temperature for 16 hrs. The reaction mixture was filtered and the filtrate was concentrated. Ethyl diethylphosphonoacetate (0.50 g) and N,N-dimethylformamide (10 ml) were added to the residue. To this mixture was added sodium hydride (60% in oil, 80 mg) at 0° C. and the mixture was stirred at 0° C. for 1 hr. The reaction mixture was poured into an aqueous dilute hydrochloric acid solution and extracted with ethyl acetate. The organic layer was washed with saturated brine, dried over anhydrous magnesium sulfate, and concentrated to give a yellow oil. A 6N aqueous hydrochloric acid solution (10 ml) and acetic acid (5 ml) were added to this yellow oil and the mixture was stirred for 3 hrs. with heating under reflux. The reaction mixture was concentrated, poured into water, and the precipitated solids were filtered, washed with water and dried to give (2E)-3-[5-(4-fluorophenyl)-1,2,3-thiadiazol-4-yl]acrylic acid (190 mg, yield: 21%) as pale-yellow crystals.

NMR(DMSO-d$_6$)δ: 6.98(1H, d, J=15.5 Hz), 7.3-7.5 (3H, m), 7.6-7.8 (2H, m), 12.67 (1H, broad s).

REFERENCE EXAMPLE 21

A mixture of 5-(4-fluorophenyl)-1-methyl-1H-pyrazole-4-carbaldehyde (350 mg), sodium hydride (60% in oil, 120 mg), ethyl diethylphosphonoacetate (673 mg) and N,N-dimethylformamide (10 ml) was stirred at room temperature for 1 hr. The reaction mixture was poured into water, and the precipitated solids were collected by filtration. After drying with airflow, the solids were dissolved in a mixed solvent of tetrahydrofuran (10 ml) and ethanol (10 ml). A 1N aqueous sodium hydroxide solution (5 ml) was added and the mixture was stirred at room temperature for 2 hrs. The reaction mixture was poured into a 10% aqueous citric acid solution and the precipitated solids were collected by filtration, washed with water and dried with airflow to give (2E)-3-[5-(4-fluorophenyl)-1-methyl-1H-pyrazol-4-yl]acrylic acid (354 mg, 84%) as crystals. Recrystallization thereof from methanol-isopropyl ether gave colorless prism crystals. melting point: 212-213° C.

In the similar manner as in Reference Examples 21, the compounds described in Reference Examples 22-31, 33-35, 37 and 40 were produced.

REFERENCE EXAMPLE 22

(2E)-3-[5-(4-Methoxyphenyl)-1-methyl-1H-pyrazol-4-yl]acrylic acid yield: 28%. Colorless prism crystals. melting point: 190-192° C. (recrystallized from methanol-diisopropyl ether).

REFERENCE EXAMPLE 23

(2E)-3-[5-(3-Chlorophenyl)-1-methyl-1H-pyrazol-4-yl]acrylic acid yield: 68%. Colorless prism crystals. melting point: 185-187° C. (recrystallized from methanol-diisopropyl ether).

REFERENCE EXAMPLE 24

(2E)-3-[5-(4-Chlorophenyl)-1-methyl-1H-pyrazol-4-yl]acrylic acid yield: 59%. Colorless prism crystals. melting point: 237-239° C. (recrystallized from methanol-diisopropyl ether).

REFERENCE EXAMPLE 25

(2E)-3-(1-Methyl-5-phenyl-1H-pyrazol-4-yl)acrylic acid yield: 70%. Colorless prism crystals. melting point: 215-216° C. (recrystallized from methanol-diisopropyl ether).

REFERENCE EXAMPLE 26

(2E)-3-{1-Methyl-5-[4-(trifluoromethyl)phenyl]-1H-pyrazol-4-yl}acrylic acid yield: 73%. Colorless prism crystals. melting point: 195-196° C. (recrystallized from methanol-diisopropyl ether).

REFERENCE EXAMPLE 27

(2E)-3-[5-(2-Fluorophenyl)-1-methyl-1H-pyrazol-4-yl]acrylic acid yield: 30%. Colorless prism crystals. melting point: 186-187° C. (recrystallized from methanol-diisopropyl ether).

REFERENCE EXAMPLE 28

(2E)-3-[5-(3-Fluorophenyl)-1-methyl-1H-pyrazol-4-yl]acrylic acid yield: 38%. Colorless prism crystals. melting point: 191-192° C. (recrystallized from methanol-diisopropyl ether).

REFERENCE EXAMPLE 29

(2E)-3-[5-(4-Bromophenyl)-1-methyl-1H-pyrazol-4-yl]acrylic acid yield: 46%. Colorless prism crystals. melting point: 246-247° C. (recrystallized from methanol-diisopropyl ether).

REFERENCE EXAMPLE 30

(2E)-3-[1-Methyl-5-(1-naphthyl)-1H-pyrazol-4-yl] acrylic acid yield: 53%. Colorless prism crystals. melting point: 216-217° C. (recrystallized from methanol-diisopropyl ether).

REFERENCE EXAMPLE 31

(2E)-3-[1-Methyl-5-(4-methylphenyl)-1H-pyrazol-4-yl]acrylic acid yield: 43%. Colorless prism crystals. melting point: 221-222° C. (recrystallized from methanol-diisopropyl ether).

REFERENCE EXAMPLE 32

A mixture of the mixture (3.9 g) of 1-benzyl-5-(4-fluorophenyl)-1H-pyrazole-4-carbaldehyde and 1-benzyl-3-(4-fluorophenyl)-1H-pyrazole-4-carbaldehyde produced in Reference Example 14, sodium hydride (60% in oil, 667 mg), ethyl diethylphosphonoacetate (3.43 g) and N,N-dimethylformamide (30 ml) was stirred at room temperature for 3 hrs. The reaction mixture was poured into water, and the mixture was extracted with ethyl acetate. The organic layer was washed with water, dried over anhydrous magnesium sulfate and concentrated to give a mixture (4.0 g, 82%) of ethyl (2E)-3-[1-benzyl-5-(4-fluorophenyl)-1H-pyrazol-4-yl]acrylate and ethyl (2E)-3-[1-benzyl-3-(4-fluorophenyl)-1H-pyrazol-4-yl]acrylate.

NMR(CDCl$_3$)δ: 1.20-1.30 (3H, m), 4.08-4.24 (2H, m), 5.20 (2H×0.7, s), 5.33 (2H×0.3, s), 6.08 (1H×0.3, d, J=16.2 Hz), 6.16 (1H×0.7, d, J=15.9 Hz), 6.96-7.60 (10H, m), 7.62 (1H×0.3, s), 7.88 (1H×0.7, s).

REFERENCE EXAMPLE 33

(2E)-3-[1-Ethyl-5-(4-fluorophenyl)-1H-pyrazol-4-yl] acrylic acid yield: 62%. Colorless prism crystals. melting point: 160-161° C. (recrystallized from methanol-diisopropyl ether).

REFERENCE EXAMPLE 34

(2E)-3-[5-(4-Fluorophenyl)-1,3-dimethyl-1H-pyrazol-4-yl]acrylic acid yield: 63%. Colorless prism crystals. melting point: 208-209° C. (recrystallized from methanol-diisopropyl ether).

REFERENCE EXAMPLE 35

(2E)-3-(5-Cyclohexyl-1-methyl-1H-pyrazol-4-yl) acrylic acid yield: 85%. Colorless prism crystals. melting point: 160° C. (decomposition)(recrystallized from methanol-diisopropyl ether).

REFERENCE EXAMPLE 36

A mixture of the mixture (4.0 g) of ethyl (2E)-3-[1-benzyl-5-(4-fluorophenyl)-1H-pyrazol-4-yl]acrylate and ethyl (2E)-3-[1-benzyl-3-(4-fluorophenyl)-1H-pyrazol-4-yl]acrylate produced in Reference Example 32, a 2N aqueous sodium hydroxide solution (11 ml) and methanol (20 ml) was stirred at 60° C. for 14 hrs. 1N Hydrochloric acid (22 ml) was poured into the reaction mixture. The precipitated solids were collected by filtration, washed with water and isopropyl ether and dried with airflow to give a mixture (3.5 g, 95%) of (2E)-3-[1-benzyl-5-(4-fluorophenyl)-1H-pyrazol-4-yl] acrylic acid and (2E)-3-[1-benzyl-3-(4-fluorophenyl)-1H-pyrazol-4-yl]acrylic acid as a powder.

NMR(CDCl$_3$)δ: 5.25 (2H×0.7, s), 5.38 (2H×0.3, s), 6.23 (1H×0.3, d, J=15.6 Hz), 6.25 (1H×0.7, d, J=15.9 Hz), 6.90-7.60 (10H, m), 8.16 (1H×0.7, s), 8.51 (1H×0.3, s).

REFERENCE EXAMPLE 37

(2E)-3-[5-(2-Furyl)-1-methyl-1H-pyrazol-4-yl] acrylic acid yield: 63%. Colorless prism crystals. melting point: 203-204° C. (recrystallized from methanol-diisopropyl ether).

REFERENCE EXAMPLE 38

Potassium bis(trimethylsilyl)amide (20% toluene solution, 1.0 g) was added to a mixture of bis(2,2,2-trifluoroethyl) (methoxycarbonylmethyl) phosphonate (318 mg), 18-crown-6 (1.32 g) and tetrahydrofuran (20 mL) at −78° C. Then 5-(4-methoxyphenyl)-1-methyl-1H-pyrazole-4-carbaldehyde (216 mg) was added and the mixture was stirred at −78° C. for 4 hrs. Aqueous ammonium chloride was added to the reaction mixture and the mixture was extracted with ethyl acetate. The organic layer was washed successively with water and saturated brine, dried over anhydrous magnesium sulfate and concentrated. Methanol (5 mL) and a 1N aqueous sodium hydroxide solution (5 mL) were added to the residue and the mixture was stirred at 60° C. for 1 hr. The reaction mixture was concentrated, 1N hydrochloric acid was added to the residue and the mixture was extracted with ethyl acetate. The organic layer was washed successively with water and saturated brine, dried over anhydrous magnesium sulfate and concentrated. Recrystallization of the residue from ethyl acetate-hexane gave (2Z)-3-[5-(4-methoxyphenyl)-1-methyl-1H-pyrazol-4-yl]acrylic acid as crystals (77 mg, yield 30%). melting point: 205-206° C.

REFERENCE EXAMPLE 39

A mixture of methyl (2Z)-3-[5-(4-fluorophenyl)-1-methyl-1H-pyrazol-4-yl]acrylate (300 mg), methanol (5 mL) and a 1N aqueous sodium hydroxide solution (5 mL) was stirred at 60° C. for 30 min. 1N Hydrochloric acid was added to the reaction mixture and the mixture was extracted with ethyl acetate. The organic layer was washed successively with water and saturated brine, dried over anhydrous magnesium sulfate and concentrated. Recrystallization of the residue from ethyl acetate-hexane gave (2Z)-3-[5-(4-fluorophenyl)-1-methyl-1H-pyrazol-4-yl]acrylic acid as crystals (220 mg, yield 78%). melting point: 205-206° C.

REFERENCE EXAMPLE 40

(2E)-3-[1-(4-Fluorophenyl)-1H-imidazol-5-yl] acrylic acid yield: 85%. Colorless crystals. melting point: decomposed at 250° C.

NMR(DMSO-$d_6$)δ: 6.17 (1H, d, J=15.5 Hz), 7.16 (1H, d, J=15.5 Hz), 7.35-7.6 (4H, m), 7.76 (1H, broad, s), 8.02 (1H, broad, s), 12.35 (1H, broad, s).

REFERENCE EXAMPLE 41

A mixture of 4-(4-fluorophenyl)-4H-1,2,4-triazole-3-carbaldehyde (3.83 g), ethyl diethylphosphonoacetate (5.60 g), sodium hydride (60% in oil, 0.88 g) and tetrahydrofuran (130 ml) was stirred at 0° C. for 1 hr. The reaction mixture was poured into an aqueous dilute hydrochloric acid solution and the mixture was extracted with ethyl acetate. The ethyl acetate layer was washed with saturated brine, dried over anhydrous magnesium sulfate and concentrated. The residue was dissolved in a 6N aqueous hydrochloric acid solution (100 ml) and stirred for 2 hrs. with heating under reflux. Disodium hydrogen phosphate was added to neutralize the reaction mixture. The precipitated solids were collected by filtration, washed with water and dried to give (2E)-3-[4-(4-fluorophenyl)-4H-1,2,4-triazol-3-yl]acrylic acid (3.60 g, yield 76%) as pale-yellow crystals. melting point: 226-229° C. (recrystallized from ethyl acetate-hexane).

REFERENCE EXAMPLE 42

Sodium hydride (60% in oil, 60 mg) was added to a mixture of 4-(4-fluorophenyl)-1-methyl-1H-pyrazole-5-carbaldehyde (168 mg), ethyl diethylphosphonoacetate (400 mg) and N,N-dimethylformamide (3 ml) at 0° C. and the mixture was stirred at room temperature for 15 min. The reaction mixture was poured into a 1N aqueous hydrochloric acid solution and the mixture was extracted with ethyl acetate. The ethyl acetate layer was concentrated and the residue was dissolved in a mixture of 6N hydrochloric acid (18 ml) and acetic acid (2 ml). The mixture was stirred for 1 hr. with heating under reflux. The reaction mixture was concentrated and poured into water. 1N Sodium hydroxide was added for neutralization. The precipitated solids were collected by filtration, washed with water, and dried to give (2E)-3-[4-(4-fluorophenyl)-1-methyl-1H-pyrazol-5-yl]acrylic acid (159 mg, 78%) as colorless crystals.

NMR(DMSO-$d_6$)δ: 3.99 (3H, s), 6.17 (1H, d, J=16 Hz), 7.2-7.3 (2H, m), 7.35-7.45 (2H, m), 7.49 (1H, d, J=16 Hz), 7.61 (1H, s).

REFERENCE EXAMPLE 43

According to the method exemplified in Reference Example 42, (2E)-3-[4-(4-fluorophenyl)-1-methyl-1H-pyrazol-3-yl]acrylic acid was synthesized from 4-(4-fluorophenyl)-1-methyl-1H-pyrazole-3-carbaldehyde. yield: 56%. Colorless crystals.

NMR(DMSO-$d_6$)δ: 3.91 (3H, s), 6.38 (1H, d, J=15.5 Hz), 7.2-7.3 (2H, m), 7.3-7.4 (2H, m), 7.41 (1H, d, J=15.5 Hz), 7.95 (1H, s).

REFERENCE EXAMPLE 44

A mixture of (2E)-3-[5-(4-fluorophenyl)-1-methyl-1H-pyrazol-4-yl]acrylic acid (0.80 g), 5% palladium-carbon (0.30 g), tetrahydrofuran (10 ml) and ethanol (10 ml) was stirred at room temperature for 6 hrs. in a hydrogen atmosphere at atmospheric pressure. Palladium-carbon was filtered off and the filtrate was concentrated to give 3-[5-(4-fluorophenyl)-1-methyl-1H-pyrazol-4-yl]propionic acid (0.78 g, yield 97%) as a colorless solid.

NMR(CDCl$_3$)δ: 2.50 (2H, t, J=7 Hz), 2.69 (2H, t, J=7 Hz), 3.71 (3H, s), 7.1-7.25 (2H, m), 7.25-7.3 (2H, m), 7.42 (1H, s).

REFERENCE EXAMPLE 45

A mixture of 2-(4-nitrophenyl)ethanethioamide (1.50 g), 1-bromo-2-butanone (1.27 g) and ethanol (50 mL) was heated under reflux for 30 min. The reaction mixture was concentrated, and ethyl acetate was added to the residue. The mixture was washed successively with saturated aqueous sodium hydrogen carbonate and saturated brine, dried over anhydrous magnesium sulfate and concentrated. The residue was subjected to silica gel column chromatography, and 4-ethyl-2-(4-nitrobenzyl)-1,3-thiazole was obtained as a brown oil (1.59 g, yield 84%) from a fraction eluted with hexane-ethyl acetate (7:1-4:1, v/v).

NMR(CDCl$_3$)δ: 1.30 (3H, t, J=7.6 Hz), 2.80 (2H, qd, J=7.6, 1.0 Hz), 4.41 (2H, s), 6.80 (1H, t, J=1.0 Hz), 7.44-7.51 (2H, m), 8.15-8.22 (2H, m).

REFERENCE EXAMPLE 46

A mixture of 2-(4-nitrophenyl)ethanethioamide (1.50 g), ethyl bromopyruvate (1.64 g) and ethanol (50 mL) was heated under reflux for 30 min. The reaction mixture was concentrated, and ethyl acetate was added to the residue. The mixture was washed successively with saturated aqueous sodium hydrogen carbonate and saturated brine, dried over anhydrous magnesium sulfate and concentrated. The residue was subjected to silica gel column chromatography, and ethyl 2-(4-nitrobenzyl)-1,3-thiazole-4-carboxylate was obtained as pale-yellow crystals (1.79 g, yield 81%) from a fraction eluted with hexane-ethyl acetate (1:1, v/v). Recrystallization thereof from ethyl acetate-hexane gave pale-yellow prism crystals. melting point: 122-123° C.

REFERENCE EXAMPLE 47

A mixture of 2-(4-nitrophenyl)ethanethioamide (0.50 g), 1-bromo-2-propanone (0.43 g) and ethanol (20 mL) was heated under reflux for 1 hr. The reaction mixture was concentrated, and saturated aqueous sodium hydrogen carbonate was added to the residue. The mixture was extracted with ethyl acetate. The organic layer was washed with saturated brine, dried over magnesium sulfate and concentrated. The residue was subjected to silica gel column chromatography, and 4-methyl-2-(4-nitrobenzyl)-1,3-thiazole was obtained as pale-yellow crystals (0.37 g, yield 63%) from a fraction eluted with hexane-ethyl acetate (2:1-1:1, v/v). Recrystallization thereof from ethyl acetate-hexane gave colorless prism crystals. melting point: 81-82° C.

REFERENCE EXAMPLE 48

A mixture of 2-(4-nitrophenyl)ethanethioamide (0.80 g), chloroacetaldehyde (40% aqueous solution, 2.88 g) and ethanol (20 mL) was heated under reflux for 15 hrs. Saturated aqueous sodium hydrogen carbonate was added to the reaction mixture, and the mixture was extracted with ethyl acetate. The organic layer was washed with saturated brine, dried over anhydrous magnesium sulfate and concentrated. The residue was subjected to silica gel column chromatography, and 2-(4-nitrobenzyl)-1,3-thiazole was obtained as an orange oil (0.35 g, yield 39%) from a fraction eluted with hexane-ethyl acetate (9:1-2:1, v/v).

NMR(CDCl$_3$)δ: 4.45 (2H, s), 7.26 (1H, d, J=3.8 Hz), 7.45-7.52 (2H, m), 7.74 (1H, d, J=3.8 Hz), 8.16-8.23 (2H, m).

REFERENCE EXAMPLE 49

A mixture of 2-(4-nitrophenyl)acetohydrazide (2.50 g), triethyl orthoformate (5.69 g), methanesulfonic acid (0.25 g) and tetrahydrofuran (50 mL) was heated under reflux for 1 hr. The reaction mixture was diluted with ethyl acetate. The mixture was washed successively with saturated aqueous sodium hydrogen carbonate and saturated brine, dried over anhydrous magnesium sulfate and concentrated. The residue was subjected to silica gel column chromatography, and 2-(4-nitrobenzyl)-1,3,4-oxadiazole was obtained as pale-yellow crystals (1.92 g, yield 73%) from a fraction eluted with hexane-ethyl acetate (3:1-1:1, v/v). Recrystallization thereof from ethyl acetate-hexane gave colorless prism crystals. melting point: 104-105° C.

REFERENCE EXAMPLE 50

A mixture of 2-(4-nitrophenyl)acetohydrazide (7.0 g), trimethyl orthobutyrate (16.01 g), methanesulfonic acid (0.69 g) and tetrahydrofuran (200 mL) was heated under reflux for 2 hrs. Water was poured into the reaction mixture, and the mixture was extracted with ethyl acetate. The organic layer was washed successively with saturated aqueous sodium hydrogen carbonate and saturated brine, dried over anhydrous magnesium sulfate and concentrated. The residue was subjected to silica gel column chromatography, and 2-(4-nitrobenzyl)-5-propyl-1,3,4-oxadiazole was obtained as a colorless oil (7.73 g, yield 87%) from a fraction eluted with hexane-ethyl acetate (3:2-1:2, v/v).

NMR(CDCl$_3$)δ: 1.00 (3H, t, J=7.2 Hz), 1.69-1.89 (2H, m), 2.79 (2H, t, J=7.2 Hz), 4.28 (2H, s), 7.47-7.53 (2H, m), 8.18-8.25 (2H, m).

REFERENCE EXAMPLE 51

A mixture of 4-nitrobenzaldehyde (15.1 g), 1,3-thiazolidine-2,4-dione (11.70 g), piperidine (1.70 g) and ethanol (300 mL) was heated under reflux for 24 hrs. The reaction mixture was concentrated. The obtained residue was washed with ethanol to give 5-(4-nitrobenzylidene)-1,3-thiazolidine-2,4-dione as yellow crystals (14.8 g, yield 59%). Recrystallization thereof from acetone-hexane gave pale-yellow prism crystals. melting point: 272-273° C.

REFERENCE EXAMPLE 52

To a mixture of 5-(4-nitrobenzylidene)-1,3-thiazolidine-2,4-dione (4.0 g) and N,N-dimethylformamide (100 mL) was added sodium hydride (60% in oil, 0.7 g) at room temperature. The reaction mixture was stirred at room temperature for 30 min. and iodomethane (6.81 g) was added to the reaction mixture. The mixture was further stirred at room temperature for 15 hrs. Water was added to the reaction mixture and the precipitated crystals were collected by filtration to give 3-methyl-5-(4-nitrobenzylidene)-1,3-thiazolidine-2,4-dione as yellow crystals (4.02 g, yield 95%). Recrystallization thereof from tetrahydrofuran-hexane gave yellow prism crystals. melting point: 233-234° C.

REFERENCE EXAMPLE 53

To a mixture of 5-(4-nitrobenzylidene)-1,3-thiazolidine-2,4-dione (3.50 g) and N,N-dimethylformamide (100 mL) was added sodium hydride (60% in oil, 0.62 g) at room temperature. The reaction mixture was stirred at room temperature for 30 min. and iodoethane (6.55 g) was added to the reaction mixture. The mixture was stirred at room temperature for 15 hrs. Water was added to the reaction mixture and the precipitated crystals were collected by filtration to give 3-ethyl-5-(4-nitrobenzylidene)-1,3-thiazolidine-2,4-dione as yellow crystals (3.81 g, yield 98%). Recrystallization thereof from acetone-hexane gave yellow prism crystals. melting point: 217-218° C.

REFERENCE EXAMPLE 54

A mixture of 3-methyl-5-(4-nitrobenzylidene)-1,3-thiazolidine-2,4-dione (1.0 g), 5% palladium carbon (1.0 g) and tetrahydrofuran (150 mL) was subjected to catalytic reduction under hydrogen pressure of 5.0 kgf·cm$^{-2}$. The catalyst was removed by filtration, and the filtrate was concentrated to give 5-(4-aminobenzyl)-3-methyl-1,3-thiazolidine-2,4-dione as colorless crystals (0.71 g, yield 79%). Recrystallization thereof from ethyl acetate-hexane gave colorless prism crystals. melting point: 91-92° C.

REFERENCE EXAMPLE 55

A mixture of 3-ethyl-5-(4-nitrobenzylidene)-1,3-thiazolidine-2,4-dione (3.60 g), 5% palladium carbon (5.0 g) and tetrahydrofuran (300 mL) was subjected to catalytic reduction under hydrogen pressure of 5.0 kgf·cm$^{-2}$. The catalyst was removed by filtration, and the filtrate was concentrated. The residue was subjected to silica gel column chromatography, and 5-(4-aminobenzyl)-3-ethyl-1,3-thiazolidine-2,4-dione was obtained as yellow crystals (3.05 g, yield 94%) from a fraction eluted with hexane-ethyl acetate (3:1-1:1, v/v). Recrystallization thereof from ethyl acetate-hexane gave yellow prism crystals. melting point: 103-104° C.

REFERENCE EXAMPLE 56

A mixture of 2-(4-nitrophenyl)acetohydrazide (0.50 g), ethyl chlorocarbonate (0.34 g) and N,N-dimethylacetamide (10 mL) was stirred at room temperature for 1 hr. Water was added to the reaction mixture, and the mixture was extracted with ethyl acetate. The organic layer was washed successively with saturated aqueous sodium hydrogen carbonate and saturated brine, dried over anhydrous magnesium sulfate, and concentrated to give colorless crystals. A mixture of the obtained crystals, diphosphorus pentaoxide (1.50 g), hexamethyldisiloxane (2.96 g) and 1,2-dichlorobenzene (10 mL) was stirred at 160° C. for 2 hrs. Water was added to the reaction mixture, and the mixture was extracted with ethyl acetate. The organic layer was washed successively with saturated aqueous sodium hydrogen carbonate and saturated brine, dried over anhydrous magnesium sulfate, and concentrated to give 5-(4-nitrobenzyl)-1,3,4-oxadiazol-2(3H)-one as pale-yellow crystals (0.29 g, yield 50%). Recrystallization thereof from ethyl acetate-hexane gave pale-yellow prism crystals. melting point: 170-171° C.

REFERENCE EXAMPLE 57

To a mixture of 3-(4-nitrophenyl)propionic acid (3.00 g), 4-methylmorpholine (2.02 g) and tetrahydrofuran (100 mL) was added dropwise isobutyl chlorocarbonate (2.95 g) at 0° C. The reaction mixture was stirred at 0° C. for 1 hr., and insoluble materials were filtered off. The filtrate was added to a mixture of hydrazine hydrate (3.85 g) and tetrahydrofuran (100 mL) at 0° C. The reaction mixture was stirred at 0° C. for 1 hr. and saturated aqueous ammonium chloride was added to the reaction mixture, and the mixture was extracted with ethyl acetate. The organic layer was washed with saturated brine, dried over anhydrous magnesium sulfate and concentrated. A mixture of the obtained residue, triethyl orthopropionate (8.14 g), methanesulfonic acid (0.30 g) and tetrahydrofuran (100 mL) was heated under reflux for 1 hr. The reaction mixture was diluted with ethyl acetate, and the organic layer was washed successively with saturated aqueous sodium hydrogen carbonate and saturated brine, dried over anhydrous magnesium sulfate and concentrated. The obtained residue was subjected to silica gel column chromatography to give 2-ethyl-5-[2-(4-nitrophenyl)ethyl]-1,3,4-oxadiazole as colorless crystals (2.28 g, yield 60%) from a fraction eluted with hexane-ethyl acetate (1:2, v/v). Recrystallization thereof from ethyl acetate-hexane gave colorless prism crystals. melting point: 65-66° C.

REFERENCE EXAMPLE 58

To a mixture of 3-(4-nitrophenyl)propionic acid (3.00 g), 4-methylmorpholine (2.02 g) and tetrahydrofuran (100 mL) was added dropwise isobutyl chlorocarbonate (2.95 g) at 0° C. The reaction mixture was stirred at 0° C. for 1 hr. and insoluble materials were filtered off. The filtrate was added to a mixture of hydrazine hydrate (3.85 g) and tetrahydrofuran (100 mL) at 0° C. The reaction mixture was stirred at 0° C. for 1 hr. and saturated aqueous ammonium chloride was added to the reaction mixture. The mixture was extracted with ethyl acetate. The organic layer was washed with saturated brine, dried over anhydrous magnesium sulfate and concentrated. A mixture of the obtained residue, triethyl orthoformate (6.84 g), ethanesulfonic acid (0.30 g) and tetrahydrofuran (100 mL) was heated under reflux for 1 hr. The reaction mixture was diluted with ethyl acetate, and the organic layer was washed successively with saturated aqueous sodium hydrogen carbonate and saturated brine, dried over anhydrous magnesium sulfate and concentrated. The obtained residue was subjected to silica gel column chromatography to give 2-[2-(4-nitrophenyl)ethyl]-1,3,4-oxadiazole as colorless crystals (2.70 g, yield 80%) from a fraction eluted with hexane-ethyl acetate (1:2, v/v). Recrystallization thereof from ethyl acetate-hexane gave colorless prism crystals. melting point: 93-94° C.

REFERENCE EXAMPLE 59

A mixture of 4-chloromethyl-1,3-oxazole hydrochloride (5.16 g), potassium carbonate (4.19 g), water (60 mL) and ethyl acetate (60 mL) was stirred for 15 min. The reaction mixture was extracted with ethyl acetate. The organic layer was washed with saturated brine, dried over anhydrous magnesium sulfate, and concentrated. A mixture of the obtained residue, triphenylphosphine (7.95 g) and acetonitrile (200 mL) was heated under reflux for 15 hrs. The reaction mixture was cooled and the precipitated crystals were washed with diethyl ether to give [(1,3-oxazol-4-yl)methyl]triphenylphosphonium chloride as colorless crystals (8.11 g, yield 68%). melting point: 268-270° C.

REFERENCE EXAMPLE 60

A mixture of 4-chloromethyl-2-ethyl-1,3-oxazole (4.87 g), triphenylphosphine (7.89 g) and acetonitrile (100 mL) was heated under reflux for 15 hrs. The reaction mixture was concentrated, and the obtained crystals were washed with diethyl ether to give [(2-ethyl-1,3-oxazol-4-yl)methyl]triphenylphosphonium chloride as colorless crystals (10.02 g, yield 79%). Recrystallization thereof from acetonitrile-diethyl ether gave colorless prism crystals. melting point: 222-223° C.

REFERENCE EXAMPLE 61

A mixture of 4-nitrobenzaldehyde (0.42 g), potassium carbonate (0.58 g), [(1,3-oxazol-4-yl)methyl]triphenylphosphonium chloride (1.65 g) and N,N-dimethylformamide (20 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The obtained residue was subjected to silica gel column chromatography to give yellow crystals from a fraction eluted with hexane-tetrahydrofuran (1:1, v/v). The obtained crystals, 5% palladium carbon (1.00 g) and tetrahydrofuran (50 mL) were subjected to catalytic reduction under a hydrogen atmosphere at atmospheric pressure. The catalyst was removed by filtration, and the filtrate was concentrated. The obtained residue was subjected to silica gel column chromatography to give 4-[2-(1,3-thiazol-4-yl)ethyl]aniline as colorless crystals (0.27 g, yield 47%) from a fraction eluted with hexane-ethyl acetate (2:1-1:1, v/v). Recrystallization thereof from ethyl acetate-hexane gave colorless prism crystals. melting point: 69-70° C.

REFERENCE EXAMPLE 62

A mixture of 4-nitrobenzaldehyde (1.0 g), potassium carbonate (1.37 g), [(2-ethyl-1,3-oxazol-4-yl)methyl]triphenylphosphonium chloride (4.20 g) and N,N-dimethylformamide (50 mL) was stirred at room temperature for 40 hrs. Water was poured into the reaction mixture, and the mixture was extracted with ethyl acetate. The organic layer was washed with saturated brine, dried over anhydrous magnesium sulfate and concentrated. The obtained residue was subjected to silica gel column chromatography to give a yellow oil from a fraction eluted with hexane-ethyl acetate (3:1-2:1, v/v). The obtained oil, 5% palladium carbon (2.00 g) and tetrahydrofuran (200 mL) were subjected to catalytic reduction under hydrogen atmosphere at atmospheric pressure. The catalyst was removed by filtration, and the filtrate was concentrated. The obtained residue was subjected to silica gel column chromatography to give 4-[2-(2-ethyl-1,3-thiazol-4-yl)ethyl]aniline as a brown oil (1.11 g, yield 73%) from a fraction eluted with hexane-ethyl acetate (2:1, v/v).

NMR(CDCl$_3$)δ: 1.39 (3H, t, J=7.6 Hz), 2.84-3.08 (6H, m), 3.56 (2H, brs), 6.59-6.66 (3H, m), 6.95-7.00 (2H, m).

REFERENCE EXAMPLE 63

A mixture of 5-(4-fluorophenyl)-1H-pyrazole-4-carbaldehyde (1.0 g), malonic acid (0.67 g), piperidine (0.54 g) and bis(2-methoxyethyl) ether (10 mL) was stirred at 110° C. for 6 hrs. Water and 1N hydrochloric acid were added to acidify the reaction mixture, and the mixture was extracted with ethyl acetate. The organic layer was washed with saturated brine, dried over anhydrous magnesium sulfate and concentrated. The obtained residue was subjected to silica gel column chromatography to give (2E)-3-[5-(4-fluorophenyl)-1H-pyrazol-4-yl]acrylic acid as colorless crystals (0.12 g, yield 10%) from a fraction eluted with hexane-ethyl acetate (1:9, v/v). Recrystallization thereof from acetone-diisopropyl ether gave colorless prism crystals. melting point: 276-277° C.

REFERENCE EXAMPLE 64

To a mixture of 3-(4-nitrophenyl)propionic acid (13.45 g), N,N-dimethylformamide (0.1 mL) and tetrahydrofuran (300 mL) was added dropwise oxalyl chloride (10.5 g) at room temperature. The reaction mixture was stirred at room temperature for 1 hr. and concentrated. The obtained residue was dissolved in tetrahydrofuran (50 mL) and added dropwise to a mixture of 25% aqueous ammonia (100 mL) and tetrahydrofuran (100 mL) at room temperature. The reaction mixture was stirred at room temperature for 2 hrs. and the mixture was extracted with ethyl acetate. The organic layer was washed with saturated brine, dried over anhydrous magnesium sulfate, and concentrated to give 3-(4-nitrophenyl)propanamide as colorless crystals (11.80 g, yield 88%). Recrystallization thereof from ethyl acetate-hexane gave colorless prism crystals. melting point: 177-178° C.

REFERENCE EXAMPLE 65

A mixture of 3-(4-nitrophenyl)propanamide (0.50 g), 2,4-bis(4-methoxyphenyl)-1,3-dithia-2,4-diphosphetane-2,4-disulfide (0.81 g) and pyridine (5 mL) was stirred at 50° C. for 15 hrs. The reaction mixture was concentrated, and 1N hydrochloric acid was added to the obtained residue and the mixture was extracted with ethyl acetate. The organic layer was washed with saturated brine, dried over anhydrous magnesium sulfate and concentrated. The residue was subjected to silica gel column chromatography to give 3-(4-nitrophenyl)propanethioamide as colorless crystals (0.40 g, yield 73%) from a fraction eluted with hexane-ethyl acetate (2:1-1:1, v/v). Recrystallization thereof from ethyl acetate-hexane gave colorless prism crystals. melting point: 157-158° C.

REFERENCE EXAMPLE 66

A mixture of 3-(4-nitrophenyl)propanethioamide (1.0 g), chloroacetaldehyde (40% aqueous solution, 2.83 g) and tert-butanol (20 mL) was heated under reflux for 2 hrs. The reaction mixture was concentrated, and saturated aqueous sodium hydrogen carbonate was added to the residue. The mixture was extracted with ethyl acetate. The organic layer was washed with saturated brine, dried over anhydrous magnesium sulfate and concentrated. The residue was subjected to silica gel column chromatography to give 2-[2-(4-nitrophenyl)ethyl]-1,3-thiazole as pale-yellow crystals (0.31 g, yield 28%) from a fraction eluted with hexane-ethyl acetate (3:1, v/v). Recrystallization thereof from ethyl acetate-hexane gave pale-yellow prism crystals. melting point: 92-93° C.

REFERENCE EXAMPLE 67

A mixture of 3-(4-nitrophenyl)propanethioamide (1.25 g), 1-bromo-2-butanone (0.98 g) and tert-butanol (30 mL) was heated under reflux for 30 min. The reaction mixture was concentrated, and saturated aqueous sodium hydrogen carbonate was added to the residue. The mixture was extracted with ethyl acetate. The organic layer was washed with saturated brine, dried over anhydrous magnesium sulfate and concentrated. The residue was subjected to silica gel column chromatography to give 4-ethyl-2-[2-(4-nitrophenyl)ethyl]-1,3-thiazole as a yellow oil (1.48 g, yield 95%) from a fraction eluted with hexane-ethyl acetate (4:1-2:1, v/v).

NMR(CDCl$_3$)δ: 1.29 (3H, t, J=7.6 Hz), 2.78 (2H, qd, J=7.6, 1.0 Hz), 3.17-3.37 (4H, m), 6.73 (1H, t, J=1.0 Hz), 7.32-7.39 (2H, m), 8.10-8.18 (2H, m).

REFERENCE EXAMPLE 68

A mixture of 4-nitrophenol (3.92 g), 4-chloromethyl-1,3-thiazole hydrochloride (4.0 g), potassium carbonate (8.13 g) and N,N-dimethylformamide (100 mL) was stirred at room temperature for 40 hrs. Water was poured into the reaction mixture, and the mixture was extracted with ethyl acetate-tetrahydrofuran. The organic layer was washed with saturated brine, dried over anhydrous magnesium sulfate and concentrated to give 4-[(4-nitrophenoxy)methyl]-1,3-thiazole as colorless crystals (3.38 g, yield 61%). Recrystallization thereof from ethyl acetate-hexane gave colorless prism crystals. melting point: 175-176° C.

REFERENCE EXAMPLE 69

A mixture of 4-nitrophenol (5.48 g), 4-chloromethyl-2-ethyl-1,3-thiazole (7.40 g), potassium carbonate (5.45 g) and N,N-dimethylformamide (50 mL) was stirred at room temperature for 15 hrs. Water was poured into the reaction mixture, and the mixture was extracted with ethyl acetate. The organic layer was washed successively with 1N aqueous sodium hydroxide solution and saturated brine, dried over anhydrous magnesium sulfate and concentrated. The residue was subjected to silica gel column chromatography to give 2-ethyl-4-[(4-nitrophenoxy)methyl]-1,3-thiazole as colorless crystals (3.60 g, yield 35%) from a fraction eluted with hexane-ethyl acetate (4:1, v/v). Recrystallization thereof from ethyl acetate-hexane gave colorless prism crystals. melting point: 79-80° C.

REFERENCE EXAMPLE 70

To a mixture of 2-(4-nitrophenoxy)acetic acid (5.0 g), 4-methylmorpholine (3.34 g) and tetrahydrofuran (100 mL) was added dropwise isobutyl chlorocarbonate (4.86 g) at 0° C. The reaction mixture was stirred at room temperature for 1 hr., and insoluble materials were filtered off. The filtrate was added dropwise to a mixture of hydrazine monohydrate (6.36 g) and tetrahydrofuran (50 mL) at 0° C. The reaction mixture was stirred at 0° C. for 2 hrs. A saturated aqueous ammonium chloride solution was added to the reaction mixture and the precipitated crystals were collected by filtration to give 2-(4-nitrophenoxy)acetohydrazide as colorless crystals (1.30 g, yield 24%). Recrystallization thereof from tetrahydrofuran-hexane gave colorless prism crystals. melting point: 191-192° C.

REFERENCE EXAMPLE 71

A mixture of 2-(4-nitrophenoxy)acetohydrazide (1.10 g), methanesulfonic acid (0.10 g), triethyl orthoformate (2.31 g) and tetrahydrofuran (50 mL) was heated under reflux for 1 hr. Water was added to the reaction mixture, and the mixture was extracted with ethyl acetate. The organic layer was washed successively with saturated aqueous sodium hydrogen carbonate and saturated brine, dried over anhydrous magnesium sulfate and concentrated. The residue was subjected to silica gel column chromatography to give 2-[(4-nitrophenoxy)methyl]-1,3,4-oxadiazole as colorless crystals (0.79 g, yield 69%) from a fraction eluted with hexane-ethyl acetate (1:1, v/v). Recrystallization thereof from ethyl acetate-hexane gave colorless prism crystals. melting point: 125-126° C.

REFERENCE EXAMPLE 72

A mixture of 2-(4-nitrophenyl)acetamide (15.0 g), 1-bromo-2-propanone (19.03 g), and N,N-dimethylformamide (2 mL) was stirred at 120° C. for 3 hrs. Water, potassium carbonate and ethyl acetate were added to basify the reaction mixture and the mixture was extracted with ethyl acetate. Insoluble materials were filtered off, and the organic layer was separated. The organic layer was washed with saturated brine, dried over anhydrous magnesium sulfate and concentrated. The residue was subjected to silica gel column chromatography to give 4-methyl-2-(4-nitrobenzyl)-1,3-oxazole as orange crystals (1.50 g, yield 8.2%) from a fraction eluted with hexane-ethyl acetate (2:1, v/v). Recrystallization thereof from ethyl acetate-hexane gave colorless prism crystals. melting point: 67-68° C.

REFERENCE EXAMPLE 73

To a mixture of 2-(4-nitrophenoxy)acetohydrazide (1.57 g) and N,N-dimethylacetamide (50 mL) was added dropwise acetyl chloride (0.70 g) at room temperature. The reaction mixture was stirred for 2 hrs. Water was added to the reaction mixture, and the mixture was extracted with ethyl acetate. The organic layer was washed with saturated brine, dried over anhydrous magnesium sulfate and concentrated. A mixture of the obtained residue, diphosphorus pentaoxide (1.76 g), hexamethyldisiloxane (4.03 g) and 1,2-dichlorobenzene (10 mL) was stirred at 140° C. for 3 hrs. Saturated aqueous sodium hydrogen carbonate was added to the reaction mixture, and the mixture was extracted with ethyl acetate. The organic layer was washed with saturated brine, dried over anhydrous magnesium sulfate and concentrated. The residue was subjected to silica gel column chromatography to give 2-methyl-5-[(4-nitrophenoxy)methyl]-1,3,4-oxadiazole as colorless crystals (0.41 g, yield 56%) from a fraction eluted with hexane-ethyl acetate (3:2-1:1, v/v). Recrystallization thereof from ethyl acetate-hexane gave colorless prism crystals. melting point: 105-106° C.

REFERENCE EXAMPLE 74

A mixture of 2-(4-nitrophenyl)acetamide (14.6 g), 1-bromo-2-butanone (20.46 g) and N,N-dimethylformamide (2 mL) was stirred at 140° C. for 2 hrs. Water, potassium carbonate and ethyl acetate were added to basify the reaction mixture and the mixture was extracted with ethyl acetate. The organic layer was washed with saturated brine, dried over anhydrous magnesium sulfate and concentrated. The residue was subjected to silica gel column chromatography to give 4-ethyl-2-(4-nitrobenzyl)-1,3-oxazole as brown crystals (2.65 g, yield 14%) from a fraction eluted with hexane-ethyl acetate (2:1, v/v). Recrystallization thereof from ethyl acetate-hexane gave brown prism crystals. melting point: 58-59° C.

REFERENCE EXAMPLE 75

To a mixture of ethyl (4-{[(benzyloxy)carbonyl]amino}phenyl)acetate (0.30 g) and tetrahydrofuran (10 mL) was added dropwise 1 M methyl magnesium bromide (1 M tetrahydrofuran solution, 10 mL) at 0° C. The reaction mixture was stirred at room temperature for 1 hr. 1N Hydrochloric acid was added to the reaction mixture and the mixture was extracted with ethyl acetate. The organic layer was washed with saturated brine, dried over anhydrous magnesium sulfate and concentrated. The residue was subjected to silica gel column chromatography to give benzyl 4-(2-hydroxy-2-methylpropyl)phenylcarbamate as colorless crystals (0.17 g, yield 59%) from a fraction eluted with hexane-ethyl acetate (4:1-2:1, v/v). Recrystallization thereof from ethyl acetate-hexane gave colorless prism crystals. melting point: 117-118° C.

REFERENCE EXAMPLE 76

To a mixture of ethyl (4-{[(benzyloxy)carbonyl]amino}phenyl)acetate (15.3 g) and tetrahydrofuran (100 mL) was added dropwise 1 M ethyl magnesium bromide (1 M tetrahydrofuran solution, 500 g) at 0° C. The reaction mixture was stirred at room temperature for 15 hrs. 1N Hydrochloric acid was added to the reaction mixture, and the mixture was extracted with ethyl acetate. The organic layer was washed with saturated brine, dried over anhydrous magnesium sulfate and concentrated. The residue was subjected to silica gel column chromatography to give benzyl 4-(2-ethyl-2-hydroxybutyl)phenylcarbamate as colorless crystals from a fraction eluted with hexane-ethyl acetate (2:1-1:1, v/v). Recrystallization thereof from ethyl acetate-hexane gave colorless prism crystals (6.86 g, yield 43%). melting point: 99-100° C.

REFERENCE EXAMPLE 77

A mixture of benzyl 4-(2-hydroxy-2-methylpropyl)phenylcarbamate (8.60 g), 10% palladium carbon (9.0 g) and tetrahydrofuran (300 mL) was subjected to catalytic reduction under a hydrogen atmosphere at atmospheric pressure.

The catalyst was removed by filtration, and the filtrate was concentrated. The residue was subjected to silica gel column chromatography to give 1-(4-aminophenyl)-2-methylpropan-2-ol as colorless crystals (3.54 g, yield 75%) from a fraction eluted with hexane-ethyl acetate (1:1, v/v). Recrystallization thereof from ethyl acetate-hexane gave colorless prism crystals. melting point: 107-108° C.

REFERENCE EXAMPLE 78

A mixture of benzyl 4-(2-ethyl-2-hydroxybutyl)phenylcarbamate (6.30 g), 10% palladium carbon (5.0 g) and tetrahydrofuran (150 mL) was subjected to catalytic reduction under a hydrogen atmosphere at atmospheric pressure. The catalyst was removed by filtration, and the filtrate was concentrated to give 3-(4-aminobenzyl)-3-pentanol as colorless crystals (3.51 g, yield 95%). Recrystallization thereof from ethyl acetate-hexane gave colorless prism crystals. melting point: 85-86° C.

REFERENCE EXAMPLE 79

To a mixture of hydroxylamine hydrochloride (21.5 g) and dimethyl sulfoxide (50 mL) was added dropwise 28% sodium methoxide methanol solution (59.6 g) at room temperature. A solution (50 mL) of (4-nitrophenyl)acetonitrile (10.0 g) in dimethyl sulfoxide was further added dropwise to the reaction mixture. The reaction mixture was stirred at 100° C. for 3 hrs. Water was added to the reaction mixture, and the mixture was extracted with ethyl acetate. The organic layer was washed with saturated brine, dried over anhydrous magnesium sulfate, and concentrated to give N'-hydroxy-2-(4-nitrophenyl)ethanimidamide as brown crystals (7.10 g, yield 59%). Recrystallization thereof from ethyl acetate-diisopropyl ether gave brown prism crystals. melting point: 170-171° C.

REFERENCE EXAMPLE 80

To a mixture of N'-hydroxy-2-(4-nitrophenyl)ethanimidamide (2.38 g) and N,N-dimethylacetamide (30 mL) was added acetyl chloride (0.96 g) at room temperature and the mixture was stirred at room temperature for 15 hrs. Water was poured into the reaction mixture, and the mixture was extracted with ethyl acetate. The organic layer was washed with saturated brine, dried over anhydrous magnesium sulfate and concentrated. A mixture of obtained residue and xylene (100 mL) was heated under reflux for 24 hrs. The reaction mixture was concentrated and ethyl acetate was added to the obtained residue. The mixture was washed with saturated brine, dried over anhydrous magnesium sulfate, and concentrated. The residue was subjected to silica gel column chromatography to give 5-methyl-3-(4-nitrobenzyl)-1,2,4-oxadiazole as orange crystals (1.00 g, yield 37%) from a fraction eluted with hexane-ethyl acetate (4:1-3:1, v/v). Recrystallization thereof from ethyl acetate-hexane gave orange prism crystals. melting point: 66-67° C.

REFERENCE EXAMPLE 81

A mixture of 5-methyl-3-(4-nitrobenzyl)-1,2,4-oxadiazole (3.89 g), Lindlar catalyst (2.0 g) and tetrahydrofuran (200 mL) was subjected to catalytic reduction under a hydrogen atmosphere at atmospheric pressure. The catalyst was removed by filtration, and the filtrate was concentrated. The residue was subjected to silica gel column chromatography to give 4-[(5-methyl-1,2,4-oxadiazol-3-yl)methyl]aniline as a brown oil (0.33 g, yield 10%) from a fraction eluted with hexane-ethyl acetate (3:1-2:1, v/v).
NMR(CDCl$_3$)δ: 2.52 (3H, s), 3.62 (2H, brs), 3.92 (2H, s), 6.62-6.66 (2H, m), 7.08-7.12 (2H, m).

REFERENCE EXAMPLE 82

A mixture of 1-bromo-3-(4-nitrophenyl)-2-propanone (0.50 g), propanethioamide (0.17 g) and ethanol (10 mL) was heated under reflux for 2 hrs. Saturated aqueous sodium hydrogen carbonate was poured into the reaction mixture, and the mixture was extracted with ethyl acetate. The organic layer was washed with saturated brine, dried over anhydrous magnesium sulfate and concentrated. The residue was subjected to silica gel column chromatography to give 2-ethyl-4-(4-nitrobenzyl)-1,3-thiazole as a colorless oil (0.45 g, yield 96%) from a fraction eluted with hexane-ethyl acetate (9:1-4:1, v/v).
NMR(CDCl$_3$)δ: 1.38 (3H, t, J=7.5 Hz), 3.02 (2H, q, J=7.5 Hz), 4.19 (2H, s), 6.74 (1H, s), 7.40-7.44 (2H, m), 8.15-8.18 (2H, m).

REFERENCE EXAMPLE 83

To a mixture of N'-hydroxy-2-(4-nitrophenyl)ethanimidamide (6.17 g) and N,N-dimethylacetamide (50 mL) was added propionyl chloride (3.22 g) at room temperature. The reaction mixture was stirred at room temperature for 2 hrs. Water was poured into the reaction mixture and the mixture was extracted with ethyl acetate. The organic layer was washed with saturated brine, dried over anhydrous magnesium sulfate and concentrated. A mixture of the obtained residue and xylene (200 mL) was heated under reflux for 15 hrs. with azeotropic dehydration. The reaction mixture was concentrated and the obtained residue was subjected to silica gel column chromatography to give 5-ethyl-3-(4-nitrobenzyl)-1,2,4-oxadiazole as brown crystals (4.40 g, yield 60%) from a fraction eluted with hexane-ethyl acetate (3:1-2:1, v/v). Recrystallization thereof from ethyl acetate-hexane gave pale-yellow prism crystals. melting point: 69-70° C.

REFERENCE EXAMPLE 84

A mixture of 5-ethyl-3-(4-nitrobenzyl)-1,2,4-oxadiazole (4.30 g), iron (reduced, 5.14 g), calcium chloride (0.20 g) and 80% ethanol (50 mL) was heated under reflux for 2 hrs.
Insoluble materials were filtered off, and the filtrate was concentrated. Water was added to the residue, and the mixture was extracted with ethyl acetate. The organic layer was washed with saturated brine, dried over anhydrous magnesium sulfate and concentrated. The residue was subjected to silica gel column chromatography to give 4-[(5-ethyl-1,2,4-oxadiazol-3-yl)methyl]aniline as an orange oil (2.73 g, yield 73%) from a fraction eluted with hexane-ethyl acetate (2:1-1:1, v/v).
NMR(CDCl$_3$)δ: 1.35 (3H, t, J=7.6 Hz), 2.86 (2H, q, J=7.6 Hz), 3.62 (2H, brs), 3.93 (2H, s), 6.61-6.66 (2H, m), 7.08-7.12 (2H, m).

REFERENCE EXAMPLE 85

A mixture of 1-bromo-3-(4-nitrophenyl)-2-propanone (0.80 g), thioacetamide (0.23 g) and ethanol (20 mL) was heated under reflux for 2 hrs. The reaction mixture was concentrated, and saturated aqueous sodium hydrogen carbonate was added to the residue. The mixture was extracted with ethyl acetate. The organic layer was washed with saturated brine, dried over anhydrous magnesium sulfate and concentrated. The residue was subjected to silica gel column chromatography to give 2-methyl-4-(4-nitrobenzyl)-1,3-thiazole as pale-yellow crystals (0.58 g, yield 79%) from a fraction eluted with hexane-ethyl acetate (3:1-2:1, v/v). Recrystallization thereof from ethyl acetate-hexane gave pale-yellow prism crystals. melting point: 118-119° C.

REFERENCE EXAMPLE 86

To a mixture of 5-(4-nitrobenzyl)-1,3,4-oxadiazol-2(3H)-one (1.0 g), iodomethane (0.97 g) and N,N-dimethylformamide (30 mL) was added sodium hydride (60% in oil, 0.20 g) at room temperature. The reaction mixture was stirred at room temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 3-methyl-5-(4-nitrobenzyl)-1,3,4-oxadiazol-2(3H)-one as colorless crystals (0.75 g, yield 71%) from a fraction eluted with hexane-ethyl acetate (3:1-2:1, v/v).

REFERENCE EXAMPLE 87

To a mixture of 5-(4-nitrobenzyl)-1,3,4-oxadiazol-2(3H)-one (1.50 g), iodoethane (1.59 g) and N,N-dimethylformamide (50 mL) was added sodium hydride (60% in oil, 0.30 g) at room temperature. The reaction mixture was stirred at room temperature for 3 hrs. Water was poured into the reaction mixture and the mixture was extracted with ethyl acetate. The organic layer was washed with saturated brine, dried over anhydrous magnesium sulfate and concentrated. The residue was subjected to silica gel column chromatography to give 3-ethyl-5-(4-nitrobenzyl)-1,3,4-oxadiazol-2(3H)-one as colorless crystals (0.99 g, yield 59%) from a fraction eluted with hexane-ethyl acetate (3:1-2:1, v/v). Recrystallization thereof from ethyl acetate-hexane gave colorless prism crystals. melting point: 108-109° C.

REFERENCE EXAMPLE 88

To a mixture of 5-(4-nitrobenzyl)-1H-tetrazole (5.0 g) and N,N-dimethylformamide (200 mL) was added sodium hydride (60% in oil, 1.17 g) at 0° C. The reaction mixture was stirred at 0° C. for 1 hr. and iodoethane (5.69 g) was added at 0° C. The reaction mixture was stirred at 0° C. for 2 hrs. and water was poured into the reaction mixture. The mixture was extracted with ethyl acetate. The organic layer was washed with saturated brine, dried over anhydrous magnesium sulfate and concentrated. The residue was subjected to silica gel column chromatography to give 2-ethyl-5-(4-nitrobenzyl)-2H-tetrazole as a brown oil (2.70 g, yield 48%) from a fraction eluted with hexane-ethyl acetate (2:1-1:2, v/v).

NMR(CDCl$_3$)δ: 1.63 (3H, t, J=7.5 Hz), 4.35 (2H, s), 4.63 (2H, q, J=7.5 Hz), 7.48-7.52 (2H, m), 8.16-8.20 (2H, m).

In addition, 1-ethyl-5-(4-nitrobenzyl)-1H-tetrazole was obtained as brown crystals (0.65 g, yield 11%) from a fraction sequentially eluted thereafter. Recrystallization thereof from ethyl acetate-hexane gave brown prism crystals. melting point: 104-105° C.

NMR(CDCl$_3$)δ: 1.44 (3H, t, J=7.4 Hz), 4.25 (2H, q, J=7.4 Hz), 4.40 (2H, s), 7.40-7.44 (2H, m), 8.20-8.24 (2H, m).

REFERENCE EXAMPLE 89

A mixture of 2-(4-nitrophenyl)ethanethioamide (1.11 g), 2-chloro-3-butanone (0.75 g) and tert-butanol (50 ml) was heated under reflux for 4 days. The reaction mixture was concentrated, and water and saturated aqueous sodium hydrogen carbonate were added to the residue. The mixture was extracted with ethyl acetate. The organic layer was washed with saturated brine, dried over anhydrous magnesium sulfate and concentrated. The residue was subjected to silica gel column chromatography to give 4,5-dimethyl-2-(4-nitrobenzyl)-1,3-thiazole as pale-yellow crystals (0.67 g, yield 47%) from a fraction eluted with hexane-ethyl acetate (2:1-1:1, v/v). Recrystallization thereof from ethyl acetate-hexane gave pale-yellow prism crystals. melting point: 93-94° C.

REFERENCE EXAMPLE 90

A mixture of 2-(4-nitrophenyl)ethanethioamide (7.0 g), 2-chloro-cyclohexanone (7.28 g) and tert-butanol (100 mL) was heated under reflux for 3 days. The reaction mixture was concentrated, and saturated aqueous sodium hydrogen carbonate was added to the residue. The mixture was extracted with ethyl acetate. The organic layer was washed with saturated brine, dried over anhydrous magnesium sulfate and concentrated. The residue was subjected to silica gel column chromatography to give 2-(4-nitrobenzyl)-4,5,6,7-tetrahydro-1,3-benzothiazole as pale-brown crystals (6.58 g, yield 66%) from a fraction eluted with hexane-ethyl acetate (3:1, v/v). Recrystallization thereof from ethyl acetate-hexane gave pale-yellow prism crystals. melting point: 118-119° C.

REFERENCE EXAMPLE 91

2-(4-Nitrobenzyl)-5-propyl-1,3,4-oxadiazole (7.70 g), 5% palladium carbon (7.0 g) and tetrahydrofuran (200 mL) were subjected to catalytic reduction under a hydrogen atmosphere at atmospheric pressure. The catalyst was removed by filtration, and the filtrate was concentrated. The residue was subjected to silica gel column chromatography to give 4-[(5-propyl-1,3,4-oxadiazol-2-yl)methyl]aniline as pale-yellow crystals (3.74 g, yield 55%) from a fraction eluted with hexane-ethyl acetate (1:1-1:2, v/v). Recrystallization thereof from ethyl acetate-hexane gave pale-yellow prism crystals. melting point: 60-61° C.

In the similar manner as in Example 91, the compounds described in Examples 92-112 were produced.

REFERENCE EXAMPLE 92

5-(4-Aminobenzyl)-1,3,4-oxadiazol-2(3H)-one was obtained as colorless crystals (yield 75%). Recrystallization thereof from ethyl acetate-hexane gave colorless prism crystals. melting point: 267-268° C.

REFERENCE EXAMPLE 93

4-[2-(5-Ethyl-1,3,4-oxadiazol-2-yl)ethyl]aniline was obtained as a colorless oil (yield 97%).

NMR(CDCl$_3$)δ: 1.35 (3H, t, J=7.6 Hz), 2.83 (2H, q, J=7.6 Hz), 2.92-3.11 (4H, m), 3.61 (2H, brs), 6.58-6.66 (2H, m), 6.95-7.02 (2H, m).

REFERENCE EXAMPLE 94

4-[2-(1,3,4-Oxadiazol-2-yl)ethyl]aniline was obtained as colorless crystals (yield 77%). Recrystallization thereof from ethyl acetate-hexane gave colorless prism crystals. melting point: 73-74° C.

REFERENCE EXAMPLE 95

4-[2-(4-Ethyl-1,3-thiazol-2-yl)ethyl]aniline was obtained as a brown oil (yield 96%).

NMR(CDCl$_3$)δ: 1.29 (3H, t, J=7.6 Hz), 2.73-2.85 (2H, m), 2.93-3.07 (2H, m), 3.18-3.27 (2H, m), 3.58 (2H, brs), 6.59-6.71 (3H, m), 6.90-7.11 (2H, m).

REFERENCE EXAMPLE 96

4-(1,3-Thiazol-4-ylmethoxy)aniline was obtained as pale-yellow crystals (yield 78%). Recrystallization thereof from ethyl acetate-hexane gave pale-yellow prism crystals. melting point: 114-115° C.

REFERENCE EXAMPLE 97

4-[(2-Ethyl-1,3-thiazol-4-yl)methoxy]aniline was obtained as a brown oil (yield 83%).

NMR(CDCl$_3$)δ: 1.40 (3H, t, J=7.2 Hz), 3.04 (2H, q, J=7.2 Hz), 3.44 (2H, brs), 5.08 (2H, d, J=0.9 Hz), 6.60-6.65 (2H, m), 6.79-6.84 (2H, m), 7.14 (1H, d, J=0.9 Hz).

REFERENCE EXAMPLE 98

4-(1,3,4-Oxadiazol-2-ylmethoxy)aniline was obtained as colorless crystals (yield 83%). Recrystallization thereof from ethyl acetate-hexane gave colorless prism crystals. melting point: 56-57° C.

REFERENCE EXAMPLE 99

4-[(4-Methyl-1,3-oxazol-2-yl)methyl]aniline was obtained as colorless crystals (yield 80%). Recrystallization thereof from ethyl acetate-hexane gave colorless prism crystals. melting point: 84-85° C.

REFERENCE EXAMPLE 100

4-[(5-Methyl-1,3,4-oxadiazol-2-yl)methoxy]aniline was obtained as a colorless oil (yield 87%).

NMR(CDCl$_3$)δ: 2.55 (3H, s), 3.49 (2H, brs), 5.13 (2H, s), 6.60-6.65 (2H, m), 6.80-6.86 (2H, m).

REFERENCE EXAMPLE 101

4-[(4-Ethyl-1,3-oxazol-2-yl)methyl]aniline was obtained as a colorless oil (yield-94%).

NMR(CDCl$_3$)δ: 1.20 (3H, t, J=7.5 Hz), 2.52 (2H, q, J=7.5 Hz), 3.63 (2H, brs), 3.96 (2H, s), 6.61-6.66 (2H, m), 7.06-7.09 (2H, m), 7.23 (1H, s).

REFERENCE EXAMPLE 102

4-[(2-Ethyl-1,3-thiazol-4-yl)methyl]aniline was obtained as a colorless oil (yield 92%).

NMR(CDCl$_3$)δ: 1.37 (3H, t, J=7.5 Hz), 3.01 (2H, q, J=7.5 Hz), 3.59 (2H, brs), 3.98 (2H, s), 6.56 (1H, s), 6.62-6.67 (2H, m), 7.04-7.08 (2H, m).

REFERENCE EXAMPLE 103

{4-[(2-Methyl-1,3-thiazol-4-yl)methyl]aniline was obtained as a colorless oil (yield 95%).

NMR(CDCl$_3$)δ: 2.68 (3H, s), 3.59 (2H, brs), 3.97 (2H, s), 6.56 (1H, s), 6.63-6.67 (2H, m), 7.04-7.07 (2H, m).

REFERENCE EXAMPLE 104

5-(4-Aminobenzyl)-3-ethyl-1,3,4-oxadiazol-2(3H)-one was obtained as colorless crystals (yield 71%). Recrystallization thereof from ethyl acetate-hexane gave colorless prism crystals. melting point: 88-89° C.

REFERENCE EXAMPLE 105

4-[(1-Methyl-1H-tetrazol-5-yl)methyl]aniline was obtained as pale-yellow crystals (yield 81%). Recrystallization thereof from ethyl acetate-hexane gave pale-yellow prism crystals. melting point: 104-105° C.

REFERENCE EXAMPLE 106

4-[(2-Methyl-2H-tetrazol-5-yl)methyl]aniline was obtained as a colorless oil (yield 94%).

NMR(CDCl$_3$)δ: 3.61 (2H, brs), 4.11 (2H, s), 4.28 (3H, s), 6.62-6.65 (2H, m), 7.08-7.13 (2H, m).

REFERENCE EXAMPLE 107

4-[(1-Ethyl-1H-tetrazol-5-yl)methyl]aniline was obtained as pale-yellow crystals (yield 78%). Recrystallization thereof from ethyl acetate-hexane gave pale-yellow prism crystals. melting point: 94-95° C.

REFERENCE EXAMPLE 108

4-[(2-Ethyl-2H-tetrazol-5-yl)methyl]aniline was obtained as a colorless oil (yield 98%).

NMR(CDCl$_3$)δ: 1.60 (3H, t, J=7.4 Hz), 3.61 (2H, brs), 4.12 (2H, s), 4.59 (2H, q, J=7.4 Hz), 6.60-6.65 (2H, m), 7.09-7.13 (2H, m).

REFERENCE EXAMPLE 109

6-Amino-1,3-benzoxazol-2(3H)-one was obtained as colorless crystals (yield 96%). Recrystallization thereof from ethyl acetate-hexane gave colorless prism crystals. melting point: 205-207° C. (decomposition).

REFERENCE EXAMPLE 110

4-(1,3-Benzoxazol-2-ylmethyl)aniline was obtained as colorless crystals (yield 78%). Recrystallization thereof from ethyl acetate-hexane gave colorless prism crystals. melting point: 105-106° C.

REFERENCE EXAMPLE 111

4-[(4,5-Dimethyl-1,3-thiazol-2-yl)methyl]aniline was obtained as colorless crystals (yield 82%). Recrystallization thereof from ethyl acetate-hexane gave colorless prism crystals. melting point: 91-92° C.

REFERENCE EXAMPLE 112

4-(4,5,6,7-Tetrahydro-1,3-benzothiazol-2-ylmethyl) aniline was obtained a pale-yellow crystals (yield 95%).

NMR(CDCl$_3$)δ: 1.80-1.85 (4H, m), 2.64-2.76 (4H, m), 3.62 (2H, brs), 4.12 (2H, s), 6.62-6.66 (2H, m), 7.08-7.20 (2H, m).

REFERENCE EXAMPLE 113

A mixture of 4'-fluoroacetophenone (4.00 g), N,N-dimethylformamide dimethylacetal (4.48 g) and N,N-dimethylformamide (4 ml) was stirred at 110° C. for 1 hr. The mixture was further stirred for 6 hrs. with removal of methanol at atmospheric pressure. After cooling to 25° C., ethyl acetate (48 ml) was added for dissolution. A solution separately prepared by dissolving p-toluenesulfonic acid monohydrate (6.06 g) in water (7 ml) and dropwise adding ethylhydrazine (1.91 g) was added at 25-30° C. over about 5 min. to the ethyl acetate solution mentioned earlier. The mixture was stirred at room temperature for 5.5 hrs. and partitioned by adding 5% aqueous sodium hydrogen carbonate. The aqueous layer was extracted with ethyl acetate. The organic layers were combined and washed successively with water and 10% brine.

The solvent was evaporated to quantitatively give 1-ethyl-5-(4-fluorophenyl)-1H-pyrazole as an oil.

NMR(CDCl$_3$)δ: 1.38-1.43 (3H, m), 4.09-4.17 (2H, m), 6.24 (1H, s), 7.14-7.17 (2H, m), 7.34-7.39 (2H, m), 7.53 (1H,s).

To a solution of the obtained oil in N,N-dimethylformamide (16 ml) was added dropwise phosphorus oxychloride (7.55 g) at 70-80° C. over about 2 hrs. The mixture was stirred at 80-85° C. for 1 hr and at 90-95° C. for 3 hrs. Water (16 ml) was added dropwise at 40° C. or below and a 4N aqueous potassium hydroxide solution was added dropwise at 30° C. or below to adjust to pH 7-8. The mixture was extracted with ethyl acetate and the organic layer was washed with water. The solvent was evaporated and the residue was subjected to silica gel column chromatography and eluted with ethyl acetate-hexane (1:5, v/v) to give 1-ethyl-5-(4-fluorophenyl)-1H-pyrazole-4-carbaldehyde (3.66 g, yield 58%) as an oil.

NMR (CDCl$_3$)δ: 1.39-1.45 (3H, m), 4.05-4.16 (2H, m), 7.26-7.29 (2H, m), 7.40-7.46 (2H, m), 8.05 (1H, s), 9.58 (1H, s).

REFERENCE EXAMPLE 114

A mixture of 4'-fluoroacetophenone (3.95 g), N,N-dimethylformamide dimethylacetal (4.43 g) and N,N-dimethylformamide (4 ml) was stirred at 110° C. for 1 hr. The mixture was further stirred for 6 hrs. with removal of methanol at atmospheric pressure. After cooling to 25° C., ethyl acetate (48 ml) was added for dissolution. A solution separately prepared by dissolving benzylhydrazine monohydrochloride (4.99 g) in water (5 ml) was added at 25-30° C. over about 5 min. to the ethyl acetate solution mentioned earlier. The mixture was stirred at room temperature for 17 hrs. and partitioned by adding 5% aqueous sodium hydrogen carbonate. The aqueous layer was extracted with ethyl acetate. The organic layers were combined and washed successively with water and 10% brine. The solvent was evaporated to quantitatively give 1-benzyl-5-(4-fluorophenyl)-1H-pyrazole as an oil.

NMR(CDCl$_3$)δ: 5.32 (2H, s), 6.32 (1H, d, J=1.84 Hz), 7.02-7.10 (4H, m), 7.24-7.31 (5H, m), 7.60 (1H, d, J=1.82 Hz).

To a solution of the obtained oil in N,N-dimethylformamide (16 ml) was added dropwise phosphorus oxychloride (7.45 g) at 70-80° C. over about 2 hrs. The mixture was stirred at 80-85° C. for 1 hr. and at 90-95° C. for 4 hrs. Water (16 ml) was added dropwise at 40° C. or below and a 4N aqueous potassium hydroxide solution was added dropwise at 30° C. or below to adjust to pH 7-8. The mixture was extracted with ethyl acetate and the organic layer was washed with water. The solvent was evaporated and the residue was subjected to silica gel column chromatography and eluted with ethyl acetate-hexane (1:5, v/v) to give 1-benzyl-5-(4-fluorophenyl)-1H-pyrazole-4-carbaldehyde (5.18 g, yield 65%) as an oil.

NMR(CDCl$_3$)δ: 5.24 (2H, s), 7.02-7.05 (2H, m), 7.15-7.21 (2H, m), 7.27-7.33 (5H, m), 8.10 (1H, s), 9.60 (1H, s).

REFERENCE EXAMPLE 115

A mixture of p-methylacetophenone (5.00 g), N,N-dimethylformamide dimethylacetal (6.66 g) and N,N-dimethylformamide (5 ml) was stirred at 110° C. for 1 hr. The mixture was further stirred for 10 hrs. with removal of methanol at atmospheric pressure. After cooling to 25° C., ethyl acetate (60 ml) was added for dissolution. A solution separately prepared by dissolving p-toluenesulfonic acid monohydrate (7.80 g) in water (7 ml) and dropwise adding methylhydrazine (1.89 g) was added at 25-30° C. over about 5 min. to the ethyl acetate solution mentioned earlier. The mixture was stirred at room temperature for 5 hrs. and partitioned by adding 5% aqueous sodium hydrogen carbonate. The aqueous layer was extracted with ethyl acetate. The organic layers were combined and washed successively with water and 10% brine. The solvent was evaporated to quantitatively give 1-methyl-5-(4-methylphenyl)-1H-pyrazole as an oil.

NMR(CDCl$_3$)δ: 2.37 (3H, s), 3.86 (3H, s), 6.26 (1H, d, J=1.88 Hz), 7.23-7.33 (4H, m), 7.49 (1H, d, J=1.86 Hz).

To a solution of the obtained oil in N,N-dimethylformamide (20 ml) was added dropwise phosphorus oxychloride (9.71 g) at 70-80° C. over about 2 hrs. The mixture was stirred at 80-85° C. for 1 hr. and at 90-95° C. for 3.5 hrs. Water (16 ml) was added dropwise at 40° C. or below and a 4N aqueous potassium hydroxide solution was added dropwise at 30° C. or below to adjust to pH 7-8. The mixture was extracted with ethyl acetate and the organic layer was washed with water. The solvent was evaporated and the residue was subjected to silica gel column chromatography and eluted with ethyl acetate-hexane (1:7-1:5, v/v) to give 1-methyl-5-(4-methylphenyl)-1H-pyrazole-4-carbaldehyde (4.52 g, yield 61%) as an oil.

NMR(CDCl$_3$)δ: 2.47 (3H, s), 3.82 (3H, s), 7.31-7.38 (4H, m), 8.03 (1H, s), 9.61 (1H, s).

REFERENCE EXAMPLE 116

A mixture of p-methoxyacetophenone (5.00 g), N,N-dimethylformamide dimethylacetal (5.95 g) and N,N-dimethylformamide (5 ml) was stirred at 110° C. for 1 hr. The mixture was further stirred for 10 hrs. with removal of methanol at atmospheric pressure. After cooling to 25° C., ethyl acetate (60 ml) was added for dissolution. A solution separately prepared by dissolving p-toluenesulfonic acid monohydrate (6.97 g) in water (7 ml) and dropwise adding methylhydrazine (1.69 g) was added at 25-30° C. over about 5 min. to the ethyl acetate solution mentioned earlier. The mixture was stirred at room temperature for 18 hrs. and partitioned by adding 5% aqueous sodium hydrogen carbonate. The aqueous layer was extracted with ethyl acetate. The organic layers were combined and washed successively with water and 10% brine. The solvent was evaporated to quantitatively give 5-(4-methoxyphenyl)-1-methyl-1H-pyrazole as an oil.

NMR(CDCl$_3$)δ: 3.85 (3H, s), 3.87 (3H, s), 6.25 (1H, s), 6.97-7.00 (2H, m), 7.33-7.36 (2H, m), 7.49 (1H, s).

To a solution of the obtained oil in N,N-dimethylformamide (20 ml) was added dropwise phosphorus oxychloride (8.55 g) at 70-80° C. over about 2 hrs. The mixture was stirred at 80-85° C. for 1 hr. and at 90-95° C. for 3 hrs. Water (20 ml) was added dropwise at 40° C. or below and a 4N aqueous potassium hydroxide solution was added dropwise at 30° C. or below to adjust to pH 7-8. The mixture was extracted with ethyl acetate and the organic layer was washed with water. The solvent was evaporated and the residue was subjected to silica gel column chromatography and eluted with ethyl acetate-hexane (1:7-1:4, v/v) to give 5-(4-methoxyphenyl)-1-methyl-1H-pyrazole-4-carbaldehyde (4.05 g, yield 56%) as an oil.

NMR (CDCl$_3$)δ: 3.81 (3H, s), 3.89 (3H, s), 7.04-7.08 (2H, m), 7.33-7.38 (2H, m), 8.02 (1H, s), 9.61 (1H, s).

REFERENCE EXAMPLE 117

A mixture of 4'-fluoroacetophenone (10.00 g), N,N-dimethylformamide dimethylacetal (11.21 g) and N,N-dimethylformamide (10 mL) was stirred at 110° C. for 1 hr. The mixture was further stirred for 8 hrs. with removal of methanol at atmospheric pressure. After cooling to 25-30° C., ethyl acetate (120 mL) was added for dissolution. A solution separately prepared by suspending p-toluenesulfonic acid monohydrate (15.1 g) in water (3 mL) and dropwise adding a 35% aqueous methylhydrazine solution (10.48 g) at 25° C. or below was added at an internal temperature of 25° C. over about 10 min. to the ethyl acetate solution mentioned earlier. The mixture was stirred at room temperature for 4 hrs., 5% aqueous sodium hydrogen carbonate was added and the mixture was extracted with ethyl acetate. The organic layer was washed successively with water and 5% brine. The solvent was evaporated to quantitatively give 5-(4-fluorophenyl)-1-methyl-1H-pyrazole as an oil.

NMR(CDCl$_3$)δ: 3.86 (3H, s), 6.27 (1H, s), 7.11-7.18 (2H, m), 7.36-7.41 (2H, m), 7.50 (1H, s).

To a solution of the obtained oil in dimethylformamide (40 mL) was added dropwise phosphorus oxychloride (18.87 g) at 70-80° C. over about 3 hrs. The mixture was stirred at 80° C. for 1 hr and at 90° C. for 4 hrs. Water (20 mL) was added dropwise at 40° C. or below and a 4N aqueous potassium hydroxide solution was added dropwise at an internal temperature of 30° C. or below to adjust to pH 7.5-8.0. Water (28 mL) was added dropwise and the mixture was stirred at 25° C. for 1 hr. The precipitated crystals were collected by filtration and washed with 20% ethanol. The obtained crystals were recrystallized from ethanol-water to give 5-(4-fluorophenyl)-1-methyl-1H-pyrazole-4-carbaldehyde (11.01 g, yield 74%).

NMR(CDCl$_3$)δ: 3.80 (3H, s), 7.22-7.28 (2H, m), 7.39-7.44 (2H, m), 8.03 (1H, s), 9.61 (1H, s).

REFERENCE EXAMPLE 118

To a mixture of 5-(4-fluorophenyl)-1-methyl-1H-pyrazole-4-carbaldehyde (3.00 g), malonic acid (1.99 g) and bis(2-methoxyethyl) ether (9 mL) was added dropwise piperidine (1.89 mL) over about 10 min. The mixture was stirred at 90-95° C. for 1 hr. and further at 105-110° C. for 4 hrs. After cooling to 25° C., toluene (12 mL) and 1N aqueous sodium hydroxide solution (15 mL) were added and the mixture was stirred. The aqueous layer was separated and the organic layer was extracted with 1N aqueous sodium hydroxide solution (6 mL). The aqueous layers were combined and washed with toluene. The layers were adjusted to pH 3.5-4.0 with 2N hydrochloric acid at 20-30° C. and water (9 mL) was added dropwise. After stirring at 25° C. for 1 hr., the precipitated crystals were collected by filtration and washed with 20% ethanol to give (2E)-3-[5-(4-fluorophenyl)-1-methyl-1H-pyrazol-4-yl]acrylic acid (3.24 g, yield 90%).

NMR(DMSO-d$_6$)δ: 3.73 (3H, s), 6.25 (1H, d, J=15.9 Hz), 7.14 (1H, d, J=15.9 Hz), 7.41-7.56 (4H, m), 8.09 (1H, s), 12.11 (1H, br).

REFERENCE EXAMPLE 119

A mixture of ethyl 3-(3-furyl)-3-oxopropionate (7.8 g) and N,N-dimethylformamide dimethylacetal (6.15 g) was stirred with heating under reflux for 1 hr. The reaction mixture was concentrated, and methylhydrazine (5.92 g) and ethanol (50 mL) were added. The mixture was stirred with heating under reflux for 30 min. The reaction mixture was concentrated, water was added to the residue, and the mixture was extracted with ethyl acetate. The organic layer was washed with water, dried over anhydrous magnesium sulfate and concentrated. The residue was subjected to silica gel column chromatography to give a pale-red oil (7.55 g) from a fraction eluted with hexane-ethyl acetate (4:1, v/v). This pale-red oil was dissolved in tetrahydrofuran (250 mL) and lithium aluminum hydride (1.3 g) was carefully added at 0° C. and the mixture was stirred at 0° C. for 30 min. A 1N aqueous sodium hydroxide solution was carefully added to the reaction mixture until a solid ceased to precipitate, and after stirring at room temperature for 30 min., the mixture was filtered. The filtrate was concentrated to give a yellow oil (4.89 g). This yellow oil was dissolved in tetrahydrofuran (200 mL), to which activated manganese dioxide (10 g) was added, and the mixture was stirred at room temperature for 14 hrs. The reaction mixture was filtered. The filtrate was concentrated and the residue was subjected to silica gel column chromatography to give 5-(3-furyl)-1-methyl-1H-pyrazole-4-carbaldehyde (4.25 g) as crystals from a fraction eluted with hexane-ethyl acetate (2:1, v/v). Recrystallization thereof from ethyl acetate-hexane gave colorless prism crystals. melting point: 70-71° C.

From the fraction eluted after the aforementioned compound, 3-(3-furyl)-1-methyl-1H-pyrazole-4-carbaldehyde (0.60 g) was obtained as crystals. Recrystallization thereof from ethyl acetate-hexane gave colorless prism crystals. melting point: 77-78° C.

REFERENCE EXAMPLE 120

A mixture of 5-(3-furyl)-1-methyl-1H-pyrazole-4-carbaldehyde (900 mg), sodium hydride (60% in oil, 245 mg), ethyl diethylphosohonoacetate (1.26 g) and N,N-dimethylformamide (10 ml) was stirred at room temperature for 1 hr. The reaction mixture was poured into water, and extracted with ethyl acetate. The organic layer was washed with water, dried over anhydrous magnesium sulfate and concentrated. Recrystallization of the residue from ethyl acetate-hexane gave ethyl (2E)-3-[5-(3-furyl)-1-methyl-1H-pyrazol-4-yl]acrylate (866 mg, 69%) as colorless prism crystals. melting point: 82-83° C.

REFERENCE EXAMPLE 121

To a mixture of ethyl (2E)-3-[5-(3-furyl)-1-methyl-1H-pyrazol-4-yl]acrylate (800 mg), tetrahydrofuran (10 ml) and ethanol (10 ml) was added 2N aqueous sodium hydroxide solution (6.5 ml) and the mixture was stirred at 60° C. for 1 hr. 1N Hydrochloric acid was poured into the reaction mixture, and the precipitated solids were collected by filtration, washed with water and dried with airflow to give (2E)-3-[5-(3-furyl)-1-methyl-1H-pyrazol-4-yl]acrylic acid (703 mg, 99%) as crystals. Recrystallization thereof from ethyl acetate-hexane gave colorless prism crystals. melting point: 218-219° C.

REFERENCE EXAMPLE 122

A mixture of ethyl 3-oxo-3-(2-thienyl)propionate (10.3 g) and N,N-dimethylformamide dimethylacetal (7.28 g) was stirred with heating under reflux for 30 min. The reaction mixture was concentrated, and methylhydrazine (7.19 g) and ethanol (50 mL) were added. The mixture was stirred with heating under reflux for 30 min. The reaction mixture was concentrated, and water was poured into the residue. The mixture was extracted with ethyl acetate and the organic layer was washed with water, dried over anhydrous magnesium sulfate, and concentrated. The residue was subjected to silica gel column chromatography to give a pale-red oil (9.37 g) from a fraction eluted with hexane-ethyl acetate (4:1, v/v). This pale-red oil was dissolved in tetrahydrofuran (250 mL) and lithium aluminum hydride (1.5 g) was added carefully at 0° C. and the mixture was stirred at 0° C. for 30 min. A 1N aqueous sodium hydroxide solution was carefully added to the reaction mixture until a solid ceased to precipitate, and after stirring at room temperature for 30 min., filtrated. The filtrate was concentrated to give a yellow oil (6.53 g). This yellow oil was dissolved in tetrahydrofuran (250 mL). Activated manganese dioxide (15 g) was added and the mixture was stirred at room temperature for 14 hrs. The reaction mixture was filtrated. The filtrate was concentrated and the residue was subjected to silica gel column chromatography to give 1-methyl-5-(2-thienyl)-1H-pyrazole-4-carbaldehyde (3.10 g) as a pale-yellow oil from a fraction eluted with hexane-ethyl acetate (2:1, v/v).

NMR(CDCl$_3$)δ: 3.92 (3H, s), 7.20-7.30 (2H, m), 7.62 (1H, dd, J=5.1, 1.2 Hz), 8.03 (1H, s), 9.74 (1H, s).

From the fraction eluted after the aforementioned compound, 1-methyl-3-(2-thienyl)-1H-pyrazole-4-carbaldehyde (1.81 g) was obtained as crystals. Recrystallization thereof from ethyl acetate-hexane gave colorless prism crystals. melting point: 71-72° C.

REFERENCE EXAMPLE 123

A mixture of 1-methyl-5-(2-thienyl)-1H-pyrazole-4-carbaldehyde (2.0 g), sodium hydride (60% in oil, 0.5 g), ethyl diethylphosphonoacetate (2.57 g) and N,N-dimethylformamide (20 ml) was stirred at room temperature for 1 hr. The reaction mixture was poured into water and the mixture was extracted with ethyl acetate. The organic layer was washed with water, dried over anhydrous magnesium sulfate and concentrated.

Recrystallization of the residue from ethyl acetate-hexane gave ethyl (2E)-3-[1-methyl-5-(2-thienyl)-1H-pyrazol-4-yl] acrylate (2.09 g, 77%) as pale-yellow prism crystals. melting point: 73-74° C.

REFERENCE EXAMPLE 124

To a mixture of ethyl (2E)-3-[1-methyl-5-(2-thienyl)-1H-pyrazol-4-yl]acrylate (2.0 g) and methanol (20 ml) was added 2N aqueous sodium hydroxide solution (7.6 ml) and the mixture was stirred at 60° C. for 30 min. 1N Hydrochloric acid was poured into the reaction mixture, and the precipitated solids were collected by filtration, washed with water and dried with airflow to give (2E)-3-[1-methyl-5-(2-thienyl)-1H-pyrazol-4-yl]acrylic acid (1.69 g, 95%) as crystals. Recrystallization thereof from methanol-isopropyl ether gave colorless prism crystals. melting point: 210-212° C.

REFERENCE EXAMPLE 125

A mixture of ethyl 3-oxo-3-(3-pyridinyl)propionate (7.58 g) and N,N-dimethylformamide dimethylacetal (6.07 g) was stirred with heating under reflux for 30 min. The reaction mixture was concentrated and methylhydrazine (5.85 g) and methanol (50 mL) were added. The mixture was stirred with heating under reflux for 30 min. The reaction mixture was concentrated, and water was poured into the residue. The mixture was extracted with ethyl acetate. The organic layer was washed with water, dried over anhydrous magnesium sulfate, and concentrated. The residue was subjected to silica gel column chromatography to give methyl 1-methyl-5-(3-pyridinyl)-1H-pyrazole-4-carboxylate (1.15 g, 13%) as a pale-yellow oil from a fraction eluted with hexane-ethyl acetate (2:1, v/v).

NMR(CDCl$_3$)δ: 3.71 (3H, s), 3.78 (3H, s), 7.44-7.50 (1H, m), 7.76-7.82 (1H, m), 8.01 (1H, s), 8.64 (1H, s), 8.72-8.76 (1H, m).

REFERENCE EXAMPLE 126

To a mixture of methyl 1-methyl-5-(3-pyridinyl)-1H-pyrazole-4-carboxylate (1.1 g) and tetrahydrofuran (20 mL) was added carefully lithium aluminum hydride (192 mg) at 0° C. and the mixture was stirred at room temperature for 30 min. A 1N aqueous sodium hydroxide solution was carefully added to the reaction mixture until a solid ceased to precipitate, and after stirring at room temperature for 30 min., filtrated. The filtrate was concentrated to give a yellow oil (0.95 g). This yellow oil was dissolved in tetrahydrofuran (50 mL). Activated manganese dioxide (3 g) was added and the mixture was stirred at room temperature for 14 hrs. The reaction mixture was filtrated, and the filtrate was concentrated. Recrystallization of the residue from ethyl acetate-hexane gave 1-methyl-5-(3-pyridinyl)-1H-pyrazole-4-carbaldehyde (770 mg, 82%) as pale-yellow prism crystals. melting point: 118-119° C.

REFERENCE EXAMPLE 127

A mixture of 1-methyl-5-(3-pyridinyl)-1H-pyrazole-4-carbaldehyde (750 mg), sodium hydride (60% in oil, 176 mg), ethyl diethylphosphonoacetate (1.08 g) and N,N-dimethylformamide (8 ml) was stirred at room temperature for 1 hr. The reaction mixture was poured into water, and the mixture was extracted with ethyl acetate. The organic layer was washed with water, dried over anhydrous magnesium sulfate, and concentrated. Recrystallization of the residue from ethyl acetate-hexane gave ethyl (2E)-3-[1-methyl-5-(3-pyridinyl)-1H-pyrazol-4-yl]acrylate (770 mg, 75%) as pale-yellow prism crystals. melting point: 159-160° C.

REFERENCE EXAMPLE 128

To a mixture of ethyl (2E)-3-[1-methyl-5-(3-pyridinyl)-1H-pyrazol-4-yl]acrylate (700 mg) and methanol (5 ml) was added a 2N aqueous sodium hydroxide solution (2.7 ml) and the mixture was stirred at 40° C. for 14 hrs. A saturated aqueous citric acid solution was poured into the reaction mixture to adjust pH to 5, and the mixture was extracted with ethyl acetate. The organic layer was washed with water, dried over anhydrous magnesium sulfate, and concentrated. The residue was recrystallized from ethyl acetate-isopropyl ether to give (2E)-3-[1-methyl-5-(3-pyridinyl)-1H-pyrazol-4-yl] acrylic acid (296 mg, 47%) as pale-yellow prism crystals. melting point: 236-237° C.

REFERENCE EXAMPLE 129

A mixture of 1,5-dimethyl-1H-pyrazole-4-carbaldehyde (400 mg), sodium hydride (60% in oil, 155 mg), ethyl diethylphosphonoacetate (795 mg) and N,N-dimethylformamide (5 ml) was stirred at room temperature for 1 hr. The reaction mixture was poured into water, and the mixture was extracted with ethyl acetate. The organic layer was washed with water, dried over anhydrous magnesium sulfate, and concentrated. Recrystallization of the residue from ethyl acetate-hexane gave ethyl (2E)-3-(1,5-dimethyl-1H-pyrazol-4-yl)acrylate (304 mg, 49%) as colorless prism crystals. melting point: 82-83° C.

REFERENCE EXAMPLE 130

To a mixture of ethyl (2E)-3-(1,5-dimethyl-1H-pyrazol-4-yl)acrylate (380 mg) and methanol (20 ml) was added a 2N aqueous sodium hydroxide solution (2.0 ml), and the mixture was stirred at 60° C. for 14 hrs. 1N Hydrochloric acid was poured into the reaction mixture, and the mixture was extracted with ethyl acetate. The organic layer was washed with water, dried over anhydrous magnesium sulfate, and concentrated. Recrystallization of the residue from ethyl acetate-hexane gave (2E)-3-(1,5-dimethyl-1H-pyrazol-4-yl) acrylic acid (283 mg, 87%) as colorless prism crystals. melting point: 217-219° C.

REFERENCE EXAMPLE 131

A mixture of 1-methyl-1H-pyrazole-4-carbaldehyde (2.59 g), sodium hydride (60% in oil, 1.13 g), ethyl diethylphosphonoacetate (5.8 g) and N,N-dimethylformamide (50 ml) was stirred at room temperature for 2 hrs. The reaction mixture was poured into water, and the mixture was extracted with ethyl acetate. The organic layer was washed with water, dried over anhydrous magnesium sulfate, and concentrated. The residue was subjected to silica gel column chromatography to give ethyl (2E)-3-(1-methyl-1H-pyrazol-4-yl)acrylate (2.72 g, 64%) as crystals from a fraction eluted with hexane-ethyl acetate (1:1, v/v). Recrystallization thereof from ethyl acetate-hexane gave colorless prism crystals. melting point: 43-44° C.

REFERENCE EXAMPLE 132

To a mixture of ethyl (2E)-3-(1-methyl-1H-pyrazol-4-yl) acrylate (2.5 g), methanol (20 ml) and tetrahydrofuran (20 ml) was added a 2N aqueous sodium hydroxide solution (13.9 ml) and the mixture was stirred at 60° C. for 3 hrs. 1N Hydrochloric acid was poured into the reaction mixture, and the mixture was extracted with ethyl acetate. The organic layer was washed with water, dried over anhydrous magnesium sulfate, and concentrated to give (2E)-3-(1-methyl-1H-pyrazol-4-yl)acrylic acid (1.75 g, 83%) as an amorphous form.

NMR(CDCl$_3$)δ: 3.93 (3H, s), 6.16 (1H, d, J=15.8 Hz), 7.57 (1H, s), 7.65 (1H, d, J=15.8 Hz), 7.72 (1H, s).

REFERENCE EXAMPLE 133

A mixture of diethyl [3-(bromomethyl)benzyl]phosphonate (10 g), potassium phthalimide (5.77 g) and N,N-dimethylformamide (100 ml) was stirred at room temperature for 14 hrs. The reaction mixture was poured into water, and the mixture was extracted with ethyl acetate. The organic layer was washed with water, dried over anhydrous magnesium sulfate, and concentrated Recrystallization of the residue from ethyl acetate-hexane gave diethyl {3-[(1,3-dioxo-1,3-dihydro-2H-isoindol-2-yl)methyl]benzyl}phosphonate (9.40 g, 78%) as colorless prism crystals. melting point: 100-101° C.

REFERENCE EXAMPLE 134

A mixture of diethyl [2-(bromomethyl)benzyl]phosphonate (11.2 g), potassium phthalimide (6.46 g) and N,N-dimethylformamide (100 ml) was stirred at room temperature for 14 hrs. The reaction mixture was poured into water, and the mixture was extracted with ethyl acetate. The organic layer was ashed with water, dried over anhydrous magnesium sulfate, and concentrated. Recrystallization of the residue from ethyl acetate-hexane gave diethyl {2-[(1,3-dioxo-1,3-dihydro-2H-isoindol-2-yl)methyl]benzyl}phosphonate (11.3 g, 83%) as colorless prism crystals. melting point: 91-92° C.

REFERENCE EXAMPLE 135

A mixture of methyl 1H-1,2,4-triazole-3-carboxylate (7.06 g), 4-nitrobenzyl bromide (10 g), potassium carbonate (16.6 g) and N,N-dimethylformamide (60 ml) was stirred at room temperature for 4 hrs. The reaction mixture was poured into water, and the mixture was extracted with ethyl acetate. The organic layer was washed with water, dried over anhydrous magnesium sulfate, and concentrated. The residue was subjected to silica gel column chromatography to give methyl 1-(4-nitrobenzyl)-1H-1,2,4-triazole-5-carboxylate (1.50 g, 12%) as crystals from a fraction eluted with hexane-ethyl acetate (1:1, v/v). Recrystallization thereof from ethyl acetate-hexane gave colorless prism crystals. melting point: 126-130° C.

From the fraction eluted after the aforementioned compound, methyl 1-(4-nitrobenzyl)-1H-1,2,4-triazole-3-carboxylate (1.49 g, 12%) was obtained as crystals. Recrystallization thereof from ethyl acetate-hexane gave colorless prism crystals. melting point: 175-177° C.

REFERENCE EXAMPLE 136

A mixture of methyl 1-(4-nitrobenzyl)-1H-1,2,4-triazole-5-carboxylate (1.3 g), 10% palladium carbon (130 mg) and ethanol (200 ml) was stirred under a hydrogen atmosphere at room temperature for 2 hrs. Palladium carbon was removed from the reaction mixture by filtration, and the filtrate was concentrated. The residue was subjected to silica gel column chromatography to give methyl 1-(4-aminobenzyl)-1H-1,2,4-triazole-5-carboxylate (0.88 g, 76%) as crystals from a fraction eluted with hexane-ethyl acetate (1:2, v/v). Recrystallization thereof from ethyl acetate-isopropyl ether gave colorless prism crystals. melting point: 101-103° C.

REFERENCE EXAMPLE 137

A mixture of 1-(2-bromoethyl)-4-nitrobenzene (18.7 g), pyrazole (5.53 g) and potassium hydroxide (4.56 g) was stirred at 140° C. for 8 min. The reaction mixture was poured into water, and the mixture was extracted with ethyl acetate. The organic layer was washed with water, dried over anhydrous magnesium sulfate, and concentrated. The residue was subjected to silica gel column chromatography to give 1-[2-(4-nitrophenyl)ethyl]-1H-pyrazole (1.37 g, 8%) as crystals from a fraction eluted with hexane-ethyl acetate (1:2, v/v). Recrystallization thereof from ethyl acetate-hexane gave yellow prism crystals. melting point: 92-93° C.

REFERENCE EXAMPLE 138

A mixture of 1-[2-(4-nitrophenyl)ethyl]-1H-pyrazole (0.8 g), 10% palladium carbon (80 mg) and ethanol (200 ml) was stirred under a hydrogen atmosphere at room temperature for 6 hrs. Palladium carbon was removed from the reaction mixture by filtration, and the filtrate was concentrated. Recrystallization of the residue from ethyl acetate-hexane gave 1-[2-(4-aminophenyl)ethyl]-1H-pyrazole (520 mg, 75%) as colorless prism crystals. melting point: 73-74° C.

REFERENCE EXAMPLE 139

A mixture of 4-nitrobenzylamine hydrochloride (8.0 g), ethyl 4-chloro-4-oxobutanoate (10.47 g), saturated aqueous sodium hydrogen carbonate (100 ml) and ethyl acetate (100 ml) was stirred at room temperature for 2 hrs. The reaction mixture was extracted with ethyl acetate. The organic layer was washed with water, dried over anhydrous magnesium sulfate, and concentrated. Recrystallization of the residue from ethyl acetate-hexane gave ethyl 4-[(4-nitrobenzyl)amino]-4-oxobutanoate (10.3 g, 87%) as colorless prism crystals. melting point: 104-106° C.

REFERENCE EXAMPLE 140

A mixture of ethyl 4-[(4-nitrobenzyl)amino]-4-oxobutanoate (10 g), 10% palladium carbon (1 g) and ethanol (300 ml) was stirred under a hydrogen atmosphere at room temperature for 14 hrs. Palladium carbon was removed from the reaction mixture by filtration, and the filtrate was concentrated. Recrystallization of the residue from ethyl acetate-hexane gave ethyl 4-[(4-aminobenzyl)amino]-4-oxobutanoate (3.6 g, 40%) as colorless prism crystals. melting point: 62-64° C.

REFERENCE EXAMPLE 141

A mixture of 2-(4-nitrobenzyl)-2H-tetrazole (5 g), 10% palladium carbon (500 mg), ethanol (100 ml) and tetrahydrofuran (100 ml) was stirred under a hydrogen atmosphere at room temperature for 4 hrs. Palladium carbon was removed from the reaction mixture by filtration, and the filtrate was concentrated. Recrystallization of the residue from ethyl acetate-hexane gave 2-(4-aminobenzyl)-2H-tetrazole (2.83 g, 66%) as yellow prism crystals. melting point: 86-87° C.

REFERENCE EXAMPLE 142

A mixture of 1-(4-nitrobenzyl)-1H-tetrazole (5 g), 10% palladium carbon (500 mg), ethanol (100 ml) and tetrahydrofuran (100 ml) was stirred under a hydrogen atmosphere at room temperature for 4 hrs. Palladium carbon was removed from the reaction mixture by filtration, and the filtrate was concentrated. Recrystallization of the residue from ethyl acetate-hexane gave 1-(4-aminobenzyl)-1H-tetrazole (3.03 g, 71%) as yellow prism crystals. melting point: 138-140° C.

REFERENCE EXAMPLE 143

A mixture of [1-(4-nitrobenzyl)-1H-imidazol-2-yl]methanol (3.6 g), 10% palladium carbon (400 mg) and ethanol (50 ml) was stirred under a hydrogen atmosphere at room temperature for 4 hrs. Palladium carbon was removed from the reaction mixture by filtration, and the filtrate was concentrated. Recrystallization of the residue from ethyl acetate-hexane gave [1-(4-aminobenzyl)-1H-imidazol-2-yl]methanol (2.53 g, 95%) as colorless prism crystals. melting point: 125° C. (decomposition)

REFERENCE EXAMPLE 144

A mixture of 4-methyl-1H-imidazole (25.5 g), 4-nitrobenzyl bromide (56 g), potassium carbonate (86 g) and N,N-dimethylformamide (500 ml) was stirred at room temperature for 14 hrs. The reaction mixture was poured into water, and the mixture was extracted with ethyl acetate. The organic layer was washed with water, dried over anhydrous magnesium sulfate, and concentrated. The residue was subjected to silica gel column chromatography to give 5-methyl-1-(4-nitrobenzyl)-1H-imidazole (1.6 g, 3%) as crystals from a fraction eluted with methanol-ethyl acetate (1:20, v/v). Recrystallization thereof from ethyl acetate-isopropyl ether gave colorless prism crystals. melting point: 120-121° C.

From the fraction eluted before the aforementioned compound, a mixture (25 g, containing 4-methyl-1-(4-nitrobenzyl)-1H-imidazole by about 75%) of 4-methyl-1-(4-nitrobenzyl)-1H-imidazole and 5-methyl-1-(4-nitrobenzyl)-1H-imidazole was obtained.

REFERENCE EXAMPLE 145

A mixture of the mixture (25 g, containing 4-methyl-1-(4-nitrobenzyl)-1H-imidazole by about 75%) of 4-methyl-1-(4-nitrobenzyl)-1H-imidazole and 5-methyl-1-(4-nitrobenzyl)-1H-imidazole obtained in the above-mentioned Reference Example 144, 10% palladium carbon (3 g) and ethanol (500 ml) was stirred under a hydrogen atmosphere at room temperature for 14 hrs. Palladium carbon was removed from the reaction mixture by filtration, and the filtrate was concentrated. The residue was recrystallized from ethyl acetate to give 1-(4-aminobenzyl)-4-methyl-1H-imidazole (3.91 g) as colorless prism crystals. melting point: 141-142° C.

REFERENCE EXAMPLE 146

A mixture of 5-methyl-1-(4-nitrobenzyl)-1H-imidazole (1.4 g), 10% palladium carbon (200 mg) and ethanol (20 ml) was stirred under a hydrogen atmosphere at room temperature for 4 hrs. Palladium carbon was removed from the reaction mixture by filtration, and the filtrate was concentrated. Recrystallization of the residue from ethyl acetate-hexane gave 1-(4-aminobenzyl)-5-methyl-1H-imidazole (1.17 g, 97%) as colorless prism crystals. melting point: 124-125° C.

REFERENCE EXAMPLE 147

A mixture of 4-ethyl-1H-imidazole (2.46 g), 4-nitrobenzyl bromide (6.08 g), potassium carbonate (7.08 g) and N,N-dimethylformamide (50 ml) was stirred at room temperature for 14 hrs. The reaction mixture was poured into water, and the mixture was extracted with ethyl acetate. The organic layer was washed with water, dried over anhydrous magnesium sulfate, and concentrated. The residue was subjected to silica gel column chromatography to give 4-ethyl-1-(4-nitrobenzyl)-1H-imidazole (1.95 g) as a yellow oil from a fraction eluted with ethyl acetate-hexane (1:1, v/v). A mixture of 4-ethyl-1-(4-nitrobenzyl)-1H-imidazole (1.95 g), 10% palladium carbon (200 mg) and ethanol (50 ml) was stirred under a hydrogen atmosphere at room temperature for 4 hrs. Palladium carbon was removed from the reaction mixture by filtration, and the filtrate was concentrated. Recrystallization of the residue from ethyl acetate-hexane gave 1-(4-aminobenzyl)-5-methyl-1H-imidazole (1.44 g) as colorless prism crystals. melting point: 137-138° C.

REFERENCE EXAMPLE 148

A mixture of 5,6-dimethyl-1H-benzimidazole (5.0 g), 4-nitrobenzyl bromide (6.16 g), potassium carbonate (7.88 g) and N,N-dimethylformamide (60 ml) was stirred at 60° C. for 14 hrs. The reaction mixture was poured into water, and the mixture was extracted with ethyl acetate. The organic layer was washed with water, dried over anhydrous magnesium sulfate, and concentrated. The residue was subjected to silica gel column chromatography to give 5,6-dimethyl-1-(4-nitrobenzyl)-1H-benzimidazole (2.6 g, 32%) as crystals from a fraction eluted with methanol-ethyl acetate (1:20, v/v). Recrystallization thereof from ethyl acetate-hexane gave pale-red prism crystals. melting point: 175-177° C.

REFERENCE EXAMPLE 149

A mixture of 5,6-dimethyl-1-(4-nitrobenzyl)-1H-benzimidazole (2.5 g), 10% palladium carbon (300 mg), ethanol (150 ml) and tetrahydrofuran (150 ml) was stirred under a hydrogen atmosphere at room temperature for 4 hrs. Palladium carbon was removed from the reaction mixture by filtration, and the filtrate was concentrated. Recrystallization of the residue from ethyl acetate-methanol gave 1-(4-aminobenzyl)-5,6-dimethyl-1H-benzimidazole (1.88 g, 84%) as colorless prism crystals. melting point: 238-239° C.

REFERENCE EXAMPLE 150

A mixture of 1-(4-nitrobenzyl)-1H-indazole (9.25 g), 10% palladium carbon (1 g), ethanol (100 ml) and tetrahydrofuran (100 ml) was stirred under a hydrogen atmosphere at room temperature for 4 hrs. Palladium carbon was removed from the reaction mixture by filtration, and the filtrate was concentrated. Recrystallization of the residue from acetone-hexane gave 4-(1H-indazol-1-ylmethyl)aniline (6.77 g, 83%) as colorless prism crystals. melting point: 110-111° C.

REFERENCE EXAMPLE 151

A mixture of 2-(4-nitrobenzyl)-2H-1,2,3-benzotriazole (1.0 g), 10% palladium carbon (100 mg) and ethanol (20 ml) was stirred under a hydrogen atmosphere at room temperature for 4 hrs. Palladium carbon was removed from the reaction mixture by filtration, and the filtrate was concentrated. The residue was subjected to silica gel column chromatography to give 4-(2H-1,2,3-benzotriazol-2-ylmethyl)aniline (313 mg, 35%) as crystals from a fraction eluted with ethyl acetate-hexane (1:1, v/v). Recrystallization thereof from ethyl acetate-hexane gave colorless prism crystals. melting point: 229-230° C.

REFERENCE EXAMPLE 152

To a mixture of 5-(4-fluorophenyl)-1-methyl-1H-pyrazole-4-carbaldehyde (4.50 g) and tetrahydrofuran (50 ml) was added dropwise methyl magnesium bromide (1 mol/L tetrahydrofuran solution, 25 ml) at 0° C. and the mixture was stirred at 0° C. for 30 min. The reaction mixture was poured into a saturated aqueous ammonium chloride solution, and the mixture was extracted with ethyl acetate. The ethyl acetate layer was dried over anhydrous magnesium sulfate and concentrated and the residue was dissolved in acetone (60 ml). This solution was cooled to 0° C. and the Jones reagent (prepared by the method described in *New Courses in Experiment Chemistry*, Vol. 15, p. 151, published by Maruzen Company, Limited) was added dropwise until the red color of the reagent no longer disappeared. Isopropyl alcohol and water were added to the reaction mixture, and the mixture was extracted with ethyl acetate. The ethyl acetate layer was dried over anhydrous magnesium sulfate and concentrated. The residue was dissolved in N,N-dimethylformamide (50 ml). To this solution were added ethyl diethylphosphonoacetate (6.0 g) and sodium hydride (60% in oil, 1.0 g) and the mixture was stirred at 80° C. for 12 hrs. The reaction mixture was poured into water, and the mixture was extracted with ethyl acetate. The ethyl acetate layer was dried over anhydrous magnesium sulfate, concentrated and the residue was purified by silica gel column chromatography to give a yellow oil from a fraction eluted with ethyl acetate-hexane (1:1, v/v). This yellow oil was dissolved in a mixture of acetic acid-37% hydrochloric acid (20-20 ml) and the mixture was stirred at 120° C. for 3 hrs. The reaction mixture was concentrated and poured into water. The precipitated crystals were collected by filtration, washed with water and dried to give (2E)-3-[5-(4-fluorophenyl)-1-methyl-1H-pyrazol-4-yl]but-2-enoic acid. (4.60 g, 80%) as colorless crystals. Recrystallization thereof from ethyl acetate-hexane gave colorless prism crystals. melting point: 123-124° C.

REFERENCE EXAMPLE 153

According to the method described in Reference Example 44, 3-[5-(4-fluorophenyl)-1-methyl-1H-pyrazol-4-yl]butanoic acid was obtained from (2E)-3-[5-(4-fluorophenyl)-1-methyl-1H-pyrazol-4-yl]but-2-enoic acid in a yield of 85%. Colorless prism crystals. melting point: 90-91° C. (recrystallized from ethyl acetate-hexane).

REFERENCE EXAMPLE 154

To a mixture of ethyl 1,5-diphenyl-1H-pyrazole-4-carboxylate (14.9 g) and tetrahydrofuran (250 ml) was added dropwise diisobutylaluminum hydride (1 mol/l toluene solution, 120 ml) under ice-cooling. The reaction mixture was stirred at room temperature for 1 hr. and poured into a 1N aqueous hydrochloric acid solution. The mixture was extracted with ethyl acetate. The ethyl acetate layer was washed successively with a 1N aqueous hydrochloric acid solution and saturated brine, dried over anhydrous magnesium sulfate, and concentrated to give (1,5-diphenyl-1H-pyrazol-4-yl)methanol (12.6 g, 99%) as colorless crystals. Recrystallization thereof from ethyl acetate-hexane gave colorless prism crystals. melting point: 147-148° C.

REFERENCE EXAMPLE 155

To a mixture of (1,5-diphenyl-1H-pyrazol-4-yl)methanol (11.78 g), triethylamine (10 ml) and ethyl acetate (300 ml) was added dropwise methanesulfonyl chloride (4.5 ml) at 0° C. The mixture was stirred at room temperature for 1 hr. and the ethyl acetate layer was washed successively with water and saturated brine, dried over anhydrous magnesium sulfate, and concentrated to give an oil. This oil was dissolved in N,N-dimethylformamide (100 ml) and the resulting solution was added dropwise to a solution of sodium diethyl malonate in N,N-dimethylformamide (prepared using diethyl malonate 20.33 g, sodium hydride (60% in oil, 4.88 g) and N,N-dimethylformamide 200 ml) at 0° C. The mixture was stirred at room temperature for 5 hrs., and poured into a 1N aqueous hydrochloric acid solution. The mixture was extracted with ethyl acetate. The ethyl acetate layer was washed successively with a 1N aqueous hydrochloric acid solution and saturated brine, dried over anhydrous magnesium sulfate, and concentrated to give an oil. A mixture of this oil, a 6N aqueous hydrochloric acid solution (100 ml) and acetic acid (50 ml) was heated under reflux for 5 hrs. The reaction mixture was cooled, concentrated and poured into water. The precipitated crystals were collected by filtration, washed with water, and dried to give 3-(1,5-diphenyl-1H-pyrazol-4-yl)propionic acid. yield: 68%. colorless needle crystals. melting point: 159-160° C. (recrystallized from acetone-hexane).

REFERENCE EXAMPLE 156

A mixture of 5-(4-chlorophenyl)-1-methyl-1H-pyrazole-4-carbaldehyde (6.68 g), ethyl diethylphosphonoacetate (7.47 g), sodium hydride (60% in oil, 1.30 g) and N,N-dimethylformamide (100 ml) was stirred at room temperature for 1 hr. The reaction mixture was poured into water, and the mixture was extracted with ethyl acetate. The organic layer was washed successively with water and saturated brine, dried over anhydrous magnesium sulfate, and concentrated to give colorless crystals (8.37 g). A mixture of the crystals (4.55 g), platinum dioxide (228 mg) and ethanol (50 ml) was stirred under a hydrogen atmosphere at atmospheric pressure at room temperature for 2 hrs. The catalyst was removed by filtration and the filtrate was concentrated and purified by silica gel column chromatography to give ethyl 3-[5-(4-chlorophenyl)-1-methyl-1H-pyrazol-4-yl]propionate (4.70 g) as a colorless oil from a fraction eluted with hexane-ethyl acetate (1:2, v/v).

Elemental analysis: Calculated ($C_{15}H_{17}ClN_2O_2$) C, 61.54; H, 5.85; N, 9.57. Found C, 61.28; H, 5.95; N, 9.21.

REFERENCE EXAMPLE 157

A mixture of ethyl 3-[5-(4-chlorophenyl)-1-methyl-1H-pyrazol-4-yl]propionate (2.35 g), a 1N aqueous sodium hydroxide solution (16 ml), tetrahydrofuran (30 ml) and ethanol (30 ml) was stirred at room temperature for 3 hrs. The reaction mixture was poured into an aqueous potassium hydrogen sulfate solution, and the mixture was extracted with ethyl acetate. The ethyl acetate layer was washed with saturated brine, dried over anhydrous magnesium sulfate, and concentrated to give: 3-[5-(4-chlorophenyl)-1-methyl-1H-pyrazol-4-yl]propionic acid (1.46 g, 69%) as a colorless powder. melting point: 138-140° C. (recrystallized from acetone-hexane).

REFERENCE EXAMPLE 158

Potassium bis(trimethylsilyl)amide (20% toluene solution, 3.05 g) was added to a mixture of bis(2,2,2-trifluoroethyl)(methoxycarbonylmethyl)phosphonate (973 mg), 18-crown-6 (4.04 g) and tetrahydrofuran (50 mL) at −78° C. Furthermore, 5-(4-fluorophenyl)-1-methyl-1H-pyrazole-4-carbaldehyde (312 mg) was added and the mixture was stirred overnight while allowing to warm from −78° C. to room temperature. Saturated aqueous ammonium chloride was added to the reaction mixture and the mixture was extracted with ethyl acetate. The organic layer was washed successively with 1N hydrochloric acid, water and saturated brine, dried over anhydrous magnesium sulfate, and concentrated. The residue was subjected to silica gel column chromatography to give methyl (2Z)-3-[5-(4-fluorophenyl)-1-methyl-1H-pyrazol-4-yl]acrylate as crystals (0.35 g, yield 95%) from a fraction eluted with hexane-ethyl acetate (4:1-1:1, v/v) (recrystallized from ethyl acetate-hexane). melting point: 108-109° C.

REFERENCE EXAMPLE 159

A mixture of 1-(4-fluorophenyl)-2-propanone (10.0 g) and N,N-dimethylformamide dimethylacetal (8.00 g) was stirred at 120° C. for 2 hrs. The reaction mixture was cooled, and hexane was added to the precipitated solids, which were collected by filtration to give 4-(dimethylamino)-3-(4-fluorophenyl)but-3-en-2-one (11.3 g, yield 83%) as a pale-yellow solid.

NMR(CDCl$_3$)δ: 1.94 (3H, s), 2.70 (6H, broad s), 6.95-7.05 (2H, m), 7.1-7.2 (2H, m), 7.58 (1H, s).

REFERENCE EXAMPLE 160

A mixture of 4-(dimethylamino)-3-(4-fluorophenyl)but-3-en-2-one (10.36 g), methylhydrazine (2.31 g) and ethanol (50 ml) was stirred for 1 hr. with heating under reflux. The reaction mixture was concentrated, poured into water and extracted with ethyl acetate. The organic layer was washed with saturated brine, dried over anhydrous magnesium sulfate and concentrated to give a yellow oil. This yellow oil was dissolved in carbon tetrachloride (100 ml), and N-bromosuccinimide (9.79 g) and 2,2'-azobis(isobutyronitrile) (50 mg) were added. The mixture was stirred for 5 hrs. with heating under reflux. The reaction mixture was concentrated, poured into water and extracted with ethyl acetate. The organic layer was washed with saturated brine, dried over anhydrous magnesium sulfate and concentrated to give a yellow oil. This yellow oil was dissolved in methanol (100 ml), and sodium formate (10.0 g) was added. The mixture was stirred for 16 hrs. with heating under reflux. The reaction mixture was concentrated, poured into water, and extracted with ethyl acetate. The organic layer was washed with saturated brine, dried over anhydrous magnesium sulfate and concentrated. The residue was purified by silica gel column chromatography and eluted with hexane-ethyl acetate (100:0-0:100, v/v) to separate the following two kinds of compounds.

[4-(4-Fluorophenyl)-1-methyl-1H-pyrazol-5-yl]methanol: (311 mg). pale-yellow solid.

NMR(CDCl$_3$)δ: 3.99 (3H, s), 4.74(2H, s), 7.05-7.15 (2H, m), 7.3-7.4 (2H, m), 7.53 (1H, s).

[4-(4-Fluorophenyl)-1-methyl-1H-pyrazol-3-yl]methanol: (60 mg). pale-yellow solid.

NMR(CDCl$_3$)δ: 3.92 (3H, s), 4.72(2H, s), 7.0-7.1 (2H, m), 7.4-7.5 (2H, m), 7.45 (1H, s).

REFERENCE EXAMPLE 161

A mixture of [4-(4-fluorophenyl)-1-methyl-1H-pyrazol-5-yl]methanol (250 mg), activated manganese dioxide (1.0 g) and tetrahydrofuran (10 ml) was stirred at room temperature for 3 hrs. The reaction mixture was filtered, and the organic layer was concentrated to give 4-(4-fluorophenyl)-1-methyl-1H-pyrazole-5-carbaldehyde (172 mg, yield 70%) as pale-yellow crystals.

NMR(CDCl$_3$)δ: 4.23 (3H, s), 7.1-7.2 (2H, m), 7.35-7.45 (2H, m), 7.59 (1H, s), 9.84 (1H, s).

REFERENCE EXAMPLE 162

4-(4-fluorophenyl)-1-methyl-1H-pyrazole-3-carbaldehyde

According to the method exemplified in Reference Example 161, the title compound was synthesized from [4-(4-fluorophenyl)-1-methyl-1H-pyrazol-3-yl]methanol.

yield: 80%. Pale-yellow solid.

NMR(CDCl$_3$)δ: 4.05 (3H, s), 7.05-7.15 (2H, m), 7.52 (1H, s), 7.55-7.6 (2H, m), 10.04 (1H, s).

REFERENCE EXAMPLE 163

A mixture of 4-(4-fluorophenyl)-1,2,3-thiadiazole-5-carbaldehyde (180 mg), ethyl diethylphosphonoacetate (450 mg), sodium hydride (60% in oil, 40 mg) and N,N-dimethylformamide (3 ml) was stirred at room temperature for 2 hrs. The reaction mixture was poured into a 1N aqueous hydrochloric acid solution and the mixture was extracted with ethyl acetate. The ethyl acetate layer was concentrated, and a 6N aqueous hydrochloric acid solution (3 ml) and acetic acid (3 ml) were added to the residue. The mixture was stirred for 3 hrs. with heating under reflux. The reaction mixture was concentrated and poured into water. The precipitated solids were collected by filtration, washed with water and dried to give (2E)-3-[4-(4-fluorophenyl)-1,2,3-thiadiazol-5-yl] acrylic acid (130 mg, yield 60%) as a pale-yellow solid.

NMR(DMSO-$d_6$)δ: 6.69(1H, d, J=15.5 Hz), 7.45-7.6 (3H, m), 7.75-7.85 (2H, m).

EXAMPLE 1

A mixture of dimethyl 4-aminobenzylphosphonate (0.86 g), (2E)-3-[5-(4-fluorophenyl)-1-methyl-1H-pyrazol-4-yl] acrylic acid (0.74 g), 1-hydroxy-1H-1,2,3-benzotriazole hydrate (0.61 g), 1-ethyl-3-(3-dimethylaminopropyl)carbodiimide hydrochloride (0.77 g) and N,N-dimethylfomamide (8 ml) was stirred at room temperature overnight. The reaction mixture was poured into a 0.5N aqueous hydrochloric acid solution and extracted with ethyl acetate. The ethyl acetate layer was washed with saturated aqueous sodium hydrogen carbonate, and then with saturated brine, dried (MgSO$_4$) and concentrated. The obtained solid was recrystallized from acetone-water to give (2E)-N-[4-(dimethylphosphonomethyl)phenyl]-3-[5-(4-fluorophenyl)-1-methyl-1H-pyrazol-4-yl]acrylamide (0.86 g, yield 65%) as colorless prism crystals. melting point: 209-210° C.

In the similar manner as in Example 1, the compounds described in Examples 2-33, 36-50, 54-62, 65, 66, 69-77 and 80-82 were produced.

EXAMPLE 2

(2E)-N-[4-(Diethylphosphonomethyl)phenyl]-3-[5-(4-fluorophenyl)-1-methyl-1H-pyrazol-4-yl]acrylamide yield: 68%. Colorless prism crystals. melting point: 208-209° C. (recrystallized from acetone-isopropyl ether).

EXAMPLE 3

(2E)-3-[5-(4-Fluorophenyl)-1-methyl-1H-pyrazol-4-yl]-N-{4-[(2-oxide-1,3,2-dioxaphosphinan-2-yl)methyl]phenyl}acrylamide yield: 25%. Colorless prism crystals. melting point: 223-227° C. (recrystallized from acetone-isopropyl ether).

EXAMPLE 4

(2E)-N-[4-(Dimethylphosphonomethyl)phenyl]-3-[5-(4-methoxyphenyl)-1-methyl-1H-pyrazol-4-yl]acrylamide yield: 55%. Colorless prism crystals. melting point: 199-200° C. (recrystallized from ethyl acetate-hexane).

EXAMPLE 5

(2E)-N-[4-(Diethylphosphonomethyl)phenyl]-3-[5-(4-methoxyphenyl)-1-methyl-1H-pyrazol-4-yl]acrylamide yield: 57%. Colorless prism crystals. melting point: 199-200° C. (recrystallized from ethyl acetate-hexane).

EXAMPLE 6

(2E)-3-[5-(3-Chlorophenyl)-1-methyl-1H-pyrazol-4-yl]-N-[4-(dimethylphosphonomethyl)phenyl]acrylamide yield: 39%. Colorless prism crystals. melting point: 248-249° C. (recrystallized from ethyl acetate-hexane).

EXAMPLE 7

(2E)-3-[5-(3-Chlorophenyl)-1-methyl-1H-pyrazol-4-yl]-N-[4-(diethylphosphonomethyl)phenyl]acrylamide yield: 51%. Colorless prism crystals. melting point: 214-216° C. (recrystallized from ethyl acetate-hexane).

EXAMPLE 8

(2E)-3-[5-(4-Chlorophenyl)-1-methyl-1H-pyrazol-4-yl]-N-[4-(dimethylphosphonomethyl)phenyl]acrylamide yield: 61%. Colorless prism crystals. melting point: 209-210° C. (recrystallized from ethyl acetate-hexane).

EXAMPLE 9

(2E)-3-[5-(4-Chlorophenyl)-1-methyl-1H-pyrazol-4-yl]-N-[4-(diethylphosphonomethyl)phenyl]acrylamide yield: 45%. Colorless prism crystals. melting point: 217-218° C. (recrystallized from ethyl acetate-hexane).

EXAMPLE 10

(2E)-N-[4-(Dimethylphosphonomethyl)phenyl]-3-(1-methyl-5-phenyl-1H-pyrazol-4-yl)acrylamide yield: 20%. Colorless prism crystals. melting point: 219-220° C. (recrystallized from ethyl acetate-hexane).

EXAMPLE 11

(2E)-N-[4-(Diethylphosphonomethyl)phenyl]-3-(1-methyl-5-phenyl-1H-pyrazol-4-yl)acrylamide yield: 61%. Colorless prism crystals. melting point: 239-240° C. (recrystallized from ethyl acetate-hexane).

EXAMPLE 12

(2E)-N-[4-(Dimethylphosphonomethyl)phenyl]-3-{1-methyl-5-[4-(trifluoromethyl)phenyl]-1H-pyrazol-4-yl}acrylamide yield: 49%. Colorless prism crystals. melting point: 212-213° C. (recrystallized from ethyl acetate-hexane).

EXAMPLE 13

(2E)-N-[4-(Diethylphosphonomethyl)phenyl]-3-{1-methyl-5-[4-(trifluoromethyl)phenyl]-1H-pyrazol-4-yl}acrylamide yield: 58%. Colorless prism crystals. melting point: 200-201° C. (recrystallized from ethyl acetate-hexane).

EXAMPLE 14

(2E)-N-[4-(Dimethylphosphonomethyl)phenyl]-3-[5-(2-fluorophenyl)-1-methyl-1H-pyrazol-4-yl]acrylamide yield: 67%. Colorless prism crystals. melting point: 220-221° C. (recrystallized from ethyl acetate-hexane).

EXAMPLE 15

(2E)-N-[4-(Diethylphosphonomethyl)phenyl]-3-[5-(2-fluorophenyl)-1-methyl-1H-pyrazol-4-yl]acrylamide yield: 43%. Colorless prism crystals. melting point: 238-240° C. (recrystallized from ethyl acetate-hexane).

EXAMPLE 16

(2E)-3-[5-(4-Bromophenyl)-1-methyl-1H-pyrazol-4-yl]-N-[4-(dimethylphosphonomethyl)phenyl]acrylamide yield: 57%. Colorless prism crystals. melting point: 212-214° C. (recrystallized from ethyl acetate-hexane).

EXAMPLE 17

(2E)-3-[5-(4-Bromophenyl)-1-methyl-1H-pyrazol-4-yl]-N-[4-(diethylphosphonomethyl)phenyl]acrylamide yield: 52%. Colorless prism crystals. melting point: 229-231° C. (recrystallized from ethyl acetate-hexane).

EXAMPLE 18

(2E)-N-[4-(Dimethylphosphonomethyl)phenyl]-3-[1-methyl-5-(1-naphthyl)-1H-pyrazol-4-yl]acrylamide yield: 30%. Colorless prism crystals. melting point: 207-209° C. (recrystallized from ethyl acetate-hexane).

EXAMPLE 19

(2E)-N-[4-(Diethylphosphonomethyl)phenyl]-3-[1-methyl-5-(1-naphthyl)-1H-pyrazol-4-yl]acrylamide yield: 33%. Colorless prism crystals. melting point: 229-231° C. (recrystallized from ethyl acetate-hexane).

EXAMPLE 20

(2E)-N-[4-(Dimethylphosphonomethyl)phenyl]-3-[5-(3-fluorophenyl)-1-methyl-1H-pyrazol-4-yl]acrylamide yield: 35%. Colorless prism crystals. melting point: 224-226° C. (recrystallized from ethyl acetate-hexane).

EXAMPLE 21

(2E)-N-[4-(Diethylphosphonomethyl)phenyl]-3-[5-(3-fluorophenyl)-1-methyl-1H-pyrazol-4-yl]acrylamide yield: 56%. Colorless prism crystals. melting point: 205-206° C. (recrystallized from ethyl acetate-hexane).

EXAMPLE 22

(2E)-N-[4-(Dimethylphosphonomethyl)phenyl]-3-[1-methyl-5-(4-methylphenyl)-1H-pyrazol-4-yl]acrylamide yield: 58%. Colorless prism crystals. melting point: 207-209° C. (recrystallized from ethyl acetate-hexane).

EXAMPLE 23

(2E)-N-[4-(Diethylphosphonomethyl)phenyl]-3-[1-methyl-5-(4-methylphenyl)-1H-pyrazol-4-yl]acrylamide yield: 57%. Colorless prism crystals. melting point: 243-245° C. (recrystallized from ethyl acetate-hexane).

EXAMPLE 24

(2E)-3-[5-(4-Fluorophenyl)-1-methyl-1H-pyrazol-4-yl]-N-{4-[(5-methyl-2-oxide-1,3,2-dioxaphosphinan-2-yl)methyl]phenyl}acrylamide yield: 36%. Colorless prism crystals. melting point: 253-254° C. (recrystallized from ethyl acetate-hexane).

EXAMPLE 25

(2E)-N-{4-[(5,5-Dimethyl-2-oxide-1,3,2-dioxaphosphinan-2-yl)methyl]phenyl}-3-[5-(4-fluorophenyl)-1-methyl-1H-pyrazol-4-yl]acrylamide yield: 69%. Colorless prism crystals. melting point: 271-273° C. (recrystallized from ethyl acetate-hexane).

EXAMPLE 26

(2E)-N-{4-[(4,6-Dimethyl-2-oxide-1,3,2-dioxaphosphinan-2-yl)methyl]phenyl}-3-[5-(4-fluorophenyl)-1-methyl-1H-pyrazol-4-yl]acrylamide yield: 62%. Colorless prism crystals. melting point: 250-252° C. (recrystallized from ethyl acetate-hexane).

EXAMPLE 27

(2E)-N-{4-[(5-Butyl-5-ethyl-2-oxide-1,3,2-dioxaphosphinan-2-yl)methyl]phenyl}-3-[5-(4-fluorophenyl)-1-methyl-1H-pyrazol-4-yl]acrylamide yield: 53%. Colorless prism crystals. melting point: 220-222° C. (recrystallized from ethyl acetate-hexane).

EXAMPLE 28

(2E)-N-[3-(Diethylphosphonomethyl)phenyl]-3-[5-(4-fluorophenyl)-1-methyl-1H-pyrazol-4-yl]acrylamide yield: 76%. Colorless prism crystals. melting point: 170-172° C. (recrystallized from ethyl acetate-hexane).

EXAMPLE 29

(2E)-N-[2-(Diethylphosphonomethyl)phenyl]-3-[5-(4-fluorophenyl)-1-methyl-1H-pyrazol-4-yl]acrylamide yield: 65%. Colorless prism crystals. melting point: 168-169° C. (recrystallized from ethyl acetate-hexane).

EXAMPLE 30

(2E)-N-[4-(Dibutylphosphonomethyl)phenyl]-3-[5-(4-fluorophenyl)-1-methyl-1H-pyrazol-4-yl]acrylamide yield: 50%. Colorless solid.
NMR(CDCl$_3$) δ: 0.89 (6H, t, J=7 Hz), 1.3-1.4 (4H, m), 1.5-1.65 (4H, m), 3.11 (2H, d, J=21.5 Hz), 3.78 (3H, s), 3.9-4.00 (4H, m), 6.35 (1H, d, J=15 Hz), 7.18-7.38 (6H, m), 7.40 (1H, d, J=15 Hz), 7.51 (2H, d, J=8. Hz), 7.66 (1H, s), 7.82 (1H, s).

EXAMPLE 31

(2E)-N-[4-(Diethylphosphono)phenyl]-3-[5-(4-fluorophenyl)-1-methyl-1H-pyrazol-4-yl]acrylamide yield: 6%. Colorless prism crystals. melting point: 174-176° C. (recrystallized from ethyl acetate-hexane).

EXAMPLE 32

(2E)-N-{4-[2-(Diethylphosphono)ethyl]phenyl}-3-[5-(4-fluorophenyl)-1-methyl-1H-pyrazol-4-yl]acrylamide yield: 19%. Colorless prism crystals. melting point: 157-158° C. (recrystallized from ethyl acetate-hexane).

EXAMPLE 33

(2E)-N-[4-(Diethylphosphonomethyl)-2-methylphenyl]-3-[5-(4-fluorophenyl)-1-methyl-1H-pyrazol-4-yl]-acrylamide yield: 50%. Colorless prism crystals. melting point: 154-155° C. (recrystallized from ethyl acetate-hexane).

EXAMPLE 34

A mixture of the mixture (250 mg) of (2E)-3-[1-benzyl-5-(4-fluorophenyl)-1H-pyrazol-4-yl]acrylic acid and (2E)-3-[1-benzyl-3-(4-fluorophenyl)-1H-pyrazol-4-yl]acrylic acid produced in Reference Example 36, 1-hydroxy-1H-1,2,3-benzotriazole hydrate (142 mg), 1-ethyl-3-(3-dimethylaminopropyl)carbodiimide hydrochloride (178 mg), diethyl 4-aminobenzylphosphonate (283 mg) and N,N-dimethylformamide (20 ml) was stirred at room temperature for 14 hrs. The reaction mixture was poured into a 1N aqueous hydrochloric acid solution, and the mixture was extracted with ethyl acetate. The ethyl acetate layer was washed with saturated aqueous sodium hydrogen carbonate, and then with saturated brine, dried (MgSO$_4$) and concentrated. The residue was subjected to silica gel column chromatography to give (2E)-3-[1-benzyl-5-(4-fluorophenyl)-1H-pyrazol-4-yl]-N-[4-(diethylphosphonomethyl)phenyl]acrylamide (106 mg) as a colorless powder from a fraction eluted with ethyl acetate. Recrystallization thereof from ethyl acetate-hexane gave colorless prism crystals. melting point: 207-208° C.

EXAMPLE 35

(2E)-3-[1-Benzyl-3-(4-fluorophenyl)-1H-pyrazol-4-yl]-N-[4-(diethylphosphonomethyl)phenyl]acrylamide (242 mg) was obtained as a colorless powder from a later-eluted fraction of (2E)-3-[1-benzyl-5-(4-fluorophenyl)-1H-pyrazol-4-yl]-N-[4-(diethylphosphonomethyl)phenyl]acrylamide obtained in Example 34. Recrystallization thereof from ethyl acetate-hexane gave colorless prism crystals. melting point: 199-200° C.

EXAMPLE 36

(2E)-N-[4-(Dimethylphosphonomethyl)phenyl]-3-[1-ethyl-5-(4-fluorophenyl)-1H-pyrazol-4-yl]acrylamide yield: 73%. Pale-yellow prism crystals. melting point: 187-189° C. (recrystallized from ethyl acetate-hexane).

EXAMPLE 37

(2E)-N-[4-(Diethylphosphonomethyl)phenyl]-3-[1-ethyl-5-(4-fluorophenyl)-1H-pyrazol-4-yl]acrylamide yield: 74%. Pale-yellow prism crystals. melting point: 226-227° C. (recrystallized from ethyl acetate-hexane).

EXAMPLE 38

(2E)-3-[5-(4-Fluorophenyl)-1,3-dimethyl-1H-pyrazol-4-yl]-N-[4-(dimethylphosphonomethyl)phenyl]acrylamide yield: 70%. Pale-yellow prism crystals. melting point: 195-198° C. (recrystallized from ethyl acetate-hexane).

EXAMPLE 39

(2E)-N-[4-(Diethylphosphonomethyl)phenyl]-3-[5-(4-fluorophenyl)-1,3-dimethyl-1H-pyrazol-4-yl]acrylamide yield: 16%. Pale-yellow prism crystals. melting point: 159-160° C. (recrystallized from ethyl acetate-hexane).

EXAMPLE 40

(2E)-3-(5-Cyclohexyl-1-methyl-1H-pyrazol-4-yl)-N-[4-(dimethylphosphonomethyl)phenyl]acrylamide yield: 19%. Pale-yellow solid
NMR(CDCl$_3$) δ: 1.2-1.85 (10H, m), 2.7-3.0 (1H, m), 3.15 (2H, d, J=21.5 Hz), 3.65 (3H, s), 3.69 (3H, s), 3.87 (3H, s), 6.15 (1H, d, J=15.9 Hz), 7.1-7.8 (7H, m).

EXAMPLE 41

(2E)-3-(5-Cyclohexyl-1-methyl-1H-pyrazol-4-yl)-N-[4-(diethylphosphonomethyl)phenyl]acrylamide yield: 13%. Pale-yellow solid. NMR(CDCl$_3$) δ: 1.2-1.85 (16H, m), 2.70-3.00 (1H, m), 3.13 (2H, d, J=21.5 Hz), 3.65 (3H, s), 3.95-4.1 (4H, m), 6.15 (1H, d, J=16 Hz), 7.1-7.8 (7H, m).

EXAMPLE 42

(2E)-N-[4-(Dimethylphosphonomethyl)phenyl]-3-[5-(2-furyl)-1-methyl-1H-pyrazol-4-yl]acrylamide yield: 72%. Colorless prism crystals. melting point: 201-202° C. (recrystallized from ethyl acetate-hexane).

EXAMPLE 43

(2E)-N-[4-(Diethylphosphonomethyl)phenyl]-3-[5-(2-furyl)-1-methyl-1H-pyrazol-4-yl]acrylamide yield: 84%. Colorless prism crystals. melting point: 195-196° C. (recrystallized from ethyl acetate-hexane).

EXAMPLE 44

(2E)-N-{4-[(5-Butyl-5-ethyl-2-oxide-1,3,2-dioxaphosphinan-2-yl)methyl]phenyl}-3-[5-(2-furyl)-1-methyl-1H-pyrazol-4-yl]acrylamide yield: 88%. Colorless prism crystals. melting point: 201-202° C. (recrystallized from ethyl acetate-hexane).

EXAMPLE 45

(2E)-N-{4-[(Diethylphosphono)(methoxy)methyl]phenyl}-3-[5-(4-fluorophenyl)-1-methyl-1H-pyrazol-4-yl]acrylamide yield: 60%. Colorless prism crystals. melting point: 200-201° C. (recrystallized from ethyl acetate-hexane).

EXAMPLE 46

(2E)-N-{4-[(Diethylphosphono)(hydroxy)methyl]phenyl}-3-[5-(4-fluorophenyl)-1-methyl-1H-pyrazol-4-yl]acrylamide yield: 15%. Colorless prism crystals. melting point: 194-195° C. (recrystallized from ethyl acetate-hexane).

EXAMPLE 47

(2E)-3-[5-(4-Fluorophenyl)-1-methyl-1H-pyrazol-4-yl]-N-{4-[(2-oxide-4,7-dihydro-1,3,2-dioxaphosphepin-2-yl)methyl]phenyl}acrylamide yield: 65%. Colorless prism crystals. melting point: 169-171° C. (recrystallized from ethyl acetate-hexane).

EXAMPLE 48

(2E)-N-{4-[(Benzyloxycarbonyl)sulfanyl]phenyl}-3-[5-(4-fluorophenyl)-1-methyl-1H-pyrazol-4-yl]acrylamide yield: 36%. Colorless solid.
NMR(CDCl$_3$)δ: 3.78 (3H, s), 5.24 (2H, s), 6.27 (1H, d, J=15.5 Hz), 7.15-7.3 (4H, m), 7.3-7.4 (6H, m), 7.5-7.6 (2H, m), 7.61 (2H, d, J=8.5 Hz), 7.83(1H, s).

EXAMPLE 49

(2E)-3-[5-(4-Fluorophenyl)-1-methyl-1H-pyrazol-4-yl]-N-{4-[hydroxy(2-pyridinyl)methyl]phenyl}acrylamide yield: 23%. Pale-yellow crystals.
NMR(CDCl$_3$)δ: 3.75 (3H, s), 5.30 (1H, broad s), 5.72 (1H, s), 6.27 (1H, d, J=15.5 Hz), 7.1-7.4 (9H, m), 7.40 (1H, d, J=15.5 Hz), 7.5-7.65 (3H, m), 7.80 (1H, s), 8.56 (1H, d, J=5 Hz).

EXAMPLE 50

(2E)-3-[5-(4-Fluorophenyl)-1-methyl-1H-pyrazol-4-yl]-N-{4-[hydroxy(6-methyl-2-pyridinyl)methyl]phenyl}acrylamide yield: 68%. Colorless crystals.
NMR(DMSO-d$_6$)δ: 2.59 (3H, s), 3.74 (3H, s), 5.81 (1H, s), 6.52 (1H, d, J=15.5 Hz), 7.14 (1H, d, J=15.5 Hz), 7.3-7.65 (11H, m), 7.89 (1H, s), 8.03 (1H, broad s), 10.06 (1H, s).

EXAMPLE 51

A mixture of (2E)-N-{4-[(benzyloxycarbonyl)sulfanyl]phenyl}-3-[5-(4-fluorophenyl)-1-methyl-1H-pyrazol-4-yl]acrylamide (488 mg), 3-(chloromethyl)-4-propyl-4H-1,2,4-triazole (240 mg), a 1N aqueous sodium hydroxide solution (3 ml) and ethanol (30 ml) was stirred at room temperature for 3 hrs. The reaction mixture was concentrated, poured into water, and extracted with ethyl acetate. The organic layer was washed with water, dried over anhydrous magnesium sulfate and concentrated to give (2E)-3-[5-(4-fluorophenyl)-1-methyl-1H-pyrazol-4-yl]-N-(4-{[(4-propyl-4H-1,2,4-triazol-3-yl)methyl]thio}phenyl)acrylamide (310 mg, 65%) as pale-yellow crystals.

NMR(CDCl$_3$)δ: 1.00 (3H, t, J=7 Hz), 1.8-1.95 (2H, m), 3.77 (3H, s), 3.97 (2H, t, J=7 Hz), 4.19 (2H, s), 6.34 (1H, d, J=15.5 Hz), 7.15-7.4 (8H, m), 7.51 (1H, d, J=8.5 Hz), 7.78 (1H, s), 8.02 (1H, broad s), 8.08 (1H, s).

EXAMPLE 52

A mixture of (2E)-3-[5-(4-fluorophenyl)-1-methyl-1H-pyrazol-4-yl]-N-(4-{[(4-propyl-4H-1,2,4-triazol-3-yl)methyl]thio}phenyl)acrylamide (96 mg), m-chloroperbenzoic acid (40 mg) and tetrahydrofuran (3 ml) was stirred at room temperature for 3 hrs. The reaction mixture was concentrated and purified by HPLC to give (2E)-3-[5-(4-fluorophenyl)-1-methyl-1H-pyrazol-4-yl]-N-(4-{[(4-propyl-4H-1,2,4-triazol-3-yl)methyl]sulfinyl}phenyl)acrylamide (36 mg, 37%) as pale-yellow crystals.

NMR(CDCl$_3$)δ: 0.96 (3H, t, J=7 Hz), 1.7-1.9 (2H, m), 3.79 (3H, s), 3.98 (2H, t, J=7.5 Hz), 4.21 (1H, d, J=9 Hz), 4.32 (1H, d, J=9 Hz), 6.34 (1H, d, J=15.5 Hz), 7.2-7.5 (8H, m), 7.73 (1H, d, J=8.5 Hz), 7.82 (1H, s), 8.01 (1H, broad s), 8.14 (1H, s).

EXAMPLE 53

In the similar manner as in Example 52 except that the amount of m-chloroperbenzoic acid used was 60 mg, (2E)-3-[5-(4-fluorophenyl)-1-methyl-1H-pyrazol-4-yl]-N-(4-{[(4-propyl-4H-1,2,4-triazol-3-yl)methyl]sulfonyl}phenyl)acrylamide was synthesized.

yield: 30%. Pale-yellow crystals.

NMR(CDCl$_3$)δ: 1.05 (3H, t, J=7 Hz), 1.9-2.0 (2H, m), 3.79 (3H, s), 4.18 (2H, t, J=7.5 Hz), 4.64 (2H, s), 6.37 (1H, d, J=15.5 Hz), 7.2-7.45 (6H, m), 7.5-7.6 (2H, m), 7.7-7.8 (3H, m), 8.24 (1H, s).

EXAMPLE 54

(2E)-N-[4-(Diethylphosphonomethyl)phenyl]-3-[3-(4-fluorophenyl)-1-methyl-1H-pyrazol-4-yl]acrylamide yield: 60%. Pale-yellow prism crystals. melting point: 197-198° C. (recrystallized from ethyl acetate-hexane).

EXAMPLE 55

(2E)-N-[4-(Diethylphosphonomethyl)phenyl]-3-[4-(4-fluorophenyl)-1-methyl-1H-pyrazol-5-yl]acrylamide yield: 74%. Pale-yellow prism crystals. melting point: 138-139° C. (recrystallized from acetone-hexane).

EXAMPLE 56

(2E)-N-[4-(Diethylphosphonomethyl)phenyl]-3-[4-(4-fluorophenyl)-1-methyl-1H-pyrazol-3-yl]acrylamide yield: 62%. Pale-yellow prism crystals. melting point: 203-204° C. (recrystallized from acetone-hexane).

EXAMPLE 57

N-[4-(Diethylphosphonomethyl)phenyl]-3-[5-(4-fluorophenyl)-1-methyl-1H-pyrazol-4-yl]propionamide yield: 53%. Colorless prism crystals. melting point: 143-144° C. (recrystallized from acetone-hexane).

EXAMPLE 58

N-[4-(Dimethylphosphonomethyl)phenyl]-3-[5-(4-fluorophenyl)-1-methyl-1H-pyrazol-4-yl]propionamide yield: 47%. Colorless prism crystals. melting point: 142-143° C. (recrystallized from acetone-hexane).

EXAMPLE 59

3-[5-(4-Chlorophenyl)-1-methyl-1H-pyrazol-4-yl]-N-[4-(diethylphosphonomethyl)phenyl]propionamide yield: 53%. Colorless crystals.

NMR(CDCl$_3$) δ: 1.24 (6H, t, J=7 Hz), 2.53 (2H, t, J=7 Hz), 2.82 (2H, t, J=7 Hz), 3.10 (2H, d, J=21.5 Hz), 3.73 (3H, s), 3.95-4.1 (4H, m), 7.17 (1H, dd, J=1.5/8.5 Hz), 7.2-7.3 (2H, m), 7.37 (2H, d, J=8.5 Hz), 7.4-7.5 (4H, m), 7.72 (1H, broad s).

EXAMPLE 60

(2E)-N-{4-[(2,4-Dioxo-1,3-thiazolidin-5-yl)methyl]phenyl}-3-[5-(4-fluorophenyl)-1-methyl-1H-pyrazol-4-yl]acrylamide yield: 53%. Colorless prism crystals. melting point: 149-150° C. (recrystallized from acetone-hexane).

EXAMPLE 61

(2E)-N-[4-(Diethylphosphonomethyl)phenyl]-3-[1-(4-fluorophenyl)-1H-imidazol-5-yl]acrylamide yield: 68%. Colorless prism crystals. melting point: 165-166° C. (recrystallized from acetone-isopropyl ether).

EXAMPLE 62

(2E)-N-[4-(Dimethylphosphonomethyl)phenyl]-3-[1-(4-fluorophenyl)-1H-imidazol-5-yl]acrylamide yield: 62%. Colorless prism crystals. melting point: 108-109° C. (recrystallized from methanol-water).

EXAMPLE 63

A mixture of (2E)-N-[4-(diethylphosphonomethyl)phenyl]-3-[1-(4-fluorophenyl)-1H-imidazol-5-yl]acrylamide (92 mg), 5% palladium-carbon (100 mg) and ethanol (10 ml) was stirred at room temperature under a hydrogen atmosphere at atmospheric pressure for 3 hrs. The reaction mixture was filtered, and the organic layer was concentrated to give N-[4-(diethylphosphonomethyl)phenyl]-3-[1-(4-fluorophenyl)-1H-imidazol-5-yl]propionamide (60 mg, 65%) as a colorless solid.

NMR(CDCl₃) δ: 1.24 (6H, t, J=7 Hz), 2.63 (2H, t, J=7 Hz), 2.92 (2H, t, J=7 Hz), 3.10 (2H, d, J=21.5 Hz), 3.9-4.1 (4H, m), 6.94 (1H, s), 7.15-7.25 (4H, m), 7.25-7.35 (2H, m), 7.39 (2H, d, J=8 Hz), 7.53 (1H, s), 7.86 (1H, broad s).

In the similar manner as in Example 63, the compounds of Examples 64, 67 and 68 were synthesized.

EXAMPLE 64

N-[4-(Dimethylphosphonomethyl)phenyl]-3-[1-(4-fluorophenyl)-1H-imidazol-5-yl]propionamide yield: 63%. Colorless solid.
NMR(CDCl₃) δ: 2.64 (2H, t, J=7 Hz), 2.91 (2H, t, J=7 Hz), 3.12 (2H, d, J=21.5 Hz), 3.64 (3H, s), 3.68 (3H, s), 6.94 (1H, s), 7.15-7.25 (4H, m), 7.25-7.35 (2H, m), 7.41 (2H, d, J=8 Hz), 7.53 (1H, s), 8.11 (1H, broad s).

EXAMPLE 65

(2E)-N-[4-(Diethylphosphonomethyl)phenyl]-3-[4-(4-fluorophenyl)-4H-1,2,4-triazol-3-yl]acrylamide yield: 64%. Colorless prism crystals. melting point: 217-218° C. (recrystallized from acetone-isopropyl ether).

EXAMPLE 66

(2E)-N-[4-(Dimethylphosphonomethyl)phenyl]-3-[4-(4-fluorophenyl)-4H-1,2,4-triazol-3-yl]acrylamide yield: 81%. Colorless prism crystals. melting point: decomposed at 250° C. or above (recrystallized from methanol-acetone).
NMR(DMSO-d₆) δ: 3.21 (2H, d, J=21.5 Hz), 3.57 (3H, s), 3.62 (3H, s), 7.08 (1H, d, J=15.5 Hz), 7.2-7.4 (3H, m), 7.4-7.7 (6H, m), 8.90 (1H, s), 10.46 (1H, broad s).

EXAMPLE 67

N-[4-(Diethylphosphonomethyl)phenyl]-3-[4-(4-fluorophenyl)-4H-1,2,4-triazol-3-yl]propionamide yield: 77%. Pale-yellow solid.
NMR(CDCl₃)δ: 1.24 (6H, t, J=7 Hz), 3.0-3.1 (4H, m), 3.10 (2H, d, J=21 Hz), 3.9-4.1 (4H, m), 7.15-7.3 (4H, m), 7.3-7.4 (2H, m), 7.48 (2H, d, J=8.5 Hz), 8.21 (1H, s), 8.8-9.0 (1H, m).

EXAMPLE 68

N-[4-(Dimethylphosphonomethyl)phenyl]-3-[4-(4-fluorophenyl)-4H-1,2,4-triazol-3-yl]propionamide yield: 54%. Pale-yellow solid.
NMR(DMSO-d₆)δ: 3.0-3.1 (4H, m), 3.11 (2H, d, J=21.5 Hz), 3.64 (3H, s), 3.67 (3H, s), 7.15-7.3 (4H, m), 7.3-7.4 (2H, m), 7.48 (2H, d, J=8.5 Hz), 8.20 (1H, s), 9.22 (1H, broad s).

EXAMPLE 69

(2E)-N-[4-(Diethylphosphonomethyl)phenyl]-3-[5-(4-fluorophenyl)-1,2,3-thiadiazol-4-yl]acrylamide yield: 45%. Pale-yellow solid.
NMR(CDCl₃) δ: 1.30 (6H, t, J=7 Hz), 3.15 (2H, d, J=21.5 Hz), 4.05-4.2 (4H, m), 7.15-7.3 (4H, m), 7.4-7.5 (2H, m), 7.5-7.6 (2H, m), 7.65-7.75 (2H, m), 9.29 (1H, broad s).

EXAMPLE 70

(2E)-N-[4-(Dimethylphosphonomethyl)phenyl]-3-[5-(4-fluorophenyl)-1,2,3-thiadiazol-4-yl]acrylamide yield: 54%. Pale-yellow crystals.
NMR(CDCl₃) δ: 3.20 (2H, d, J=22 Hz), 3.71 (3H, s), 3.75 (3H, s), 7.2-7.3 (4H, m), 7.4-7.5 (3H, m), 7.58 (2H, d, J=8.5 Hz), 7.73 (1H, d, J=15 Hz), 8.06 (1H, broad s).

EXAMPLE 71

(2E)-N-[4-(Diethylphosphonomethyl)phenyl]-3-[4-(4-fluorophenyl)-1,2,3-thiadiazol-5-yl]acrylamide yield: 37%. Pale-yellow prism crystals. melting point: 173-175° C. (recrystallized from acetone-hexane).

EXAMPLE 72

(2E)-N-[4-(Dimethylphosphonomethyl)phenyl]-3-[4-(4-fluorophenyl)-1,2,3-thiadiazol-5-yl]acrylamide yield: 53%. Pale-yellow prism crystals. melting point: 196-197° C. (recrystallized from acetone-hexane).

EXAMPLE 73

(2E)-N-[4-(Diethylphosphonomethyl)phenyl]-3-[5-(4-fluorophenyl)-1-methyl-1H-pyrazol-4-yl]but-2-enamide yield: 65%. Pale-yellow crystals.
NMR(CDCl₃) δ: 1.23 (6H, t, J=7 Hz), 2.29 (3H, s), 3.10 (2H, d, J=21.5 Hz), 3.70 (3H, s), 3.95-4.15 (4H, m), 5.78 (1H, s), 7.1-7.4 (7H, m), 7.4-7.5 (2H, m), 7.64 (1H, s).

EXAMPLE 74

N-[4-(Diethylphosphonomethyl)phenyl]-3-[5-(4-fluorophenyl)-1-methyl-1H-pyrazol-4-yl]butanamide yield: 68%. Colorless crystals.
NMR(CDCl₃) δ: 1.2-1.3 (9H, m), 2.4-2.6 (2H, m), 3.10 (2H, d, J=21.5 Hz), 3.15-3.25 (1H, m), 3.68 (3H, s), 3.95-4.1 (4H, m), 7.1-7.2 (4H, m), 7.2-7.3 (2H, m), 7.34 (2H, d, J=8.5 Hz), 7.48 (1H, s), 7.5-7.6 (1H, m).

EXAMPLE 75

(2Z)-N-[4-(Diethylphosphonomethyl)phenyl]-3-[5-(4-methoxyphenyl)-1-methyl-1H-pyrazol-4-yl]acrylamide yield: 76%. Colorless prism crystals. melting point: 187-188° C. (recrystallized from ethyl acetate-hexane).

EXAMPLE 76

(2Z)-N-[4-(Dimethylphosphonomethyl)phenyl]-3-[5-(4-methoxyphenyl)-1-methyl-1H-pyrazol-4-yl]acrylamide yield: 76%. Colorless prism crystals. melting point: 172-173° C. (recrystallized from ethyl acetate-hexane).

EXAMPLE 77

(2Z)-N-[4-(Diethylphosphonomethyl)phenyl]-3-[5-(4-fluorophenyl)-1-methyl-1H-pyrazol-4-yl]acrylamide yield: 68%. Colorless prism crystals. melting point: 208-209° C. (recrystallized from ethyl acetate-hexane).

EXAMPLE 78

In the similar manner as in Example 51, (2E)-3-[5-(4-fluorophenyl)-1-methyl-1H-pyrazol-4-yl]-N-(4-{[(1-propyl-1H-imidazol-5-yl)methyl]thio}phenyl)acrylamide was produced.

yield: 65%. Pale-yellow amorphous form.
NMR(CDCl$_3$) δ: 0.97 (3H, t, J=7 Hz), 1.8-1.9 (2H, m), 3.77 (3H, s), 3.92 (2H, t, J=7 Hz), 3.97 (2H, s), 6.33 (1H, d, J=15.5 Hz), 6.67 (1H, s), 7.15-7.4 (7H, m), 7.4-7.45 (2H, m), 7.51 (1H, d, J=8.5 Hz), 7.78 (1H, s), 7.95-8.05 (1H, m).

EXAMPLE 79

A mixture of 2-(ethoxycarbonyloxy)-3-[4-({(2E)-3-[5-(4-fluorophenyl)-1-methyl-1H-pyrazol-4-yl]-2-propenoyl}amino)phenyl]propionamide (420 mg), 1,8-diazabicyclo[5.4.0]-7-undecene (266 mg) and acetonitrile (10 ml) was stirred at room temperature for 1 hr. The reaction mixture was concentrated and diluted with ethyl acetate. The mixture was successively washed with a 1N aqueous hydrochloric acid solution, water and saturated brine. The organic layer was dried over anhydrous magnesium sulfate and concentrated to give (2E)-N-{4-[(2,4-dioxo-1,3-oxazolidin-5-yl)methyl]phenyl}-3-[5-(4-fluorophenyl)-1-methyl-1H-pyrazol-4-yl]acrylamide (293 mg, 77%) as colorless crystals.

NMR(CDCl$_3$)δ: 2.95-3.2 (2H, m), 3.74 (3H, s), 5.15-5.25 (1H, m), 6.52 (1H, d, J=15.5 Hz), 7.05-7.2 (3H, m), 7.35-7.6 (6H, m), 7.89 (1H, s), 10.04 (1H, s), 11.70 (1H, broad s).

EXAMPLE 80

N-[4-(Diethylphosphonomethyl)phenyl]-3-(1,5-diphenyl-1H-pyrazol-4-yl)propionamide yield: 92%. Colorless prism crystals. melting point: 157-159° C. (recrystallized from ethyl acetate-hexane).

EXAMPLE 81

N-[4-(Ethoxycarbonylmethyl)phenyl]-3-(1,5-diphenyl-1H-pyrazol-4-yl)propionamide yield: 92%. Colorless prism crystals. melting point: 143-144° C. (recrystallized from ethyl acetate-hexane).

EXAMPLE 82

N-[4-(Methoxycarbonyl)phenyl]-3-(1,5-diphenyl-1H-pyrazol-4-yl)propionamide yield: 97%. Colorless prism crystals, melting point: 196-197° C. (recrystallized from ethyl acetate-hexane).

EXAMPLE 83

A mixture of N-[4-(ethoxycarbonylmethyl)phenyl]-3-(1,5-diphenyl-1H-pyrazol-4-yl)propionamide (0.76 g), a 1N aqueous sodium hydroxide solution (5 ml) and ethanol (5 ml) was stirred at 50° C. for 3 hrs. The reaction mixture was poured into a 1N aqueous hydrochloric acid solution and the precipitated crystals were collected by filtration, washed with water and dried to give (4-{[3-(1,5-diphenyl-1H-pyrazol-4-yl)propanoyl]amino}phenyl)acetic acid.

yield: 94%. Colorless prism crystals. melting point: 199-201° C. (recrystallized from ethyl acetate-hexane).

EXAMPLE 84

In the similar manner as in Example 83, 4-{[3-(1,5-diphenyl-1H-pyrazol-4-yl)propanoyl]amino}benzoic acid was produced.

yield: 93%. Colorless prism crystals. melting point: 254-256° C. (recrystallized from acetone-hexane).

EXAMPLE 85

To a mixture of (2E)-3-[5-(4-fluorophenyl)-1-methyl-1H-pyrazol-4-yl]acrylic acid (0.50 g), N,N-dimethylformamide (0.05 mL) and tetrahydrofuran (15 mL) was added dropwise oxalyl chloride (0.30 g) at room temperature. The reaction mixture was stirred at room temperature for 30 min. and concentrated. A mixture of the obtained residue, 4-[(5-propyl-1,3,4-oxadiazol-2-yl)methyl]aniline (0.48 g) and N,N-dimethylacetamide (20 mL) was stirred at room temperature for 2 hrs. Water was poured into the reaction mixture, and the mixture was extracted with ethyl acetate. The organic layer was washed successively with 1N hydrochloric acid, saturated aqueous sodium hydrogen carbonate and saturated brine, dried over anhydrous magnesium sulfate, and concentrated to give (2E)-3-[5-(4-fluorophenyl)-1-methyl-1H-pyrazol-4-yl]-N-{4-[(5-propyl-1,3,4-oxadiazol-2-yl)methyl]phenyl}acrylamide as colorless crystals (0.81 g, yield 91%). Recrystallization thereof from acetone-hexane gave colorless prism crystals. melting point: 154-155° C.

In the similar manner as in Example 85, the compounds described in Examples 86-108 were produced.

EXAMPLE 86

(2E)-3-[5-(4-Fluorophenyl)-1-methyl-1H-pyrazol-4-yl]-N-{4-[(5-oxo-4,5-dihydro-1,3,4-oxadiazol-2-yl)methyl]phenyl}acrylamide was obtained as colorless crystals (yield 83%). Recrystallization thereof from acetone-hexane gave colorless prism crystals. melting point: 262-263° C.

EXAMPLE 87

(2E)-3-[5-(4-Fluorophenyl)-1-methyl-1H-pyrazol-4-yl]-N-[4-(1H-tetrazol-5-ylmethyl)phenyl]acrylamide was obtained as pale-yellow crystals (yield 84%). Recrystallization thereof from acetone-methanol gave pale-yellow prism crystals. melting point: 252-253° C.

EXAMPLE 88

(2E)-N-{4-[2-(5-Ethyl-1,3,4-oxadiazol-2-yl)ethyl]phenyl}-3-[5-(4-fluorophenyl)-1-methyl-1H-pyrazol-4-yl]acrylamide was obtained as colorless crystals (yield 93%). Recrystallization thereof from ethyl acetate-hexane gave colorless prism crystals. melting point: 167-168° C.

EXAMPLE 89

(2E)-3-[5-(4-Fluorophenyl)-1-methyl-1H-pyrazol-4-yl]-N-{4-[2-(1,3,4-oxadiazol-2-yl)ethyl]phenyl}acrylamide was obtained as colorless crystals (yield 87%). Recrystallization thereof from ethyl acetate-hexane gave colorless prism crystals. melting point: 177-178° C.

EXAMPLE 90

(2E)-N-{4-[2-(2-Ethyl-1,3-thiazol-4-yl)ethyl]phenyl}-3-[5-(4-fluorophenyl)-1-methyl-1H-pyrazol-4-yl]acrylamide was obtained as colorless crystals (yield 74%). Recrystallization thereof from ethyl acetate-hexane gave colorless prism crystals. melting point: 190-191° C.

EXAMPLE 91

(2E)-3-[5-(4-Fluorophenyl)-1-methyl-1H-pyrazol-4-yl]-N-{4-[2-(1,3-thiazol-4-yl)ethyl]phenyl}acrylamide was obtained as colorless crystals (yield 65%). Recrystallization thereof from ethyl acetate-hexane gave colorless prism crystals. melting point: 211-212° C.

EXAMPLE 92

(2E)-3-[5-(4-Fluorophenyl)-1-methyl-1H-pyrazol-4-yl]-N-[4-(1,3-thiazol-4-ylmethoxy)phenyl]acrylamide was obtained as pale-yellow crystals (yield 91%). Recrystallization thereof from acetone-hexane gave colorless prism crystals. melting point: 171-172° C.

EXAMPLE 93

(2E)-N-{4-[(2-Ethyl-1,3-thiazol-4-yl)methoxy]phenyl}-3-[5-(4-fluorophenyl)-1-methyl-1H-pyrazol-4-yl]acrylamide was obtained as colorless crystals (yield 97%). Recrystallization thereof from ethyl acetate-hexane gave colorless prism crystals. melting point: 98-99° C.

EXAMPLE 94

(2E)-3-[5-(4-Fluorophenyl)-1-methyl-1H-pyrazol-4-yl]-N-[4-(1,3,4-oxadiazol-2-ylmethoxy)phenyl]acrylamide was obtained as colorless crystals (yield 76%). Recrystallization thereof from ethyl acetate-hexane gave colorless prism crystals. melting point: 154-155° C.

EXAMPLE 95

(2E)-3-[5-(4-Fluorophenyl)-1-methyl-1H-pyrazol-4-yl]-N-{4-[(4-methyl-1,3-oxazol-2-yl)methyl]phenyl}acrylamide was obtained as colorless crystals (yield 68%). Recrystallization thereof from ethyl acetate-diisopropyl ether gave colorless prism crystals. melting point: 220-221° C.

EXAMPLE 96

(2E)-3-[5-(4-Fluorophenyl)-1-methyl-1H-pyrazol-4-yl]-N-[4-(pyridin-2-ylmethyl)phenyl]acrylamide was obtained as colorless crystals (yield 87%). Recrystallization thereof from ethyl acetate-hexane gave colorless prism crystals. melting point: 215-216° C.

EXAMPLE 97

(2E)-3-[5-(4-Fluorophenyl)-1-methyl-1H-pyrazol-4-yl]-N-{4-[(5-methyl-1,3,4-oxadiazol-2-yl)methoxy] phenyl}acrylamide was obtained as colorless crystals (yield 74%). Recrystallization thereof from acetone-hexane gave colorless prism crystals. melting point: 117-118° C.

EXAMPLE 98

(2E)-N-{4-[(4-Ethyl-1,3-oxazol-2-yl)methyl]phenyl}-3-[5-(4-fluorophenyl)-1-methyl-1H-pyrazol-4-yl]acrylamide was obtained as colorless crystals (yield 88%). Recrystallization thereof from ethyl acetate-hexane gave colorless prism crystals. melting point: 174-175° C.

EXAMPLE 99

(2E)-N-{4-[(2-Ethyl-1,3-thiazol-4-yl)methyl]phenyl}-3-[5-(4-fluorophenyl)-1-methyl-1H-pyrazol-4-yl]acrylamide was obtained as colorless crystals (yield 35%). Recrystallization thereof from acetone-hexane gave colorless prism crystals. melting point: 178-179° C.

EXAMPLE 100

(2E)-3-[5-(4-Fluorophenyl)-1-methyl-1H-pyrazol-4-yl]-N-{4-[(2-methyl-1,3-thiazol-4-yl)methyl] phenyl}acrylamide was obtained as colorless crystals (yield 63%). Recrystallization thereof from acetone-hexane gave colorless prism crystals. melting point: 192-193° C.

EXAMPLE 101

(2E)-3-[5-(4-Fluorophenyl)-1-methyl-1H-pyrazol-4-yl]-N-{4-[(1-methyl-1H-tetrazol-5-yl)methyl] phenyl}acrylamide was obtained as colorless crystals (yield 32%). Recrystallization thereof from acetone-hexane gave colorless prism crystals. melting point: 243-244° C.

EXAMPLE 102

(2E)-3-[5-(4-Fluorophenyl)-1-methyl-1H-pyrazol-4-yl]-N-{4-[(2-methyl-2H-tetrazol-5-yl)methyl] phenyl}acrylamide was obtained as colorless crystals (yield 96%). Recrystallization thereof from acetone-hexane gave colorless prism crystals. melting point: 159-161° C.

EXAMPLE 103

(2E)-N-{4-[(1-Ethyl-1H-tetrazol-5-yl)methyl]phenyl}-3-[5-(4-fluorophenyl)-1-methyl-1H-pyrazol-4-yl]acrylamide was obtained as colorless crystals (yield 87%). Recrystallization thereof from acetone-hexane gave colorless prism crystals. melting point: 206-207° C.

EXAMPLE 104

(2E)-N-{4-[(2-Ethyl-2H-tetrazol-5-yl)methyl]phenyl}-3-[5-(4-fluorophenyl)-1-methyl-1H-pyrazol-4-yl]acrylamide was obtained as colorless crystals (yield 61%). Recrystallization thereof from acetone-hexane gave colorless prism crystals. melting point: 187-188° C.

EXAMPLE 105

(2E)-3-[5-(4-Fluorophenyl)-1-methyl-1H-pyrazol-4-yl]-N-(4-neopentylphenyl)acrylamide was obtained as colorless crystals (yield 27%). Recrystallization thereof from ethyl acetate-hexane gave colorless prism crystals. melting point: 150-151° C.

EXAMPLE 106

(2E)-3-[5-(4-Fluorophenyl)-1-methyl-1H-pyrazol-4-yl]-N-(2-oxo-2,3-dihydro-1,3-benzoxazol-6-yl)acrylamide was obtained as colorless crystals (yield 70%). Recrystallization thereof from tetrahydrofuran-hexane gave colorless prism crystals. melting point: >300° C.

EXAMPLE 107

(2E)-N-[4-(1,3-Benzoxazol-2-ylmethyl)phenyl]-3-[5-(4-fluorophenyl)-1-methyl-1H-pyrazol-4-yl]acrylamide was obtained as colorless crystals (yield 50%). Recrystallization thereof from acetone-hexane gave colorless prism crystals. melting point: 195-196° C.

EXAMPLE 108

(2E)-N-[4-(1H-Benzimidazol-2-ylmethyl)phenyl]-3-[5-(4-fluorophenyl)-1-methyl-1H-pyrazol-4-yl]acrylamide was obtained as colorless crystals (yield 56%). Recrystallization thereof from N,N-dimethylformamide-water gave colorless prism crystals. melting point: >300° C.

EXAMPLE 109

A mixture of ethyl (4-aminophenyl)acetate (0.88 g), (2E)-3-[5-(4-fluorophenyl)-1-methyl-1H-pyrazol-4-yl]acrylic acid (1.0 g), 1-hydroxy-1H-1,2,3-benzotriazole hydrate (0.81 g), 1-ethyl-3-(3-dimethylaminopropyl)carbodiimide hydrochloride (1.02 g) and N,N-dimethylformamide (30 mL) was stirred at room temperature for 15 hrs. Water was poured into the reaction mixture, and the mixture was extracted with ethyl acetate. The organic layer was washed successively with 1N hydrochloric acid, saturated aqueous sodium hydrogen carbonate and saturated brine, dried over anhydrous magnesium sulfate, and concentrated to give ethyl [4-({(2E)-3-[5-(4-fluorophenyl)-1-methyl-1H-pyrazol-4-yl]prop-2-enoyl}amino)phenyl]acetate as colorless crystals (1.49 g, yield 89%). Recrystallization thereof from ethyl acetate-hexane gave colorless prism crystals. melting point: 177-178° C.

In the similar manner as in Example 109, the compounds described in Examples 110-124 were produced.

EXAMPLE 110

(2E)-3-[5-(4-Fluorophenyl)-1-methyl-1H-pyrazol-4-yl]-N-{4-[(3-methyl-2,4-dioxo-1,3-thiazolidin-5-yl)methyl]phenyl}acrylamide was obtained as colorless crystals (yield 65%). Recrystallization thereof from acetone-hexane gave colorless prism crystals. melting point: 228-229° C.

EXAMPLE 111

(2E)-N-{4-[(3-Ethyl-2,4-dioxo-1,3-thiazolidin-5-yl)methyl]phenyl}-3-[5-(4-fluorophenyl)-1-methyl-1H-pyrazol-4-yl]acrylamide was obtained as colorless crystals (yield 40%). Recrystallization thereof from acetone-hexane gave colorless prism crystals. melting point: 214-215° C.

EXAMPLE 112

Diethyl 4-({(2E)-3-[5-(4-fluorophenyl)-1H-pyrazol-4-yl]prop-2-enoyl}amino)benzylphosphonate was obtained as colorless crystals (yield 50%). Recrystallization thereof from ethyl acetate-hexane gave colorless prism crystals. melting point: 181-182° C.

EXAMPLE 113

(2E)-N-{4-[2-(4-Ethyl-1,3-thiazol-2-yl) ethyl]phenyl}-3-[5-(4-fluorophenyl)-1-methyl-1H-pyrazol-4-yl]acrylamide was obtained as colorless crystals (yield 38%). Recrystallization thereof from ethyl acetate-hexane gave colorless prism crystals. melting point: 200-201° C.

EXAMPLE 114

(2E)-3-[5-(4-Fluorophenyl)-1-methyl-1H-pyrazol-4-yl]-N-[4-(2-hydroxy-2-methylpropyl)phenyl]acrylamide was obtained as colorless crystals (yield 89%). Recrystallization thereof from ethyl acetate-hexane gave colorless prism crystals. melting point: 188-189° C.

EXAMPLE 115

(2E)-N-[4-(2-Ethyl-2-hydroxybutyl)phenyl]-3-[5-(4-fluorophenyl)-1-methyl-1H-pyrazol-4-yl]acrylamide was obtained as colorless crystals (yield 55%). Recrystallization thereof from acetone-hexane gave colorless prism crystals. melting point: 150-151° C.

EXAMPLE 116

(2E)-3-[5-(4-Fluorophenyl)-1-methyl-1H-pyrazol-4-yl]-N-{4-[(5-methyl-1,2,4-oxadiazol-3-yl)methyl]phenyl}acrylamide was obtained as pale-yellow crystals (yield 57%). Recrystallization thereof from acetone-hexane gave colorless prism crystals. melting point: 183-184° C.

EXAMPLE 117

(2E)-N-(4-{[Acetyl(methyl)amino]methyl}phenyl)-3-[5-(4-fluorophenyl)-1-methyl-1H-pyrazol-4-yl]acrylamide was obtained as colorless crystals (yield 58%). Recrystallization thereof from acetone-hexane gave colorless prism crystals. melting point: 192-193° C.

EXAMPLE 118

(2E)-N-{4-[(5-Ethyl-1,2,4-oxadiazol-3-yl)methyl]phenyl}-3-[5-(4-fluorophenyl)-1-methyl-1H-pyrazol-4-yl]acrylamide was obtained as colorless crystals (yield 51%). Recrystallization thereof from acetone-hexane gave colorless prism crystals. melting point: 150-152° C.

EXAMPLE 119

(2E)-3-[5-(4-Fluorophenyl)-1-methyl-1H-pyrazol-4-yl]-N-{4-[(4-methyl-5-oxo-4,5-dihydro-1,3,4-oxadiazol-2-yl)methyl]phenyl}acrylamide was obtained as colorless crystals (yield 54%). Recrystallization thereof from acetone-hexane gave colorless prism crystals. melting point: 200-201° C.

EXAMPLE 120

(2E)-N-{4-[(4-Ethyl-5-oxo-4,5-dihydro-1,3,4-oxadiazol-2-yl)methyl]phenyl}-3-[5-(4-fluorophenyl)-1-methyl-1H-pyrazol-4-yl]acrylamide was obtained as colorless crystals (yield 73%). Recrystallization thereof from acetone-hexane gave colorless prism crystals. melting point: 149-150° C.

EXAMPLE 121

(2E)-3-[5-(4-Fluorophenyl)-1-methyl-1H-pyrazol-4-yl]-N-[4-(2-oxopropyl)phenyl]acrylamide was obtained as colorless crystals (yield 17%). Recrystallization thereof from acetone-hexane gave colorless prism crystals. melting point: 186-187° C.

EXAMPLE 122

(2E)-3-[5-(4-Fluorophenyl)-1-methyl-1H-pyrazol-4-yl]-N-(3-methyl-2-oxo-2,3-dihydro-1,3-benzoxazol-6-yl)acrylamide was obtained as colorless crystals (yield 56%). Recrystallization thereof from tetrahydrofuran-hexane gave colorless prism crystals. melting point: 265-266° C.

EXAMPLE 123

(2E)-N-{4-[(4,5-Dimethyl-1,3-thiazol-2-yl)methyl]phenyl}-3-{5-(4-fluorophenyl)-1-methyl-1H-pyrazol-4-yl}acrylamide was obtained as colorless crystals (yield 56%). Recrystallization thereof from ethyl acetate-hexane gave colorless prism-crystals. melting point: 210-211° C.

EXAMPLE 124

(2E)-3-[5-(4-Fluorophenyl)-1-methyl-1H-pyrazol-4-yl]-N-[4-(4,5,6,7-tetrahydro-1,3-benzothiazol-2-ylmethyl)phenyl]acrylamide was obtained as colorless crystals (yield 73%). Recrystallization thereof from acetone-hexane gave colorless prism crystals. melting point: 205-206° C.

EXAMPLE 125

4-Ethyl-2-(4-nitrobenzyl)-1,3-thiazole (0.50 g), 5% palladium carbon (0.50 g) and tetrahydrofuran (30 mL) were subjected to catalytic reduction under a hydrogen atmosphere at atmospheric pressure. The catalyst was removed by filtration, and the filtrate was concentrated. A mixture of the obtained residue, (2E)-3-[5-(4-fluorophenyl)-1-methyl-1H-pyrazol-4-yl]acrylic acid (0.49 g), 1-hydroxy-1H-1,2,3-benzotriazole hydrate (0.46 g), 1-ethyl-3-(3-dimethylaminopropyl)carbodiimide hydrochloride (0.58 g) and N,N-dimethylformamide (10 mL) was stirred at room temperature for 15 hrs. Water was poured into the reaction mixture, and the mixture was extracted with ethyl acetate. The organic layer was washed successively with 0.1N hydrochloric acid, saturated aqueous sodium hydrogen carbonate and saturated brine, dried over anhydrous magnesium sulfate and concentrated. The residue was subjected to silica gel column chromatography to give (2E)-N-{4-[(4-ethyl-1,3-thiazol-2-yl) methyl]phenyl}-3-[5-(4-fluorophenyl)-1-methyl-1H-pyrazol-4-yl]acrylamide as colorless crystals (0.35 g, yield 39%) from a fraction eluted with hexane-ethyl acetate (1:5, v/v). Recrystallization thereof from acetone-hexane gave colorless prism crystals. melting point: 211-212° C.

In the similar manner as in Example 125, the compounds described in Examples 126-130 were produced.

EXAMPLE 126

Ethyl 2-[4-({(2E)-3-[5-(4-fluorophenyl)-1-methyl-1H-pyrazol-4-yl]prop-2-enoyl}amino)benzyl]-1,3-thiazole-4-carboxylate was obtained as colorless crystals (yield 23%). Recrystallization thereof from ethyl acetate-hexane gave colorless prism crystals. melting point: 189-190° C.

EXAMPLE 127

(2E)-3-[5-(4-Fluorophenyl)-1-methyl-1H-pyrazol-4-yl]-N-(4-[(4-methyl-1,3-thiazol-2-yl)methyl)phenyl]acrylamide was obtained as colorless crystals (yield 31%). Recrystallization thereof from acetone-hexane gave colorless prism crystals. melting point: 217-218° C.

EXAMPLE 128

(2E)-3-[5-(4-Fluorophenyl)-1-methyl-1H-pyrazol-4-yl]-N-{4-[(1,3-thiazol-2-yl)methyl]phenyl}acrylamide was obtained as colorless crystals (yield 22%). Recrystallization thereof from acetone-hexane gave colorless prism crystals. melting point: 209-210° C.

EXAMPLE 129

(2E)-3-[5-(4-Fluorophenyl)-1-methyl-1H-pyrazol-4-yl]-N-[4-(1,3,4-oxadiazol-2-ylmethyl)phenyl]acrylamide was obtained as colorless crystals (yield 63%). Recrystallization thereof from acetone-hexane gave colorless prism crystals. melting point: 223-224° C.

EXAMPLE 130

(2E)-3-[5-(4-Fluorophenyl)-1-methyl-1H-pyrazol-4-yl]-N-(4-[2-(1,3-thiazol-2-yl)ethyl]phenyl}acrylamide was obtained as colorless crystals (yield 24%). Recrystallization thereof from ethyl acetate-hexane gave colorless prism crystals. melting point: 201-202° C.

EXAMPLE 131

A mixture of ethyl 2-[4-({(2E)-3-[5-(4-fluorophenyl)-1-methyl-1H-pyrazol-4-yl]prop-2-enoyl}amino)benzyl]-1,3-thiazole-4-carboxylate (0.52 g), a 1N aqueous sodium hydroxide solution (2 mL), tetrahydrofuran (2 mL) and ethanol (2 mL) was stirred at 50° C. for 30 min. 1N Hydrochloric acid (2 mL) and water were added to the reaction mixture and the precipitated crystals were collected by filtration to give 2-[4-({(2E)-3-[5-(4-fluorophenyl)-1-methyl-1H-pyrazol-4-yl]prop-2-enoyl }amino)benzyl]-1,3-thiazole-4-carboxylic acid as colorless crystals (0.41 g, yield 80%). Recrystallization thereof from acetone-hexane gave colorless prism crystals. melting point: 226-227° C.

EXAMPLE 132

A mixture of 2-[4-({(2E)-3-[5-(4-fluorophenyl)-1-methyl-1H-pyrazol-4-yl]prop-2-enoyl}amino)benzyl]-1,3-thiazole-4-carboxylic acid (0.24 g), a 1-hydroxy-1H-1,2,3-benzotriazole ammonia complex (0.12 g), 1-ethyl-3-(3-dimethylaminopropyl) carbodiimide hydrochloride (0.15 g) and N,N-dimethylformamide (5 mL) was stirred at room temperature for 3 days. Water was poured into the reaction mixture, and the mixture was extracted with ethyl acetate. The organic layer was washed successively with 0.1N hydrochloric acid, saturated aqueous sodium hydrogen carbonate and saturated brine, dried over anhydrous magnesium sulfate, and concentrated to give 2-[4-({(2E)-3-[5-(4-fluorophenyl)-1-methyl-1H-pyrazol-4-yl]prop-2-enoyl}amino)benzyl]-1,3-thiazole-4-carboxamide as colorless crystals (0.21 g, yield 88%). Recrystallization thereof from acetone-hexane gave colorless prism crystals. melting point: 159-160° C.

EXAMPLE 133

A mixture of ethyl [4-({(2E)-3-[5-(4-fluorophenyl)-1-methyl-1H-pyrazol-4-yl]prop-2-enoyl}amino)phenyl]acetate (1.33 g), a 1N aqueous sodium hydroxide solution (5 mL), tetrahydrofuran (5 mL) and ethanol (5 mL) was stirred at room temperature for 1 hr. 1N Hydrochloric acid (5 mL) and water were added to the reaction mixture and the precipitated crystals were collected by filtration to give [4-({(2E)-3-[5-(4-fluorophenyl)-1-methyl-1H-pyrazol-4-yl]prop-2-enoyl]amino}phenyl]acetic acid as colorless crystals (1.14 g, yield 91%). Recrystallization thereof from acetone-hexane gave colorless prism crystals. melting point: 245-246° C.

EXAMPLE 134

To a mixture of [4-({(2E)-3-[5-(4-fluorophenyl)-1-methyl-1H-pyrazol-4-yl]prop-2-enoyl}amino)phenyl]acetic acid (0.40 g), 4-methylmorpholine (0.14 g) and tetrahydrofuran (10 mL) was added dropwise a solution (5 mL) of isobutyl chlorocarbonate (0.20 g) in tetrahydrofuran at 0° C. The reaction mixture was stirred at 0° C. for 1 hr. and insoluble materials were filtered off. The filtrate was added to a mixture of hydrazine hydrate (0.28 g) and tetrahydrofuran (10 mL) at 0° C. The reaction mixture was stirred at 0° C. for 1 hr. and saturated aqueous ammonium chloride was added to the reaction mixture. The precipitated crystals were filtered to give colorless crystals.

A mixture of the obtained crystals, triethyl orthopropionate (0.58 g), methanesulfonic acid (0.02 g) and tetrahydrofuran (10 mL) was heated under reflux for 1 hr. The reaction mixture was diluted with ethyl acetate, and the organic layer was washed successively with saturated aqueous sodium hydrogen carbonate and saturated brine, dried over anhydrous magnesium sulfate and concentrated. The obtained residue was subjected to silica gel column chromatography to give (2E)-N-{4-[(5-ethyl-1,3,4-oxadiazol-2-yl)methyl]phenyl}-3-[5-(4-fluorophenyl)-1-methyl-1H-pyrazol-4-yl]acrylamide as colorless crystals (0.24 g, yield 51%) from a fraction eluted with ethyl acetate-methanol (20:1, v/v). Recrystallization thereof from acetone-hexane gave colorless prism crystals. melting point: 164-165° C.

EXAMPLE 135

To a mixture of [4-({(2E)-3-[5-(4-fluorophenyl)-1-methyl-1H-pyrazol-4-yl]prop-2-enoyl}amino)phenyl]acetic acid (5.5 g), 4-methylmorpholine (1.91 g) and tetrahydrofuran (100 mL) was added dropwise a solution (10 mL) of isobutyl chlorocarbonate (2.98 g) in tetrahydrofuran at 0° C. The reaction mixture was stirred at room temperature for 1 hr. and insoluble materials were filtered off. The filtrate was added dropwise to a mixture of hydrazine monohydrate (3.63 g) and tetrahydrofuran (30 mL) at 0° C. The reaction mixture was stirred at 0° C. for 2 hrs. and saturated aqueous sodium hydrogen carbonate was added. The precipitated crystals were collected by filtration to give (2E)-3-[5-(4-fluorophenyl)-1-methyl-1H-pyrazol-4-yl]-N-[4-(2-hydrazino-2-oxoethyl)phenyl]acrylamide as pale-yellow crystals (4.97 g, yield 87%). Recrystallization thereof from N,N-dimethylformamide-water gave colorless prism crystals. melting point: 273-274° C.

EXAMPLE 136

A mixture of (2E)-3-[5-(4-fluorophenyl)-1-methyl-1H-pyrazol-4-yl]-N-[4-(2-hydrazino-2-oxoethyl)phenyl]acrylamide (0.50 g), triethyl orthoacetate (0.63 g), methanesulfonic acid (0.025 g), and tetrahydrofuran (10 mL) was heated under reflux for 1 hr. The reaction mixture was diluted with ethyl acetate, washed successively with saturated aqueous sodium hydrogen carbonate and saturated brine, dried over anhydrous magnesium sulfate and concentrated. The residue was subjected to silica gel column chromatography to give (2E)-3-[5-(4-fluorophenyl)-1-methyl-1H-pyrazol-4-yl]-N-{4-[(5-methyl-1,3,4-oxadiazol-2-yl) methyl]phenyl}acrylamide as pale-yellow crystals (0.25 g, yield 46%) from a fraction eluted with ethyl acetate-methanol (100:0-20:1, v/v). Recrystallization thereof from ethyl acetate-hexane gave pale-yellow prism crystals. melting point: 151-152° C.

EXAMPLE 137

A mixture of tert-butyl [4-({(2E)-3-[5-(4-fluorophenyl)-1-methyl-1H-pyrazol-4-yl]prop-2-enoyl}amino)benzyl]carbamate (2.0 g) and 4N hydrogenchloride in ethyl acetate (80 mL) was stirred at 70° C. for 15 hrs. The precipitated crystals were collected by filtration and washed with ethyl acetate. A 1N aqueous sodium hydroxide solution (50 mL) was added to the obtained crystals (0.30 g) and the mixture was extracted with ethyl acetate-tetrahydrofuran. The organic layer was washed with saturated brine, dried over anhydrous magnesium sulfate, and concentrated to give (2E)-N-[4-(aminomethyl)phenyl]-3-[5-(4-fluorophenyl)-1-methyl-1H-pyrazol-4-yl]acrylamide as colorless crystals (0.18 g). Recrystallization thereof from ethyl acetate-hexane gave colorless prism crystals. melting point: 201-202° C.

EXAMPLE 138

A mixture of tert-butyl [4-({(2E)-3-[5-(4-fluorophenyl)-1-methyl-1H-pyrazol-4-yl]prop-2-enoyl}amino)benzyl]carbamate (2.0 g) and 4N hydrogenchloride in ethyl acetate (80 mL) was stirred at 70° C. for 15 hrs. The precipitated crystals were collected by filtration, and washed with ethyl acetate. Triethylamine (0.39 g) was added to a solution (10 mL) of the obtained crystals (1.00 g) in N,N-dimethylacetamide at room temperature. The reaction mixture was stirred at room temperature for 30 min. and propionyl chloride (0.27 g) was added. The reaction mixture was further stirred at room temperature for 2.5 days. Water was poured into the reaction mixture, and the mixture was extracted with ethyl acetate-tetrahydrofuran. The organic layer was washed successively with 1N hydrochloric acid, saturated aqueous sodium hydrogen carbonate and saturated brine, dried over anhydrous magnesium sulfate, and concentrated to give (2E)-3-[5-(4-fluorophenyl)-1-methyl-1H-pyrazol-4-yl]-N-{4-[(propionylamino)methyl]phenyl}acrylamide as colorless crystals (0.51 g). Recrystallization thereof from acetone-hexane gave colorless prism crystals. melting point: 271-272° C.

In the similar manner as in Example 138, the compounds described in Examples 139-142 were produced.

EXAMPLE 139

(2E)-3-[5-(4-Fluorophenyl)-1-methyl-1H-pyrazol-4-yl]-N-{4-[(isobutyrylamino)methyl]phenyl}acrylamide was obtained as colorless crystals. Recrystallization thereof from acetone-hexane gave colorless prism crystals. melting point: 258-259° C.

EXAMPLE 140

(2E)-N-{4-[(Butyrylamino)methyl]phenyl}-3-[5-(4-fluorophenyl)-1-methyl-1H-pyrazol-4-yl]acrylamide was obtained as colorless crystals. Recrystallization thereof from acetone-hexane gave colorless prism crystals. melting point: 259-260° C.

EXAMPLE 141

(2E)-3-[5-(4-Fluorophenyl)-1-methyl-1H-pyrazol-4-yl]-N-(4-{[(3-methylbutanoyl)amino]methyl}phenyl)acrylamide was obtained as colorless crystals. Recrystallization thereof from acetone-hexane gave colorless prism crystals. melting point: 226-227° C.

EXAMPLE 142

N-[4-({(2E)-3-[5-(4-Fluorophenyl)-1-methyl-1H-pyrazol-4-yl]prop-2-enoyl}amino)benzyl]benzamide was obtained as colorless crystals. Recrystallization thereof from acetone-hexane gave colorless prism crystals. melting point: 250-251° C.

EXAMPLE 143

A mixture of dimethylamine (2M tetrahydrofuran solution, 1.7 mL), [4-({(2E)-3-[5-(4-fluorophenyl)-1-methyl-1H-pyrazol-4-yl]prop-2-enoyl}amino)phenyl]acetic acid (0.70 g), 1-hydroxy-1H-1,2,3-benzotriazole hydrate (0.35 g), 1-ethyl-3-(3-dimethylaminopropyl) carbodiimide hydrochloride (0.44 g) and N,N-dimethylformamide (20 mL) was stirred at room temperature for 15 hrs. Water was poured into the reaction mixture, and the mixture was extracted with ethyl acetate. The organic layer was washed successively with 1N hydrochloric acid, saturated aqueous sodium hydrogen carbonate and saturated brine, dried over anhydrous magnesium sulfate and concentrated. The residue was subjected to silica gel column chromatography to give (2E)-N-{4-[2-(dimethylamino)-2-oxoethyl]phenyl}-3-[5-(4-fluorophenyl)-1-methyl-1H-pyrazol-4-yl]acrylamide as colorless crystals (0.36 g, yield 49%) from a fraction eluted with ethyl acetate-methanol (20:1, v/v). Recrystallization thereof from acetone-diisopropyl ether gave colorless prism crystals. melting point: 209-210° C.

EXAMPLE 144

A mixture of diethylamine (0.17 g), [4-({(2E)-3-[5-(4-fluorophenyl)-1-methyl-1H-pyrazol-4-yl]prop-2-enoyl}amino)phenyl]acetic acid (0.70 g), 1-hydroxy-1H-1,2,3-benzotriazole hydrate (0.35 g), 1-ethyl-3-(3-dimethylaminopropyl) carbodiimide hydrochloride (0.44 g) and N,N-dimethylformamide (20 mL) was stirred at room temperature for 15 hrs. Water was poured into the reaction mixture, and the mixture was extracted with ethyl acetate. The organic layer was washed successively with 1N hydrochloric acid, saturated aqueous sodium hydrogen carbonate and saturated brine, dried over anhydrous magnesium sulfate and concentrated. The residue was subjected to silica gel column chromatography to give ((2E)-N-{4-[2-(diethylamino)-2-oxoethyl]phenyl}-3-[5-(4-fluorophenyl)-1-methyl-1H-pyrazol-4-yl]acrylamide as colorless crystals (0.48 g, yield 62%) from a fraction eluted with ethyl acetate-methanol (20:1, v/v). Recrystallization thereof from acetone-hexane gave colorless prism crystals. melting point: 175-176° C.

EXAMPLE 145

To a mixture of (2E)-3-[5-(4-fluorophenyl)-1-methyl-1H-pyrazol-4-yl]acrylic acid (35.0 g), acetonitrile (245 mL) and dimethylformamide (0.175 mL) was added thionyl chloride (11.4 mL) at 40-45° C. and the mixture was stirred for 1 hr. Then diethyl 4-aminobenzylphosphonate (36.3 g) was added at 5° C. and diisopropylethylamine (61.9 mL) was further added dropwise. The mixture was stirred at room temperature for 1 hr. A 1N aqueous sodium hydroxide solution (140 mL) was added to neutralize the reaction mixture and water (472.5 mL) was further added. The mixture was stirred at room temperature for 1 hr. The precipitated crystals were collected by filtration and washed with 30% acetonitrile to give diethyl [4-({(2E)-3-[5-(4-fluorophenyl)-1-methyl-1H-pyrazol-4-yl]prop-2-enoyl}amino)benzyl]phosphonate (61.5 g, yield 92%).

The obtained crystals were dissolved in 90% ethanol by heating, warm water was added at 60-65° C., a seed crystal was added with stirring and the mixture was cooled to room temperature to give crystals. melting point: 208-209° C.

EXAMPLE 146

A mixture of dimethyl 4-aminobenzylphosphonate (258 mg), (2E)-3-[5-(3-furyl)-1-methyl-1H-pyrazol-4-yl]acrylic acid (218 mg), 1-hydroxy-1H-1,2,3-benzotriazole hydrate (184 mg), 1-ethyl-3-(3-dimethylaminopropyl)carbodiimide hydrochloride (230 mg) and N,N-dimethylformamide (8 mL) was stirred overnight at room temperature. The reaction mixture was poured into a 0.5N aqueous hydrochloric acid solution, and the mixture was extracted with ethyl acetate. The ethyl acetate layer was washed with saturated aqueous sodium hydrogen carbonate and then with saturated brine, dried ($MgSO_4$) and concentrated. The obtained solid was recrystallized from ethyl acetate-hexane to give dimethyl 4-{[(2E)-3-[5-(3-furyl)-1-methyl-1H-pyrazol-4-yl]prop-2-enoyl]amino}benzylphosphonate (123 mg, yield 30%) as colorless prism crystals. melting point: 176-177° C.

In the similar manner as in Example 146, the compounds described in Examples 147-155 were produced.

EXAMPLE 147

Diethyl 4-[{(2E)-3-[5-(3-furyl)-1-methyl-1H-pyrazol-4-yl]prop-2-enoyl) amino]benzylphosphonate yield: 37%. Colorless prism crystals. melting point: 208-210° C. (recrystallized from ethyl acetate-hexane).

EXAMPLE 148

Dimethyl 4-({(2E)-3-[1-methyl-5-(2-thienyl)-1H-pyrazol-4-yl]prop-2-enoyl}amino)benzylphosphonate yield: 24%. Colorless prism crystals. melting point: 247-248° C. (recrystallized from ethyl acetate-hexane).

EXAMPLE 149

Diethyl [4-({(2E)-3-[1-methyl-5-(2-thienyl)-1H-pyrazol-4-yl]prop-2-enoyl}amino)benzyl]phosphonate yield: 31%. Colorless prism crystals. melting point: 262-263° C. (recrystallized from ethyl acetate-hexane).

EXAMPLE 150

Diethyl 4-({(2E)-3-[1-methyl-5-(3-pyridinyl)-1H-pyrazol-4-yl]prop-2-enoyl}amino)benzylphosphonate yield: 37%. Colorless prism crystals. melting point: 211-214° C. (recrystallized from ethanol-ethyl acetate).

EXAMPLE 151

Diethyl 4-{[(2E)-3-(1,5-dimethyl-1H-pyrazol-4-yl)prop-2-enoyl]amino}benzylphosphonate yield: 29%. Colorless prism crystals. melting point: 228-230° C. (recrystallized from ethyl acetate-hexane).

EXAMPLE 152

Diethyl 4-{[(2E)-3-(1-methyl-1H-pyrazol-4-yl)prop-2-enoyl]amino}benzylphosphonate yield: 34%. Colorless prism crystals. melting point: 201-202° C. (recrystallized from ethyl acetate-hexane).

EXAMPLE 153

(2E)-3-[5-(4-Fluorophenyl)-1-methyl-1H-pyrazol-4-yl]-N-[4-(hydroxymethyl) phenyl]acrylamide yield: 74%. Colorless prism crystals. melting point: 117-118° C. (recrystallized from ethyl acetate-isopropyl ether).

EXAMPLE 154

Diethyl 4-[({(2E)-3-[5-(4-fluorophenyl)-1-methyl-1H-pyrazol-4-yl]prop-2-enoyl)amino)methyl]benzylphosphonate yield: 74%. Amorphous form.
NMR(CDCl$_3$)δ: 1.25 (6H, t, J=7.0 Hz), 3.11 (2H, d, J=21.6 Hz), 3.76 (3H, s), 3.93-4.08 (4H, m), 4.46-4.50 (2H, m), 5.96-6.02 (1H, m), 6.15 (1H, d, J=15.4 Hz), 7.15-7.36 (9H, m), 7.74 (1H, s).

EXAMPLE 155

(2E)-N-(4-[(2,4-Dioxo-1,3-thiazolidin-3-yl)methyl]phenyl}-3-3-[5-(4-fluorophenyl)-1-methyl-1H-pyrazol-4-yl]acrylamide yield: 75%. Colorless prism crystals. melting point: 245-247° C. (recrystallized from ethyl acetate-hexane).

EXAMPLE 156

A mixture of (2E)-3-[5-(4-fluorophenyl)-1-methyl-1H-pyrazol-4-yl]-N-[4-(hydroxymethyl)phenyl]acrylamide (8.4 g), thionyl chloride (2.59 mL) and tetrahydrofuran (70 mL) was heated under reflux for 3 hrs. The reaction mixture was poured into saturated aqueous sodium hydrogen carbonate, and the mixture was extracted with ethyl acetate. The ethyl acetate layer was washed with water and then saturated brine, dried (MgSO$_4$) and concentrated to give a solid (6.22 g). To a mixture of 1,3-oxazolidine-2,4-dione (123.3 mg) and N,N-dimethylformamide (5 mL) was added sodium hydride (60% in oil, 48.8 mg) and the mixture was stirred at room temperature for 30 min. The obtained solid (300 mg) was added to the reaction mixture and the mixture was further stirred overnight at room temperature. Water was added to the reaction mixture, and the mixture was extracted with ethyl acetate. The organic layer was washed successively with 0.1N hydrochloric acid, water and saturated brine, dried over anhydrous magnesium sulfate, and concentrated. The residue was recrystallized from ethyl acetate-hexane to give (2E)-N-{4-[(2,4-dioxo-1,3-oxazolidin-3-yl)methyl]phenyl}-3-[5-(4-fluorophenyl)-1-methyl-1H-pyrazol-4-yl]acrylamide as yellow prism crystals (132 mg, yield 37%). melting point: 239-240° C.

In the similar manner as in Example 146, the compounds described in Examples 157-158 were produced.

EXAMPLE 157

(2E)-N-{4-[(2,5-Dioxo-1-imidazolidinyl)methyl]phenyl}-3-[5-(4-fluorophenyl)-1-methyl-1H-pyrazol-4-yl]acrylamide yield: 53%. Yellow prism crystals. melting point: 249-250° C. (recrystallized from ethyl acetate-hexane).

EXAMPLE 158

(2E)-N-{4-[(2,6-Dioxo-1-piperidinyl)methyl]phenyl}-3-[5-(4-fluorophenyl)-1-methyl-1H-pyrazol-4-yl]acrylamide yield: 65%. Colorless prism crystals. melting point: 218-220° C. (recrystallized from ethyl acetate-hexane).

EXAMPLE 159

A mixture of (2E)-3-[5-(4-fluorophenyl)-1-methyl-1H-pyrazol-4-yl]acrylic acid (1.0 g), oxalyl chloride (618 mg), tetrahydrofuran (60 mL) and N,N-dimethylformamide (2 drops) was stirred at room temperature for 2 hrs. The reaction mixture was concentrated and diluted with N,N-dimethylacetamide (50 mL). 4-(1H-Imidazol-1-ylmethyl)aniline (844 mg) was added and the mixture was stirred overnight at room temperature. Water was poured into the reaction mixture, and the mixture was extracted with ethyl acetate. The ethyl acetate layer was washed with water, dried (MgSO$_4$) and concentrated. The obtained solid was recrystallized from acetone-hexane to give (2E)-3-[5-(4-fluorophenyl)-1-methyl-1H-pyrazol-4-yl]-N-[4-(1H-imidazol-1-ylmethyl) phenyl] acrylamide as pale-yellow prism crystals (1.41 g, yield 86%). melting point: 213-214° C.

In the similar manner as in Example 146, the compounds described in Examples 160-179 were produced.

EXAMPLE 160

(2E)-N-[4-(2-Amino-2-oxoethyl)phenyl]-3-[5-(4-fluorophenyl)-1-methyl-H-pyrazol-4-yl]acrylamide yield: 46%. Colorless prism crystals. melting point: 253-255° C. (recrystallized from ethyl acetate-hexane).

EXAMPLE 161

(2E)-3-[5-(4-Fluorophenyl)-1-methyl-1H-pyrazol-4-yl]-N-[4-(1H-pyrazol-1-ylmethyl)phenyl]acrylamide yield: 86%. Colorless prism crystals. melting point: 189-191° C. (recrystallized from acetone-hexane).

EXAMPLE 162

(2E)-3-[5-(4-Fluorophenyl)-1-methyl-1H-pyrazol-4-yl]-N-{4-[(2-isopropyl-1H-imidazol-1-yl)methyl]phenyl}acrylamide yield: 74%. Colorless prism crystals. melting point: 271-272° C. (recrystallized from acetone-hexane).

EXAMPLE 163

(2E)-3-[5-(4-Fluorophenyl)-1-methyl-1H-pyrazol-4-yl]-N-[4-(1H-1,2,4-triazol-1-ylmethyl)phenyl]acrylamide yield: 90%. Colorless prism crystals. melting point: 225-226° C. (recrystallized from acetone-hexane).

EXAMPLE 164

Methyl 1-[4-({(2E)-3-[5-(4-fluorophenyl)-1-methyl-1H-pyrazol-4-yl]prop-2-enoyl}amino)benzyl]-1H-1,2,4-triazole-5-carboxylate yield: 87%. Colorless prism crystals. melting point: 203-205° C. (recrystallized from acetone-hexane).

EXAMPLE 165

(2E)-N-(4-Acetylphenyl)-3-[5-(4-fluorophenyl)-1-methyl-1H-pyrazol-4-yl)acrylamide yield: 65%. Colorless prism crystals. melting point: 204-205° C. (recrystallized from acetone-hexane).

EXAMPLE 166

(2E)-N-[4-(Acetylamino)phenyl]-3-[5-(4-fluorophenyl)-1-methyl-1H-pyrazol-4-yl]acrylamide yield: 87%. Colorless prism crystals. melting point: 281-282° C. (recrystallized from acetone-hexane).

EXAMPLE 167

(2E)-3-[5-(4-Fluorophenyl)-1-methyl-1H-pyrazol-4-yl]-N-[4-(2-hydroxyethyl) phenyl]acrylamide yield: 85%. Colorless prism crystals. melting point: 198-200° C. (recrystallized from acetone-hexane).

EXAMPLE 168

(2E)-3-[5-(4-Fluorophenyl)-1-methyl-1H-pyrazol-4-yl]-N-(4-methylphenyl) acrylamide yield: 85%. Colorless prism crystals. melting point: 178-180° C. (recrystallized from acetone-hexane).

EXAMPLE 169

(2E)-3-[5-(4-Fluorophenyl)-1-methyl-1H-pyrazol-4-yl]-N-[3-(hydroxymethyl) phenyl)acrylamide yield: 42%. Colorless prism crystals. melting point: 130-132° C. (recrystallized from acetone-hexane).

EXAMPLE 170 tert-Butyl 4-({(2E)-3-[5-(4-fluorophenyl)-1-methyl-1H-pyrazol-4-yl]prop-2-enoyl]amino)benzylcarbamate yield: 69%. Colorless prism crystals. melting point: 222-223° C. (recrystallized from acetone-isopropyl ether).

EXAMPLE 171

(2E)-N-{4-[(4-Ethyl-1H-imidazol-1-yl)methyl]phenyl}-3-[5-(4-fluorophenyl)-1-methyl-1H-pyrazol-4-yl]acrylamide yield: 30%. Colorless prism crystals. melting point: 224-226° C. (recrystallized from acetone-hexane).

EXAMPLE 172

(2E)-N-(4-[(5,6-Dimethyl-1H-benzimidazol-1-yl)methyl]phenyl}-3-[5-(4-fluorophenyl)-1-methyl-1H-pyrazol-4-yl]acrylamide yield: 74%. Colorless prism crystals. melting point: 279-280° C. (recrystallized from acetone-methanol).

EXAMPLE 173

(2E)-3-[5-(4-Fluorophenyl)-1-methyl-1H-pyrazol-4-yl]-N-{4-[(2-methyl-1H-benzimidazol-1-yl)methyl]phenyl}acrylamide yield: 58%. Colorless prism crystals. melting point: 263-264° C. (recrystallized from acetone-methanol).

EXAMPLE 174

(2E)-3-[5-(4-Fluorophenyl)-1-methyl-1H-pyrazol-4-yl]-N-{4-[hydroxy(phenyl)methyl]phenyl}acrylamide yield: 50%. Colorless prism crystals. melting point: 192-195° C. (recrystallized from ethyl acetate).

EXAMPLE 175

(2E)-N-(4-Benzylphenyl)-3-[5-(4-fluorophenyl)-1-methyl-1H-pyrazol-4-yl]acrylamide yield: 28%. Colorless prism crystals. melting point: 226-227° C. (recrystallized from acetone-hexane).

EXAMPLE 176

(2E)-3-[5-(4-Fluorophenyl)-1-methyl-1H-pyrazol-4-yl]-N-[4-(1H-indazol-1-ylmethyl)phenyl]acrylamide yield: 71%. Colorless prism crystals. melting point: 146-148° C. (recrystallized from acetone-hexane).

EXAMPLE 177

(2E)-N-[4-(1H-1,2,3-Benzotriazol-1-ylmethyl)phenyl]-3-[5-(4-fluorophenyl)-1-methyl-1H-pyrazol-4-yl]acrylamide yield: 41%. Colorless prism crystals. melting point: 226-227° C. (recrystallized from acetone-hexane).

EXAMPLE 178

(2E)-3-[5-(4-Fluorophenyl)-1-methyl-1H-pyrazol-4-yl]-N-[4-(2H-indazol-2-ylmethyl)phenyl]acrylamide yield: 53%. Colorless prism crystals. melting point: 231-232° C. (recrystallized from acetone-hexane).

EXAMPLE 179

(2E)-N-[4-(2H-1,2,3-Benzotriazol-2-ylmethyl)phenyl]-3-[5-(4-fluorophenyl)-1-methyl-1H-pyrazol-4-yl]acrylamide yield: 50%. Colorless prism crystals. melting point: 222-223° C. (recrystallized from acetone-hexane).

EXAMPLE 180

A mixture of (2E)-3-[5-(4-fluorophenyl)-1-methyl-1H-pyrazol-4-yl]acrylic acid (600 mg), oxalyl chloride (260 µL), tetrahydrofuran (10 mL) and N,N-dimethylformamide (2 drops) was stirred at room temperature for 3 hrs. The reaction mixture was concentrated and diluted with N,N-dimethylacetamide (10 mL). Ethyl 4-aminobenzoate (482 mg) was added and the mixture was stirred at room temperature for 3 hrs. The reaction mixture was poured into a 0.1N aqueous hydrochloric acid solution, and the mixture was extracted with ethyl acetate. The ethyl acetate layer was washed with saturated aqueous sodium hydrogen carbonate, and then with saturated brine, dried ($MgSO_4$) and concentrated. The obtained solid was recrystallized from acetone-hexane to give ethyl 4-({(2E)-3-[5-(4-fluorophenyl)-1-methyl-1H-pyrazol-4-yl]prop-2-enoyl}amino)benzoate (810 mg, yield 84%) as colorless needle crystals. melting point: 202-203° C.

In the similar manner as in Example 180, the compounds described in Examples 181-206 were produced.

EXAMPLE 181

(2E)-N-[4-(Aminosulfonyl)phenyl]-3-[5-(4-fluorophenyl)-1-methyl-1H-pyrazol-4-yl]acrylamide yield: 39%. Pale-yellow prism crystals. melting point: 300-305° C. (decomposition)(recrystallized from acetone-isopropyl ether).

EXAMPLE 182

(2E)-3-[5-(4-Fluorophenyl)-1-methyl-1H-pyrazol-4-yl]-N-(4-hydroxyphenyl) acrylamide yield: 65%. Colorless prism crystals. melting point: 259-260° C. (recrystallized from ethyl acetate-hexane).

EXAMPLE 183

4-({(2E)-3-[5-(4-Fluorophenyl)-1-methyl-1H-pyrazol-4-yl]prop-2-enoyl}amino)benzamide yield: 76%. Colorless prism crystals. melting point: 276-278° C. (recrystallized from acetone-hexane).

EXAMPLE 184

(2E)-3-[5-(4-Fluorophenyl)-1-methyl-1H-pyrazol-4-yl]-N-[2-(hydroxymethyl) phenyl]acrylamide yield: 22%. Colorless prism crystals. melting point: 119-120° C. (recrystallized from acetone-hexane).

EXAMPLE 185

(2E)-N-[4-(1H-Benzimidazol-1-ylmethyl)phenyl]-3-[5-(4-fluorophenyl)-1-methyl-1H-pyrazol-4-yl]acrylamide yield: 79%. Pale-yellow prism crystals. melting point: 243-244° C. (recrystallized from acetone-hexane).

EXAMPLE 186

(2E)-3-[5-(4-Fluorophenyl)-1-methyl-1H-pyrazol-4-yl]-N-{4-[2-(1H-pyrazol-1-yl)ethyl]phenyl}acrylamide yield: 82%. Colorless prism crystals. melting point: 205-206° C. (recrystallized from ethyl acetate-hexane).

EXAMPLE 187

(2E)-3-{5-(4-Fluorophenyl)-1-methyl-1H-pyrazol-4-yl}-N-{4-[2-(1H-imidazol-1-yl)ethyl]phenyl}acrylamide yield: 71%. Colorless prism crystals. melting point: 160-162° C. (recrystallized from ethyl acetate-hexane).

EXAMPLE 188

Ethyl 4-{[4-({(2E)-3-[5-(4-fluorophenyl)-1-methyl-1H-pyrazol-4-yl]prop-2-enoyl}amino)benzyl]amino}-4-oxobutanoate yield: 57%. Colorless prism crystals. melting point: 195-197° C. (recrystallized from acetone-hexane).

EXAMPLE 189

(2E)-N-{4-[(Acetylamino)methyl]phenyl}-3-[5-(4-fluorophenyl)-1-methyl-1H-pyrazol-4-yl]acrylamide yield: 62%. Colorless prism crystals. melting point: 233-234° C. (recrystallized from acetone-hexane).

EXAMPLE 190

(2E)-3-[5-(4-Fluorophenyl)-1-methyl-1H-pyrazol-4-yl]-N-{4-[(2-methyl-1H-imidazol-1-yl)methyl]phenyl}acrylamide yield: 63%. Colorless prism crystals. melting point: 232-233° C. (recrystallized from ethanol-hexane).

EXAMPLE 191

(2E)-N-{4-[(2-Ethyl-1H-imidazol-1-yl)methyl]phenyl}-3-[5-(4-fluorophenyl)-1-methyl-1H-pyrazol-4-yl]acrylamide yield: 56%. Colorless prism crystals. melting point: 237-238° C. (recrystallized from ethanol-hexane).

EXAMPLE 192

(2E)-3-[5-(4-Fluorophenyl)-1-methyl-1H-pyrazol-4-yl]-N-[4-(4-morpholinylmethyl) phenyl]acrylamide yield: 75%. Colorless prism crystals. melting point: 202-203° C. (recrystallized from ethanol-hexane).

EXAMPLE 193

(2E)-3-[5-(4-Fluorophenyl)-1-methyl-1H-pyrazol-4-yl]-N-[4-(1-pyrrolidinylmethyl) phenyl]acrylamide yield: 25%. Colorless prism crystals. melting point: 192-193° C. (recrystallized from ethanol-hexane).

EXAMPLE 194

(2E)-3-[5-(4-Fluorophenyl)-1-methyl-1H-pyrazol-4-yl]-N-[4-(1H-1,2,3-triazol-1-ylmethyl)phenyl]acrylamide yield: 50%. Colorless prism crystals. melting point: 252-253° C. (recrystallized from ethanol-hexane).

EXAMPLE 195

(2E)-3-[5-(4-Fluorophenyl)-1-methyl-1H-pyrazol-4-yl]-N-[4-1H-imidazol-1-yl)phenyl]acrylamide yield: 10%. Colorless prism crystals. melting point: 238-239° C. (recrystallized from ethanol-ethyl acetate).

EXAMPLE 196

(2E)-3-[5-(4-Fluorophenyl)-1-methyl-1H-pyrazol-4-yl]-N-[4-(2H-1,2,3-triazol-2-ylmethyl)phenyl]acrylamide yield: 74%. Colorless prism crystals. melting point: 178-179° C. (recrystallized from ethyl acetate-hexane).

EXAMPLE 197

(2E)-3-[5-(4-Fluorophenyl)-1-methyl-1H-pyrazol-4-yl]-N-[4-(1H-pyrazol-1-yl)phenyl]acrylamide yield: 63%. Pale-yellow prism crystals. melting point: 200-201° C. (recrystallized from ethyl acetate-hexane).

EXAMPLE 198

(2E)-3-[5-(4-Fluorophenyl)-1-methyl-1H-pyrazol-4-yl]-N-[4-(2H-tetrazol-2-ylmethyl)phenyl]acrylamide yield: 83%. Pale-yellow prism crystals. melting point: 210-211° C. (recrystallized from ethyl acetate-hexane).

EXAMPLE 199

(2E)-3 [5-(4-Fluorophenyl)-1-methyl-1H-pyrazol-4-yl]-N-[4-(1H-tetrazol-1-ylmethyl)phenyl]acrylamide yield: 78%. Colorless prism crystals. melting point: 233-234° C. (recrystallized from ethyl acetate-hexane).

EXAMPLE 200

(2E)-3-[5-(4-Fluorophenyl)-1-methyl-1H-pyrazol-4-yl]-N-(4-{[2-(hydroxymethyl)-1H-imidazol-1-yl]methyl}phenyl)acrylamide yield: 38%. Colorless prism crystals. melting point: 229-230° C. (recrystallized from acetone-hexane).

EXAMPLE 201

(2E)-3-[5-(4-Fluorophenyl)-1-methyl-1H-pyrazol-4-yl]-N-{4-[(5-methyl-1H-imidazol-1-yl)methyl]phenyl}acrylamide yield: 50%. Colorless prism crystals. melting point: 260-261° C. (recrystallized from acetone-hexane).

EXAMPLE 202

(2E)-3-[5-(4-Fluorophenyl)-1-methyl-1H-pyrazol-4-yl]-N-{4-[(4-methyl-1H-imidazol-1-yl)methyl]phenyl}acrylamide yield: 57%. Colorless prism crystals. melting point: 202-203° C. (recrystallized from acetone-hexane).

EXAMPLE 203

(2E)-N-{4-[(1,1-Dioxide-4-thiomorpholinyl)methyl]phenyl}-3-[5-(4-fluorophenyl)-1-methyl-1H-pyrazol-4-yl]acrylamide yield: 73%. Colorless prism crystals. melting point: 237-238° C. (recrystallized from acetone-hexane).

EXAMPLE 204

(2E)-3-[5-(4-Fluorophenyl)-1-methyl-1H-pyrazol-4-yl]-N-[4-(methylthio) phenyl]acrylamide yield: 76%. Colorless prism crystals. melting point: 164-165° C. (recrystallized from ethyl acetate-hexane).

EXAMPLE 205

(2E)-N-(4-Benzoylphenyl)-3-[5-(4-fluorophenyl)-1-methyl-1H-pyrazol-4-yl]acrylamide yield: 82%. Colorless prism crystals. melting point: 110-112° C. (recrystallized from acetone-hexane).

EXAMPLE 206

(2E)-3-[5-(4-Fluorophenyl)-1-methyl-1H-pyrazol-4-yl]-N-[4-(phenylsulfonyl) phenyl]acrylamide yield: 61%. Colorless prism crystals. melting point: 169-172° C. (recrystallized from acetone-hexane).

EXAMPLE 207

A mixture of (2E)-3-[5-(4-fluorophenyl)-1-methyl-1H-pyrazol-4-yl]-N-[4-(hydroxymethyl)phenyl]acrylamide (8.4 g), thionyl chloride (2.59 mL) and tetrahydrofuran (70 mL) was heated under reflux for 3 hrs. The reaction mixture was poured into saturated aqueous sodium hydrogen carbonate, and the mixture was extracted with ethyl acetate. The ethyl acetate layer was washed with water and then saturated brine, dried ($MgSO_4$) and concentrated to give a solid (6.22 g). A mixture of this solid (1.0 g), sodium thiomethoxide (0.57 g) and N,N-dimethylformamide (10 mL) was stirred at 40° C. for 14 hrs. The reaction mixture was poured into a 0.1N aqueous hydrochloric acid solution, and the mixture was extracted with ethyl acetate. The ethyl acetate layer was washed with saturated aqueous sodium hydrogen carbonate, and then with saturated brine, dried ($MgSO_4$) and concentrated. The residue was subjected to silica gel column chromatography to give (2E)-3-{1-methyl-5-[4-(methylthio) phenyl]-1H-pyrazol-4-yl}-N-{4-[(methylthio)methyl] phenyl}acrylamide as crystals (650 mg) from a fraction eluted with hexane-ethyl acetate (2:1-1:1, v/v). Recrystallization thereof from acetone-hexane gave colorless prism crystals. melting point: 145-146° C.

EXAMPLE 208

A mixture of (2E)-3-[5-(4-fluorophenyl)-1-methyl-1H-pyrazol-4-yl]-N-[4-(hydroxymethyl)phenyl]acrylamide (8.4 g), thionyl chloride (2.59 mL) and tetrahydrofuran (70 mL) was heated under reflux for 3 hrs. The reaction mixture was poured into saturated aqueous sodium hydrogen carbonate, and the mixture was extracted with ethyl acetate. The ethyl acetate layer was washed with water and then saturated brine, dried ($MgSO_4$) and concentrated to give a solid (6.22 g). A mixture of this solid (300 mg), sodium thiomethoxide (56.9 mg) and N,N-dimethylformamide (10 mL) was stirred at room temperature for 30-min. The reaction mixture was poured into a 0.1N aqueous hydrochloric acid solution, and the mixture was extracted with ethyl acetate. The ethyl acetate layer was washed with saturated aqueous sodium hydrogen carbonate, and then with saturated brine, dried ($MgSO_4$) and concentrated. The residue was subjected to silica gel column chromatography to give (2E)-3-[5-(4-fluorophenyl)-1-methyl-1H-pyrazol-4-yl]-N-{4-[(methylthio)methyl] phenyl}acrylamide as crystals (125 mg) from a fraction eluted wit hexane-ethyl acetate (1:1-0:1, v/v). Recrystallization thereof from acetone-hexane gave colorless prism crystals. melting point: 165-168° C.

In the similar manner as in Example 208, the compounds described in Examples 209-214 were produced.

EXAMPLE 209

(2E)-3-[5-(4-Fluorophenyl)-1-methyl-1H-pyrazol-4-yl]-N-[4-(methoxymethyl) phenyl]acrylamide Colorless prism crystals. melting point: 170-171° C. (recrystallized from acetone-hexane).

EXAMPLE 210

(2E)-N-{4-[(Ethylthio)methyl]phenyl}-3-[5-(4-fluorophenyl)-1-methyl-1H-pyrazol-4-yl]acrylamide Colorless prism crystals. melting point: 157-158° C. (recrystallized from ethyl acetate-hexane).

EXAMPLE 211

(2E)-N-{4-[(tert-Butylthio)methyl]phenyl}-3-[5-(4-fluorophenyl)-1-methyl-1H-pyrazol-4-yl]acrylamide Colorless prism crystals. melting point: 166-168° C. (recrystallized from acetone-hexane).

EXAMPLE 212

(2E)-3-[5-(4-Fluorophenyl)-1-methyl-1H-pyrazol-4-yl]-N-{4-[(phenylthio)methyl]phenyl}acrylamide Colorless prism crystals. melting point: 197-198° C. (recrystallized from acetone-hexane).

EXAMPLE 213

(2E)-3-[5-(4-Fluorophenyl)-1-methyl-1H-pyrazol-4-yl]-N-(4-[(1H-1,2,3-triazol-4-ylthio)methyl)phenyl] acrylamide Colorless prism crystals. melting point: 182-183° C. (recrystallized from acetone-hexane).

EXAMPLE 214

(2E)-3-[5-(4-Fluorophenyl)-1-methyl-1H-pyrazol-4-yl]-N-(4-[[(1-methyl-1H-tetrazol-5-yl)thio]methyl] phenyl)acrylamide Colorless prism crystals. melting point: 150-152° C. (recrystallized from acetone-hexane).

EXAMPLE 215

A mixture of (2E)-3-[5-(4-fluorophenyl)-1-methyl-1H-pyrazol-4-yl]-N-{4-[(methylthio)methyl] phenyl}acrylamide (600 mg), m-chloroperbenzoic acid (387 mg) and tetrahydrofuran (50 mL) was stirred at 0° C. for 20 min. A saturated aqueous sodium sulfite solution was added to the reaction mixture, and the mixture was extracted with ethyl acetate. The ethyl acetate layer was washed with saturated aqueous sodium hydrogen carbonate, and then with saturated brine, dried ($MgSO_4$) and concentrated. The obtained solid was recrystallized from acetone-hexane to give (2E)-3-(5-(4-fluorophenyl)-1-methyl-1H-pyrazol-4-yl)-N-(4-((methylsulfinyl)methyl)phenyl)acrylamide (340 mg, yield 54%) as colorless prism crystals. melting point: 240-241° C.

In the similar manner as in Example 215, the compounds described in Examples 216-221 were produced.

EXAMPLE 216

(2E)-N-{4-[(Ethylsulfinyl)methyl]phenyl}-3-[5-(4-fluorophenyl)-1-methyl-1H-pyrazol-4-yl]acrylamide yield: 66%. Colorless prism crystals. melting point: 228-229° C. (recrystallized from ethyl acetate-hexane).

EXAMPLE 217

(2E)-3-[5-(4-Fluorophenyl)-1-methyl-1H-pyrazol-4-yl]-N-[4-(methylsulfinyl) phenyl]acrylamide yield: 62%. Colorless prism crystals. melting point: 260-261° C. (recrystallized from acetone-hexane).

EXAMPLE 218

(2E)-N-{4-[(tert-Butylsulfinyl)methyl]phenyl}-3-[5-(4-fluorophenyl)-1-methyl-1H-pyrazol-4-yl]acrylamide yield: 33%. Colorless prism crystals. melting point: 242-243° C. (recrystallized from acetone-hexane).

EXAMPLE 219

(2E)-3-[5-(4-Fluorophenyl)-1-methyl-1H-pyrazol-4-yl]-N-{4-[(phenylsulfinyl)methyl]phenyl}acrylamide yield: 47%. Colorless prism crystals. melting point: 236-237° C. (recrystallized from acetone-methanol).

EXAMPLE 220

(2E)-3-[5-(4-Fluorophenyl)-1-methyl-1H-pyrazol-4-yl]-N-(4-{[(1-methyl-1H-tetrazol-5-yl)sulfinyl]methyl}phenyl)acrylamide yield: 66%. Colorless prism crystals. melting point: 179-183° C. (recrystallized from acetone-hexane).

EXAMPLE 221

(2E)-3-[5-(4-Fluorophenyl)-1-methyl-1H-pyrazol-4-yl]-N-{4-[(1H-1,2,3-triazol-4-yl)sulfinyl]methyl}phenyl)acrylamide yield: 54%. Colorless prism crystals. melting point: 179-183° C. (recrystallized from acetone-hexane).

EXAMPLE 222

A mixture of (2E)-3-[5-(4-fluorophenyl)-1-methyl-1H-pyrazol-4-yl]-N-{4-[(methylthio)methyl]phenyl}acrylamide (600 mg), m-chloroperbenzoic acid (780 mg) and tetrahydrofuran (50 mL) was stirred at 0° C. for 20 min. A saturated aqueous sodium sulfite solution was added to the reaction mixture, and the mixture was further stirred for 10 min. and extracted with ethyl acetate. The ethyl acetate layer was washed with saturated aqueous sodium hydrogen carbonate, and then with saturated brine, dried (MgSO$_4$) and concentrated. The obtained solid was recrystallized from acetone-hexane to give (2E)-3-[5-(4-fluorophenyl)-1-methyl-1H-pyrazol-4-yl]-N-(4-[(methylsulfonyl) methyl]phenyl)acrylamide (490 mg, yield 75%) as colorless prism crystals. melting point: 251-252° C.

In the similar manner as in Example 222, the compounds described in Examples 223-227 were produced.

EXAMPLE 223

(2E)-N-{4-[(Ethylsulfonyl)methyl]phenyl}-3-[5-(4-fluorophenyl)-1-methyl-1H-pyrazol-4-yl]acrylamide yield: 64%. Colorless prism crystals. melting point: 257-258° C. (recrystallized from ethyl acetate-hexane).

EXAMPLE 224

(2E)-N-{4-[(tert-Butylsulfonyl)methyl]phenyl}-3-[5-(4-fluorophenyl)-1-methyl-1H-pyrazol-4-yl]acrylamide yield: 71%. Colorless prism crystals. melting point: 260-261° C. (recrystallized from acetone-hexane).

EXAMPLE 225

(2E)-3-[5-(4-Fluorophenyl)-1-methyl-1H-pyrazol-4-yl]-N-{4-[(phenylsulfonyl)methyl] phenyl}acrylamide yield: 66%. Colorless prism crystals. melting point: 223-224° C. (recrystallized from acetone-hexane).

EXAMPLE 226

(2E)-3-(5-(4-Fluorophenyl)-1-methyl-1H-pyrazol-4-yl]-N-(4-{[(1-methyl-1H-tetrazol-5-yl)sulfonyl]methyl}phenyl)acrylamide yield: 21%. Colorless prism crystals. melting point: 224-225° C. (recrystallized from acetone-hexane).

EXAMPLE 227

(2E)-3-[5-(4-Fluorophenyl)-1-methyl-1H-pyrazol-4-yl]-N-{4-[(1H-1,2,3-triazol-4-ylsulfonyl)methyl]phenyl}acrylamide yield: 45%. Colorless prism crystals. melting point: 204-206° C. (recrystallized from acetone-hexane).

EXAMPLE 228

A mixture of diethyl {3-[(1,3-dioxo-1,3-dihydro-2H-isoindol-2-yl)methyl]benzyl}phosphonate (8.0 g), hydrazine hydrate (4 mL) and methanol (100 mL) was heated under reflux for 14 hrs. The reaction mixture was cooled and the precipitated crystals were removed by filtration. The filtrate was concentrated and a 1N aqueous sodium hydroxide solution (50 mL) was added to the residue. The mixture was extracted with ethyl acetate. The ethyl acetate layer was washed with water and then with saturated brine, dried (MgSO$_4$) and concentrated to give a colorless oil (2.0 g). A mixture of this oil (310 mg), (2E)-3-[5-(4-fluorophenyl)-1-methyl-1H-pyrazol-4-yl]acrylic acid (246 mg), 1-hydroxy-1H-1,2,3-benzotriazole hydrate (184 mg), 1-ethyl-3-(3-dimethylaminopropyl)carbodiimide hydrochloride (230 mg) and N,N-dimethylformamide (8 mL) was stirred overnight at room temperature. The reaction mixture was poured into a 0.5N aqueous hydrochloric acid solution, and the mixture was extracted with ethyl acetate. The ethyl acetate layer was washed with saturated aqueous sodium hydrogen carbonate, and then with saturated brine, dried (MgSO$_4$) and concentrated. The residue was subjected to silica gel column chromatography to give diethyl 3-[({(2E)-3-[5-(4-fluorophenyl)-1-methyl-1H-pyrazol-4-yl]prop-2-enoyl}amino)methyl]benzylphosphonate (391 mg) as an amorphous form from a fraction eluted with hexane-ethyl acetate (4:1-1:1, v/v).

NMR(CDCl$_3$)δ: 1.24 (6H, t, J=7.0 Hz), 3.12 (2H, d, J=21.6 Hz), 3.76 (3H, s), 3.93-4.08 (4H, m), 4.27 (2H, d, J=5.8 Hz), 5.95-6.10 (1H, m), 6.16 (1H, d, J=15.6 Hz), 7.15-7.37 (9H, m), 7.76 (1H, s).

In the similar manner as in Example 228, the compound described in Example 229 was produced.

EXAMPLE 229

Diethyl 2-[({(2E)-3-[5-(4-fluorophenyl)-1-methyl-1H-pyrazol-4-yl]prop-2-enoyl}amino)methyl]benzylphosphonate was obtained as an amorphous form (357 mg).

NMR(CDCl$_3$)δ: 1.28 (6H, t, J=7.0 Hz), 3.23 (2H, d, J=21.6 Hz), 3.74 (3H, s), 3.91-4.11 (4H, m), 4.52 (2H, d, J=5.4 Hz), 6.22 (1H, d, J=15.4 Hz), 7.14-7.42 (9H, m), 7.79 (1H, s), 7.89 (1H, brs).

In the similar manner as in Example 1, the compounds described in Examples 230-231 were produced.

EXAMPLE 230

3-[5-(4-Chlorophenyl)-1-methyl-1H-pyrazol-4-yl]-N-[4-(dimethylphosphonomethyl)phenyl]propionamide yield: 97%. Colorless crystals.
HPLC analysis: purity 99.6% (retention time: 3.389 min.)
MS(ESI+): 462 (M+H)

EXAMPLE 231

Methyl 3-[4-({(2E)-3-[5-(4-fluorophenyl)-1-methyl-1H-pyrazol-4-yl]prop-2-enoyl}amino)phenyl]-2-hydroxypropionate yield 97%. Colorless crystals.
HPLC analysis: purity 80% (retention time: 3.385 min.)
MS(ESI+): 424(M+H)

EXAMPLE 232

A mixture of methyl 3-[4-({(2E)-3-[5-(4-fluorophenyl)-1-methyl-1H-pyrazol-4-yl]prop-2-enoyl}amino)phenyl]-2-hydroxypropionate (1.34 g), a 2N aqueous sodium hydroxide solution (10 ml) and methanol (20 ml) was stirred at room temperature for 1 hr. The reaction mixture was poured into a 1N aqueous hydrochloric acid solution (100 ml). The precipitated solids were collected by filtration, washed with water and dried to give 3-[4-({(2E)-3-[5-(4-fluorophenyl)-1-methyl-1H-pyrazol-4-yl]prop-2-enoyl}amino)phenyl]-2-hydroxypropionic acid (800 mg, 62%) as colorless crystals.

HPLC analysis: purity 100% (retention time: 3.216 min.)
MS(ESI+): 410(M+H)

EXAMPLE 233

A mixture of 3-[4-({(2E)-3-[5-(4-fluorophenyl)-1-methyl-1H-pyrazol-4-yl]prop-2-enoyl}amino)phenyl]-2-hydroxypropionic acid (409 mg), ethyl chlorocarbonate (324 mg), triethylamine (405 mg) and ethyl acetate (10 ml) was stirred at 0° C. for 1 hr. Conc. aqueous ammonia (10 ml) was added to the reaction mixture and the mixture was stirred at room temperature for 1 hr. The reaction mixture was concentrated, and the precipitated solids were collected by filtration, washed with water and dried to give 2-(ethoxycarbonyloxy)-3-[4-({(2E)-3-[5-(4-fluorophenyl)-1-methyl-1H-pyrazol-4-yl]prop-2-enoyl}amino)phenyl]propionamide (471 mg, 98%) as colorless crystals.

HPLC analysis: purity 94.7% (retention time: 3.398 min.)
MS(ESI+): 481(M+H)

EXAMPLE 234

A mixture of ethyl 4-({(2E)-3-[5-(4-fluorophenyl)-1-methyl-1H-pyrazol-4-yl]prop-2-enoyl}amino)benzoate (510 mg), a 2N aqueous sodium hydroxide solution (1.29 mL) and ethanol (20 mL) was stirred at 50° C. for 14 hrs. 1N Hydrochloric acid (2.6 mL) was added to the reaction mixture, and the mixture was extracted with ethyl acetate. The ethyl acetate layer was washed with saturated aqueous sodium hydrogen carbonate, and then with saturated brine, dried (MgSO$_4$) and concentrated. The obtained solid was recrystallized from acetone-hexane to give 4-({(2E)-3-[5-(4-fluorophenyl)-1-methyl-1H-pyrazol-4-yl]prop-2-enoyl}amino)benzoic acid (390 mg, yield 82%) as colorless prism crystals. melting point: 291-292° C.

Of the compounds obtained in the aforementioned Examples, the compounds having different names are indicated in the following by the different names.

EXAMPLE 1

Dimethyl, [4-({(2E)-3-[5-(4-fluorophenyl)-1-methyl-1H-pyrazol-4-yl]prop-2-enoyl}amino)benzyl]phosphonate

EXAMPLE 2

Diethyl [4-({(2E)-3-[5-(4-fluorophenyl)-1-methyl-1H-pyrazol-4-yl]prop-2-enoyl}amino)benzyl]phosphonate

EXAMPLE 4

Dimethyl [4-({(2E)-3-[5-(4-methoxyphenyl)-1-methyl-1H-pyrazol-4-yl]prop-2-enoyl}amino)benzyl]phosphonate

EXAMPLE 5

Diethyl [4-({(2E)-3-[5-(4-methoxyphenyl)-1-methyl-1H-pyrazol-4-yl]prop-2-enoyl}amino)benzyl]phosphonate

EXAMPLE 6

Dimethyl [4-({(2E)-3-[5-(3-chlorophenyl)-1-methyl-1H-pyrazol-4-yl]prop-2-enoyl}amino)benzyl]phosphonate

EXAMPLE 7

Diethyl [4-({(2E)-3-[5-(3-chlorophenyl)-1-methyl-1H-pyrazol-4-yl]prop-2-enoyl}amino)benzyl]phosphonate

EXAMPLE 8

Dimethyl [4-({(2E)-3-[5-(4-chlorophenyl)-1-methyl-1H-pyrazol-4-yl]prop-2-enoyl}amino)benzyl]phosphonate

EXAMPLE 9

Diethyl [4-({(2E)-3-[5-(4-chlorophenyl)-1-methyl-1H-pyrazol-4-yl]prop-2-enoyl}amino)benzyl]phosphonate

EXAMPLE 10

Dimethyl (4-{[(2E)-3-(1-methyl-5-phenyl-1H-pyrazol-4-yl)prop-2-enoyl]amino}benzyl)phosphonate

EXAMPLE 11

Diethyl (4-{[(2E)-3-(1-methyl-5-phenyl-1H-pyrazol-4-yl)prop-2-enoyl]amino}benzyl)phosphonate

EXAMPLE 12

Dimethyl {4-[((2E)-3-{1-methyl-5-[4-(trifluoromethyl)phenyl]-1H-pyrazol-4-yl}prop-2-enoyl)amino]benzyl}phosphonate

EXAMPLE 13

Diethyl {4-[((2E)-3-{1-methyl-5-[4-(trifluoromethyl)phenyl]-1H-pyrazol-4-yl}prop-2-enoyl)amino]benzyl}phosphonate

EXAMPLE 14

Dimethyl [4-({(2E)-3-[5-(2-fluorophenyl)-1-methyl-1H-pyrazol-4-yl]prop-2-enoyl}amino)benzyl]phosphonate

EXAMPLE 15

Diethyl [4-({(2E)-3-[5-(2-fluorophenyl)-1-methyl-1H-pyrazol-4-yl]prop-2-enoyl}amino)benzyl]phosphonate

EXAMPLE 16

Dimethyl [4-({(2E)-3-[5-(4-bromophenyl)-1-methyl-1H-pyrazol-4-yl]prop-2-enoyl}amino)benzyl]phosphonate

EXAMPLE 17

Diethyl [4-({(2E)-3-[5-(4-bromophenyl)-1-methyl-1H-pyrazol-4-yl]prop-2-enoyl}amino)benzyl]phosphonate

EXAMPLE 18

Dimethyl [4-({(2E)-3-[1-methyl-5-(1-naphthyl)-1H-pyrazol-4-yl]prop-2-enoyl}amino)benzyl]phosphonate

EXAMPLE 19

Diethyl [4-({(2E)-3-[1-methyl-5-(1-naphthyl)-1H-pyrazol-4-yl]prop-2-enoyl}amino)benzyl]phosphonate

EXAMPLE 20

Dimethyl [4-({(2E)-3-[5-(3-fluorophenyl)-1-methyl-1H-pyrazol-4-yl]prop-2-enoyl}amino)benzyl]phosphonate

EXAMPLE 21

Diethyl [4-({(2E)-3-[5-(3-fluorophenyl)-1-methyl-1H-pyrazol-4-yl]prop-2-enoyl}amino)benzyl]phosphonate

EXAMPLE 22

Dimethyl [4-({(2E)-3-[1-methyl-5-(4-methylphenyl)-1H-pyrazol-4-yl]prop-2-enoyl}amino)benzyl]phosphonate

EXAMPLE 23

Diethyl [4-({(2E)-3-[1-methyl-5-(4-methylphenyl)-1H-pyrazol-4-yl]prop-2-enoyl}amino)benzyl]phosphonate

EXAMPLE 28

Diethyl [3-({(2E)-3-[5-(4-fluorophenyl)-1-methyl-1H-pyrazol-4-yl]prop-2-enoyl}amino)benzyl]phosphonate

EXAMPLE 29

Diethyl [2-({(2E)-3-[5-(4-fluorophenyl)-1-methyl-1H-pyrazol-4-yl]prop-2-enoyl}amino)benzyl]phosphonate

EXAMPLE 30

Dibutyl [4-({(2E)-3-[5-(4-fluorophenyl)-1-methyl-1H-pyrazol-4-yl]prop-2-enoyl}amino)benzyl]phosphonate

EXAMPLE 31

Diethyl [4-({(2E)-3-[5-(4-fluorophenyl)-1-methyl-1H-pyrazol-4-yl]prop-2-enoyl}amino)phenyl]phosphonate

EXAMPLE 32

Diethyl {2-[4-({(2E)-3-[5-(4-fluorophenyl)-1-methyl-1H-pyrazol-4-yl]prop-2-enoyl}amino)phenyl]ethyl}phosphonate

EXAMPLE 33

Diethyl [4-({(2E)-3-[5-(4-fluorophenyl)-1-methyl-1H-pyrazol-4-yl]prop-2-enoyl}amino)-3-methylbenzyl]phosphonate

EXAMPLE 34

Diethyl [4-({(2E)-3-[1-benzyl-5-(4-fluorophenyl)-1H-pyrazol-4-yl]prop-2-enoyl}amino)benzyl]phosphonate

EXAMPLE 35

Diethyl [4-({(2E)-3-[1-benzyl-3-(4-fluorophenyl)-1H-pyrazol-4-yl]prop-2-enoyl}amino)benzyl]phosphonate

EXAMPLE 36

Dimethyl [4-({(2E)-3-[1-ethyl-5-(4-fluorophenyl)-1H-pyrazol-4-yl]prop-2-enoyl}amino)benzyl]phosphonate

EXAMPLE 37

Diethyl [4-({(2E)-3-[1-ethyl-5-(4-fluorophenyl)-1H-pyrazol-4-yl]prop-2-enoyl}amino)benzyl]phosphonate

EXAMPLE 38

Dimethyl [4-({(2E)-3-[5-(4-fluorophenyl)-1,3-dimethyl-1H-pyrazol-4-yl]prop-2-enoyl}amino)benzyl]phosphonate

EXAMPLE 39

Diethyl [4-({(2E)-3-[5-(4-fluorophenyl)-1,3-dimethyl-1H-pyrazol-4-yl]prop-2-enoyl}amino)benzyl]phosphonate

EXAMPLE 40

Dimethyl {4-{[(2E)-3-(5-cyclohexyl-1-methyl-1H-pyrazol-4-yl) prop-2-enoyl]amino}benzyl)phosphonate

EXAMPLE 41

Diethyl (4-{[(2E)-3-(5-cyclohexyl-1-methyl-1H-pyrazol-4-yl)prop-2-enoyl]amino}benzyl)phosphonate

EXAMPLE 42

Dimethyl [4-({(2E)-3-[5-(2-furyl)-1-methyl-1H-pyrazol-4-yl]prop-2-enoyl}amino)benzyl]phosphonate

EXAMPLE 43

Diethyl [4-({(2E)-3-[5-(2-furyl)-1-methyl-1H-pyrazol-4-yl]prop-2-enoyl}amino)benzyl]phosphonate

EXAMPLE 45

Diethyl [{4-({(2E)-3-[5-(4-fluorophenyl)-1-methyl-1H-pyrazol-4-yl]prop-2-enoyl}amino)phenyl}(methoxy)methyl]phosphonate

EXAMPLE 46

Diethyl {[4-({(2E)-3-[5-(4-fluorophenyl)-1-methyl-1H-pyrazol-4-yl]prop-2-enoyl}amino)phenyl](hydroxy)methyl}phosphonate

EXAMPLE 48

O-Benzyl S-[4-({(2E)-3-[5-(4-fluorophenyl)-1-methyl-1H-pyrazol-4-yl]prop-2-enoyl}amino)phenyl]thiocarbonate

EXAMPLE 54

Diethyl [4-({(2E)-3-[3-(4-fluorophenyl)-1-methyl-1H-pyrazol-4-yl]prop-2-enoyl}amino)benzyl]phosphonate

EXAMPLE 55

Diethyl [4-({(2E)-3-[4-(4-fluorophenyl)-1-methyl-1H-pyrazol-5-yl]prop-2-enoyl}amino)benzyl]phosphonate

EXAMPLE 56

Diethyl [4-({(2E)-3-[4-(4-fluorophenyl)-1-methyl-1H-pyrazol-3-yl]prop-2-enoyl}amino)benzyl]phosphonate

EXAMPLE 57

Diethyl [4-({3-[5-(4-fluorophenyl)-1-methyl-1H-pyrazol-4-yl]propanoyl}amino)benzyl]phosphonate

EXAMPLE 58

Dimethyl [4-({3-[5-(4-fluorophenyl)-1-methyl-1H-pyrazol-4-yl]propanoyl}amino)benzyl]phosphonate

EXAMPLE 59

Diethyl [4-({3-[5-(4-chlorophenyl)-1-methyl-1H-pyrazol-4-yl]propanoyl}amino)benzyl]phosphonate

EXAMPLE 61

Diethyl [4-({(2E)-3-[1-(4-fluorophenyl)-1H-imidazol-5-yl]prop-2-enoyl}amino)benzyl]phosphonate

EXAMPLE 62

Dimethyl [4-({(2E)-3-[1-(4-fluorophenyl)-1H-imidazol-5-yl]prop-2-enoyl}amino)benzyl]phosphonate

EXAMPLE 63

Diethyl [4-({3-[1-(4-fluorophenyl)-1H-imidazol-5-yl]propanoyl}amino)benzyl]phosphonate

EXAMPLE 64

Dimethyl [4-({3-[1-(4-fluorophenyl)-1H-imidazol-5-yl]propanoyl}amino)benzyl]phosphonate

EXAMPLE 65

Diethyl [4-({(2E)-3-[4-(4-fluorophenyl)-4H-1,2,4-triazol-3-yl]prop-2-enoyl}amino)benzyl]phosphonate

EXAMPLE 66

Dimethyl [4-({(2E)-3-[4-(4-fluorophenyl)-4H-1,2,4-triazol-3-yl]prop-2-enoyl}amino)benzyl]phosphonate

EXAMPLE 67

Diethyl [4-({3-[4-(4-fluorophenyl)-4H-1,2,4-triazol-3-yl]propanoyl}amino)benzyl]phosphonate

EXAMPLE 68

Dimethyl [4-({3-[4-(4-fluorophenyl)-4H-1,2,4-triazol-3-yl]propanoyl}amino)benzyl]phosphonate

EXAMPLE 69

Diethyl [4-({(2E)-3-[5-(4-fluorophenyl)-1,2,3-thiadiazol-4-yl]prop-2-enoyl}amino)benzyl]phosphonate

EXAMPLE 70

Dimethyl [4-({(2E)-3-[5-(4-fluorophenyl)-1,2,3-thiadiazol-4-yl]prop-2-enoyl}amino)benzyl]phosphonate

EXAMPLE 71

Diethyl [4-({(2E)-3-[4-(4-fluorophenyl)-1,2,3-thiadiazol-5-yl]prop-2-enoyl}amino)benzyl]phosphonate

EXAMPLE 72

Dimethyl [4-({(2E)-3-[4-(4-fluorophenyl)-1,2,3-thiadiazol-5-yl]prop-2-enoyl}amino)benzyl]phosphonate

EXAMPLE 73

Diethyl [4-({(2E)-3-[5-(4-fluorophenyl)-1-methyl-1H-pyrazol-4-yl]but-2-enoyl}amino)benzyl]phosphonate

EXAMPLE 74

Diethyl [4-({3-[5-(4-fluorophenyl)-1-methyl-1H-pyrazol-4-yl]butanoyl}amino)benzyl]phosphonate

EXAMPLE 75

Diethyl [4-({(2Z)-3-[5-(4-methoxyphenyl)-1-methyl-1H-pyrazol-4-yl]prop-2-enoyl}amino)benzyl]phosphonate

EXAMPLE 76

Dimethyl [4-({(2Z)-3-[5-(4-methoxyphenyl)-1-methyl-1H-pyrazol-4-yl]prop-2-enoyl}amino)benzyl]phosphonate

EXAMPLE 77

Diethyl [4-({(2Z)-3-[5-(4-fluorophenyl)-1-methyl-1H-pyrazol-4-yl]prop-2-enoyl}amino)benzyl]phosphonate

EXAMPLE 80

Diethyl [4-{[3-(1,5-diphenyl-1H-pyrazol-4-yl)propanoyl]amino}benzyl]phosphonate

EXAMPLE 81

Ethyl (4-{[3-(1,5-diphenyl-1H-pyrazol-4-yl)propanoyl]amino}phenyl)acetate

EXAMPLE 82

Methyl 4-{[3-(1,5-diphenyl-1H-pyrazol-4-yl)propanoyl]amino}benzoate

EXPERIMENTAL EXAMPLE 1

Using rat C6 glioma cells, the GDNF production promoting action of the compound of the present invention was evaluated.

Rat C6 glioma cells (ATCC) were grown in Dulbecco's Modified Eagle's Medium (DMEM) containing 10% FBS (Fetal Bovine Serum) in a collagen type 1 coated 75 cm$^2$ culture flask (SUMITOMO BAKELITE Co., Ltd.) until near confluent, detached by trypsin treatment and washed once with DMEM containing 10% FBS.

The cells after washing were diluted with 10% FBS-containing DMEM to a concentration of $5 \times 10^4$/mL and seeded at 0.3 mL/well in each well of collagen type 1 coated 48 well culture dish (SUMITOMO BAKELITE Co., Ltd.). After 3 days, the culture in the culture dish was placed in a 1% BSA (bovine serum albumin, Sigma)-containing DMEM medium supplemented with various concentrations of test compound, and further cultured for 2 days. The culture supernatant was recovered and preserved at −80° C. until measurement of GDNF.

The content of GDNF in the culture supernatant was measured by the following ELISA Method.

Anti-GDNF antibody (MAB212, R&D) was diluted with TBS (Tris buffered physiological saline: 25 mmol/L Tris-HCl (pH 8.0), 150 mmol/L NaCl) to 2 µg/mL and dispensed at 0.1 mL/well to each well of a 96-well immunoplate. The 96-well immunoplate was incubated overnight at 4° C. and washed once with TBS containing Tween 20 at 0.05% (hereinafter to be abbreviated as TBST). A blocking solution (TBS containing 1% BSA and 5% sucrose) was added at 0.2 mL/well to each well after washing, and the plate was incubated at room temperature for 1 hr., after which each well was washed twice with TBST. The culture supernatant (0.1 mL) of the aforementioned C6 cells was added to each well after washing and the plate was incubated at room temperature for 3 hrs., after which the wells were washed 5 times with TBST. The 500-fold diluted anti-GDNF antibody (G2791, Promega) was added by 0.1 mL to each well after washing, incubated at room temperature for 2 hrs. and washed 5 times with TBST. A 5000-fold diluted horseradish peroxidase-labeled anti-chicken IgY antibody (G1351, Promega) was added at 0.1 mL/well to each well after washing, incubated at room temperature for 2 hrs. and washed 5 times with TBST. A substrate solution (TMB substrate solution, BIO-RAD) was added at 0.1 mL/well to each well after washing and allowed to develop color at room temperature for 8 min. To stop the reaction, 0.1 mL of 1 mol/L phosphoric acid was added to each well in coloring developing reaction. The absorbance of the reaction solution at 450 nm wavelength was measured.

In the same manner as above except the test compound was not used, the ELISA Method was performed and this was used as a control group.

Using various concentrations of GDNF (Promega), ELISA Method was performed in the same manner as above and standard line was prepared.

From the aforementioned absorbance and standard line, GDNF content in a sample was calculated and the concentration ($EC_{50}$), which causes 50% increase of GDNF relative to the control group was calculated from the regression line. The results are shown in Table 1.

TABLE 1

| Example number | $EC_{50}$ value (µmol/L) |
|---|---|
| 1 | 0.2 |
| 2 | 0.4 |
| 5 | 1.0 |
| 9 | 2.5 |
| 11 | 0.9 |
| 27 | 0.5 |
| 49 | 1.6 |
| 50 | 0.4 |
| 60 | 0.8 |
| 61 | 0.4 |
| 71 | 1.7 |
| 91 | 0.49 |
| 110 | 0.31 |
| 121 | 0.18 |
| 140 | 0.22 |
| 147 | 0.46 |
| 149 | 0.51 |
| 159 | 0.12 |
| 161 | 0.13 |
| 163 | 0.19 |
| 185 | 0.3 |
| 190 | 0.59 |
| 192 | 0.54 |
| 193 | 0.16 |
| 195 | 0.12 |
| 222 | 0.12 |
| 223 | 0.036 |

As shown in Table 1, the compound of the present invention has GDNF production promoting action.

EXPERIMENTAL EXAMPLE 2

Using PC12 cells, the neuroprotective action of the compound of the present invention was evaluated.

PC12 cells were precultured for one day in a DMEM (Dulbecco's Modified Eagle's Medium) culture solution containing 10% FCS (Fetal Calf Serum) in an incubator at 37° C., 5% $CO_2$, and seeded at $5 \times 10^3$/well in a 24 well plate (Falcon) in the same medium. After the cells adhered to the bottom surface, the culture was changed to a DMEM culture solution containing 0.5% FCS and 2 ng/mL of NGF (Wako Pure Chemical Industries, Ltd.). After culturing overnight, the test compound was added at a concentration of 0.3-3.0 µmol/L and the cells were cultured for two more days. Gultalaldehyde was added to the cultured to a final concentration of 2% and the cells were fixed for 1 hr., after which stained with a Diff-Quick (International Reagents Corporation). The cells were washed, dried with air and observed under a microscope.

As a result, the cells treated with the compounds of Example 2, Example 49, Example 60, Example 110, Example 149, Example 159, Example 161, Example 185, Example 192, Example 222 and Example 223 showed promoted formation of neurite network, which demonstrated that these compounds have a neuroprotective action.

FORMULATION EXAMPLE 1

Production of Capsule

| 1) compound of Example 1 | 30 mg |
|---|---|
| 2) cellulose fine powder | 10 mg |
| 3) lactose | 19 mg |
| 4) magnesium stearate | 1 mg |
| total | 60 mg |

1), 2), 3) and 4) were mixed and filled in gelatin capsules.

FORMULATION EXAMPLE 2

Production of Tablet

| 1) compound of Example 1 | 30 g |
|---|---|
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of 1), 2) and 3) and 30 g of 4) were kneaded with water and, after drying in vacuo, granulated. The granules were mixed with 14 g of 4) and 1 g of 5) and punched with a tableting machine. In this way, 1000 tablets containing 30 mg of the compound of Example 1 per tablet are obtained.

INDUSTRIAL APPLICABILITY

The compound of the present invention has superior neurotrophic factor production or secretion promoting action and is useful for the prophylaxis or treatment of neuropathy and the like.

This application is based on a patent application No. 2002-320153 filed in Japan, the contents of which are all hereby incorporated by reference.

The references cited herein, including patents and patent applications, are hereby incorporated in their entireties by reference, to the extent that they have been disclosed herein.

The invention claimed is:

1. Diethyl [4-({(2E)-3-[5-(4-fluorophenyl)-1-methyl-1H-pyrazol-4-yl]prop-2-enoyl}amino)benzyl]phosphonate or salt thereof.

2. A pharmaceutical composition comprising the compound of claim 1 or a salt thereof together with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,423,159 B2 | Page 1 of 1 |
| APPLICATION NO. | : 10/532667 | |
| DATED | : September 9, 2008 | |
| INVENTOR(S) | : Yu Momose et al. | |

It is certified that error appears in the above-identified patent and that said Letters Patent is hereby corrected as shown below:

In column 146, line 53, claim 1, before "salt" insert --a--.

Signed and Sealed this

Twenty-fourth Day of February, 2009

JOHN DOLL
*Acting Director of the United States Patent and Trademark Office*